(12) United States Patent
Crawford et al.

(10) Patent No.: US 11,135,022 B2
(45) Date of Patent: Oct. 5, 2021

(54) SURGICAL ROBOT PLATFORM

(71) Applicant: GLOBUS MEDICAL, INC., Audubon, PA (US)

(72) Inventors: Neil R. Crawford, Chandler, AZ (US); Nicholas Theodore, Paradise Valley, AZ (US); Mitchell A. Foster, Scottsdale, AZ (US)

(73) Assignee: Globus Medical, Inc., Audubon, PA (US)

( * ) Notice: Subject to any disclaimer, the term of this patent is extended or adjusted under 35 U.S.C. 154(b) by 972 days.

(21) Appl. No.: 15/449,260

(22) Filed: Mar. 3, 2017

(65) Prior Publication Data

US 2017/0231702 A1  Aug. 17, 2017

Related U.S. Application Data

(63) Continuation of application No. 13/924,505, filed on Jun. 21, 2013, now Pat. No. 9,782,229.
(Continued)

(51) Int. Cl.
*A61B 5/05* (2021.01)
*A61B 34/30* (2016.01)
(Continued)

(52) U.S. Cl.
CPC .............. *A61B 34/30* (2016.02); *A61B 5/066* (2013.01); *A61B 10/02* (2013.01);
(Continued)

(58) Field of Classification Search
CPC . A61B 10/02; A61B 10/0233; A61B 10/0275; A61B 17/025; A61B 17/1615;
(Continued)

(56) References Cited

U.S. PATENT DOCUMENTS 4,150,293 A  4/1979 Franke
5,246,010 A  9/1993 Gazzara et al.
(Continued)

FOREIGN PATENT DOCUMENTS

EP  2286729 A2  2/2011
JP  898843 A  4/1996
(Continued)

OTHER PUBLICATIONS

US 8,231,638 B2, 07/2012, Swarup et al. (withdrawn)

*Primary Examiner* — Mark D Remaly

(57) ABSTRACT

A medical robot system, including a robot coupled to an effectuator element with the robot configured for controlled movement and positioning. The system may include a transmitter configured to emit one or more signals, and the transmitter is coupled to an instrument coupled to the effectuator element. The system may further include a motor assembly coupled to the robot and a plurality of receivers configured to receive the one or more signals emitted by the transmitter. A control unit is coupled to the motor assembly and the plurality of receivers, and the control unit is configured to supply one or more instruction signals to the motor assembly. The instruction signals can be configured to cause the motor assembly to selectively move the effectuator element and is further configured to (i) calculate a position of the at least one transmitter by analysis of the signals received by the plurality of receivers; (ii) display the position of the at least one transmitter with respect to the body of the patient; and (iii) selectively control actuation of the motor assembly in response to the signals received by the plurality of receivers.

20 Claims, 113 Drawing Sheets

Related U.S. Application Data

(60) Provisional application No. 61/800,527, filed on Mar. 15, 2013, provisional application No. 61/662,702, filed on Jun. 21, 2012.

(51) Int. Cl.

| | | |
|---|---|---|
| *A61B 5/06* | (2006.01) | |
| *A61B 10/02* | (2006.01) | |
| *A61N 1/05* | (2006.01) | |
| *A61B 34/00* | (2016.01) | |
| *A61B 90/14* | (2016.01) | |
| *A61B 90/00* | (2016.01) | |
| *A61B 17/02* | (2006.01) | |
| *A61B 17/16* | (2006.01) | |
| *A61B 34/32* | (2016.01) | |
| *A61B 34/20* | (2016.01) | |
| *A61B 46/20* | (2016.01) | |
| *A61B 50/13* | (2016.01) | |
| *A61B 17/88* | (2006.01) | |
| *A61B 17/17* | (2006.01) | |
| *A61B 34/10* | (2016.01) | |
| *A61B 17/70* | (2006.01) | |
| *A61M 5/172* | (2006.01) | |
| *A61B 17/00* | (2006.01) | |

(52) U.S. Cl.
CPC ...... *A61B 10/0233* (2013.01); *A61B 10/0275* (2013.01); *A61B 17/025* (2013.01); *A61B 17/1615* (2013.01); *A61B 17/1671* (2013.01); *A61B 17/1703* (2013.01); *A61B 17/1757* (2013.01); *A61B 17/7082* (2013.01); *A61B 17/8866* (2013.01); *A61B 34/10* (2016.02); *A61B 34/20* (2016.02); *A61B 34/25* (2016.02); *A61B 34/32* (2016.02); *A61B 34/70* (2016.02); *A61B 34/74* (2016.02); *A61B 34/76* (2016.02); *A61B 46/20* (2016.02); *A61B 50/13* (2016.02); *A61B 90/14* (2016.02); *A61B 90/37* (2016.02); *A61B 90/39* (2016.02); *A61M 5/172* (2013.01); *A61N 1/0529* (2013.01); *A61B 2010/0208* (2013.01); *A61B 2017/00119* (2013.01); *A61B 2017/00203* (2013.01); *A61B 2017/00207* (2013.01); *A61B 2017/0256* (2013.01); *A61B 2034/107* (2016.02); *A61B 2034/2051* (2016.02); *A61B 2034/2055* (2016.02); *A61B 2034/2072* (2016.02); *A61B 2034/301* (2016.02); *A61B 2034/741* (2016.02); *A61B 2034/742* (2016.02); *A61B 2034/743* (2016.02); *A61B 2034/744* (2016.02); *A61B 2090/034* (2016.02); *A61B 2090/064* (2016.02); *A61B 2090/365* (2016.02); *A61B 2090/374* (2016.02); *A61B 2090/378* (2016.02); *A61B 2090/3762* (2016.02); *A61B 2090/3764* (2016.02); *A61B 2090/395* (2016.02); *A61B 2090/3937* (2016.02); *A61B 2090/3941* (2016.02); *A61B 2090/3945* (2016.02); *A61B 2090/3966* (2016.02); *A61B 2090/3975* (2016.02); *A61B 2090/3979* (2016.02); *A61B 2090/3983* (2016.02)

(58) Field of Classification Search
CPC ........... A61B 17/1671; A61B 17/1703; A61B 17/1757; A61B 17/7082; A61B 17/8866; A61B 2010/0208; A61B 2017/00119; A61B 2017/00203; A61B 2017/00207; A61B 2017/0256; A61B 2034/107; A61B 2034/2051; A61B 2034/2055; A61B 2034/2072; A61B 2034/301; A61B 2034/741; A61B 2034/742; A61B 2034/743; A61B 2034/744; A61B 2090/034; A61B 2090/064; A61B 2090/365; A61B 2090/374; A61B 2090/3762; A61B 2090/3764; A61B 2090/378; A61B 2090/3937; A61B 2090/3941; A61B 2090/3945; A61B 2090/395; A61B 2090/3966; A61B 2090/3975; A61B 2090/3979; A61B 2090/3983; A61B 34/10; A61B 34/20; A61B 34/25; A61B 34/30; A61B 34/32; A61B 34/70; A61B 34/74; A61B 34/76; A61B 46/20; A61B 50/13; A61B 5/066; A61B 90/14; A61B 90/37; A61B 90/39; A61M 5/172; A61N 1/0529
See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wrignt et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,161 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,276,471 B1 | 8/2001 | Kratzenberg et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessrnan et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |

(56) References Cited

U.S. PATENT DOCUMENTS

| | | |
|---|---|---|
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessrnan et al. |
| 6,692,090 B1 | 2/2004 | Heyn et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Lehner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,787,699 B2 | 6/2010 | Mahesh et al. |
| 7,751,865 B2 | 7/2010 | Jascab et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |

(56) References Cited

U.S. PATENT DOCUMENTS

| | | |
|---|---|---|
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavailee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |

(56) References Cited

U.S. PATENT DOCUMENTS

| | | |
|---|---|---|
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,627,996 B2 | 9/2014 | Scott et al. |
| 8,644,789 B2 | 9/2014 | Shelton, IV et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Frisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,683,210 B2 | 11/2014 | Truncale et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2003/0055049 A1 | 3/2003 | Brock |
| 2003/0153829 A1 | 8/2003 | Sarin et al. |
| 2004/0024311 A1 | 2/2004 | Quaid |
| 2004/0068172 A1 | 4/2004 | Nowinsk et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0215879 A1* | 9/2005 | Chuanggui ............ A61B 90/36 600/407 |
| 2005/0245820 A1 | 11/2005 | Sarin |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0154389 A1 | 6/2008 | Smith et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2006/0300477 | 12/2008 | Lloyd et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadeni et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |

(56) References Cited

U.S. PATENT DOCUMENTS

| | | |
|---|---|---|
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0209290 A1 | 8/2012 | Selover et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinder et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0066944 A1 | 3/2014 | Taylor et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarrnent |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2014/0379130 A1 | 12/2014 | Lee et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |

(56) References Cited

U.S. PATENT DOCUMENTS

| | | |
|---|---|---|
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucker et al. |

FOREIGN PATENT DOCUMENTS

| | | | |
|---|---|---|---|
| JP | 8313304 | A | 11/1996 |
| JP | 2008538184 | A | 10/2008 |
| JP | 2015528713 | A | 10/2015 |
| WO | 02071369 | A1 | 9/2002 |
| WO | 2017127202 | A1 | 7/2017 |

\* cited by examiner

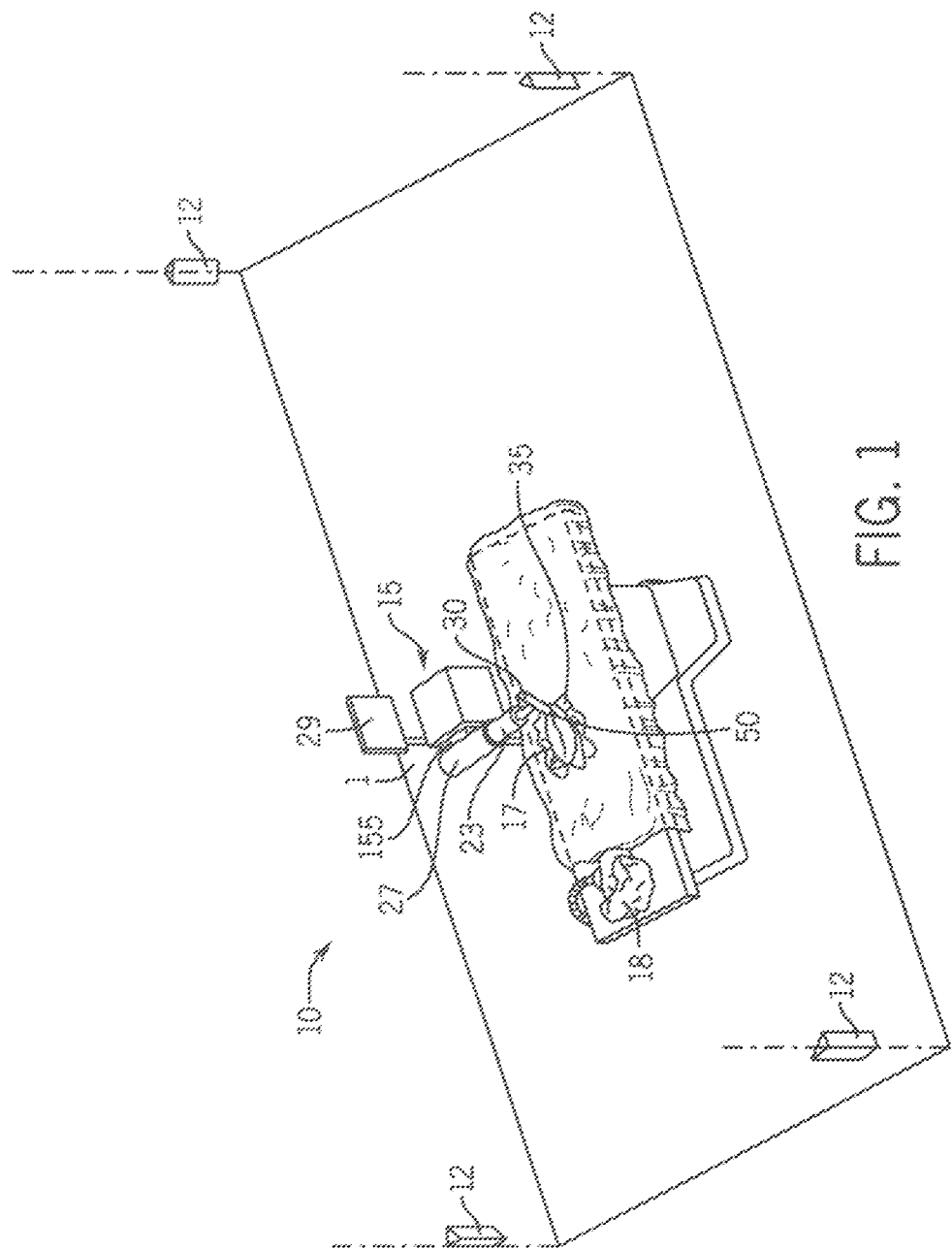

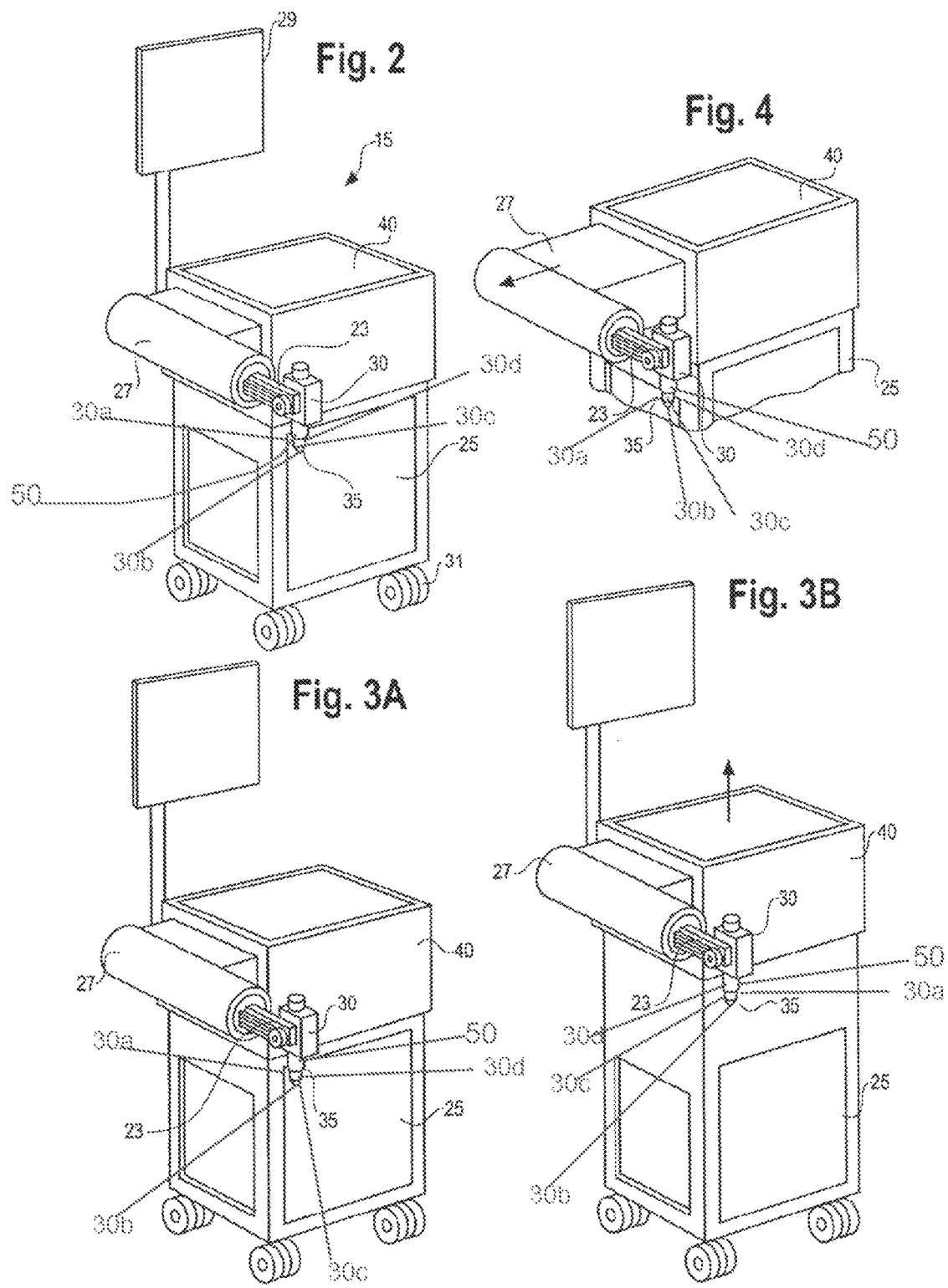

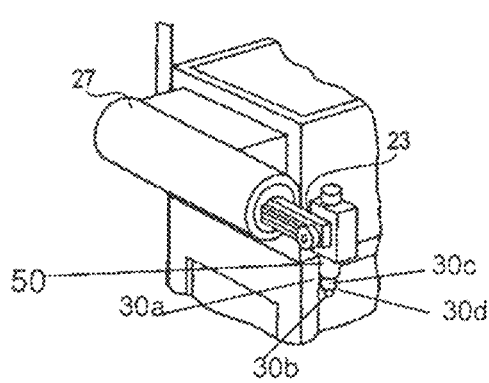
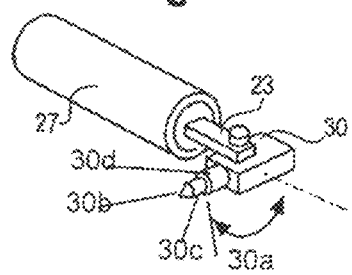
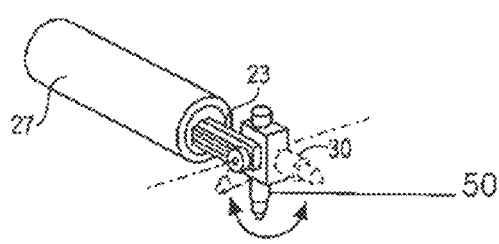
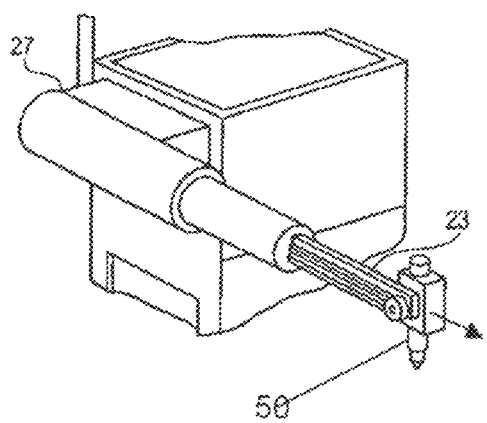
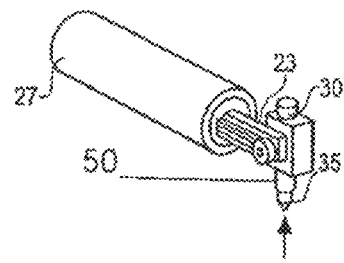
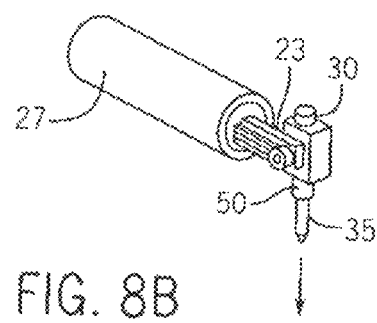

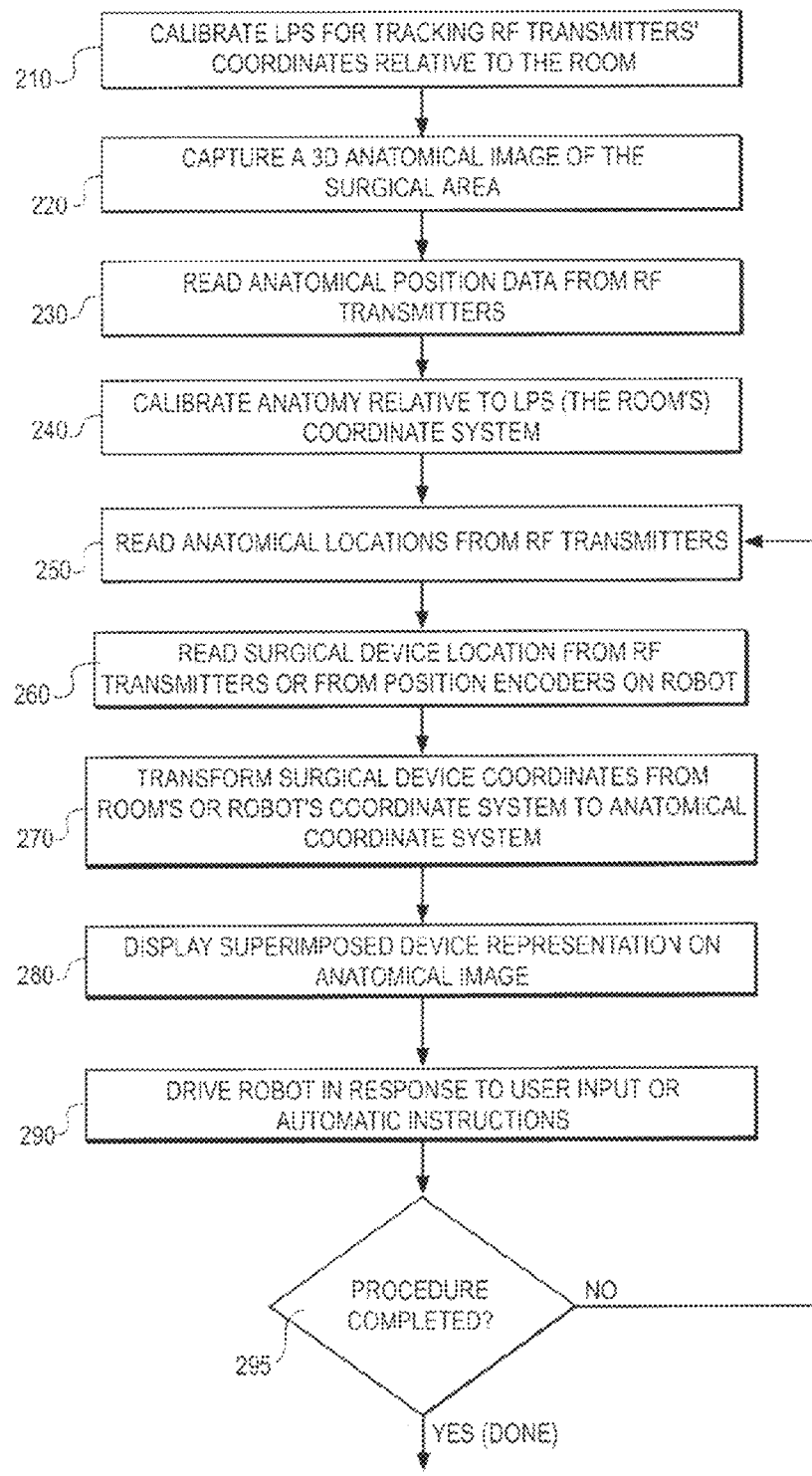

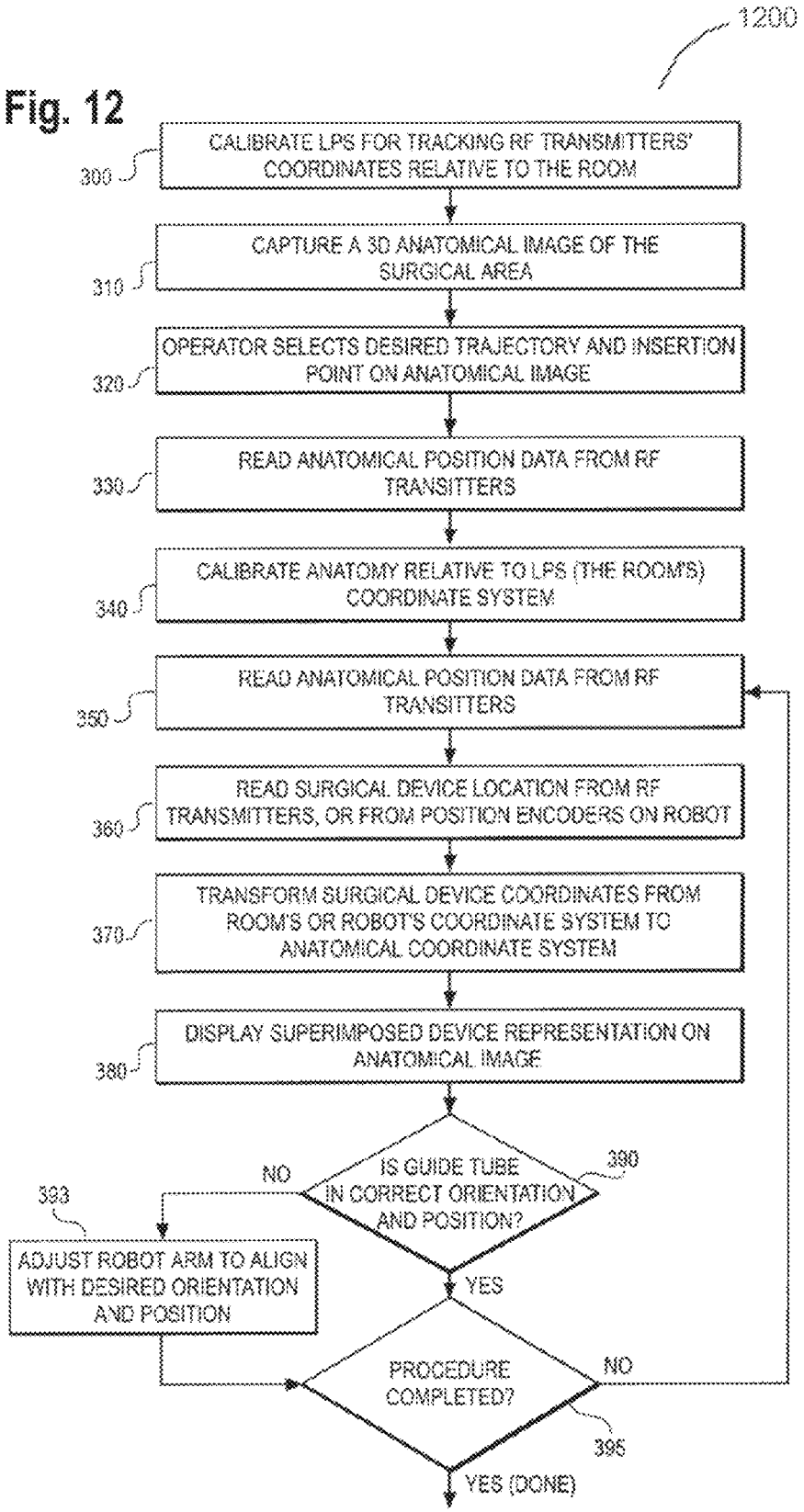

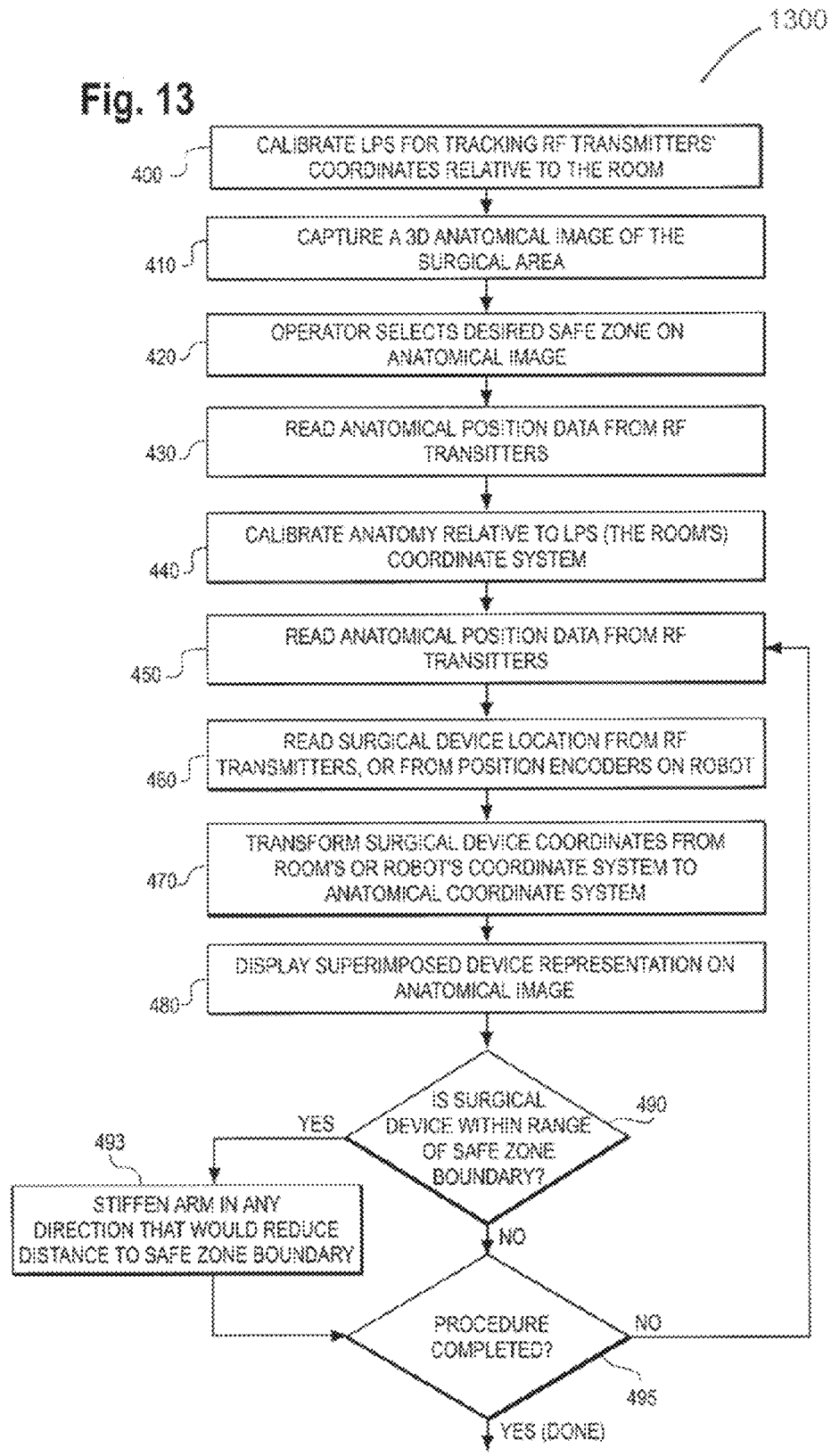

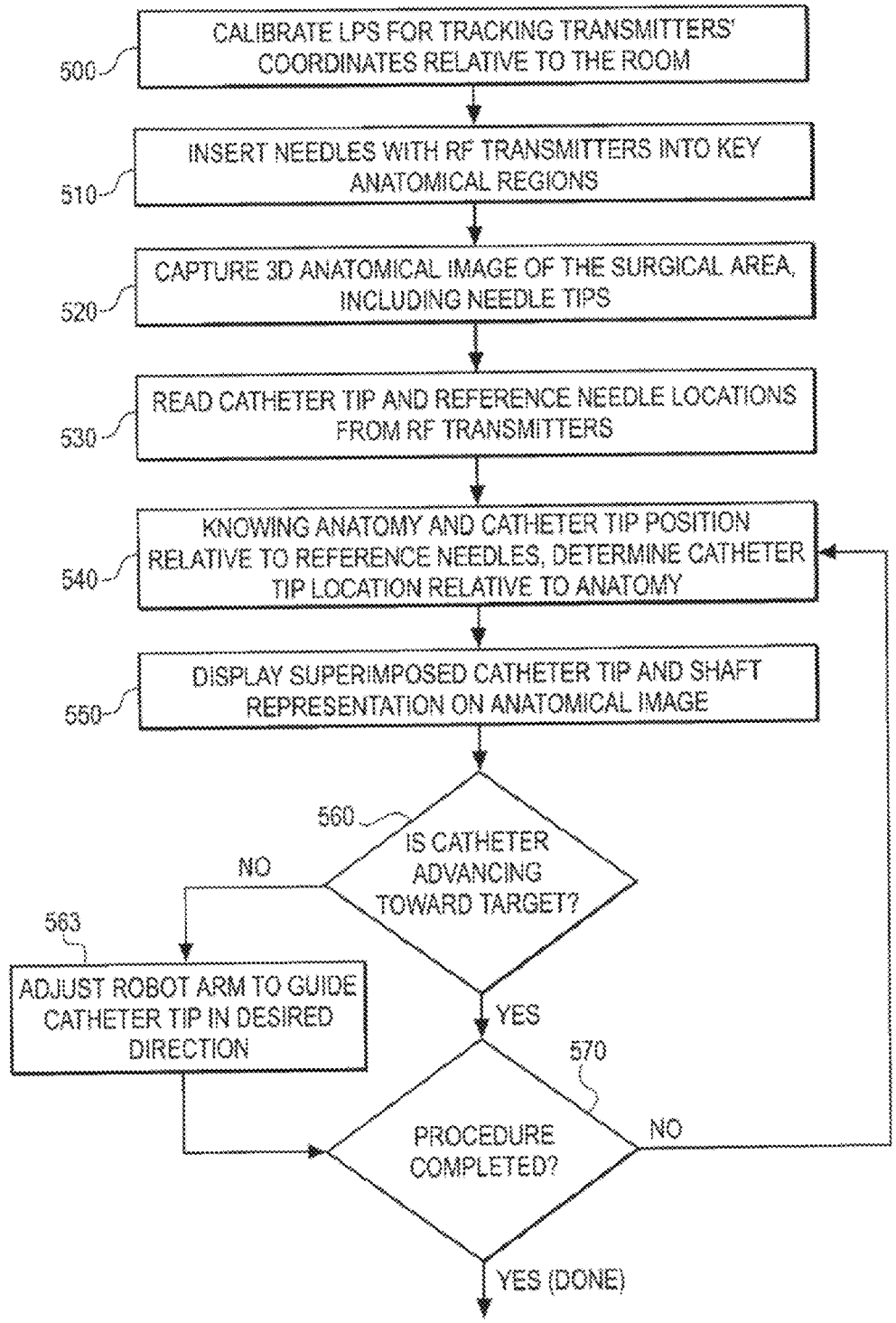

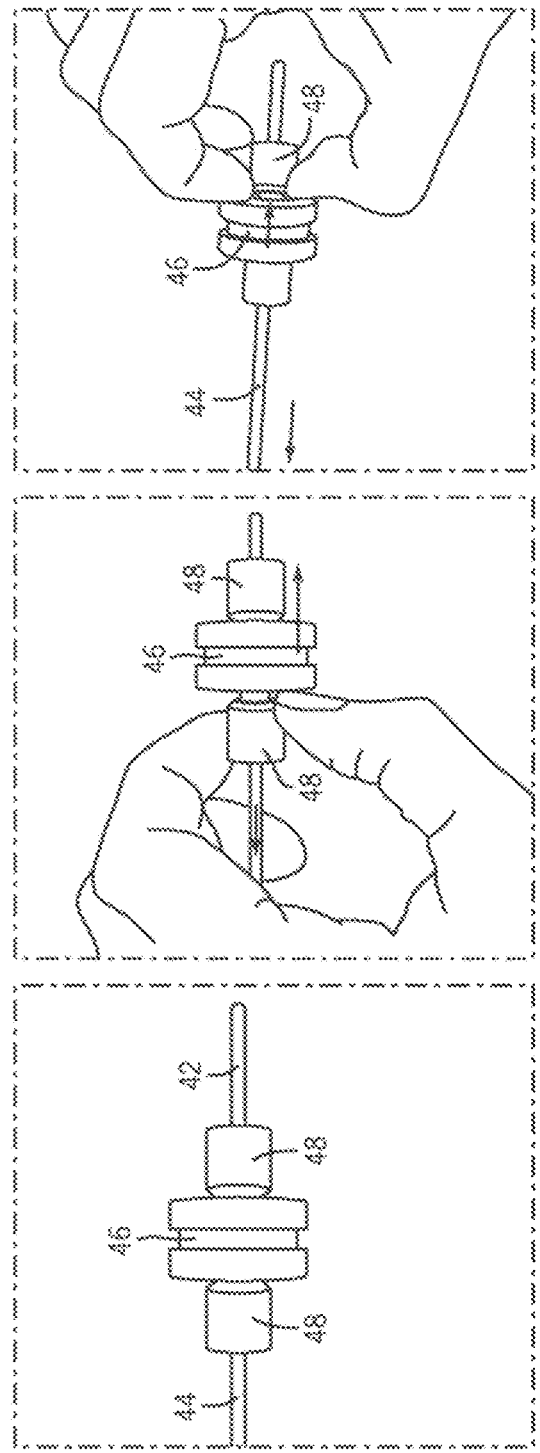

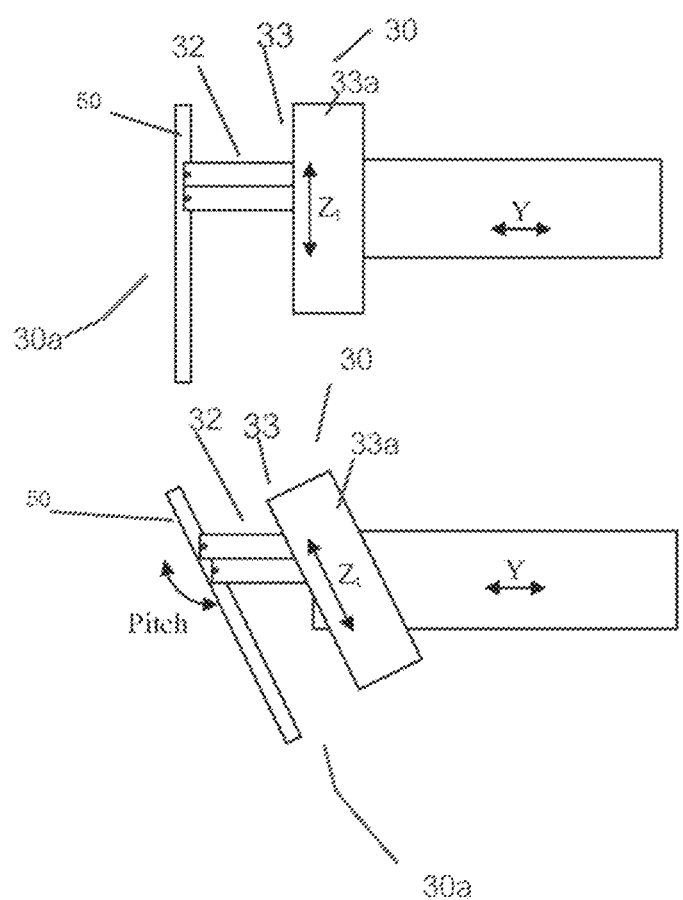

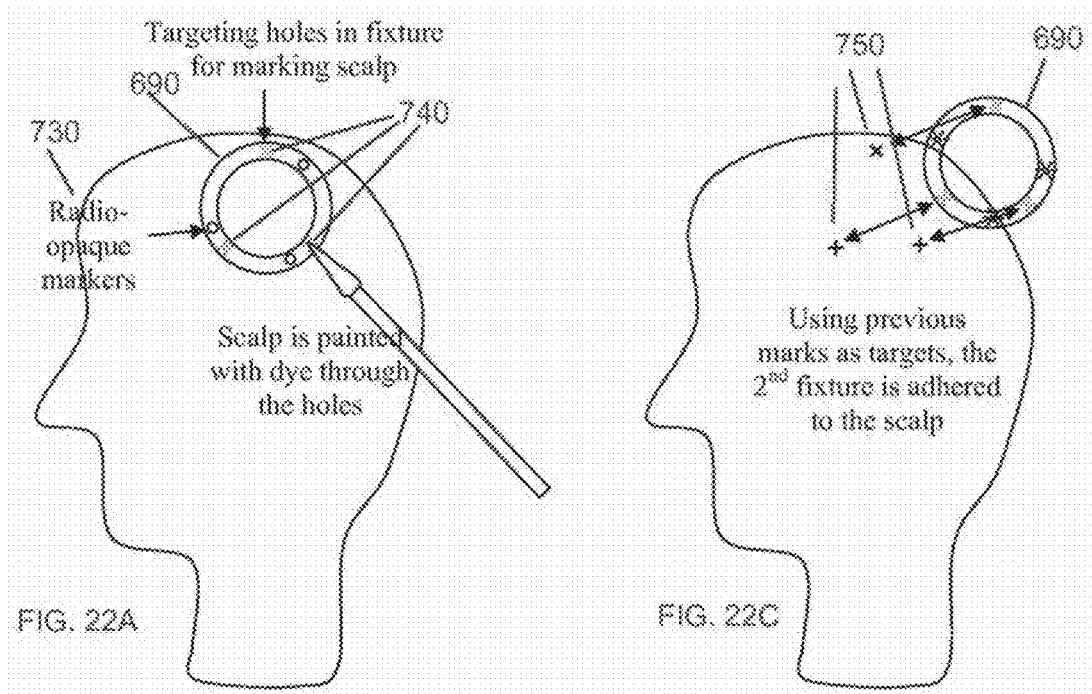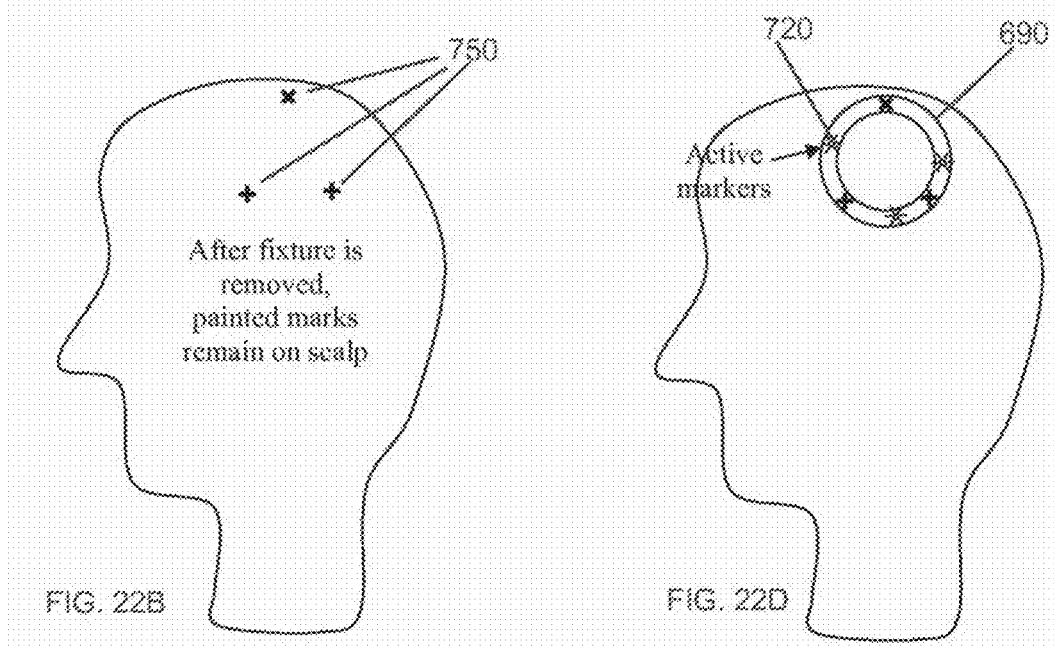

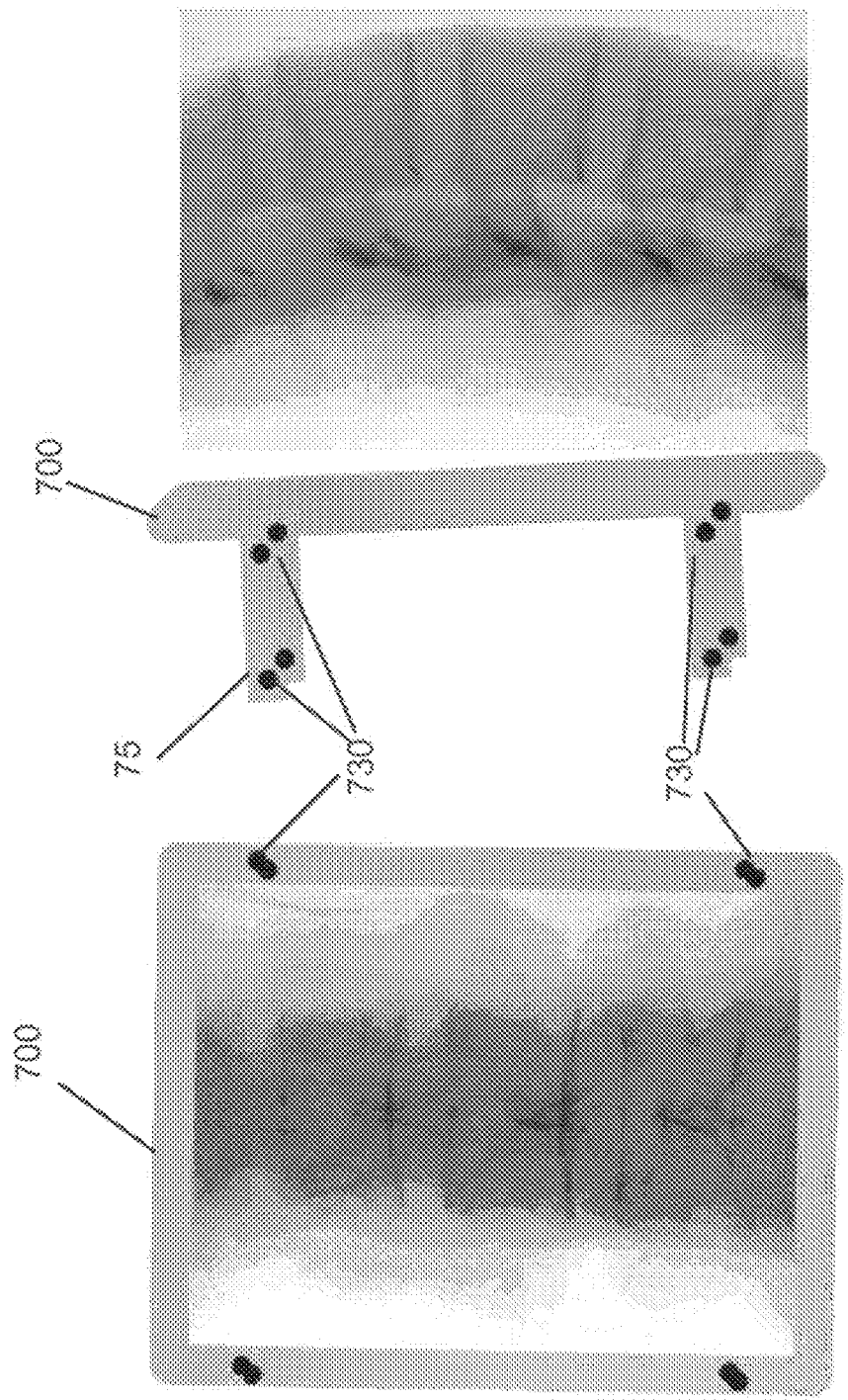

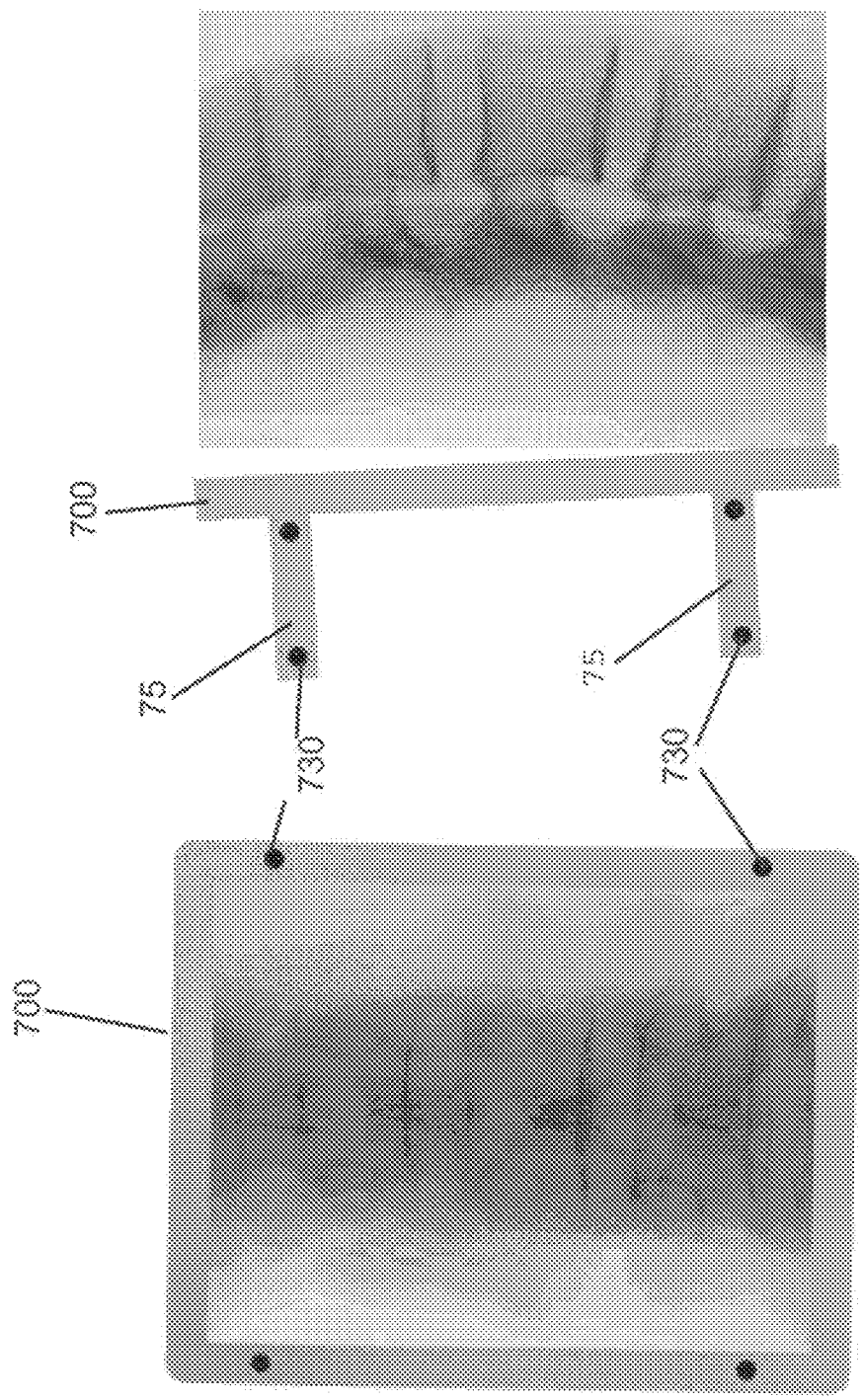

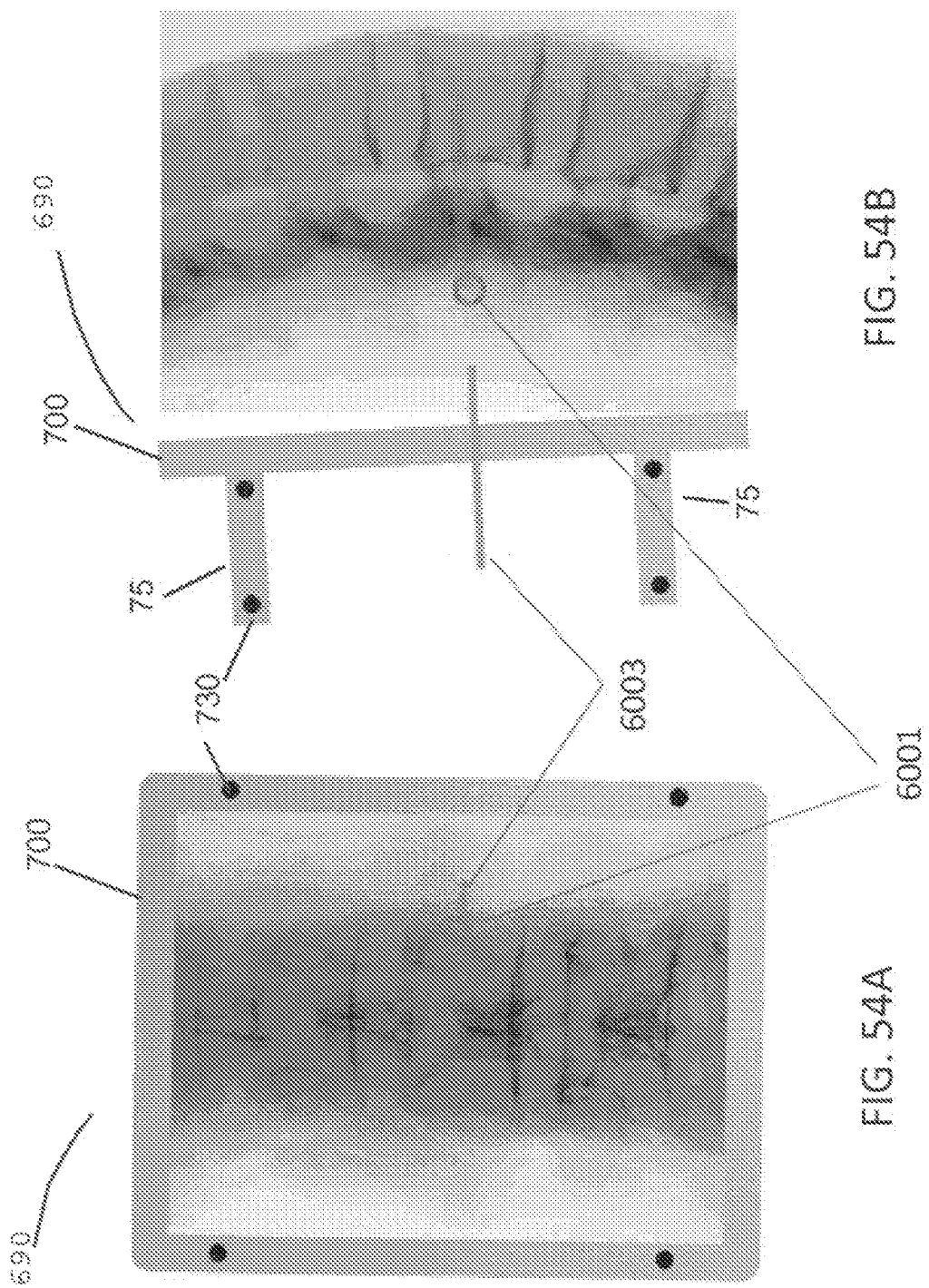

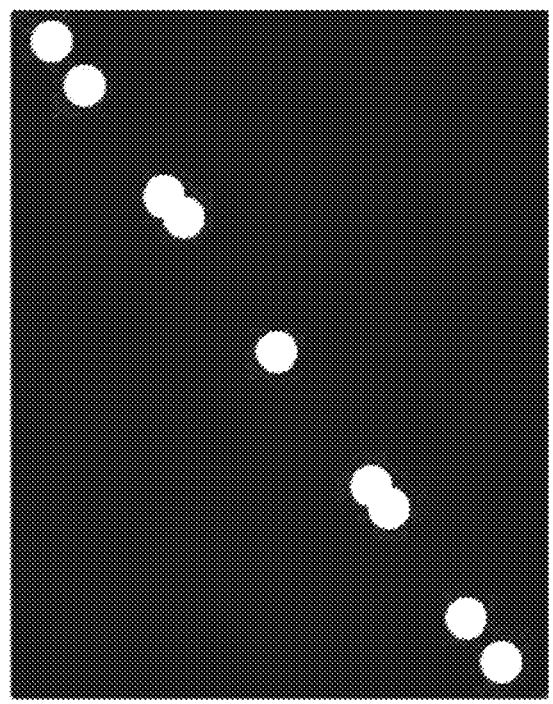
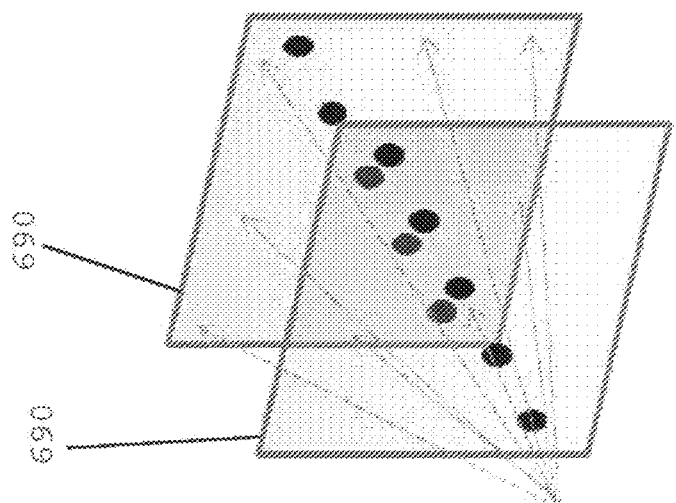
FIG. 59B
FIG. 59A

SURGICAL ROBOT PLATFORM

RELATED APPLICATIONS

This application is continuation of U.S. patent application Ser. No. 13/924,505 filed on Jun. 21, 2013 which claims priority under 35 U.S.C. § 119 to U.S. Provisional Patent Application No. 61/662,702 filed on Jun. 21, 2012 and U.S. Provisional Patent Application No. 61/800,527 filed on Mar. 15, 2013, which are incorporated herein by reference in their entirety.

BACKGROUND

Various medical procedures require the precise localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Limited robotic assistance for surgical procedures is currently available. For example, the da Vinci® medical robot system (da Vinci® is a registered trademark of Intuitive Surgical) is a robot used in certain surgical applications. In the da Vinci® system, the user controls manipulators that control a robotic actuator. The system converts the surgeon's gross movements into micro-movements of the robotic actuator. Although the da Vinci® system eliminates hand tremor and provides the user with the ability to work through a small opening, like many of the robots commercially available today, it is expensive, obtrusive, and the setup is cumbersome. Further, for procedures such as thoracolumbar pedicle screw insertion, these conventional methods are known to be error-prone and tedious.

One of the characteristics of many of the current robots used in surgical applications which make them error prone is that they use an articular arm based on a series of rotational joints. The use of an articular system may create difficulties in arriving at an accurately targeted location because the level of any error is increased over each joint in the articular system.

SUMMARY

Some embodiments of the invention provide a surgical robot (and optionally an imaging system) that utilizes a Cartesian positioning system that allows movement of a surgical instrument to be individually controlled in an x-axis, y-axis and z-axis. In some embodiments, the surgical robot can include a base, a robot arm coupled to and configured for articulation relative to the base, as well as an end-effectuator coupled to a distal end of the robot arm. The effectuator element can include the surgical instrument or can be configured for operative coupling to the surgical instrument. Some embodiments of the invention allow the roll, pitch and yaw rotation of the end-effectuator and/or surgical instrument to be controlled without creating movement along the x-axis, y-axis, or z-axis.

In some embodiments, the end-effectuator can include a guide tube, a tool, and/or a penetrating shaft with a leading edge that is either beveled (shaft cross-cut at an angle) or non-beveled (shaft ending in a pointed tip). In some embodiments, a non-beveled end-effectuator element can be employed to ablate a pathway through tissue to reach the target position while avoiding the mechanical forces and deflection created by a typical bevel tissue cutting system.

Some embodiments of the surgical robot can include a motor assembly comprising three linear motors that separately control movement of the effectuator element and/or surgical instrument on the respective x-, y- and z-axes. These separate motors can provide a degree of accuracy that is not provided by conventional surgical robots, thereby giving the surgeon the capability of more exactly determining position and strike angles on a three dimensional image.

In some embodiments, at least one RF transmitter can be mounted on the effectuator element and/or the surgical instrument. Three or more RF receivers can be mounted in the vicinity of the surgical robot. The location of the RF transmitter and, therefore, the surgical instrument, can be accurately determined by analyzing the RF signals that are emitted from the RF transmitter. For example, by measuring the time of flight of the RF signal from the transmitter to the RF receivers that are positioned at known locations, the position of the end-effectuator element with respect to a patient can be determined. In some embodiments, a physician or surgeon can perform epidural injections of steroids into a patient to alleviate back pain without the use of x-rays as is currently required with x-ray fluoroscopic techniques.

Some embodiments of the invention use RF feedback to actively control the movement of the surgical robot. For example, RF signals can be sent by the RF transmitter on an iterative basis and then analyzed in an iterative process to allow the surgical robot to automatically move the effectuator element and/or surgical instrument to a desired location within a patient's body. The location of the effectuator element and/or surgical instrument can be dynamically updated and, optionally, can be displayed to a user in real-time.

In some embodiments, at least one RF transmitter can be disposed on other elements of the surgical robot, or anywhere in the room where an invasive procedure is taking place, in order to track other devices.

Some embodiments of the invention dispose one or more RF transmitters on the anatomical part of the patient that is the target of the invasive procedure. This system can be used to correct the movement of the surgical robot in the event the anatomical target moves during the procedure.

In some embodiments, the system can be configured to automatically position and rigidly hold the end-effectuator and/or the surgical instrument in accurate alignment with a required trajectory, such as, for example, a selected trajectory of a pedicle screw during pedicle screw insertion procedures. In case of movement of the patient, the system can be configured to automatically adjust the position of the robot to maintain desired alignment relative to an anatomical region of interest.

DESCRIPTION OF THE DRAWINGS

FIG. 1 is a partial perspective view of a room in which a medical procedure is taking place by using a surgical robot, the movement of which is controlled by analysis of RF signals that are emitted from an inside the patient and received by RF receivers mounted therein.

FIG. 2 is a perspective view of a surgical robot according to an embodiment of the invention.

FIGS. 3A-3B are perspective views of the surgical robot illustrated in FIG. 2, which show the movement of the base of the surgical robot in the z-axis direction in accordance with an embodiment of the invention.

FIG. 4 is a partial perspective view of the surgical robot of FIG. 2 which shows how the robot arm can be moved in the x-axis direction.

FIGS. 5A-5B are partial perspective views of the surgical robot of FIG. 2, which show how the robot arm can be moved in the y-axis direction.

FIG. 6 is a perspective view of a portion of the robot arm of FIG. 2 showing how an effectuator element can be twisted about a y-axis.

FIG. 7 is a perspective view of a portion of a robot arm of FIG. 2 showing how an effectuator element can be pivoted about a pivot axis that is perpendicular to the y-axis.

FIGS. 8A-8B are partial perspective views of the surgical robot of FIG. 2, which show the movement of a surgical instrument 35 along the z-axis from an effectuator element.

FIG. 11 is a flow chart diagram for general operation of a surgical robot in accordance with one embodiment of the invention.

FIG. 12 is a flow chart diagram for a closed screw/needle insertion performed using a surgical robot in accordance with one embodiment of the invention.

FIG. 13 is a flow chart diagram of a safe zone surgery performed using a surgical robot as described herein in accordance with one embodiment of the invention.

FIG. 14 is a flow chart diagram of a flexible catheter insertion procedure performed using a surgical robot as described herein in accordance with one embodiment of the invention.

FIGS. 17C-17E illustrate tools for manually adjusting a drill stop with reference to drill bit markings in accordance with one embodiment of the invention.

FIGS. 18A-18B depicts an end-effectuator having a clearance mechanism in accordance with one embodiment of the invention.

FIGS. 22A-22D depict a targeting fixture and method configured for application to the skull of a patient in accordance with one embodiment of the invention.

FIGS. 52A-52B illustrates expected images on anteroposterior and lateral x-rays of the spine with a misaligned fluoroscopy (x-ray) machine in accordance with one embodiment of the invention.

FIGS. 53A-53B illustrates expected images on anteroposterior and lateral x-rays of the spine with a well aligned fluoroscopy (x-ray) machine in accordance with one embodiment of the invention.

FIGS. 54A-54B illustrates expected images on anteroposterior and lateral x-rays of the spine with a well aligned fluoroscopy (x-ray) machine including overlaid computer-generated graphical images showing the planned trajectory and the current actual position of the robot end-effectuator in accordance with one embodiment of the invention.

FIG. 59A illustrates two parallel plates with identically positioned radio-opaque markers in accordance with one embodiment of the invention.

FIG. 59B illustrates resulting expected x-ray demonstrating how marker overlay is affected due to parallax using the two parallel plates as shown in FIG. 59A in accordance with one embodiment of the invention.

DETAILED DESCRIPTION

Figure 9:
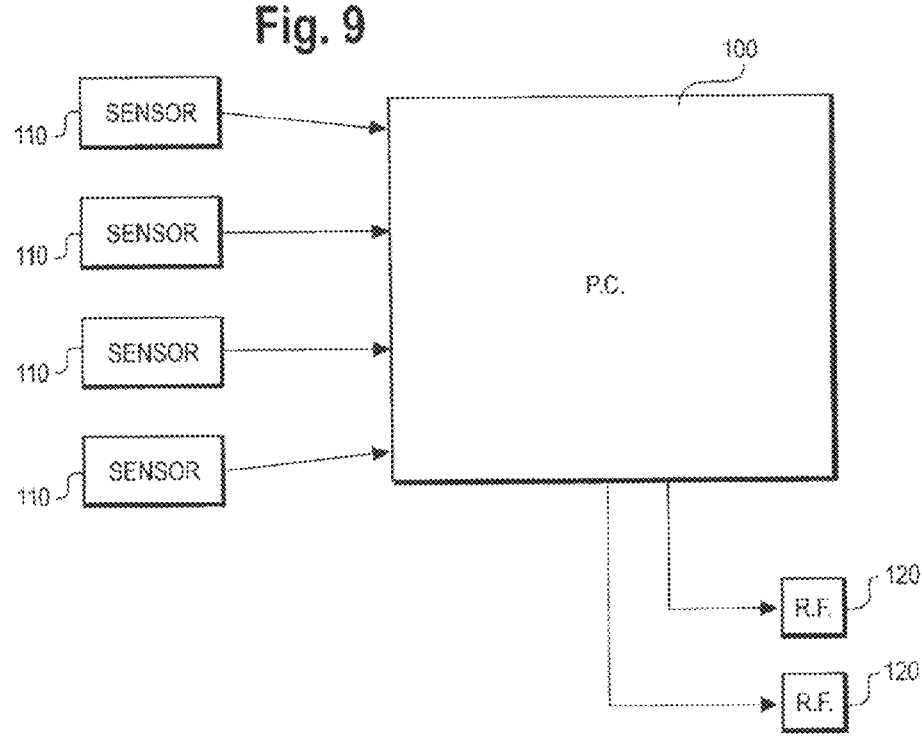
FIG. 9 is a system diagram which shows local positioning sensors, a controlling PC, and a Radiofrequency (RF) transmitter in accordance with an embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a delivery conduit" can include two or more such delivery conduits unless the context indicates otherwise.

As used herein, the terms "optional" or "optionally" mean that the subsequently described event or circumstance may or may not occur, and that the description includes instances where said event or circumstance occurs and instances where it does not.

In some embodiments, the disclosed devices and systems can comprise elements of the devices and systems described in U.S. Patent Publication Nos. 2007/0238985, 2008/0154389, and 2008/0215181, the disclosures of which are incorporated herein by reference in their entireties.

As employed in this specification and annexed drawings, the terms "unit," "component," "interface," "system," "platform," and the like are intended to include a computer-related entity or an entity related to an operational apparatus with one or more specific functionalities, wherein the computer-related entity or the entity related to the operational apparatus can be either hardware, a combination of hardware and software, software, or software in execution. One or more of such entities are also referred to as "functional elements." As an example, a unit may be, but is not limited to being, a process running on a processor, a processor, an object, an executable computer program, a thread of execution, a program, a memory (e.g., a hard disc drive), and/or a computer. As another example, a unit can be an apparatus with specific functionality provided by mechanical parts operated by electric or electronic circuitry which is operated by a software application or a firmware application executed by a processor, wherein the processor can be internal or external to the apparatus and executes at least a part of the software or firmware application. In addition or in the alternative, a unit can provide specific functionality based on physical structure or specific arrangement of hardware elements. As yet another example, a unit can be an apparatus that provides specific functionality through electronic functional elements without mechanical parts, the electronic functional elements can include a processor therein to execute software or firmware that provides at least in part the functionality of the electronic functional elements. An illustration of such apparatus can be control circuitry, such as a programmable logic controller. The foregoing example and related illustrations are but a few examples and are not intended to be limiting. Moreover, while such illustrations are presented for a unit, the foregoing examples also apply to a component, a system, a platform, and the like. It is noted that in certain embodiments, or in connection with certain aspects or features thereof, the terms "unit," "component," "system," "interface," "platform" can be utilized interchangeably.

Throughout the description and claims of this specification, the word "comprise" and variations of the word, such as "comprising" and "comprises," means "including but not limited to," and is not intended to exclude, for example, other additives, components, integers or steps.

Figure 35A:
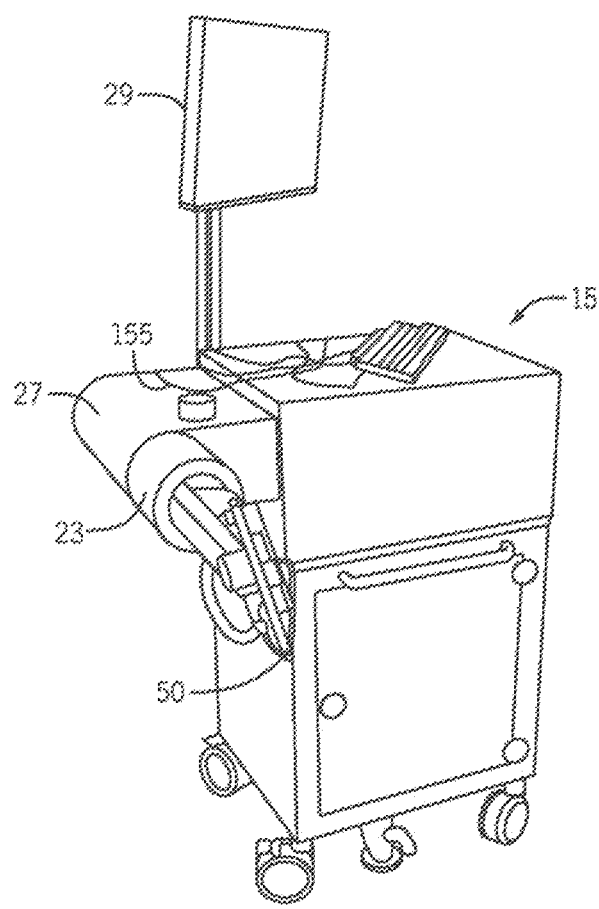
FIGS. 35A-35B display a surgical robot in accordance with one embodiment of the invention.

Referring now to FIGS. 1 and 35A, some embodiments include a surgical robot system 1 is disclosed in a room 10 where a medical procedure is occurring. In some embodiments, the surgical robot system 1 can comprise a surgical robot 15 and one or more positioning sensors 12. In this aspect, the surgical robot 15 can comprise a display means 29 (including for example a display 150 shown in FIG. 10), and a housing 27. In some embodiments a display 150 can be attached to the surgical robot 15, whereas in other embodiments, a display means 29 can be detached from surgical robot 15, either within surgical room 10 or in a remote location. In some embodiments, the housing 27 can comprise a robot arm 23, and an end-effectuator 30 coupled to the robot arm 23 controlled by at least one motor 160. For example, in some embodiments, the surgical robot system 1 can include a motor assembly 155 comprising at least one motor (represented as 160 in FIG. 10). In some embodiments, the end-effectuator 30 can comprise a surgical instrument 35. In other embodiments, the end-effectuator 30 can be coupled to the surgical instrument 35. As used herein, the term "end-effectuator" is used interchangeably with the terms "end-effectuator," "effectuator element," and "effectuator element." In some embodiments, the end-effectuator 30 can comprise any known structure for effecting the movement of the surgical instrument 35 in a desired manner.

Figure 34:
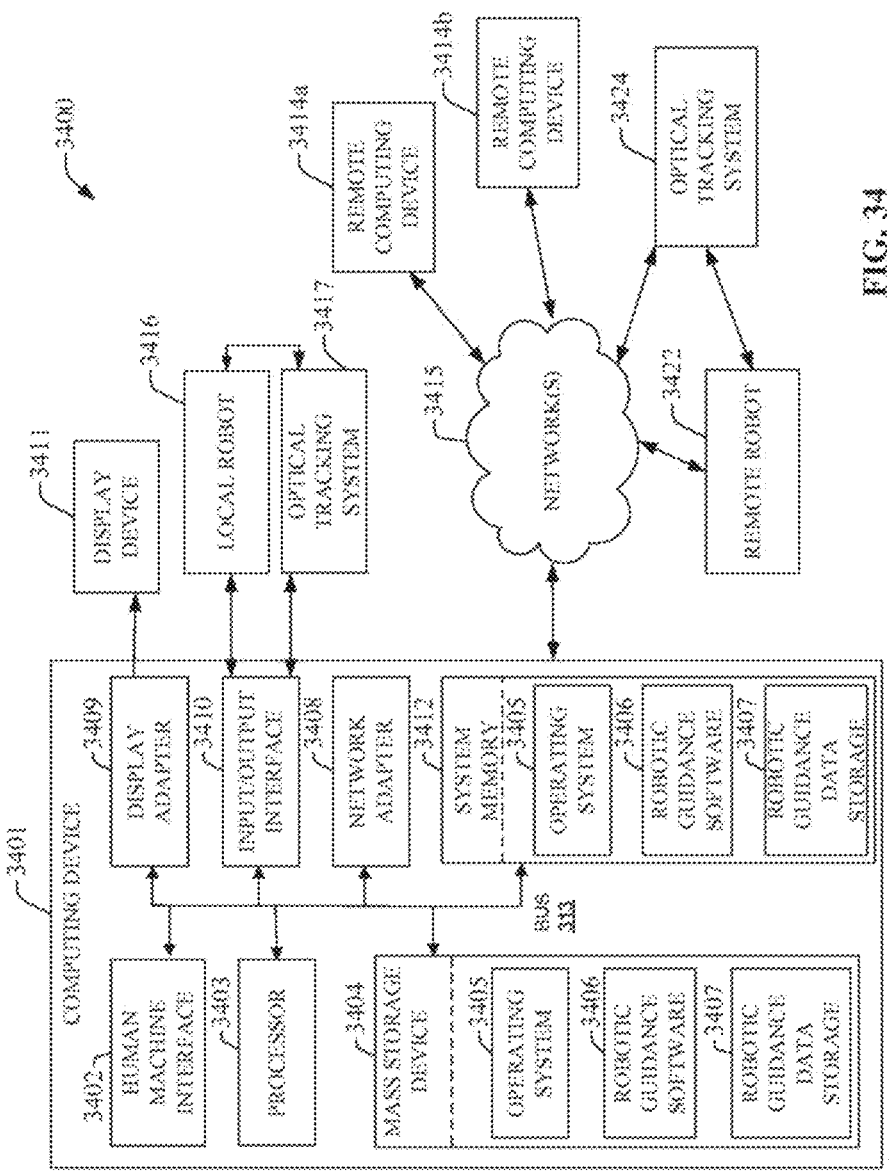
FIG. 34 illustrates a computing platform that enables implementation of various embodiments of the invention.

In some embodiments, prior to performance of an invasive procedure, a three-dimensional ("3D") image scan can be taken of a desired surgical area of the patient 18 and sent to a computer platform in communication with surgical robot 15 as described herein (see for example the platform 3400 including the computing device 3401 shown in FIG. 34). In some embodiments, a physician can then program a desired point of insertion and trajectory for surgical instrument 35 to reach a desired anatomical target within or upon the body of patient 18. In some embodiments, the desired point of insertion and trajectory can be planned on the 3D image scan, which in some embodiments, can be displayed on display means 29. In some embodiments, a physician can plan the trajectory and desired insertion point (if any) on a computed tomography scan (hereinafter referred to as "CT scan") of a patient 18. In some embodiments, the CT scan can be an isocentric C-arm type scan, an O-arm type scan, or intraoperative CT scan as is known in the art. However, in some embodiments, any known 3D image scan can be used in accordance with the embodiments of the invention described herein.

In some embodiments, the surgical robot system 1 can comprise a local positioning system ("LPS") subassembly to track the position of surgical instrument 35. The LPS subassembly can comprise at least one radio-frequency (RF) transmitter 120 that is coupled were affixed to the end-effectuator 30 or the surgical instrument 35 at a desired location. In some embodiments, the at least one RF transmitter 120 can comprise a plurality of transmitters 120, such as, for example, at least three RF transmitters 120. In another embodiment, the LPS subassembly can comprise at least one RF receiver 110 configured to receive one or more RF signals produced by the at least one RF transmitter 120. In some embodiments, the at least one RF receiver 110 can comprise a plurality of RF receivers 110, such as, for example, at least three RF receivers 110. In these embodiments, the RF receivers 110 can be positioned at known locations within the room 10 where the medical procedure is to take place. In some embodiments, the RF receivers 110 can be positioned at known locations within the room 10 such that the RF receivers 110 are not coplanar within a plane that is parallel to the floor of the room 10.

In some embodiments, during use, the time of flight of an RF signal from each RF transmitter 120 of the at least one RF transmitter 120 to each RF receiver 110 of the at least one RF receiver 110 (e.g., one RF receiver, two RF receivers, three RF receivers, etc.) can be measured to calculate the position of each RF transmitter 120. Because the velocity of the RF signal is known, the time of flight measurements result in at least three distance measurements for each RF transmitter 120 (one to each RF receiver 110).

In some embodiments, the surgical robot system 1 can comprise a control device (for example a computer 100 having a processor and a memory coupled to the processor). In some embodiments, the processor of the control device 100 can be configured to perform time of flight calculations as described herein. Further, in some embodiments, can be configured to provide a geometrical description of the location of the at least one RF transmitter 120 with respect to an operative end of the surgical instrument 35 or end-effectuator 30 that is utilized to perform or assist in performing an invasive procedure. In some further embodiments, the position of the RF transmitter 120, as well as the dimensional profile of the surgical instrument 35 or the effectuator element 30 can be displayed on a monitor (for example on a display means 29 such as the display 150 shown in FIG. 10). In one embodiment, the end-effectuator 30 can be a tubular element (for example a guide tube 50) that is positioned at a desired location with respect to, for example, a patient's 18 spine to facilitate the performance of a spinal surgery. In some embodiments, the guide tube 50 can be aligned with the z axis 70 defined by a corresponding robot motor 160 or, for example, can be disposed at a selected angle relative to the z-axis 70. In either case, the processor of the control device (i.e. the computer 100) can be configured to account for the orientation of the tubular element and the position of the RF transmitter 120. As further described herein, in some embodiments, the memory of the control device (computer 100 for example) can store software for performing the calculations and/or analyses required to perform many of the surgical method steps set forth herein.

Figure 35B:
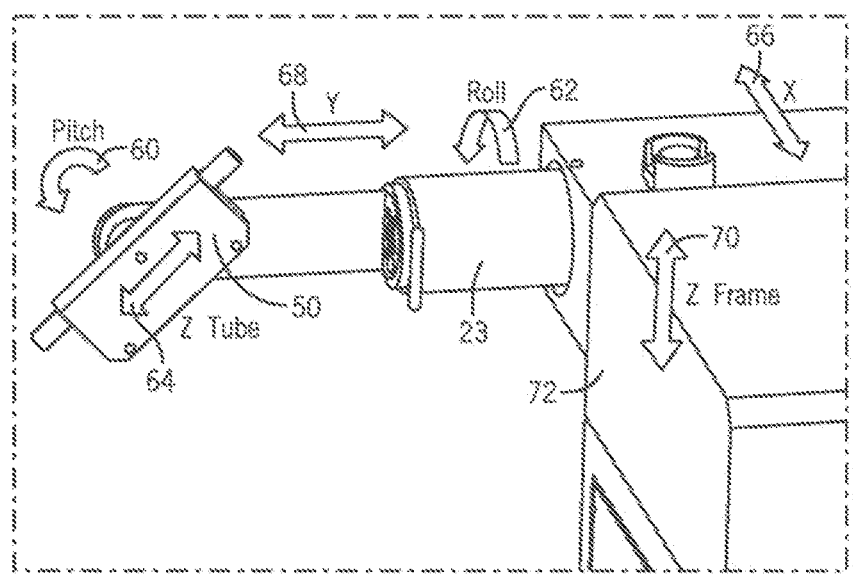

Another embodiment of the disclosed surgical robot system 1 involves the utilization of a robot 15 that is capable of moving the end-effectuator 30 along x-, y-, and z-axes (see 66, 68, 70 in FIG. 35B). In this embodiment, the x-axis 66 can be orthogonal to the y-axis 68 and z-axis 70, the y-axis 68 can be orthogonal to the x-axis 66 and z-axis 70, and the z-axis 70 can be orthogonal to the x-axis 66 and the y-axis 68. In some embodiments, the robot 15 can be configured to effect movement of the end-effectuator 30 along one axis independently of the other axes. For example, in some embodiments, the robot 15 can cause the end-effectuator 30 to move a given distance along the x-axis 66 without causing any significant movement of the end-effectuator 30 along the y-axis 68 or z-axis 70.

In some further embodiments, the end-effectuator 30 can be configured for selective rotation about one or more of the x-axis 66, y-axis 68, and z-axis 70 (such that one or more of the Cardanic Euler Angles (e.g., roll, pitch, and/or yaw) associated with the end-effectuator 30 can be selectively controlled). In some embodiments, during operation, the end-effectuator 30 and/or surgical instrument 35 can be aligned with a selected orientation axis (labeled "Z Tube" in FIG. 35B) that can be selectively varied and monitored by an agent (for example computer 100 and platform 3400) that can operate the surgical robot system 1. In some embodiments, selective control of the axial rotation and orientation of the end-effectuator 30 can permit performance of medical procedures with significantly improved accuracy compared to conventional robots that utilize, for example, a six degree of freedom robot arm 23 comprising only rotational axes.

In some embodiments, as shown in FIG. 1, the robot arm 23 that can be positioned above the body of the patient 18, with the end-effectuator 30 selectively angled relative to the z-axis toward the body of the patient 18. In this aspect, in some embodiments, the robotic surgical system 1 can comprise systems for stabilizing the robotic arm 23, the end-effectuator 30, and/or the surgical instrument 35 at their respective positions in the event of power failure. In some embodiments, the robotic arm 23, end-effectuator 30, and/or surgical instrument 35 can comprise a conventional worm-drive mechanism (not shown) coupled to the robotic arm 23, configured to effect movement of the robotic arm along the z-axis 70. In some embodiments, the system for stabilizing the robotic arm 23, end-effectuator 30, and/or surgical instrument 35 can comprise a counterbalance coupled to the robotic arm 23. In another embodiment, the means for maintaining the robotic arm 23, end-effectuator 30, and/or surgical instrument 35 can comprise a conventional brake mechanism (not shown) that is coupled to at least a portion of the robotic arm 23, such as, for example, the end-effectuator 30, and that is configured for activation in response to a loss of power or "power off" condition of the surgical robot 15.

Referring to FIG. 1, in some embodiments, the surgical robot system 1 can comprise a plurality of positioning sensors 12 configured to receive RF signals from the at least one conventional RF transmitter (not shown) located within room 10. In some embodiments, the at least one RF transmitter 120 can be disposed on various points on the surgical robot 15 and/or on patient 18. For example, in some embodiments, the at least one RF transmitter 120 can be attached to one or more of the housing 27, robot arm 23, end-effectuator 30, and surgical instrument 35. Some embodiments include positioning sensors 12 that in some embodiments comprise RF receivers 110. In some embodiments, RF receivers 110 are in communication with a computer platform as described herein (see for example 3400 comprising a computing device 3401 FIG. 34) that receives the signal from the RF transmitters 120. In some embodiments, each transmitter 120 of the at least one RF transmitter 120 can transmit RF energy on a different frequency so that the identity of each transmitter 120 in the room 10 can be determined. In some embodiments, the location of the at least one RF transmitter 120, and, consequently, the objects to which the transmitters 120 are attached, are calculated by the computer (e.g., computing device 3401 in FIG. 34) using time-of-flight processes.

In some embodiments, the computer (not shown in FIG. 1) is also in communication with surgical robot 15. In some embodiments, a conventional processor (not shown) of the computer 100 of the computing device 3401 can be configured to effect movement of the surgical robot 15 according to a preplanned trajectory selected prior to the procedure. For example, in some embodiments, the computer 100 of the computing device 3401 can use robotic guidance software 3406 and robotic guidance data storage 3407 (shown in FIG. 34) to effect movement of the surgical robot 15.

In some embodiments, the position of surgical instrument 35 can be dynamically updated so that surgical robot 15 is aware of the location of surgical instrument 35 at all times during the procedure. Consequently, in some embodiments, the surgical robot 15 can move the surgical instrument 35 to the desired position quickly, with minimal damage to patient 18, and without any further assistance from a physician (unless the physician so desires). In some further embodiments, the surgical robot 15 can be configured to correct the path of surgical instrument 35 if the surgical instrument 35 strays from the selected, preplanned trajectory.

In some embodiments, the surgical robot 15 can be configured to permit stoppage, modification, and/or manual control of the movement of the end-effectuator 30 and/or surgical instrument 35. Thus, in use, in some embodiments, an agent (e.g., a physician or other user) that can operate the system 1 has the option to stop, modify, or manually control the autonomous movement of end-effectuator 30 and/or surgical instrument 35. Further, in some embodiments, tolerance controls can be preprogrammed into the surgical robot 15 and/or processor of the computer platform 3400 (such that the movement of the end-effectuator 30 and/or surgical instrument 35 is adjusted in response to specified conditions being met). For example, in some embodiments, if the surgical robot 15 cannot detect the position of surgical instrument 35 because of a malfunction in the at least one RF transmitter 120, then the surgical robot 15 can be configured to stop movement of end-effectuator 30 and/or surgical instrument 35. In some embodiments, if surgical robot 15 detects a resistance, such as a force resistance or a torque resistance above a tolerance level, then the surgical robot 15 can be configured to stop movement of end-effectuator 30 and/or surgical instrument 35.

In some embodiments, the computer 100 for use in the system (for example represented by computing device 3401), as further described herein, can be located within surgical robot 15, or, alternatively, in another location within surgical room 10 or in a remote location. In some embodiments, the computer 100 can be positioned in operative communication with positioning sensors 12 and surgical robot 15.

In some further embodiments, the surgical robot 15 can also be used with existing conventional guidance systems. Thus, alternative conventional guidance systems beyond those specifically disclosed herein are within the scope and spirit of the invention. For instance, a conventional optical tracking system 3417 for tracking the location of the surgical device, or a commercially available infrared optical tracking system 3417, such as Optotrak® (Optotrak® is a registered trademark of Northern Digital Inc. Northern Digital, Waterloo, Ontario, Canada), can be used to track the patient 18 movement and the robot's base 25 location and/or intermediate axis location, and used with the surgical robot system 1. In some embodiments in which the surgical robot system 1 comprises a conventional infrared optical tracking system 3417, the surgical robot system 1 can comprise conventional optical markers attached to selected locations on the end-effectuator 30 and/or the surgical instrument 35 that are configured to emit or reflect light. In some embodiments, the light emitted from and/or reflected by the markers can be read by cameras (for example with cameras 8200 shown in FIG. 81) and/or optical sensors and the location of the object can be calculated through triangulation methods (such as stereo-photogrammetry).

Referring now to FIG. 2, it is seen that, in some embodiments, the surgical robot 15 can comprise a base 25 connected to wheels 31. The size and mobility of these embodiments can enable the surgical robot to be readily moved from patient to patient and room to room as desired. As shown, in some embodiments, the surgical robot 15 can further comprise a case 40 that is slidably attached to base 25 such that the case 40 can slide up and down along the z-axis 70 substantially perpendicular to the surface on which base 25 sits. In some embodiments, the surgical robot 15 can include a display means 29, and a housing 27 which contains robot arm 23.

As described earlier, the end-effectuator 30 can comprise a surgical instrument 35, whereas in other embodiments, the end-effectuator 30 can be coupled to the surgical instrument 35. In some embodiments, it is arm 23 can be connected to the end-effectuator 30, with surgical instrument 35 being removably attached to the end-effectuator 30.

Referring now to FIGS. 2, 3A-3B, 4, 5A-5B, 6, 7, and 8A-8B, in some embodiments, the effectuator element 30 can include an outer surface 30*d*, and can comprise a distal end 30*a* defining a beveled leading edge 30*b* and a non-beveled leading edge 30*c*. In some embodiments, the surgical instrument 35 can be any known conventional instrument, device, hardware component, and/or attachment that is used during performance of a an invasive or non-invasive medical procedure (including surgical, therapeutic, and diagnostic procedures). For example and without limitation, in some embodiments, the surgical instrument 35 can be embodied in or can comprise a needle 7405, 7410, a conventional probe, a conventional screw, a conventional drill, a conventional tap, a conventional catheter, a conventional scalpel forceps, or the like. In addition or in the alternative, in some embodiments, the surgical instrument 35 can be a biological delivery device, such as, for example and without limitation, a conventional syringe, which can distribute biologically acting compounds throughout the body of a patient 18. In some embodiments, the surgical instrument 35 can comprise a guide tube 50 (also referred to herein as a "Z-tube 50") that defines a central bore configured for receipt of one or more additional surgical instruments 35.

In some embodiments, the surgical robot 15 is moveable in a plurality of axes (for instance x-axis 66, y-axis 68, and z-axis 70) in order to improve the ability to accurately and precisely reach a target location. Some embodiments include a robot 15 that moves on a Cartesian positioning system; that is, movements in different axes can occur relatively independently of one another instead of at the end of a series of joints.

Referring now to FIGS. 3A and 3B, the movement of case 40 relative to base 25 of surgical robot 15 is represented as a change of height of the system 1 and the position of the case 40 with respect to the base 25. As illustrated, in some embodiments, case 40 can be configured to be raised and lowered relative to the base 25 along the z-axis. Some embodiments include a housing 27 that can be attached to case 40 and be configured to move in the z-direction (defined by z-frame 72) with case 40 when case 40 is raised and lowered. Consequently, in some embodiments, arm 23, the end-effectuator 30, and surgical instrument 35 can be configured to move with case 40 as case 40 is raised and lowered relative to base 25.

In a further embodiment, referring now to FIG. 4, housing 27 can be slidably attached to case 40 so that it can extend and retract along the x-axis 66 relative to case 40 and substantially perpendicularly to the direction case 40 moves relative to base 25. Consequently, in some embodiments, the robot arm 23, the end-effectuator 30, and surgical instrument 35 can be configured to move with housing 27 as housing 27 is extended and retracted relative to case 40.

Referring now to FIGS. 5A and 5B, the extension of arm 23 along the y-axis 68 is shown. In some embodiments, robot arm 23 can be extendable along the y-axis 68 relative to case 40, base 25, and housing 27. Consequently, in some embodiments, the end-effectuator 30 and surgical instrument 35 can be configured to move with arm 23 as arm 23 is extended and retracted relative to housing 27. In some embodiments, arm 23 can be attached to a low profile rail system (not shown) which is encased by housing 27.

Referring now to FIGS. 6, 7 and FIGS. 8A-B, the movement of the end-effectuator 30 is shown. FIG. 6 shows an embodiment of an end-effectuator 30 that is configured to rotate about the y-axis 68, performing a rotation having a specific roll 62. FIG. 7 shows an embodiment of an end-effectuator 30 that is configured to rotate about the x-axis 66, performing a rotation having a specific pitch 60. FIG. 8 shows an embodiment of an end-effectuator 30 that is configured to raise and lower surgical instrument 35 along a substantially vertical axis, which can be a secondary movable axis 64, referred to as "Z-tube axis 64". In some embodiments, the orientation of the guide tube 50 can be initially aligned with z-axis 70, but such orientation can change in response to changes in roll 62 and/or pitch 60.

FIG. 9 shows a system diagram of the 3D positioning sensors 110, computer 100, and RF transmitters 120 in accordance with some embodiments of the invention is provided. As shown, computer 100 is in communication with positioning sensors 110. In some embodiments, during operation, RF transmitters 120 are attached to various points on the surgical robot 15. In some embodiments, the RF transmitters 120 can also be attached to various points on or around an anatomical target of a patient 18. In some embodiments, computer 100 can be configured to send a signal to the RF transmitters 120, prompting the RF transmitters 120 to transmit RF signals that are read by the positioning sensors 110. In some embodiments, the computer 100 can be coupled to the RF transmitters 120 using any conventional communication means, whether wired or wireless. In some embodiments, the positioning sensors 110 can be in communication with computer 100, which can be configured to calculate the location of the positions of all the RF transmitters 120 based on time-of-flight information received from the positioning sensors 110. In some embodiments, computer 100 can be configured to dynamically update the calculated location of the surgical instrument 35 and/or end-effectuator 30 being used in the procedure, which can be displayed to the agent.

Figure 10:
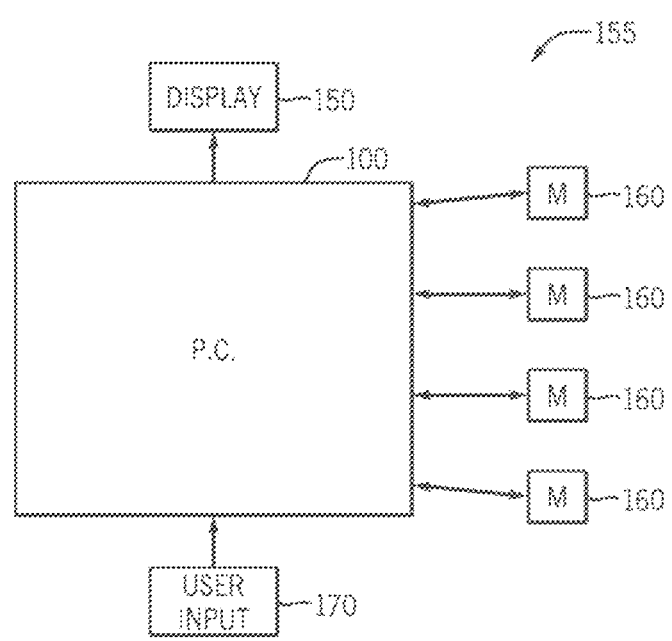
FIG. 10 is a system diagram of the controlling PC, user input, and motors for controlling the robot in accordance with an embodiment of the invention.

Some embodiments can include a system diagram of surgical robot system 1 having a computer 100, a display means 29 comprising a display 150, user input 170, and motors 160, provided as illustrated in FIG. 10. In some embodiments, motors 160 can be installed in the surgical robot 15 and control the movement of the end-effectuator 30 and/or surgical instrument 35 as described above. In some embodiments, computer 100 can be configured to dynamically update the location of the surgical instrument 35 being used in the procedure, and can be configured to send appropriate signals to the motors 160 such that the surgical robot 15 has a corresponding response to the information received by computer 100. For example, in some embodiments, in response to information received by computer 100, the computer 100 can be configured to prompt the motors 160 to move the surgical instrument 35 along a preplanned trajectory.

In some embodiments, prior to performance of a medical procedure, such as, for example, an invasive surgical procedure, user input 170 can be used to plan the trajectory for a desired navigation. After the medical procedure has commenced, if changes in the trajectory and/or movement of the end-effectuator 30 and/or surgical instrument 35 are desired, a user can use the user input 170 to input the desired changes, and the computer 100 can be configured to transmit corresponding signals to the motors 160 in response to the user input 170.

In some embodiments, the motors 160 can be or can comprise conventional pulse motors. In this aspect, in some embodiments, the pulse motors can be in a conventional direct drive configuration or a belt drive and pulley combination attached to the surgical instrument 35. Alternatively, in other embodiments, the motors 160 can be conventional pulse motors that are attached to a conventional belt drive rack-and-pinion system or equivalent conventional power transmission component.

In some embodiments, the use of conventional linear pulse motors within the surgical robot 15 can permit establishment of a non-rigid position for the end-effectuator 30 and/or surgical instrument 35. Thus, in some embodiments, the end-effectuator 30 and/or surgical instrument 35 will not be fixed in a completely rigid position, but rather the end-effectuator 30 and/or the surgical instrument 35 can be configured such that an agent (e.g., a surgeon or other user) can overcome the x-axis 66 and y-axis 68, and force the end-effectuator 30 and/or surgical instrument 35 from its current position. For example, in some embodiments, the amount of force necessary to overcome such axes can be adjusted and configured automatically or by an agent. In some embodiments, the surgical robot 15 can comprise circuitry configured to monitor one or more of: (a) the position of the robot arm 23, the end-effectuator 30, and/or the surgical instrument 35 along the x-axis 66, y-axis 68, and z-axis 70; (b) the rotational position (e.g., roll 62 and pitch 60) of the robot arm 23, the end-effectuator 30, and/or the surgical instrument 35 relative to the x-(66), y-(68), and z-(70) axes; and (c) the position of the end-effectuator 30, and/or the surgical instrument 35 along the travel of the re-orientable axis that is parallel at all times to the end-effectuator 30 and surgical instrument 35 (the Z-tube axis 64).

In one embodiment, circuitry for monitoring the positions of the x-axis 66, y-axis 68, z-axis 70, Z-tube axis 64, roll 62, and/or pitch 60 can comprise relative or absolute conventional encoder units (also referred to as encoders) embedded within or functionally coupled to conventional actuators and/or bearings of at least one of the motors 160. Optionally, in some embodiments, the circuitry of the surgical robot 15 can be configured to provide auditory, visual, and/or tactile feedback to the surgeon or other user when the desired amount of positional tolerance (e.g., rotational tolerance, translational tolerance, a combination thereof, or the like) for the trajectory has been exceeded. In some embodiments, the positional tolerance can be configurable and defined, for example, in units of degrees and/or millimeters.

In some embodiments, the robot 15 moves into a selected position, ready for the surgeon to deliver a selected surgical instrument 35, such as, for example and without limitation, a conventional screw, a biopsy needle 8110, and the like. In some embodiments, as the surgeon works, if the surgeon inadvertently forces the end-effectuator 30 and/or surgical instrument 35 off of the desired trajectory, then the system 1 can be configured to provide an audible warning and/or a visual warning. For example, in some embodiments, the system 1 can produce audible beeps and/or display a warning message on the display means 29, such as "Warning: Off Trajectory," while also displaying the axes for which an acceptable tolerance has been exceeded.

In some embodiments, in addition to, or in place of the audible warning, a light illumination may be directed to the end-effectuator 30, the guide tube 50, the operation area (i.e. the surgical field 17) of the patient 18, or a combination of these regions. For example, some embodiments include at least one visual indication 900 capable of illuminating a surgical field 17 of a patient 18. Some embodiments include at least one visual indication 900 capable of indicating a target lock by projecting an illumination on a surgical field 17. In some embodiments, the system 1 can provide feedback to the user regarding whether the robot 15 is locked on target. In some other embodiments, the system 1 can provide an alert to the user regarding whether at least one marker 720 is blocked, or whether the system 1 is actively seeking one or more markers 720.

Figure 80:
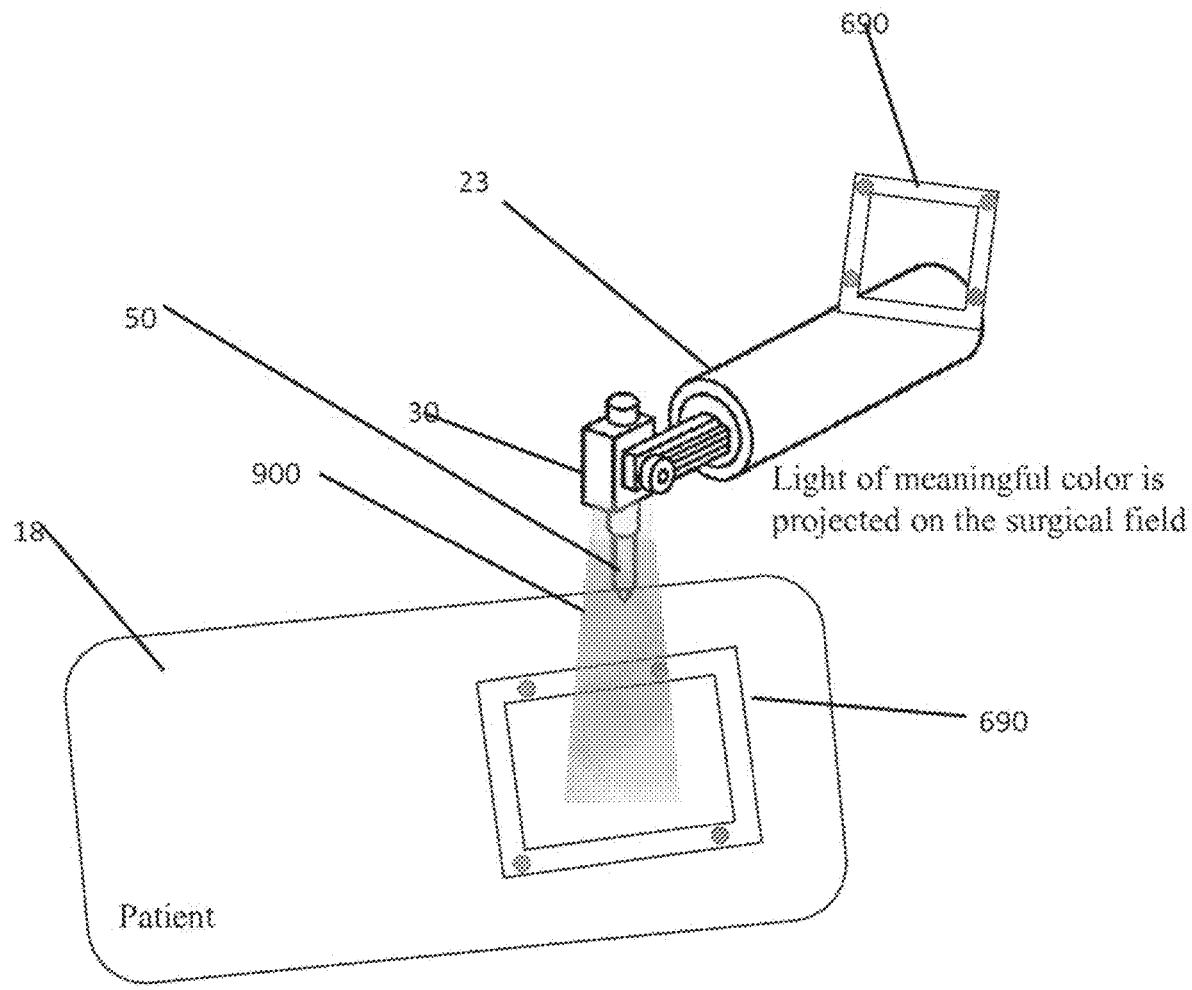
FIG. 80 illustrates a partial view of a surgical robot system including a visual indicator comprising lights projected on the surgical field in accordance with one embodiment of the invention.

In some embodiments, the visual indication 900 can be projected by one or more conventional light emitting diodes mounted on or near the robot end-effectuator 30. In some embodiments, the visual indication can comprise lights projected on the surgical field 17 including a color indicative of the current situation (see for example, FIG. 80). In some embodiments, a green projected light could represent a locked-on-target situation, whereas in some embodiments, a red illumination could indicate a trajectory error, or obscured markers 720. In some other embodiments, a yellow illumination could indicate the system 1 is actively seeking one or more markers 720.

In some embodiments, if the surgeon attempts to exceed the acceptable tolerances, the robot 15 can be configured to provide mechanical resistance ("push back" or haptic feedback) to the movement of the end-effectuator 30 and/or surgical instrument 35 in this manner, thereby promoting movement of the end-effectuator 30 and/or surgical instrument 35 back to the correct, selected orientation. In some embodiments, when the surgeon then begins to correct the improper position, the robot 15 can be configured to substantially immediately return the end-effectuator 30 and/or surgical instrument 35 back to the desired trajectory, at which time the audible and visual warnings and alerts can be configured to cease. For example, in some embodiments, the visual warning could include a visual indication 900 that may include a green light if no tolerances have been exceeded, or a red light if tolerances are about to, or have been exceeded.

As one will appreciate, a conventional worm-drive system would be absolutely rigid, and a robot 15 having such a worm-drive system would be unable to be passively moved (without breaking the robot 15) no matter how hard the surgeon pushed. Furthermore, a completely rigid articulation system can be inherently unsafe to a patient 18. For example, if such a robot 15 were moving toward the patient 18 and inadvertently collided with tissues, then these tissues could be damaged. Although conventional sensors can be placed on the surface of such a robot 15 to compensate for these risks, such sensors can add considerable complexity to the overall system 1 and would be difficult to operate in a fail-safe mode. In contrast, during use of the robot 15 described herein, if the end-effectuator 30 and/or surgical instrument 35 inadvertently collides with tissues of the patient 18, a collision would occur with a more tolerable force that would be unlikely to damage such tissues. Additionally, in some embodiments, auditory and/or visual feedback as described above can be provided to indicate an increase in the current required to overcome the obstacle. Furthermore, in some embodiments, the end-effectuator 30 of the robot 15 can be configured to displace itself (move away) from the inadvertently contacted tissue if a threshold required motor 160 current is encountered. In some embodiments, this threshold could be configured (by a control component, for example) for each axis such that the moderate forces associated with engagement between the tissue and the end-effectuator 30 can be recognized and/or avoided.

In some embodiments, the amount of rigidity associated with the positioning and orientation of the end-effectuator 30 and/or the surgical instrument 35 can be selectively varied. For example, in some embodiments, the robot 15 can be configured to shift between a high-rigidity mode and a low-rigidity mode. In some embodiments, the robot 15 can be programmed so that it automatically shifts to the low-rigidity mode as the end-effectuator 30 and surgical instrument 35 are shifted from one trajectory to another, from a starting position as they approach a target trajectory and/or target position. Moreover, in some embodiment, once the end-effectuator 30 and/or surgical instrument 35 is within a selected distance of the target trajectory and/or target position, such as, for example, within about 1° and about 1 mm of the target, the robot 15 can be configured to shift to the high-rigidity mode. In some embodiments, this mechanism may improve safety because the robot 15 would be unlikely to cause injury if it inadvertently collided with the patient 18 while in the low-rigidity mode.

Some embodiments include a robot 15 that can be configured to effect movement of the end-effectuator 30 and/or surgical instrument 35 in a selected sequence of distinct movements. In some embodiments, during movement of the end-effectuator 30 and/or surgical instrument 35 from one trajectory to another trajectory, the x-axis 66, y-axis 68, roll 62, and 60 pitch 60 orientations are all changed simultaneously, and the speed of movement of the end-effectuator 30 can be increased. Consequently, because of the range of positions through which the end-effectuator 30 travels, the likelihood of a collision with the tissue of the patient 18 can also be increased. Hence, in some embodiments, the robot 15 can be configured to effect movement of the end-effectuator 30 and/or surgical instrument 35 such that the position of the end-effectuator 30 and/or surgical instrument 35 within the x-axis 66 and the y-axis 68 are adjusted before the roll 62 and pitch 60 of the end-effectuator 30 and/or surgical instrument 35 are adjusted. In some alternative embodiments, the robot 15 can be configured to effect movement of the end-effectuator 30 and/or surgical instrument 35 so that the roll 62 and pitch 60 are shifted to 0°. The position of the end-effectuator 30 and/or surgical instrument 35 within the x-axis 66 and the y-axis 68 are adjusted, and then the roll 62 and pitch 60 of the end-effectuator 30 and/or surgical instrument 35 are adjusted.

Some embodiments include a robot 15 that can be optionally configured to ensure that the end-effectuator 30 and/or surgical instrument 35 are moved vertically along the z-axis 70 (away from the patient 18) by a selected amount before a change in the position and/or trajectory of the end-effectuator 30 and/or surgical instrument 35 is effected. For example, in some embodiments, when an agent (for example, a surgeon or other user, or equipment) changes the trajectory of the end-effectuator 30 and/or surgical instrument 35 from a first trajectory to a second trajectory, the robot 15 can be configured to vertically displace the end-effectuator 30 and/or surgical instrument 35 from the body of the patient 18 along the z-axis 70 by the selected amount (while adjusting x-axis 66 and y-axis 68 configurations to remain on the first trajectory vector, for example), and then effecting the change in position and/or orientation of the end-effectuator 30 and/or surgical instrument 35. This ensures that the end-effectuator 30 and/or surgical instrument 35 do not move laterally while embedded within the tissue of the patient 18. Optionally, in some embodiments, the robot 15 can be configured to produce a warning message that seeks confirmation from the agent (for example, a surgeon or other user, or equipment) that it is safe to proceed with a change in the trajectory of the end-effectuator 30 and/or surgical instrument 35 without first displacing the end-effectuator 30 and/or surgical instrument 35 along the z-axis.

In some embodiments, at least one conventional force sensor (not shown) can be coupled to the end-effectuator 30 and/or surgical instrument 35 such that the at least one force sensor receives forces applied along the orientation axis (Z-tube axis 64) to the surgical instrument 35. In some embodiments, the at least one force sensor can be configured to produce a digital signal. In some embodiments for example, the digital signal can be indicative of the force that is applied in the direction of the Z-tube axis 64 to the surgical instrument 35 by the body of the patient 18 as the surgical instrument 35 advances into the tissue of the patient 18. In some embodiments, the at least one force sensor can be a small conventional uniaxial load cell based on a conventional strain gauge mechanism. In some embodiments, the uniaxial load cell can be coupled to, for example, analog-to-digital filtering to supply a continuous digital data stream to the system 1. Optionally, in some embodiments, the at least one force sensor can be configured to substantially continuously produce signals indicative of the force that is currently being applied to the surgical instrument 35. In some embodiments, the surgical instrument 35 can be advanced into the tissue of the patient 18 by lowering the z-axis 70 while the position of the end-effectuator 30 and/or surgical instrument 35 along the x-axis 66 and y-axes 68 is adjusted such that alignment with the selected trajectory vector is substantially maintained. Furthermore, in some embodiments, the roll 62 and pitch 60 orientations can remain constant or self-adjust during movement of the x-(66), y-(68), and z-(70) axes such that the surgical instrument 35 remains oriented along the selected trajectory vector. In some embodiments, the position of the end-effectuator 30 along the z-axis 70 can be locked at a selected mid-range position (spaced a selected distance from the patient 18) as the surgical instrument 35 advances into the tissue of the patient 18. In some embodiments, the stiffness of the end-effectuator 30 and/or the surgical instrument 35 can be set at a selected level as further described herein. For example, in some embodiments, the stiffness of the Z-tube axis 64 position of the end-effectuator 30 and/or the surgical instrument 35 can be coupled to a conventional mechanical lock (not shown) configured to impart desired longitudinal stiffness characteristics to the end-effectuator 30 and/or surgical instrument 35. In some embodiments, if the end-effectuator 30 and/or surgical instrument 35 lack sufficient longitudinal stiffness, then the counterforce applied by the tissue of the patient 18 during penetration of the surgical instrument 35 can oppose the direction of advancement of the surgical instrument 35 such that the surgical instrument 35 cannot advance along the selected trajectory vector. In other words, as the z-axis 70 advances downwards, the Z-tube axis 64 can be forced up and there can be no net advancement of the surgical instrument 35. In some embodiments, the at least one force sensor can permit an agent (for example, a surgeon or other user, or equipment) to determine, (based on sudden increase in the level of applied force monitored by the force sensor at the end-effectuator 30 and/or the surgical instrument 35), when the surgical instrument 35 has encountered a bone or other specific structure within the body of the patient 18.

In some alternative embodiments, the orientation angle of the end-effectuator 30 and/or surgical instrument 35 and the x-axis 66 and y-axis 68 can be configured to align the Z-tube axis 64 with the desired trajectory vector at a fully retracted Z-tube position, while a z-axis 70 position is set in which the distal tip of the surgical instrument 35 is poised to enter tissue. In this configuration, in some embodiments, the end-effectuator 30 can be positioned in a manner that the end-effectuator 30 can move, for example, exactly or substantially exactly down the trajectory vector if it were advanced only along guide tube 50. In such scenario, in some embodiments, advancing the Z-tube axis 64 can cause the guide tube 50 to enter into tissue, and an agent (a surgeon or other user, equipment, etc.) can monitor change in force from the load sensor. Advancement can continue until a sudden increase in applied force is detected at the time the surgical instrument 35 contacts bone.

In some embodiments, the robot 15 can be configured to deactivate the one or more motors 160 that advance the Z-tube axis 64 such that the end-effectuator 30 and/or the surgical instrument 35 can move freely in the Z-tube axis 64 direction while the position of the end-effectuator 30 and/or the surgical instrument 35 continues to be monitored. In some embodiments, the surgeon can then push the end-effectuator 30 down along the Z-tube axis 64, (which coincides with the desired trajectory vector) by hand. In some embodiments, if the end-effectuator 30 position has been forced out of alignment with the trajectory vector, the position of the surgical instrument 35 can be corrected by adjustment along the x-(66) and/or y-(68) axes and/or in the roll 62 and/or pitch 60 directions. In some embodiments, when motor 160 associated with the Z-tube 50 movement of the surgical instrument 35 is deactivated, the agent (for example, a surgeon or other user, or equipment) can manually force the surgical instrument 35 to advance until a tactile sense of the surgical instrument 35 contacts bone, or another known region of the body).

In some further embodiments, the robotic surgical system 1 can comprise a plurality of conventional tracking markers 720 configured to track the movement of the robot arm 23, the end-effectuator 30, and/or the surgical instrument 35 in three dimensions. It should be appreciated that three dimensional positional information from tracking markers 720 can be used in conjunction with the one dimensional linear positional information from absolute or relative conventional linear encoders on each axis of the robot 15 to maintain a high degree of accuracy. In some embodiments, the plurality of tracking markers 720 can be mounted (or otherwise secured) thereon an outer surface of the robot 15, such as, for example and without limitation, on the base 25 of the robot 15, or the robot arm 23. In some embodiments, the plurality of tracking markers 720 can be configured to track the movement of the robot 15 arm, the end-effectuator 30, and/or the surgical instrument 35. In some embodiments, the computer 100 can utilize the tracking information to calculate the orientation and coordinates of the distal tip 30a of the surgical instrument 35 based on encoder counts along the x-axis 66, y-axis 68, z-axis 70, the Z-tube axis 64, and the roll 62 and pitch 60 axes. Further, in some embodiments, the plurality of tracking markers 720 can be positioned on the base 25 of the robot 15 spaced from the surgical field 17 to reduce the likelihood of being obscured by the surgeon, surgical tools, or other parts of the robot 15. In some embodiments, at least one tracking marker 720 of the plurality of tracking markers 720 can be mounted or otherwise secured to the end-effectuator 30. In some embodiments, the positioning of one or more tracking markers 720 on the end-effectuator 30 can maximize the accuracy of the positional measurements by serving to check or verify the end-effectuator 30 position (calculated from the positional information from the markers on the base 25 of the robot 15 and the encoder counts of the x-(66), y-(68), roll 62, pitch 60, and Z-tube axes 64).

Figure 16:
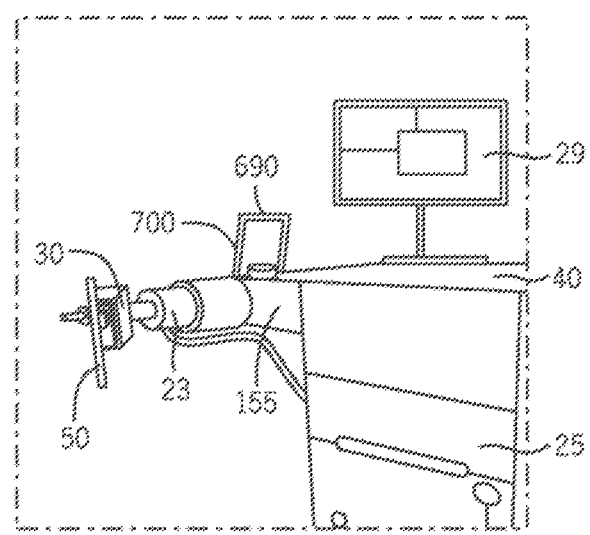
FIG. 16 depicts a surgical robot having a plurality of optical markers mounted for tracking movement in an x-direction in accordance with one embodiment of the invention.

In some further embodiments, at least one optical marker of the plurality of optical tracking markers 720 can be positioned on the robot 15 between the base 25 of the robot 15 and the end-effectuator 30 instead of, or in addition to, the markers 720 on the base 25 of the robot 15, (see FIG. 16). In some embodiments, the at least one tracking marker 720 can be mounted to a portion of the robot 15 that effects movement of the end-effectuator 30 and/or surgical instrument 35 along the x-axis to enable the tracking marker 720 to move along the x-axis 66 as the end-effectuator 30 and surgical instrument 35 move along the x-axis 66 (see FIG. 76). The placement of the tracking markers 720 in this way can reduce the likelihood of a surgeon blocking the tracking marker 720 from the cameras or detection device, or the tracking marker 720 becoming an obstruction to surgery. In certain embodiments, because of the high accuracy in calculating the orientation and position of the end-effectuator 30 based on the tracking marker 720 outputs and/or encoder counts from each axis, it can be possible to very accurately determine the position of the end-effectuator 30. For example, in some embodiments, without requiring knowledge of the counts of axis encoders for the z-axis 70, which is between the x-axis 66 and the base 25, knowing only the position of the markers 720 on the x-axis 66 and the counts of encoders on the y-(68), roll 62, pitch 60, and Z-tube axes 64 can enable computation of the position of the end-effectuator 30. In some embodiments, the placement of markers 720 on any intermediate axis of the robot 15 can permit the exact position of the end-effectuator 30 to be calculated based on location of such markers 720 and counts of encoders on axes (66, 62, 60, 64) between the markers 720 and the end-effectuator 30. In some embodiments, from the configuration of the robot 15 (see for example, FIG. 2), the order of axes from the base 25 to the end-effectuator 30 is z-(70) then x-(66) then y-(68) then roll 62 then pitch 60 then Z-tube 64. Therefore, for example, within embodiments in which tracking markers 720 are placed on the housing 27 of the robot 15 that moves with the roll 62 axis, the locations of such tracking markers 720 and the encoder counts of the pitch 60 and Z-tube axes 64 can be sufficient to calculate the end-effectuator 30 position.

Figure 17A:
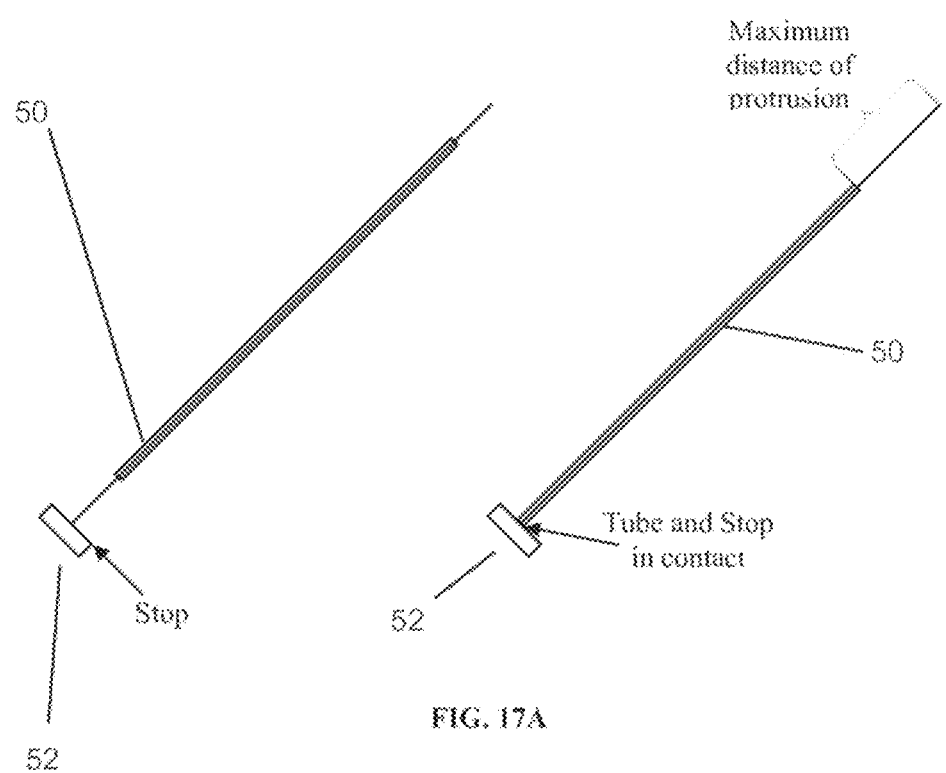
FIGS. 17A-17B depict surgical instruments having a stop mechanism in accordance with one embodiment of the invention.
Figure 17B:
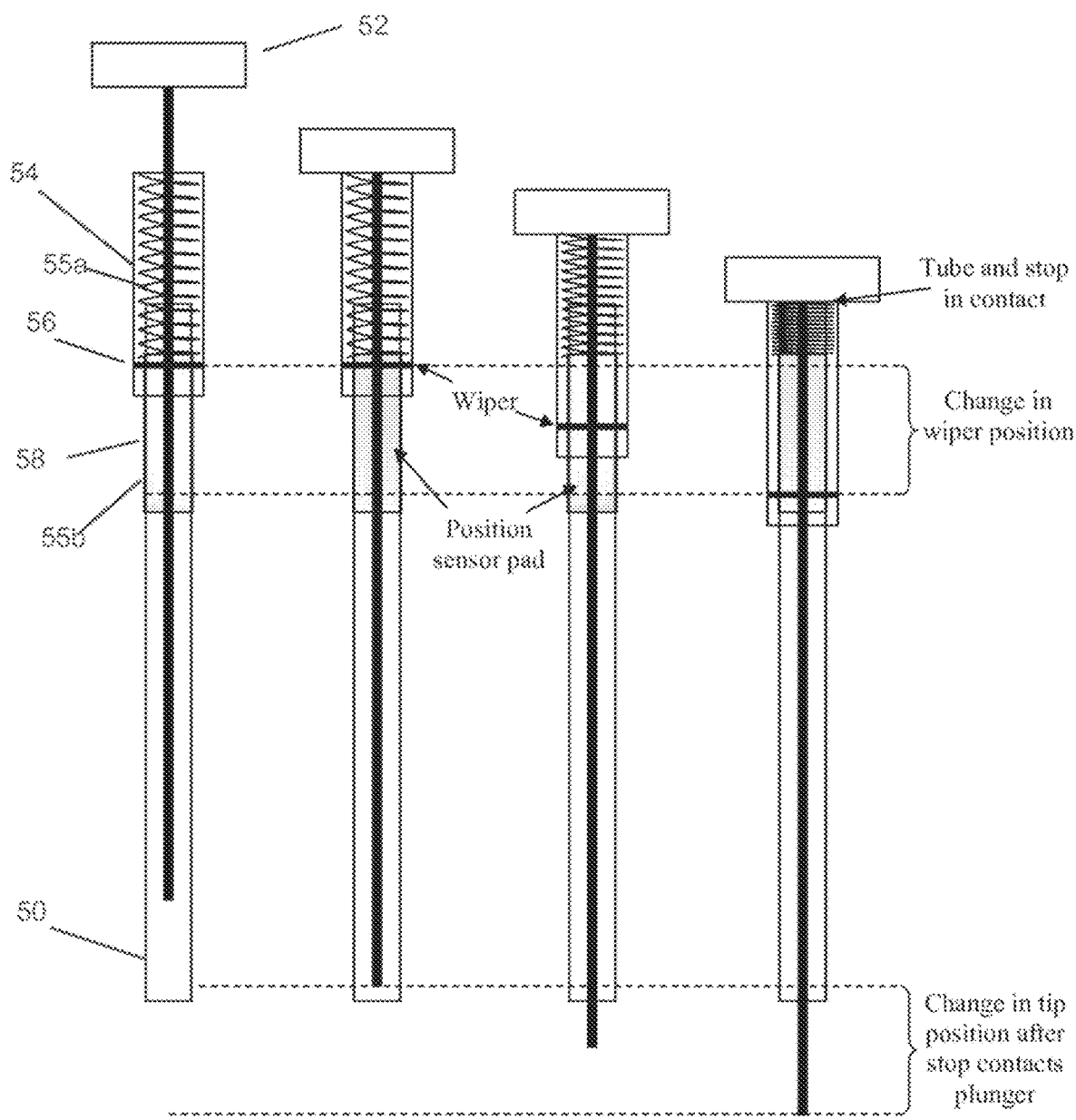
Figure 17F:
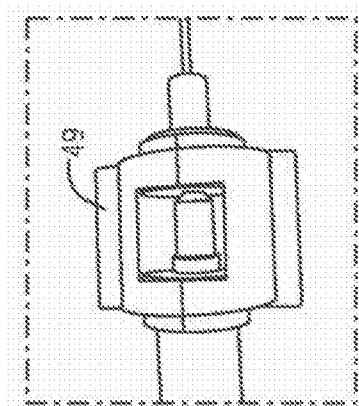
FIGS. 17F-J illustrate tools for locking and holding a drill bit in a set position in accordance with one embodiment of the invention.
Figure 17G:
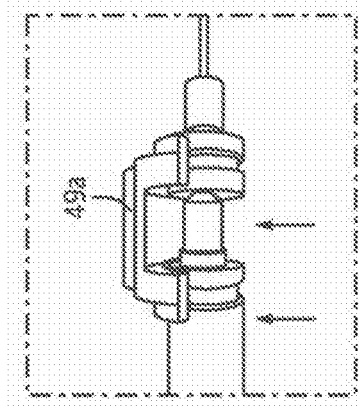
Figure 17H:
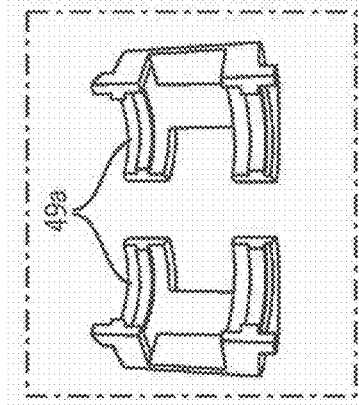
Figure 17J:
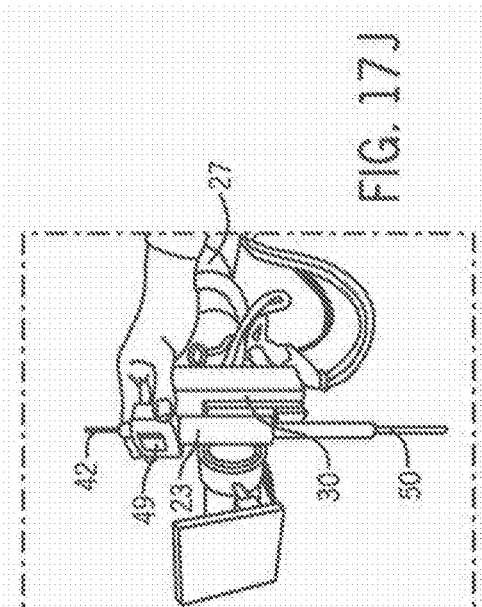
Figure 17I:
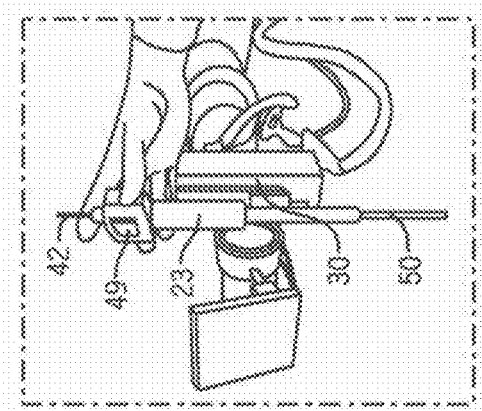

In some embodiments, when the surgical instrument 35 is advanced into the tissue of the patient 18 with the assistance of a guide tube 50, the surgical instrument 35 can comprise a stop mechanism 52 that is configured to prevent the surgical instrument 35 from advancing when it reaches a predetermined amount of protrusion (see for example, FIGS. 17A-B). In some embodiments, by knowing the lengths of the guide tube 50 and the surgical instrument 35, the distance between the respective ends of the surgical instrument 35, and the location where the stop mechanism 52 is attached, it is possible to determine the maximum distance past the end of the guide tube 50 that the surgical instrument 35 can protrude.

In some embodiments, it can be desirable to monitor not just the maximum protrusion distance of the surgical instrument 35, but also the actual protrusion distance at any instant during the insertion process. Therefore, in some embodiments, the robot 15 can substantially continuously monitor the protrusion distance, and in some embodiments, the distance can be displayed on a display (such as display means 29). In some embodiments, protrusion distance can be substantially continuously monitored using a spring-loaded plunger 54 including a spring-loaded mechanism 55a and sensor pad 55b that has a coupled wiper 56 (see for example FIG. 17B). In some embodiments, the stop mechanism 52 on the surgical instrument 35 can be configured to contact the spring-loaded mechanism 55 well before it encounters the end of the guide tube 50. In some embodiments, when the wiper 56 moves across the position sensor pad 55b, its linear position is sampled, thereby permitting calculation of the distance by which the surgical instrument 35 protrudes past the end of the guide tube 50 substantially in real-time. In some embodiments, any conventional linear encoding mechanism can be used to monitor the plunger's depth of depression and transmit that information to the computer 100 as further described herein.

Some embodiments include instruments that enable the stop on a drill bit 42 to be manually adjusted with reference to markings 44 on the drill bit 42. For example, FIGS. 17C-17E depict tools for manually adjusting a drill stop 46 with reference to drill bit markings 44 in accordance with one embodiment of the invention. As shown, in some embodiments, the drill bit 42 can include release mechanisms 48 on each end of the drill stop 46. In some embodiments, if the release 48 on one end of the drill stop 46 is pulled, it is possible to move the drill stop 46 up the shaft of the drill bit 42. In some embodiments, if the release 48 on the other end of the drill stop 46 is pulled, it is possible to move the drill stop 46 down the shaft (see the direction of movement in FIGS. 17D and 17E). In some embodiments, if neither release mechanism 48 is pulled, the drill stop 46 will not move in either direction, even if bumped.

Some embodiments include the ability to lock and hold the drill bit 42 in a set position relative to the tube 50 in which it is housed. For example, in some embodiments, the drill bit 42 can be locked by locking the drill stop 46 relative to the tube 50 using a locking mechanism. FIGS. 17F-J illustrates tools for locking and holding a drill bit 42 in a set position in accordance with one embodiment of the invention. In some embodiments, the locking mechanism 49 shown in FIG. 17H can comprise two clam shells 49 (shown in FIG. 17F). In some embodiments, a drill bit 42 can be locked into position by assembling the clam shells around the drill stop 46 (shown in FIG. 17G). This feature allows the user to lock the drill bit 42 in a position such that the tip slightly protrudes past the end of the tube 50 (see FIGS. 17I and 17J). In this position, the user can force the tube 50 to penetrate through soft tissues to force the tube 50 to contact bone (for example during a percutaneous spine screw insertion).

In some further embodiments, the end-effectuator 30 can be configured not block the tracking optical markers 720 or interfere with the surgeon. For example, in some embodiments, the end-effectuator 30 can comprise a clearance mechanism 33 including an actuator 33a that permits this configuration, as depicted in FIGS. 18A and 18B. As shown, the guide tube 50 can be secured within a housing of the end-effectuator 30 with two shafts 32. In some embodiments, the shafts 32 move relative to one other, due to a parallelogram effect of the clearance mechanism 33, the position of the guide tube 50 can mimic the position of the end-effectuator 30 (see FIG. 18B).

Figure 19A:
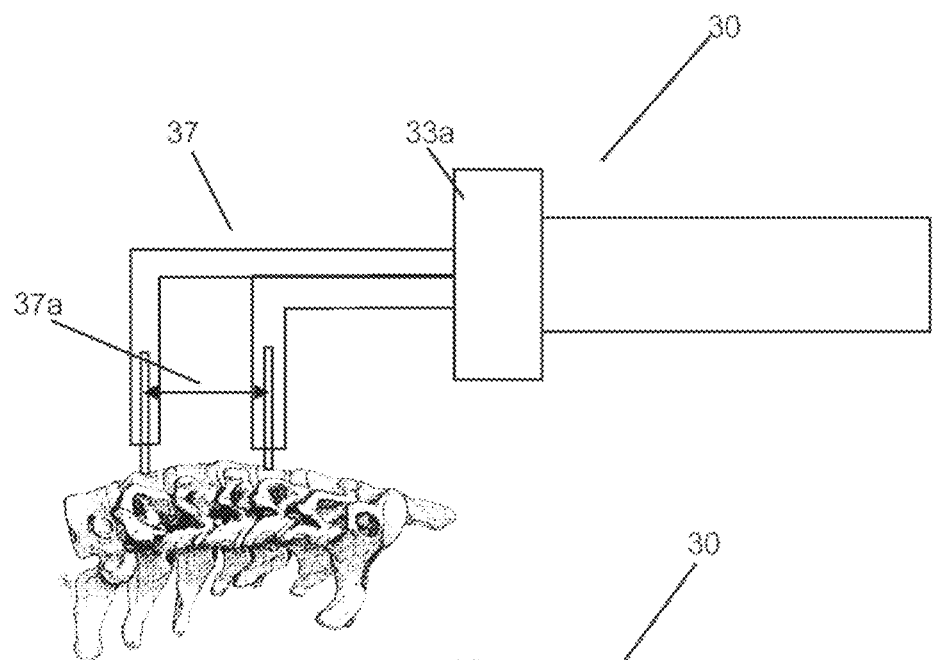
FIG. 19A-19B depicts an end-effectuator having an attachment element for applying distraction and/or compression forces in accordance with one embodiment of the invention.
Figure 19B:
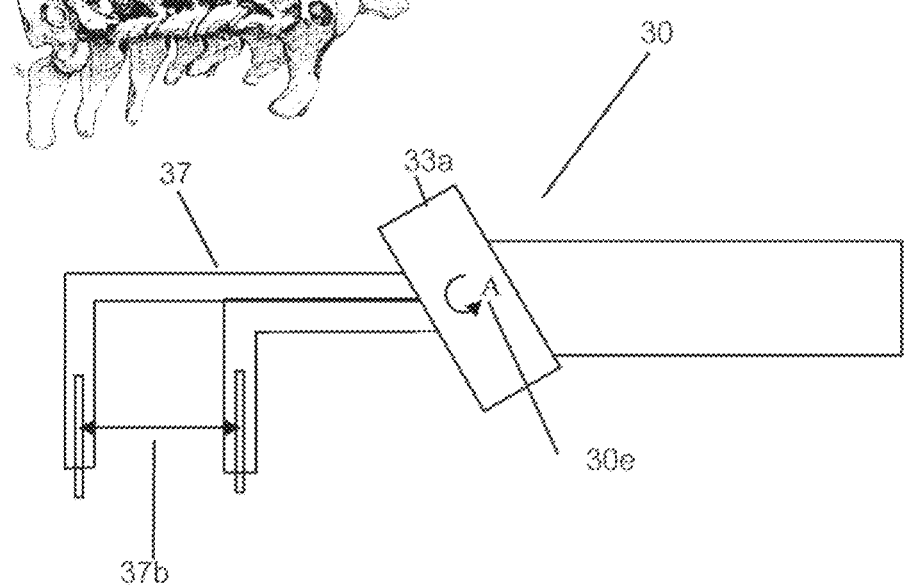

In applications such as cervical or lumbar fusion surgery, it can be beneficial to apply distraction or compression across one or more levels of the spine (anteriorly or posteriorly) before locking hardware in place. In some embodiments, the end-effectuator 30 can comprise an attachment element 37 that is configured to apply such forces (see for example FIGS. 19A-B). In some embodiments, the end-effectuator 30 attachment element 37 can be configured for coupling to the end-effectuator 30 at substantially the same location as the clearance mechanism 33. In some embodiments, the end-effectuator 30 with attachment element 37 snaps into the same place as the end-effectuator 30 without the attachment element 37. In some embodiments, during use of the end-effectuator 30 attachment element 37, the relative movement of the two shafts 32 caused by angulation 30e will not cause movement in the pitch 60 direction and will instead cause distraction (illustrated as moving from an attachment element 37 distance 37a in FIG. 19A to distance 37b in FIG. 19B). Further, although shaft 32 movement as shown in FIGS. 19A-B would cause distraction, rotation of the actuator 33a in the opposite direction to that represented by 30e would cause compression (i.e. the distance 37b in FIG. 19B would move towards the distance 37a in FIG. 19A).

In view of the embodiments described hereinbefore, some embodiments that can be implemented in accordance with the disclosed subject matter can be better appreciated with reference to the flowcharts in FIGS. 24-33. For purposes of simplicity of explanation, the method disclosed by the embodiments described herein is presented and described as a series of steps; however, it is to be understood and appreciated that the claimed subject matter is not limited by the order of acts, as some acts may occur in different orders and/or concurrently with other acts from that shown and described herein. For example, the various methods or processes of some embodiments of the invention can alternatively be represented as a series of interrelated states or events, such as in a state diagram. Furthermore, not all illustrated acts may be required to implement a method in accordance with some embodiments of the invention. Further yet, two or more of the disclosed methods or processes can be implemented in combination with each other, to accomplish one or more features or advantages herein described.

It should be further appreciated that the methods disclosed in the various embodiments described throughout the subject specification can be stored on an article of manufacture, or computer-readable medium, to facilitate transporting and transferring such methods to a computing device (e.g., a desktop computer, a mobile computer, a mobile telephone, a blade computer, a programmable logic controller, and the like) for execution, and thus implementation, by a processor of the computing device or for storage in a memory thereof.

In some embodiments, the surgical robot 15 can adjust its position automatically continuously or substantially continuously in order to move the end-effectuator 30 to an intended (i.e. planned) position. For example, in some embodiments, the surgical robot 15 can adjust its position automatically continuously or substantially continuously based on the current position of the end-effectuator 30 and surgical target as provided by a current snapshot of tracking markers, LPS, or other tracking data. It should further be appreciated that certain position adjustment strategies can be inefficient. For example, an inefficient strategy for the robot 15 to find a target location can be an iterative algorithm to estimate the necessary direction of movement, move toward the target location, and then assess a mismatch between a current location and the target location (the mismatch referred to as an error), and estimate a new direction, repeating the cycle of estimate-movement-assessment until the target location is reached within a satisfactory error. Conversely, the position adjustment strategies in accordance with some embodiments of the invention are substantively more efficient than iterative strategies. For example, in some embodiments, a surgical robot 15 can make movements and adjust its location by calibrating the relative directions of motions in each axis (permitting computation via execution of software or firmware with the computer 100) at each frame of tracking data, of a unique set of necessary motor encoder counts that can cause each of the individual axes to move to the correct location. In some embodiments, the Cartesian design of the disclosed robot 15 can permit such a calibration to be made by establishing a coordinate system for the robot 15 and determining key axes of rotation.

As described in greater detail below, in some embodiments, methods for calibrating the relative directions of the robot's 15 axes can utilize a sequence of carefully planned movements, each in a single axis. In some embodiments, during these moves, temporary tracking markers 720 are attached to the end-effectuator 30 to capture the motion of the end-effectuator 30. It should be appreciated that the disclosed methods do not require the axes of the robot 15 to be exactly or substantially perpendicular, nor do they require the vector along which a particular axis moves (such as the x-axis 66) to coincide with the vector about which rotation occurs (such as pitch 60, which occurs primarily about the x-axis 66). In certain embodiments, the disclosed methods include motion along a specific robot 15 axis that occurs in a straight line. In some embodiments, the disclosed methods for calibrating the relative directions of movement of the robot's 15 axes can utilize one or more frames of tracking data captured at the ends of individual moves made in x-(66), y-(68), roll (62), pitch (60), and Z-tube axes 64 from markers 720 temporarily attached to the end-effectuator's 30 guide tube 50. In some embodiments, when moving individual axes, all other axes can be configured at the zero position (for example, the position where the encoder for the axis reads 0 counts). Additionally or alternatively, one or more frames of tracking data with all robot 15 axes at 0 counts (neutral position) may be necessary, and one or more frames of data with the temporary markers 720 rotated to a different position about the longitudinal axis of the guide tube 50 may be necessary. In some embodiments, the marker 720 positions from these moves can be used to establish a Cartesian coordinate system for the robot 15 in which the origin (0, 0, 0) is through the center of the end-effectuator 30 and is at the location along the end-effectuator 30 closest to where pitch 60 occurs. Additionally or alternatively, in some embodiments, this coordinate system can be rotated to an alignment in which y-axis 68 movement of the robot 15 can occur exactly or substantially along the coordinate system's y-axis 68, while x-axis 66 movement of the robot 15 occurs substantially perpendicular to the y-axis 68, but by construction of the coordinate system, without resulting in any change in the z-axis 70 coordinate. In certain embodiments, the steps for establishing the robot's 15 coordinate system based at least on the foregoing individual moves can comprise the following: First, from the initial and final positions of the manual rotation of tracking markers 720 about the long axis of the end-effectuator 30, a finite helical axis of motion is calculated, which can be represented by a vector that is centered in and aligned with the end-effectuator 30. It should be appreciated that methods for calculating a finite helical axis of motion from two positions of three or more markers are described in the literature, for example, by Spoor and Veldpaus (Spoor, C. W. and F. E. Veldpaus, "Rigid body motion calculated from spatial co-ordinates of markers," J Biomech 13(4): 391-393 (1980)). In some embodiments, rather than calculating the helical axis, the vector that is centered in and aligned with the end-effectuator 30 can be defined, or constructed, by interconnecting two points that are attached to two separate rigid bodies that can be temporarily affixed to the entry and exit of the guide tube 50 on the Z-tube axis 64. In this instance, each of the two rigid bodies can include at least one tracking marker 720 (e.g., one tracking marker 720, two tracking markers 720, three tracking markers 720, more than three tracking markers 720, etc.), and a calibration can be performed that provides information indicative of the locations on the rigid bodies that are adjacent to the entry and exit of the guide tube 50 relative to the tracking markers.

A second helical axis can be calculated from the pitch 60 movements, providing a vector substantially parallel to the x-axis of the robot 15 but also close to perpendicular with the first helical axis calculated. In some embodiments, the closest point on the first helical axis to the second helical axis (or vector aligned with the end-effectuator 30) is calculated using simple geometry and used to define the origin of the robot's coordinate system (0, 0, 0). A third helical axis is calculated from the two positions of the roll 62 axis. In certain scenarios, it cannot be assumed that the vector about which roll occurs (third helical axis) and the vector along which the y-axis 68 moves are exactly or substantially parallel. Moreover, it cannot be assumed that the vector about which pitch 60 occurs and the vector along which x-axis 66 motion occurs are exactly or substantially parallel. Vectors for x-axis 66 and y-axis 68 motion can be determined from neutral and extended positions of x-axis 66 and y-axis 68 and stored separately. As described herein, in some embodiments, the coordinate system can be realigned to enable y-axis movement of the robot 15 to occur exactly or substantially in the y-axis 68 direction of the coordinate system, and x-axis 66 movement of the robot 15 without any change in the z-coordinate (70). In general, to perform such a transformation of coordinate systems, a series of rotations about a coordinate axis is performed and applied to every point of interest in the current coordinate system. Each point is then considered to be represented in the new coordinate system. In some embodiments, to apply a rotation of a point represented by a 3×1 vector about a particular axis, the vector can be pre-multiplied by a 3×3 rotation matrix. The 3×3 rotation matrix for a rotation of Rx degrees about the x-axis is:

$$\begin{bmatrix} 1 & 0 & 0 \\ 0 & \cos R_x & -\sin R_x \\ 0 & \sin R_x & \cos R_x \end{bmatrix}$$

The 3×3 rotation matrix for a rotation of $R_y$ degrees about the y-axis is:

$$\begin{bmatrix} \cos R_y & 0 & \sin R_y \\ 0 & 1 & 0 \\ -\sin R_y & 0 & \cos R_y \end{bmatrix}$$

The 3×3 rotation matrix for a rotation of $R_z$ degrees about the z-axis is:

$$\begin{bmatrix} \cos R_z & -\sin R_z & 0 \\ \sin R_z & \cos R_z & 0 \\ 0 & 0 & 1 \end{bmatrix}$$

In some embodiments, to transform coordinate systems, a series of three rotations can be performed. For example, such rotations can be applied to all vectors and points of interest in the current coordinate system, including the x-movement vector, y-movement vector and each of the helical axe, to align the y movement vector with the new coordinate system's y-axis, and to align the x movement vector as closely as possible to the new coordinate system's x-axis at z=0. It should be appreciated that more than one possible sequence of three rotations can be performed to achieve substantially the same goal. For example, in some embodiments, a sequence of three rotations can comprise (1) a rotation about x using an $R_x$ value appropriate to rotate the y-movement vector until its z coordinate equal 0, followed by (2) a rotation about z using an $R_z$ value appropriate to rotate the y-movement vector until its x coordinate equal 0, followed by (3) a rotation about y using an $R_y$ value appropriate to rotate the x-movement vector until its z coordinate equals 0. In some embodiments, to find the rotation angle appropriate to achieve a given rotation, the arctangent function can be utilized. For example, in some embodiments, the angle needed to rotate a point or vector (x1, y1, z1) about the z axis to y1=0 is −arctan(y1/x1).

It should be appreciated that after transformation of the coordinate system, in some embodiments, although the new coordinate system is aligned such that the y-movement axis of the surgical robot 15 is exactly or substantially exactly aligned with the coordinate system's y-axis 68, the roll 62 rotation movement of the robot 15 should not be assumed to occur exactly or substantially exactly about a vector aligned with the coordinate system's y-axis 68. Similarly, in some embodiments, the pitch 60 movement of the surgical robot 15 should not be assumed to occur exactly or substantially exactly about a vector aligned with the coordinate system's x-axis. In some embodiments, in roll 62 and pitch 60 rotational movement there can be linear and orientational "offsets" from the helical axis of motion to the nearest coordinate axis. In some embodiments, from the helical axes determined above using tracked markers, such offsets can be calculated and retained (e.g., stored in a computing device's memory) so that for any rotation occurring during operation, the offsets can be applied, rotation can be performed, and then negative offsets can be applied so that positional change occurring with rotation motion accounts for the true center of rotation.

In some embodiments, during tracking, the desired trajectory can be first calculated in the medical image coordinate system, then transformed to the robot 15 coordinate system based at least on known relative locations of active markers. For example, in some embodiments, conventional light-emitting markers and/or conventional reflective markers associated with an optical tracking system 3417 can be used (see for example active markers 720 in FIG. 20A). In other embodiments, conventional electromagnetic sensors associated with an electromagnetic tracking system can be used. In some other embodiments, radio-opaque markers (for example markers 730 shown in FIG. 20A) can be used with a CT imaging system. In some embodiments, radio-opaque markers 730 (spheres formed, at least in part from metal or other dense material), can be used to provide a marker 730 that can at least partially absorb x-rays to produce a highly contrasted image of the sphere in a CT scan image.

In some embodiments, the necessary counts for the end-effectuator 30 to reach the desired position in the robot's 15 coordinate system can be calculated based on the following example process. First the necessary counts to reach the desired angular orientation can be calculated. In some embodiments, a series of three rotations can be applied to shift the coordinate system temporarily to a new coordinate system in which the y-axis 68 coincides or substantially coincides with the helical axis of motion for roll 62, and the x-axis 66 is largely aligned with the helical axis of motion for pitch 60 and by definition, and the helical axis of motion for pitch 60 has constant z=0. Then, the number of counts necessary to achieve the desired pitch 60 can be determined, keeping track of how this pitch 60 can affect roll 62. In one implementation, to find the necessary counts to achieve the desired pitch, the change in pitch angle 60 can be multiplied by the previously calibrated motor counts per degree for pitch. The change in roll 62 caused by this change in pitch 60 can be calculated from the orientation of the helical axis and the rotation angle (pitch) about the helical axis. Then, the necessary roll 62 to get to the desired roll 62 to reach the planned trajectory alignment can be calculated, with the benefit that applying roll 62 does not, by definition of the coordinate system, result in any further change in pitch. The coordinate system is then shifted back to the previously described robot 15 coordinate system by the inverse of the three rotations applied above. Then the necessary counts to reach the desired x-axis 66 position can be calculated, also keeping track of how this x-axis 66 position change will affect y-axis 68 position. Then the necessary y-axis 68 counts to reach the desired y-axis position can be readily calculated with the benefit that changing the y-axis 68 coordinate can have no effect on any other axis since the y-axis motion vector is by definition aligned with the robot's y-axis 68. In a scenario in which the Z-tube 50 position is being actively controlled, the orientation of the Z-tube 50 movement vector is adjusted when adjusting roll 62 and pitch 60 and the counts necessary to move it to the desired position along the trajectory vector is calculated from the offset. In some embodiments, after the necessary counts to achieve the desired positions in all axes are calculated as described, these counts can be sent as computer-accessible instructions (e.g., computer-readable and/or computer-executable instructions) to respective controllers for each axis in order to move the axes to the computed positions.

Figure 24:
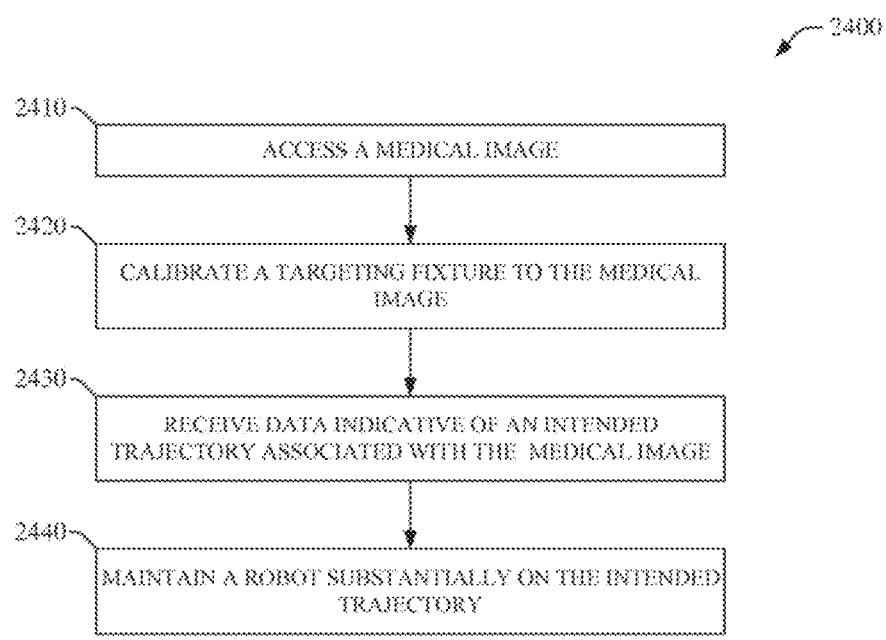
FIGS. 24-33 illustrate methods in accordance with one embodiment of the invention.

FIG. 24 is a flowchart of a method 2400 for positioning and advancing through soft tissue in accordance with one or more aspects according to one embodiment of the invention. As shown, in some embodiments, at block 2410, a medical image is accessed (e.g., received, retrieved, or otherwise acquired). As described herein, the medical image can be a 3D anatomical image scan including, but not limited to a CT scan, a magnetic resonance imaging scan (hereinafter referred to as an "MRI scan"), an X-ray image, or other anatomical scan. It should be appreciated that any 3D anatomical scan may be utilized with the surgical robot 15 and is within the scope of the present invention. In some embodiments, at block 2420, a targeting fixture 690 is calibrated to the medical image. In some embodiments, the calibration can be semi-automated or automated. In some embodiments, at block 2430, data indicative of an intended trajectory associated with the medical image is received. In some embodiments, at block 2440, a robot 15 is substantially maintained on the intended trajectory. In some embodiments, a control platform (for example, platform 3400 shown in FIG. 34) can adjust movement of the robot 15 in order to substantially maintain the intended trajectory.

Figure 25:
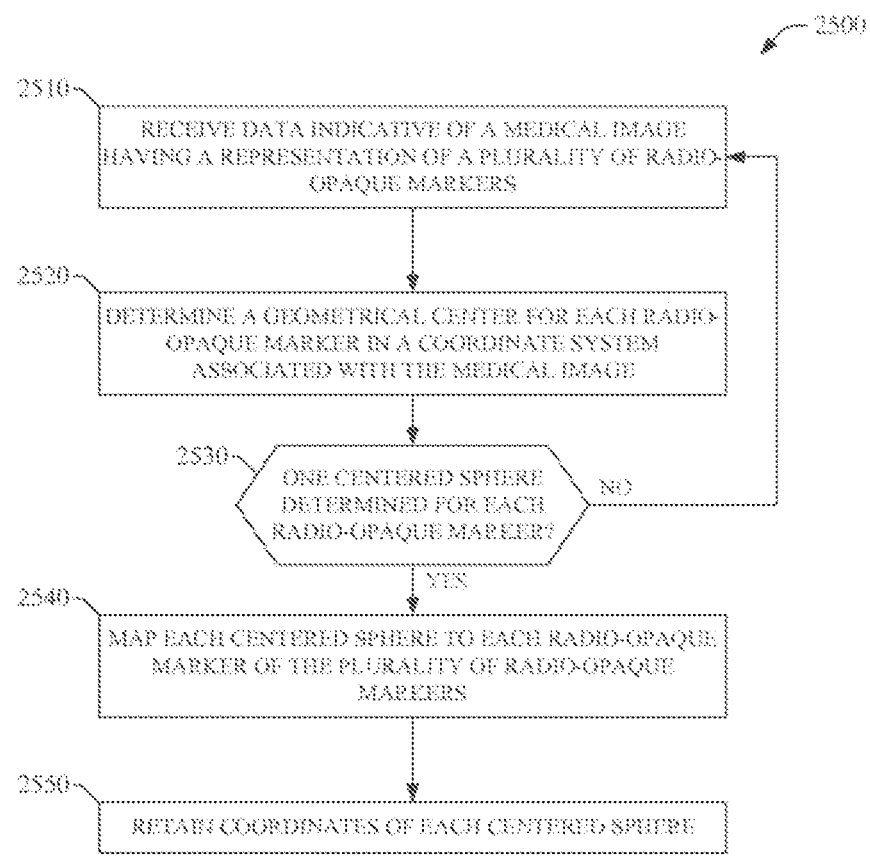
Figure 26:
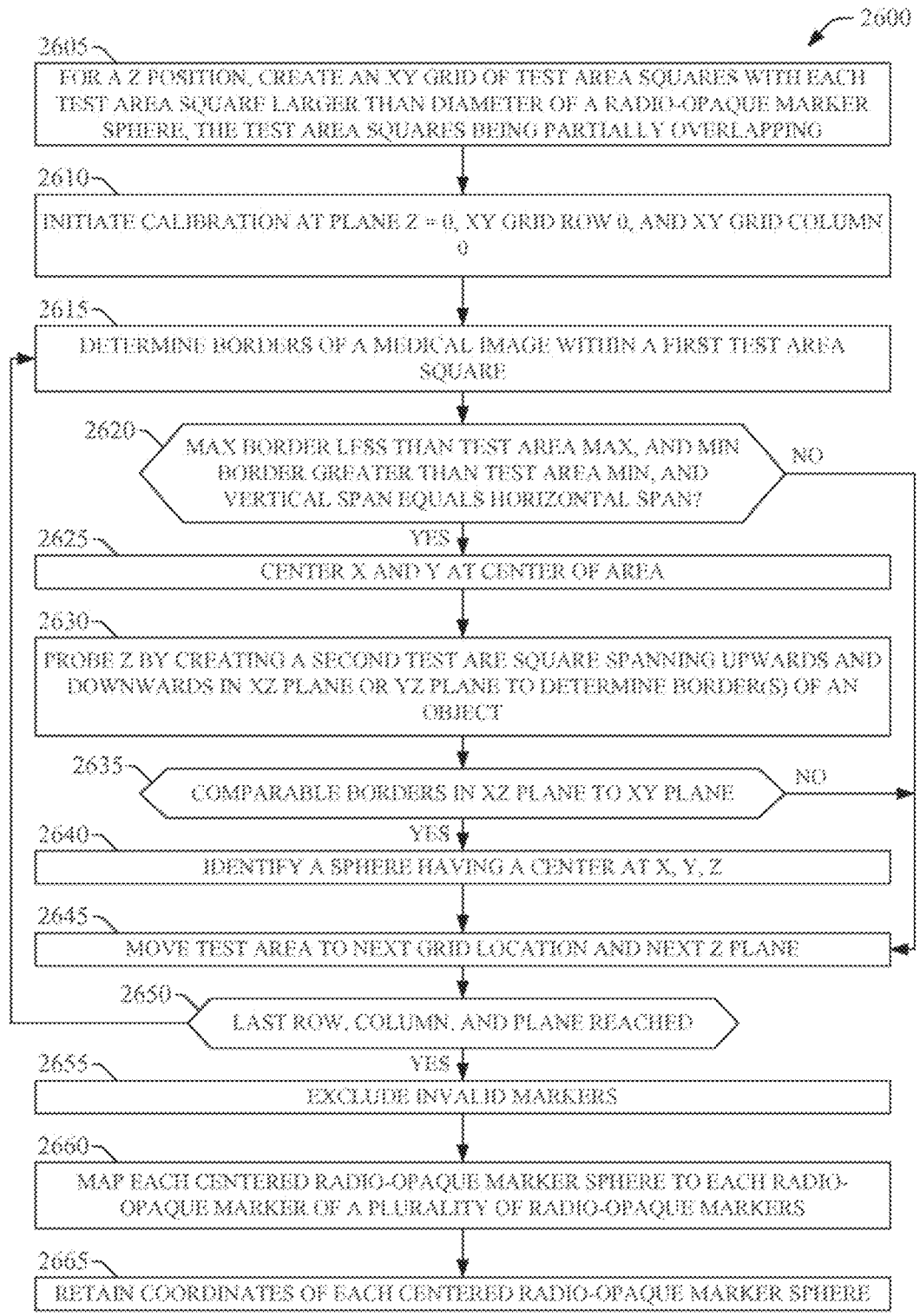

FIGS. 25-26 are flowcharts of methods for calibrating a targeting fixture 690 to a medical image in accordance with one or more embodiments of the invention. As shown in FIG. 25, in some embodiments, the method 2500 can embody a semi-automated calibration method and can be implemented (e.g., executed) as part of block 2420 in certain scenarios. In some embodiments, at block 2510, data indicative of a medical image having a representation of a plurality of radio-opaque markers (for example radio-opaque markers 730) is received. In one embodiment, as described herein, such plurality can contain four radio-opaque markers 730. In some embodiments, at block 2520, a geometrical center for each radio-opaque marker 730 is determined in a coordinate system associated with the medical image. In some embodiments, image thresholding can be utilized to define one or more edges of each radio-opaque marker 730 and a geometrical center thereof. Thresholding refers to an image processing technique in which pixel intensity within a 2D region can be monitored. For example, the x, y positions (for instance expressed in mm) of pixels of an intensity that reach a predetermined value can be retrieved. Stated similarly, the threshold refers to the transition pixel intensity from light to dark. In some embodiments, on 2D slices of the medical image, the radio-opaque marker 730 can appear light and the adjacent space (such as tissue or air) can appear dark. In some embodiments, displaying pixels that satisfy a thresholding criterion at an intensity encountered at the edge of a radio-opaque marker can yield a largely circular trace outlining the marker on the medical image. Since in some embodiments, markers 730 can be spherical, a method for finding the center of the marker 730 in a 2D view can include firstly restricting the 2D view to a sampling region with the high-intensity image of the sphere toward the center of the region and pixels of lower intensity toward the outer edges of the region. Secondly, the method can include finding the mean x threshold position (e.g., the maximum x coordinate of pixels satisfying the threshold criterion plus minimum x coordinate of pixels satisfying the threshold criterion divided by two), and finding the mean y threshold position using a similar method. In some embodiments, the center of the sphere can be found by determining 2D centers of slices through the same marker 730 in two orthogonal views. For example, in some embodiments, the method can include finding mean x and mean y from an xy slice, then finding mean x and mean z from an xz slice to get a mean x, y, and z axis coordinate representing the center of the marker 730. Further, upon or after the mean x, mean y, and mean z are found, new xy and xz slices can be evaluated again and the maximum and minimum x, y, and z threshold values can be again determined to evaluate the dimensions of the thresholded object in each view. It can be appreciated from this method that in some embodiments, a non-spherical object of high intensity, such as a small process of cortical bone extending away from the side of the spine, may fail to satisfy (1) a condition where there is high intensity near the middle of the region, but low intensity all around, since the process may extend out of the region in one or more directions; or (2) a condition where the dimensions in x, y, and z of the centered object do not match each other (e.g., non-spherical case).

As shown in FIG. 25, in some embodiments, at block 2530, it is ascertained if one centered sphere is determined for each radio-opaque marker 730 for the fixture being calibrated. In some embodiments, when at least one such sphere is not determined, or identified, the threshold setting is adjusted and flow is directed to block 2510. In some embodiments, at block 2540, each centered sphere is mapped to each radio-opaque marker 730 of the plurality of radio-opaque markers 730. As shown, in some embodiments, block 2540 can represent a mapping action which, in some embodiments, can comprise implementing a sorting process to establish a specific centered sphere is associated with a specific one of the plurality of radio-opaque markers 730. In some embodiments, a plurality of radio-opaque markers 730 contains four radio-opaque markers 730 (represented, for example, as OP1, OP2, OP3, and OP4). In some embodiments, the sorting process can map each one of four centered markers 730 to one of OP1, OP2, OP3, or OP4. In some embodiments, the sorting process can distinguish a specific marker 730 by measuring inter-marker distances from mean positions of the four unidentified markers 730, and comparing such distances to extant inter-marker distances (for example, those that are pre-measured and retained in memory, such as mass storage device 3404) for each marker 730 on a marker fixture. In some embodiments, the opaque markers 730 on the fixture 690 can be placed asymmetrically, each marker 730 can be identified from a unique set of inter-marker distances corresponding to such marker 730. For example, in some embodiments where the sum of inter-marker distances of one unknown marker 730 relative to the other threes markers 730 measured from the medical image is D, a single physical marker 730 (one of OP1, OP2, OP3, or OP4) can have a matching inter-marker distance sum within a specified tolerance (such as ±1 mm) of D. In some embodiments, at block 2550, coordinates of each centered sphere can be retained (for example in memory of a computer platform 3400). As described herein, in some embodiments, such coordinates can be utilized in a process for tracking movement of a robot 15.

Some embodiments include method 2600 (shown as a flowchart in FIG. 26) that can embody an automated calibration method and can be implemented (e.g., executed) as part of block 2420 in certain scenarios. In some embodiments, at block 2605, for a Z position, an x-y grid of test area squares is created. In some embodiments, each test area square can be larger than the diameter of a sphere (a radio-opaque marker 730) associated with a targeting fixture 690 comprised of material that, when imaged, appears as opaque. In some embodiments, each test area square can be at least partially overlapping with at least one adjacent test area square. In one embodiment of the invention, a nearly half the surface of a test area square can overlap with the surface of an adjacent test area square. In some embodiments, at block 2610, calibration is initiated at place Z=0, x-y grid row 0, x-y grid column 0. In some embodiments, at block 2615, borders of a medical image within a first test area square are determined. It should be appreciated that in some embodiments, a sphere can be rendered as a circular area, but a section of bone represented in the medical image can be asymmetrical. In some embodiments, a thresholding process in accordance with one or more aspects described herein can be implemented to exclude one or more invalid markers 730 by assessing if the x, y, and z axes boundaries of the object are of substantially equivalent dimensions, consistent with the shape being spherical.

In some embodiments, at block 2620, it is determined if a maximum (max) border coordinate is less than the maximum coordinate of the test area, and a minimum (min) border coordinate is greater than the minimum coordinate of the test area, and vertical span of features rendered in the image are equal or substantially equal to horizontal span of such features. As shown in FIG. 26, in some embodiments, in the negative case, flow is directed to block 2645, at which the first test area is moved to next grid location and next Z plane. Conversely, in case the three foregoing conditions are fulfilled, flow is directed to block 2625, at which X coordinate and Y coordinate are centered at the center of the current test area. In some embodiments, at block 2630, Z coordinate is probed by creating a second test area square spanning upwards and downwards in XZ plane and/or YZ plane to determine one or more borders of an object. In some embodiments, at block 2635, it is determined if borders of the object observed in XZ plane are of substantially equivalent relative spacing (vertically and horizontally) to borders in the x-y plane, consistent with the shape of the object being spherical. In some embodiments, when such borders are of different spacing, flow is directed to block 2645. Conversely, when spacing of such borders is substantially equivalent between views, a sphere having a center at X coordinate, Y coordinate, and Z coordinate is identified at block 2640 and flow is directed to block 2645.

In some embodiments, at block 2650, it is determined if last row and column in x-y grid are reached and last Z plane is reached as a result of updating the first test area at block 2645. In some embodiments, in the negative case, flow is directed to block 2615, in which the first area is the updated instance of a prior first area, with the flow reiterating one or more of blocks 2620 through 2645. Conversely, in the affirmative case, flow is directed to block 2655 at which invalid marker(s) 730 can be excluded. In some embodiments, a paring process can be implemented to exclude one or more invalid markers 730. For this paring process, in some embodiments, the known spacings between each of the N radio-opaque markers 730 (with N a natural number) on the targeting fixture 690 and each other radio-opaque marker 730 on the targeting fixture 690 can be compared to the markers 730 that have been found on the medical image. In a scenario in which more than N number of markers 730 can be found on the medical image, any sphere found on the medical image that does not have spacings relative to N−1 other markers 730 that are within an acceptable tolerance of known spacings retained, for example, on a list can be considered to be invalid. For example, if a targeting fixture 690 has four radio-opaque markers 730, there are six known spacings, with each marker 730 having a quantifiable spacing relative to three other markers 730: the inter-marker spacings for markers 1-2, 1-3, 1-4, 2-3, 2-4, and 3-4. On the 3D medical image of the targeting fixture 690, in some embodiments, if five potential markers 730 are found on the medical image, their inter-marker spacings can be calculated. In this scenario, there are 10 inter-marker spacings: 1-2, 1-3, 1-4, 1-5, 2-3, 2-4, 2-5, 3-4, 3-5, and 4-5, with each sphere having a quantifiable spacing relative to four other markers 730. Considering each of the five potential markers 730 individually, if any one of such five markers 730 does not have three of its four inter-marker spacings within a very small distance of the spacings on the list of six previously quantified known spacings, it is considered invalid.

In some embodiments, at block 2660, each centered radio-opaque marker 730, identified at block 2640, can be mapped to each radio-opaque marker 730 of a plurality of radio-opaque markers 730. In some embodiments, a sorting process in accordance with one or more aspects described herein can be implemented to map such markers 730 to radio opaque markers 730. In some embodiments, at block 2665, coordinates of each centered sphere can be retained (e.g., in memory of a computer platform 3400). As described herein, in some embodiments, such coordinates can be utilized in a process for tracking movement of a robot 15. In some embodiments, during tracking, the established (e.g., calibrated) spatial relationship between active markers 720 and radio-opaque markers 730 can be utilized to transform the coordinate system from the coordinate system of the medical image to the coordinate system of the tracking system 3417, or vice versa. Some embodiments include a process for transforming coordinates from the medical image's coordinate system to the tracking system's coordinate system can include a fixture 690 comprising four radio-opaque markers OP1, OP2, OP3, and OP4 (for example radio-opaque markers 730) in a rigidly fixed position relative to four active markers AM1, AM2, AM3, AM4 (for example, active markers 720). In some embodiments, at the time the calibration of the fixture 690 occurred, this positional relationship can be retained in a computer memory (e.g., system memory 3412) for later access on real-time or substantially on real-time in a set of four arbitrary reference Cartesian coordinate systems that can be readily reachable through transformations at any later frame of data. In some embodiments, each reference coordinate system can utilize an unambiguous positioning of three of the active markers 720. Some embodiments can include a reference coordinate system for AM1, AM2, and AM3 can be coordinate system in which AM1 can be positioned at the origin (e.g., the three-dimensional vector (0, 0, 0)); AM2 can be positioned on the x-axis (e.g., x-coordinate AM2x>0, y-coordinate AM2y=0, and z-coordinate AM2z=0); and AM3 can be positioned on the x-y plane (e.g., x-coordinate AM3x unrestricted, y-coordinate AM3y>0, and z-coordinated AM3z=0). Some embodiments include a method to generate a transformation to such coordinate system can comprise (1) translation of AM1, AM2, AM3, OP1, OP2, OP3, and OP4 in a manner that AM1 vector position is (0, 0, 0); (2) rotation about the x-axis by an angle suitable to position AM2 at z=0 (e.g., rotation applied to AM2, AM3 and OP1-OP4); (3) rotation about the z-axis by an angle suitable to position AM2 at y=0 and x>0 (e.g., rotation applied to AM2, AM3 and OP1-OP4); (4) rotation about the x-axis by an angle suitable to position AM3 at z=0 and y>0 (e.g., rotation applied to AM3 and OP1-OP4). It should be appreciated that, in some embodiments, it is unnecessary to retain these transformations in computer memory, for example; rather, the information retained for later access can be the coordinates of AM1-AM3 and OP1-OP4 in such reference coordinate system. In some embodiments, another such reference coordinate system can transform OP1-OP4 by utilizing AM2, AM3, and AM4. In some embodiments, another such reference coordinate system can transform OP1-OP4 by utilizing AM1, AM3, and AM4. In some further embodiments, another such reference coordinate system can transform OP1-OP4 by utilizing AM1, AM2, and AM4.

In some embodiments, at the time of tracking, during any given frame of data, the coordinates of the active markers AM1-AM4 can be provided by the tracking system 3417. In some embodiments, by utilizing markers AM1, AM2, and AM3, transformations suitable to reach the conditions of the reference coordinate system can be applied. In some embodiments, such transformations can position AM1, AM2, and AM3 on the x-y plane in a position in proximity to the position that was earlier stored in computer memory for this reference coordinate system. In some embodiments, for example, to achieve a best fit of the triad of active markers 720 on their stored location, a least squares algorithm can be utilized to apply an offset and rotation to the triad of markers 720. In one implementation, the least squares algorithm can be implemented as described by Sneath (Sneath P. H. A., Trend-surface analysis of transformation grids, J. Zoology 151, 65-122 (1967)). In some embodiments, transformations suitable to reach the reference coordinate system, including the least squares adjustment, can be retained in memory (e.g., system memory 3412 and/or mass storage device 3404). In some embodiments, the retained coordinates of OP1-OP4 in such reference coordinate system can be retrieved and the inverse of the retained transformations to reach the reference coordinate system can be applied to such coordinates. It should be appreciated that the new coordinates of OP1-OP4 (the coordinates resulting from application of the inverse of the transformations) are in the coordinate system of the tracking system 3417. Similarly, in some embodiments, by utilizing the remaining three triads of active markers 720, the coordinates of OP1-OP4 can be retrieved.

In some embodiments, the four sets of OP1-OP4 coordinates in the tracking system's coordinate system that can be calculated from different triads of active markers 720 are contemplated to have coordinates that are approximately equivalent. In some embodiments, when coordinates are not equivalent, the data set can be analyzed to determine which of the active markers 720 provides non-suitable (or poor) data by assessing how accurately each triad of active markers 720 at the current frame overlays onto the retained positions of active markers 720. In some other embodiments, when the coordinates are nearly equivalent, a mean value obtained from the four sets can be utilized for each radio-opaque marker 730. In some embodiments, to transform coordinates of other data (such as trajectories from the medical image coordinate system) to the tracking system's coordinate system, the same transformations can be applied to the data. For example, in some embodiments, the tip and tail of a trajectory vector can be transformed to the four reference coordinate systems and then retrieved with triads of active markers 720 at any frame of data and transformed to the tracking system's coordinate system.

Figure 27:
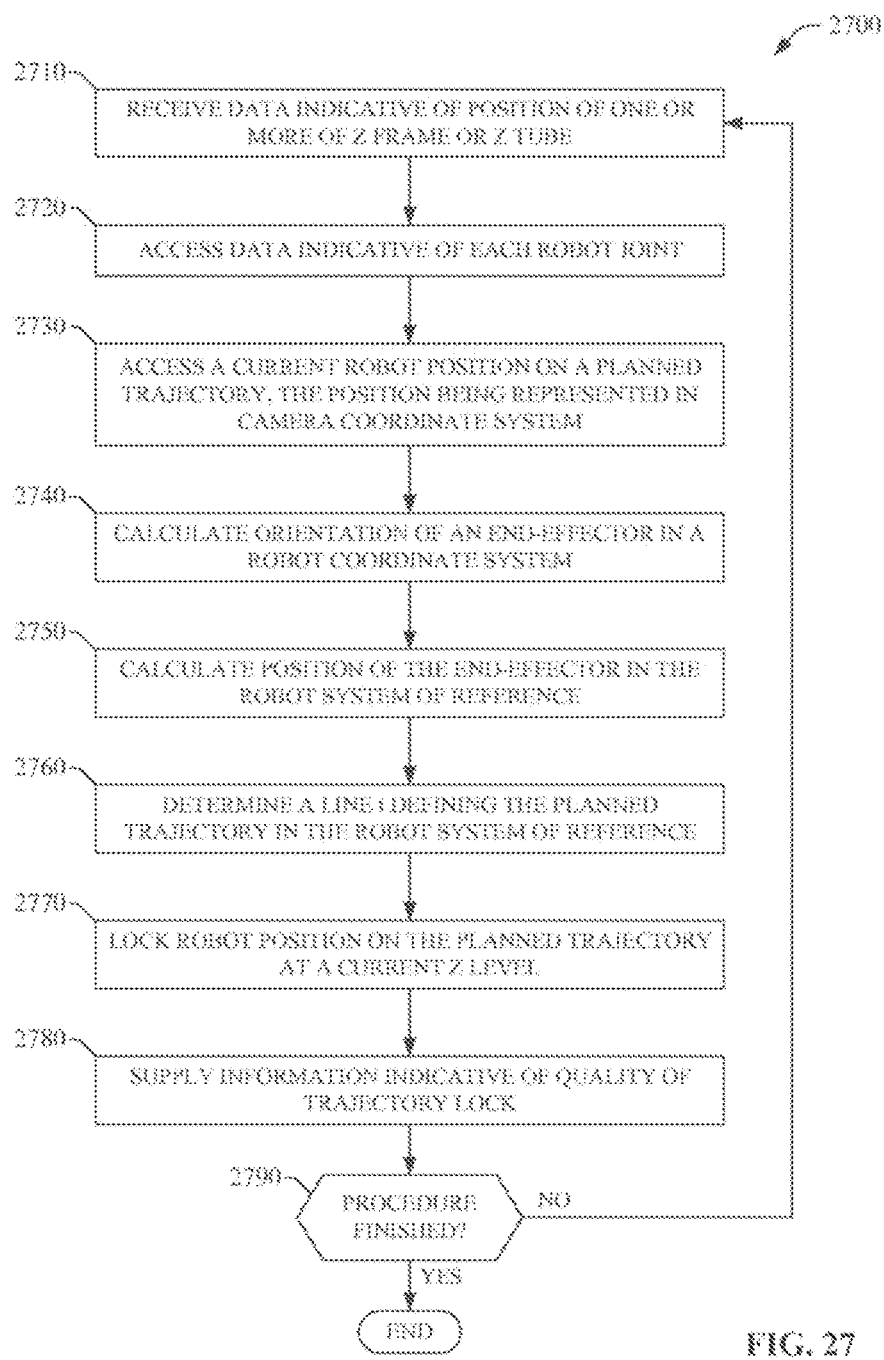

FIG. 27 is a flowchart of a method 2700 for automatically maintaining a surgical robot 15 substantially on a trajectory in accordance some embodiments of the invention. In some embodiments, at block 2710, data indicative of position of one or more of Z-frame 72 or Z-tube 50 are received. In some embodiments, at block 2720, data indicative of each robot 15 joint in the surgical robot 15, such as encoder counts from each axis motor 160, are accessed. In some embodiments, at block 2730, a current robot 15 position on a planned trajectory is accessed (the position being represented in a camera coordinate system or the coordinate system of other tracking device). In one embodiment, the planned trajectory can be generated by an operator. For example, the operator (e.g., a surgeon) can scroll and rotate through the image slices until the desired anatomy can be viewed on three windows representing three orthogonal planes (typically sagittal, coronal, and axial slices). The operator can then draw a line at the desired slope and location on one window; the line simultaneously is calculated and appears on the other two windows, constrained by the views of the screens and orientation on the window on which it was drawn.

In another embodiment, a line (e.g., referred to as line t) that is fixed on the image both in angle and position represents the desired trajectory; the surgeon has to rotate and scroll the images to align this trajectory to the desired location and orientation on the anatomy. At least one advantage of such embodiment is that it can provide a more complete, holistic picture of the anatomy in relationship to the desired trajectory that may not require the operator to erase and start over or nudge the line after it is drawn, and this process was therefore adopted. In some embodiments, a planned trajectory can be retained in a memory of a computing device (for example, computing device 3401) that controls the surgical robot 15 or is coupled thereto for use during a specific procedure. In some embodiments, each planned trajectory can be associated with a descriptor that can be retained in memory with the planned trajectory. As an example, the descriptor can be the level and side of the spine where screw insertion is planned.

In another embodiment, the line t that is (fixed on the image both in angle and position representing the desired trajectory) is dictated by the current position of the robot's end effectuator 30, or by an extrapolation of the end effectuator guide tube 50 if an instrument 35 were to extend from it along the same vector. In some embodiments, as the robot 15 is driven manually out over the patient 18 by activating motors 160 controlling individual or combined axes 64, 66, 68, 70, the position of this extrapolated line (robot's end effectuator 30) is updated on the medical image, based on markers 720 attached to the robot, conventional encoders showing current position of an axis, or a combination of these registers. In some embodiments, when the desired trajectory is reached, that vector's position in the medical image coordinate system is stored into the computer memory (for example in memory of a computer platform 3400) so that later, when recalled, the robot 15 will move automatically in the horizontal plane to intersect with this vector. In some embodiments, instead of manually driving the robot 15 by activating motors 160, the robot's axes can be put in a passive state. In some embodiments, in the passive state, the markers 720 continue to collect data on the robot arm 23 position and encoders on each axis 64, 66, 68, 70 continue to provide information regarding the position of the axis; therefore the position of an extrapolated line can be updated on the medical image as the passive robot 15 is dragged into any orientation and position in the horizontal plane. In some embodiments, when a desired trajectory is reached, the position can be stored into the computer memory. Some embodiments include conventional software control or a conventional switch activation capable of placing the robot 15 into an active state to immediately rigidly hold the position or trajectory, and to begin compensating for movement of the patient 18.

In some further embodiments, the computing device that implements the method 2700 or that is coupled to the surgical robot 15 can render one or more planned trajectories. Such information can permit confirming that the trajectories planned are within the range of the robot's 15 reach by calculating the necessary motor 160 encoder counts to reach each desired trajectory, and assessing if the counts are within the range of possible counts of each axis.

In some embodiments, information including whether each trajectory is in range, and how close each trajectory is to being out of range can be provided to an agent (such as a surgeon or other user, or equipment). For example, in some embodiments, a display means 29 (such as a display device 3411) can render (i.e. display) the limits of axis counts or linear or angular positions of one or more axes and the position on each axis where each targeted trajectory is currently located.

In another embodiment, the display device 3411 (for example, a display 150) can render a view of the horizontal work field as a rectangle with the robot's x-axis 66 movement and y-axis 68 movement ranges defining the horizontal and vertical dimensions of the rectangle, respectively. In some embodiments, marks (for example, circles) on the rectangle can represent the position of each planned trajectory at the current physical location of the robot 15 relative to the patient 18. In another embodiment, a 3D Cartesian volume can represent the x-axis 66 movement, y-axis 68 movement and z-axis 70 movement ranges of the robot 15. In some embodiments, line segments or cylinders rendered in the volume can represent the position of each planned trajectory at the current location of the robot 15 relative to the patient 18. Repositioning of the robot 15 or a patient 18 is performed at this time to a location that is within range of the desired trajectories. In other embodiments, the surgeon can adjust the Z Frame 72 position, which can affect the x-axis 66 range and the y-axis 68 range of trajectories that the robot 15 is capable of reaching (for example, converging trajectories require less x-axis 66 or y-axis reach the lower the robot 15 is in the z-axis 70). During this time, simultaneously, a screen shows whether tracking markers on the patient 18 and robot 15 are in view of the detection device of the tracking system (for example, optical tracking system 3417 shown in FIG. 34 and cameras 8200 in FIG. 81). Repositioning of the cameras 8200, if necessary, is also performed at this time for good visibility or optimal detection of tracking sensors.

In some embodiments, at block 2740, orientation of an end-effectuator 30 in a robot 15 coordinate system is calculated. In some embodiments, at block 2750, position of the end-effectuator 30 in the robot 15 coordinate system is calculated. In some embodiments, at block 2760, a line t defining the planned trajectory in the robot 15 coordinate system is determined. In some embodiments, at block 2770, robot 15 position is locked on the planned trajectory at a current Z level. In some embodiments, at block 2780, information indicative of quality of the trajectory lock can be supplied. In some embodiments, actual coordinate(s) of the surgical robot 15 can be rendered in conjunction with respective coordinate(s) of the planned trajectory. In some embodiments, aural indicia can be provided based on such quality. For instance, in some embodiments, a high-frequency and/or high-amplitude noise can embody aural indicia suitable to represent a low-quality lock. In some alternative embodiments, a brief melody may be repeatedly played, such as the sound associated with successful recognition of a USB memory device by a computer, to indicate successful lock on the planned trajectory. In other embodiments, a buzz or other warning noise may be played if the robot 15 is unable to reach its target due to the axis being mechanically overpowered, or if the tracking markers 720 are undetectable by cameras 8200 or other marker position sensors.

In some embodiments, at block 2790, it is determined if a surgical procedure is finished and, in the affirmative case, the flow terminates. In other embodiments, the flow is directed to block 2710. In some embodiments, the method 2700 can be implemented (i.e., executed) as part of block 2440 in certain scenarios. It should be appreciated that in some embodiments, the method 2700 also can be implemented for any robot 15 having at least one feature that enable movement of the robot 15.

Figure 28A:
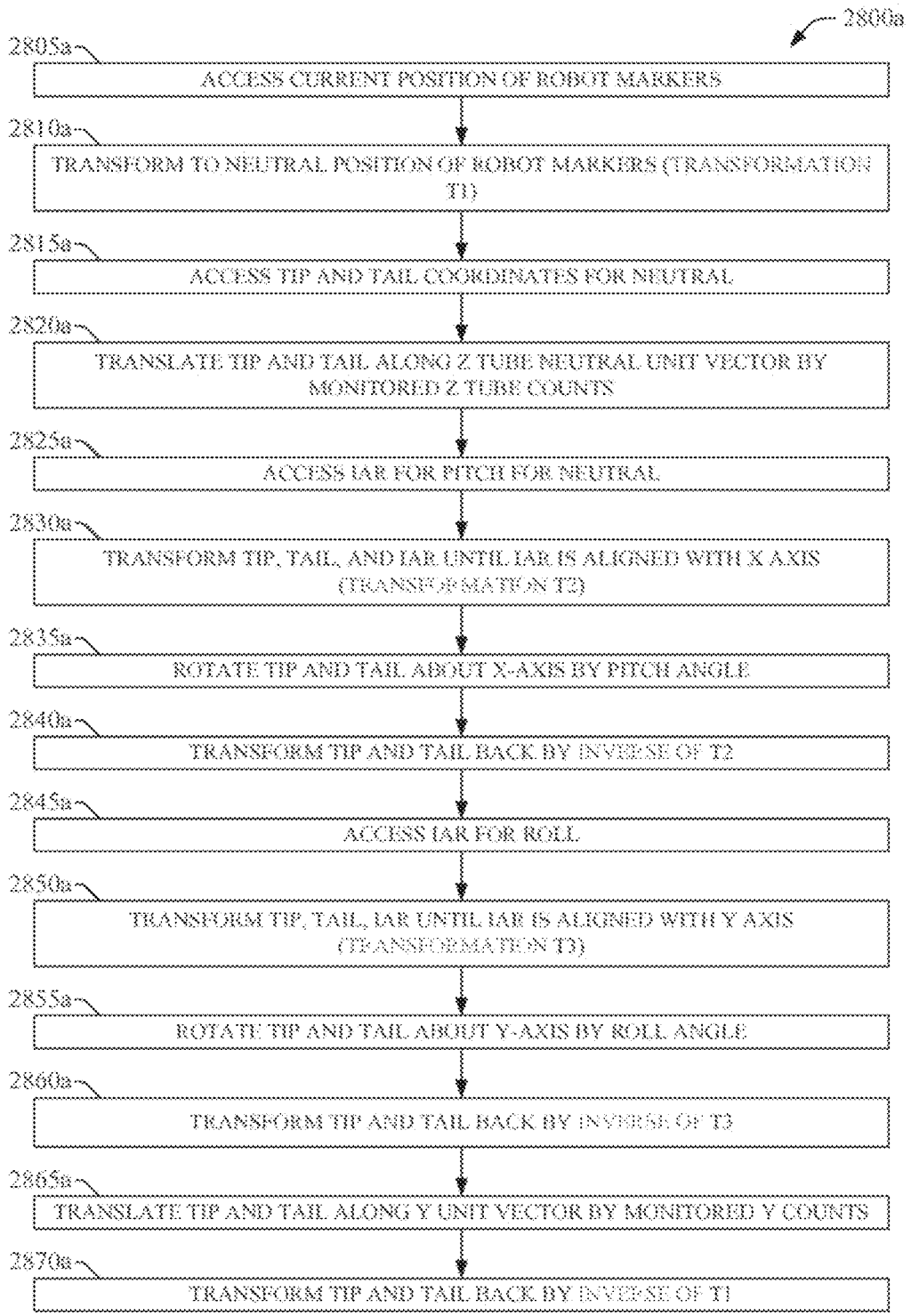

FIG. 28A is a flowchart of a method 2800a for calculating position and/or orientation of an end-effectuator 30 in a robot 15 according to one at least one embodiment of the invention. In some embodiments, the position and/or orientation can be calculated based at least on monitored position of a tracking array 690 mounted on the robot's x-axis 66 and monitored counts of encoders on the y-axis 68, roll 62, pitch 60, and Z-tube axis 64 actuators. In some embodiments, position and/or orientation are calculated in a robot 15 coordinate system. In some embodiments, the method 2800a can embody one or more of blocks 2740 or 2750. In some embodiments, at block 2805a, the current position (i.e., 3D position) of x-axis 66 mounted robot 15 tracking markers is accessed. In some embodiments, at block 2810a, the current position of the tracking array 690 mounted to the robot 15 is transformed to neutral position. This is a position that was previously stored and represents the position of the tracking array 690 when the robot 15 was at zero counts on each axis between the tracker 690 and the robot 15 base (x-axis 66 and z-axis 70 in this configuration). In some embodiments, the set of transformations (T1) to transform from the current position to the neutral position can be retained in computer memory (for example, the system memory 3412 and/or mass storage device 3404). In some embodiments, a tip and tail of a line segment representing the vector in line with the end-effectuator 30 can be computed based at least on the process described herein. In some embodiments, this process can establish a robot 15 coordinate system and calibrate the relative orientations of the axes of movement of the robot 15 where tracking markers 720 can be attached temporarily to the end-effectuator 30. In some embodiments, the vector's position in space can be determined by finding the finite helical axis of motion of markers 720 manually rotated to two positions around the guide tube 50. In some embodiments, the vector's position in space can be determined by connecting a point located at the entry of the guide tube 50 (identified by a temporarily mounted rigid body 690 with tracking markers 720) to a point located at the exit of the guide tube 50 (identified by a second temporarily mounted rigid body 690 with tracking markers 720).

In some embodiments, the tip of the line segment can be obtained as the point along the vector that is closest to the vector representing the helical axis of motion during pitch. In some embodiments, the tail of the line segment can be set an arbitrary distance (for example about 100 mm) up the vector aligned with the guide tube 50 and/or first helical axis. In some embodiments, the Cartesian coordinates of such tip and tail positions can be transformed to a coordinate system described herein in which the y-axis 68 movement can coincide with the y-axis 68 of the coordinate system, and the x-axis 66 can be aligned such that x-axis 66 movement can cause the greatest change in direction in the x-axis 66, moderate change in the y-axis 68, and no change in the z-axis 70. In some embodiments, these coordinates can be retained in a computer memory (for example system memory 3412) for later retrieval. In some embodiments, at block 2815a, tip and tail coordinates for neutral are accessed (i.e., retrieved). In some embodiments, at block 2820a, tip and tail are translated along Z-tube 50 neutral unit vector by monitored Z-tube 50 counts. In some embodiments, at block 2825a, an instantaneous axis of rotation ("IAR") is accessed. The IAR is the same as the helical axis of motion ignoring the element of translation along the helical axis for pitch 60 for neutral. As described earlier, in some embodiments, the vectors for this IAR were previously stored in computer memory at the time the coordinate system of the robot 15 was calibrated. In some embodiments, at block 2830a, tip coordinate, tail coordinate, and IAR vector direction and location coordinates are transformed (for example, iteratively transformed) to a new coordinate system in which IAR is aligned with X axis. In some embodiments, data indicative of such transformations (T2) can be stored. In some embodiments, at block 2835a, tip coordinate and tail coordinate are rotated about X axis by pitch 60 angle. In some embodiments, at block 2840a, tip coordinate and tail coordinate are transformed back by inverse of T2 to the previous coordinate system. In some embodiments, at block 2845a, previously stored vectors that represent the IAR for roll 62 are accessed. In some embodiments, at block 2850a, tip coordinate, tail coordinate, IAR coordinate are transformed (for example, iteratively transformed) to a new coordinate system in which IAR is aligned with y-axis 68. In some embodiments, data indicative of such transformation(s) (T3) can be retained in memory. In some embodiments, at block 2855a, tip coordinate and tail coordinate are rotated about y-axis 68 by roll 62 angle. In some embodiments, at block 2860a, tip coordinate and tail coordinate are transformed back by inverse of T3 to the previous coordinate system. In some embodiments, at block 2865a, tip coordinate and tail coordinate are translated along a y-axis 68 unit vector (e.g., a vector aligned in this coordinate system with the y-axis 68) by monitored counts. In some embodiments, at block 2870a, tip coordinate and tail coordinate are transformed back by inverse of T1 to the current coordinate system monitored by the tracking system 3417.

Figure 28B:
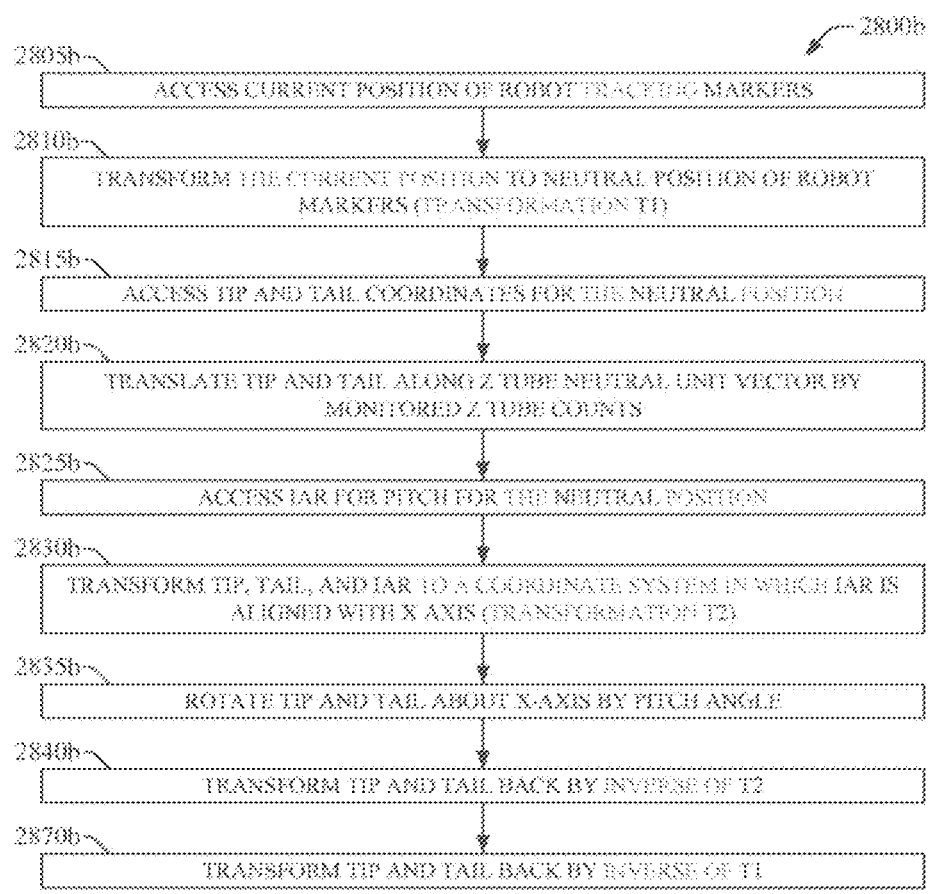

FIG. 28B is a flowchart of a method 2800b for calculating position and/or orientation of an end-effectuator 30 in a robot 15 in accordance with one embodiment of the invention. In some embodiments, the position and/or the orientation can be calculated based at least on monitored position of a tracking array 690 mounted on the robot's 15 roll 62 axis and monitored counts of encoders on the pitch 60 and Z-tube 50 actuators. In some embodiments, position and/or orientation can be calculated in a robot 15 coordinate system. In accordance with some embodiments of the invention, the method 2800B can embody one or more of blocks 2740 or 2750. In some embodiments, at block 2805b, current position of an array of one or more robot 15 tracking markers 720 is accessed. In some embodiments, the current position is a 3D position and the array of robot 15 tracking markers 720 can be mounted to the roll 62 axis of the robot 15. In some embodiments, at block 2810b, the current position of the array of robot 15 tracking markers 720 mounted to the robot 15 is transformed to neutral position. In some embodiments, the neutral position can be a position that was previously stored and can represent the position of the robot 15 tracking array 690 when the robot 15 had zero counts on each axis between the tracker 690 and the robot base 25 (e.g., z-axis 70, x-axis 68, y-axis 66, and roll 62 axis in this configuration). In some embodiments, data indicative of a set of transformations (T1) to go from the current position to the neutral position can be stored in a computer memory (for example, mass storage device 3404 or system memory 3412).

In some embodiments, in order to establish a robot 15 coordinate system and calibrate the relative orientations of the axes of movement of the robot 15, a tip and tail of a line segment representing the vector in line with the end-effectuator 30 with temporarily attached tracking markers 720 is located. In some embodiments, the vector's position in space can be determined by finding the finite helical axis of motion of markers manually rotated to two positions around the guide tube 50. In other embodiments, the vector's position in space can be determined by connecting a point located at the entry of the guide tube 50 (identified by a temporarily mounted rigid body 690 with tracking markers 720) to a point located at the exit of the guide tube 50 (identified by a second temporarily mounted rigid body 690 with tracking markers 720).

In some embodiments, the tip of the line segment can be found as the point along the vector that is closest to the vector representing the helical axis of motion during pitch. In some embodiments, the tail of the line segment can be set an arbitrary distance (for example, nearly 100 mm) up the vector aligned with the guide tube/first helical axis. In some embodiments, the Cartesian coordinates of these tip and tail positions can be transformed to a coordinate system described herein in which the y-axis 68 movement substantially coincides with the y-axis 68 of the coordinate system, and the x-axis 66 movement is aligned in a manner that, in some embodiments, x-axis 66 movement causes the greatest change in direction in the x-axis 66, slight change in y-axis 68, and no change in the z-axis 70. It should be appreciated that such coordinates can be retained in memory (for example system memory 3412) for later retrieval. In some embodiments, at block 2815b, tip and tail coordinates for the neutral position are accessed (i.e., retrieved or otherwise obtained). In some embodiments, at block 2820b, tip and tail are translated along Z-tube 50 neutral unit vector by monitored Z-tube 50 counts. In some embodiments, at block 2825b, IAR is accessed. In one implementation, the vectors for this IAR may be available in a computer memory, for example, such vectors may be retained in the computer memory at the time the coordinate system of the robot 15 is calibrated in accordance with one or more embodiments described herein. In some embodiments, at block 2830b, tip coordinate, tail coordinate, and IAR vector direction and location coordinates are transformed to a new coordinate system in which IAR is aligned with x-axis 66. In some embodiments, data indicative of the applied transformations (T2) can be retained in a computer memory. In some embodiments, at block 2835*b*, tip coordinate and tail coordinate are rotated about x-axis 66 by pitch 60 angle. In some embodiments, at block 2840*b*, tip coordinate and tail coordinate are transformed back by applying the inverse of T2 to the previous coordinate system. In some embodiments, at block 2870*b*, tip coordinate and tail coordinate are transformed back by applying the inverse of T1 to the current coordinate system monitored by the tracking system 3417.

Figure 29:
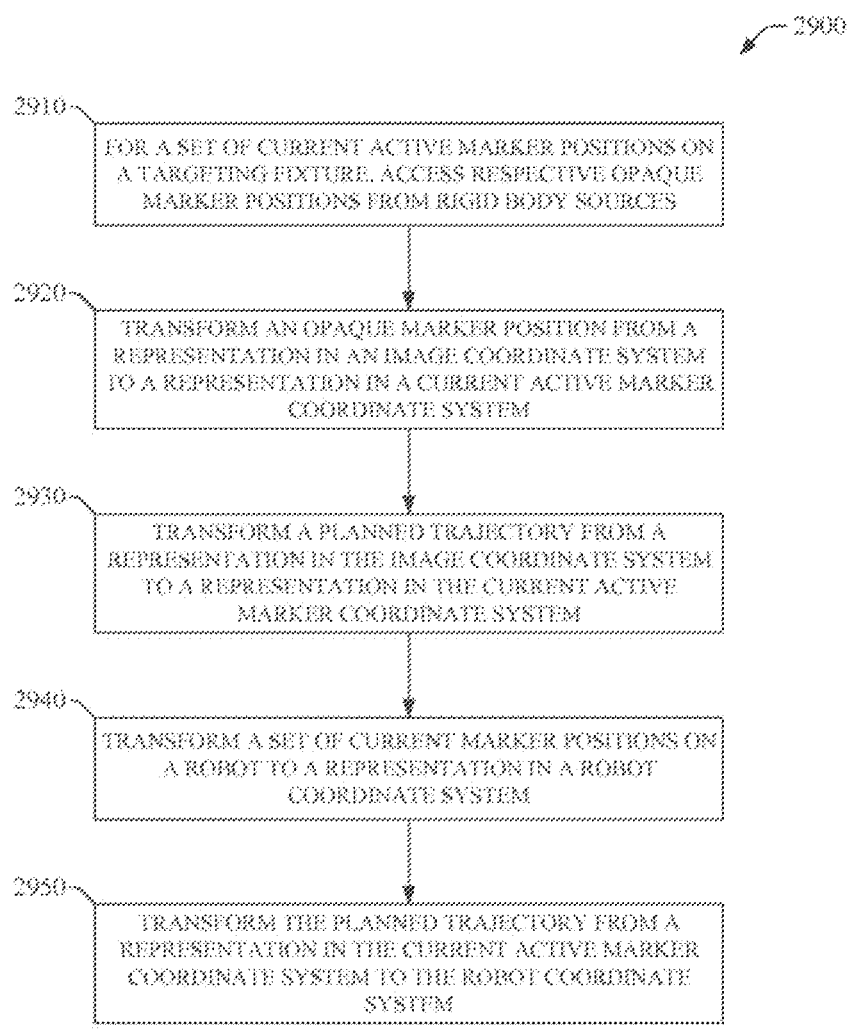

FIG. 29 is a flowchart of a method 2900 for determining a line indicative of a trajectory in a robot 15 coordinate system in accordance with one embodiment of the invention. In some embodiments, the trajectory can be a planned trajectory associated with a surgical procedure. In some embodiments, at block 2910, for a set of current active marker 720 positions on a targeting fixture 690, respective opaque marker 730 positions are accessed from a rigid body source (such as a fixture 690). In some embodiments, at block 2920, an opaque marker 730 position is transformed from a representation in an image coordinate system to a representation in a current active marker 720 coordinate system. In some embodiments, at block 2930, a planned trajectory is transformed from a representation in the image coordinate system to a representation in the current active maker 720 coordinate system. In some embodiments, at block 2940, a set of current marker 720 positions on a robot 15 is transformed to a representation in a robot 15 coordinate system. In some embodiments, at block 2950, the planned trajectory is transformed from a representation in the current active marker 720 coordinate system to the robot 15 coordinate system.

Figure 30:
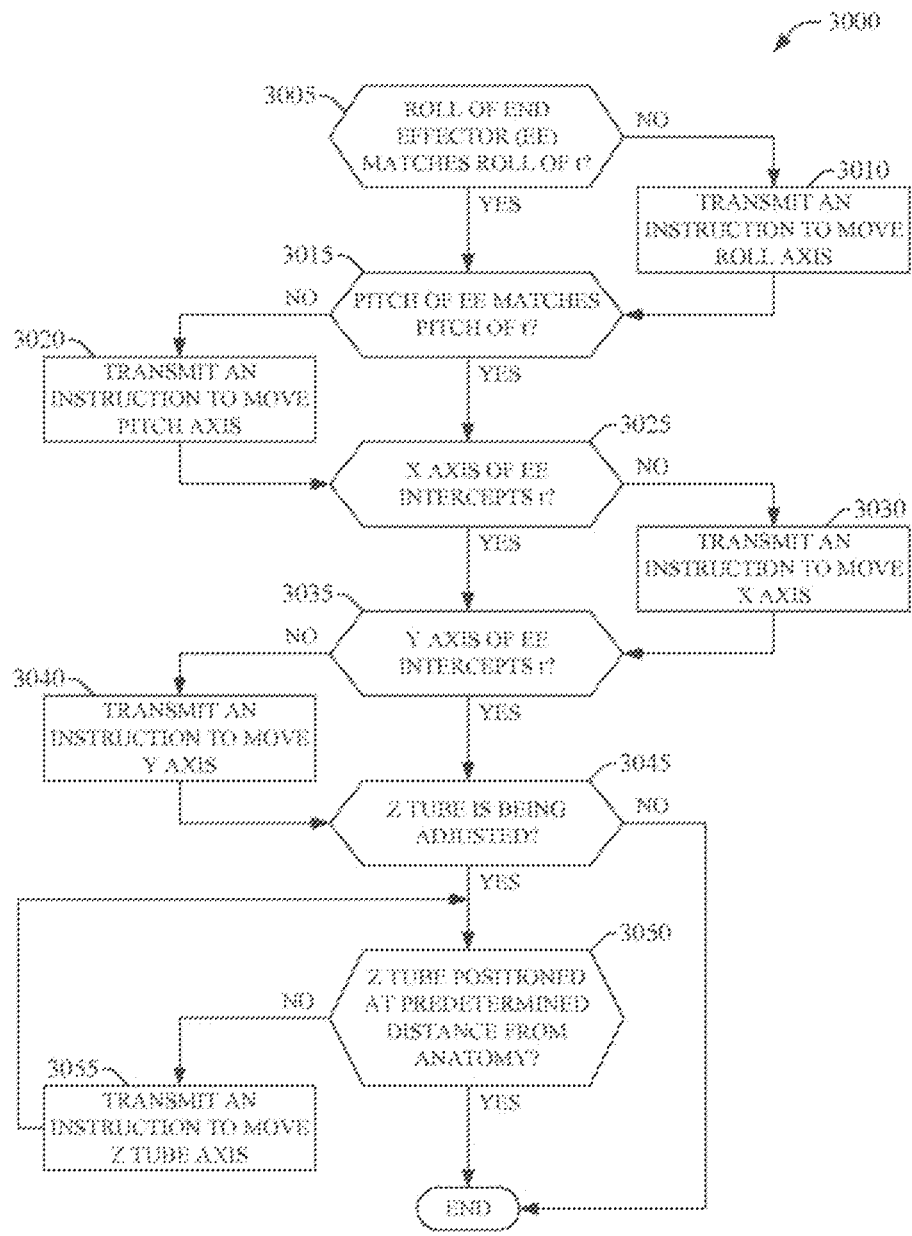

FIG. 30 is a flowchart of a method 3000 for adjusting a robot 15 position to lock on a trajectory in accordance in accordance with one embodiment of the invention. As illustrated, in some embodiments, the trajectory can be locked at a current Z plane, or level above the surgical field 17. In some embodiments, at block 3005, it is determined if roll 62 of an end-effectuator 30 matches roll of the trajectory (represented by a line t (or t)). In the negative case, in some embodiments, an instruction to move a roll 62 axis is transmitted at block 3010 and flow is directed to block 3015. Conversely, in the affirmative case, in some embodiments, flow is directed to block 3015 where it is determined if the pitch 60 of the end-effectuator 30 has matched the pitch of the trajectory. In the negative case, an instruction to move a pitch 60 axis is transmitted at block 3020 and flow is directed to block 3025. In the affirmative case, in some embodiments, flow is directed to block 3025 where it is determined if x-axis 66 coordinates of points on the vector of the end-effectuator 30 intercept the x-axis 66 coordinates of the desired trajectory vector. In the negative case, in some embodiments, an instruction to move the x-axis 66 can be transmitted and flow is directed to 3035. In the affirmative case, in some embodiments, flow is directed to block 3035 where it is determined if y-axis 68 coordinates of points on the vector of the end-effectuator 30 intercept the y-axis 68 coordinates of the desired trajectory vector. In the negative case, in some embodiments, an instruction to move the y-axis 68 can be transmitted at block 3040 and flow is directed to block 3045. In the affirmative case, in some embodiments, flow is directed to block 3045 in which it is determined if a Z-tube 50 is being adjusted. In some embodiments, an end-user can configure information (i.e., data or metadata) indicative of the Z-tube 50 being adjusted to control it to a desired position, for example. In the negative case, in some embodiments, flow is terminated. In the affirmative case, in some embodiments, flow is directed to block 3050 where it is determined if the Z-tube 50 is positioned at a predetermined distance from anatomy. In the affirmative case, in some embodiments, flow terminates and the Z-tube 50 is located at a desired position with respect to a target location in the anatomy (bone, biopsy site, etc.). In the negative case, in some embodiments, an instruction to move the Z-tube axis 64 is transmitted at block 3055 and the flow is directed to block 3050. It should be noted that the subject method 3000 in some embodiments, but not all embodiments, may require that movement in each of the indicated axes (x-axis 66, y-axis 68, Z-tube axis 64, roll 62, and pitch 60) occurs without affecting the other axes earlier in the method flow. For example, in some embodiments, the y-axis 68 movement at block 3040 should not cause change in the position of x-axis 66 coordinate, which was already checked at block 3025. In some embodiments, the method 3000 can be implemented iteratively in order to reach a desired final position in instances where the axes do not move completely independently. In certain embodiments, the method 3000 can account for all axis positions nearly simultaneously, and can determine the exact amount of movement necessary in each axis, and thus it can be more efficient.

Figure 31:
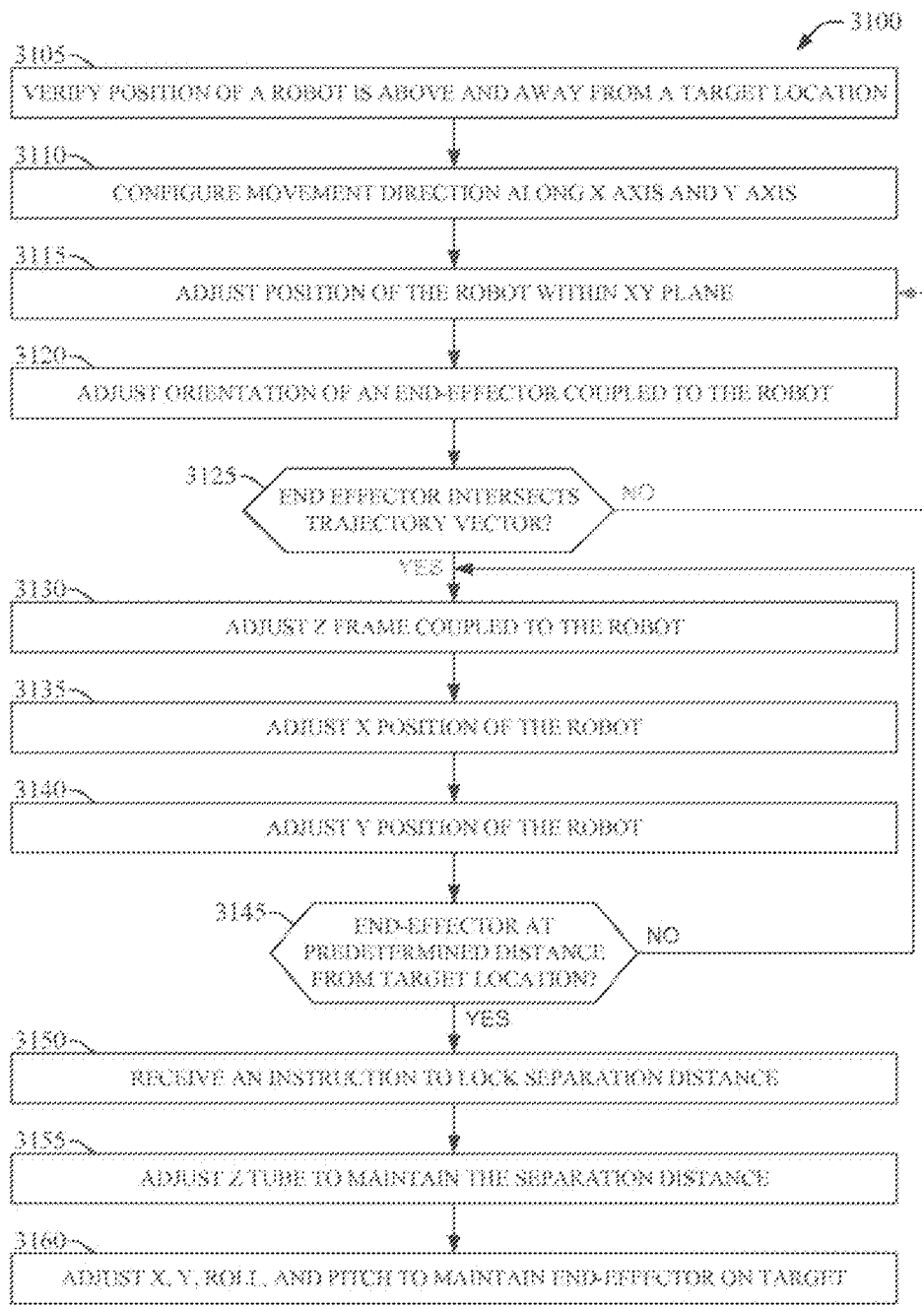
Figure 32:
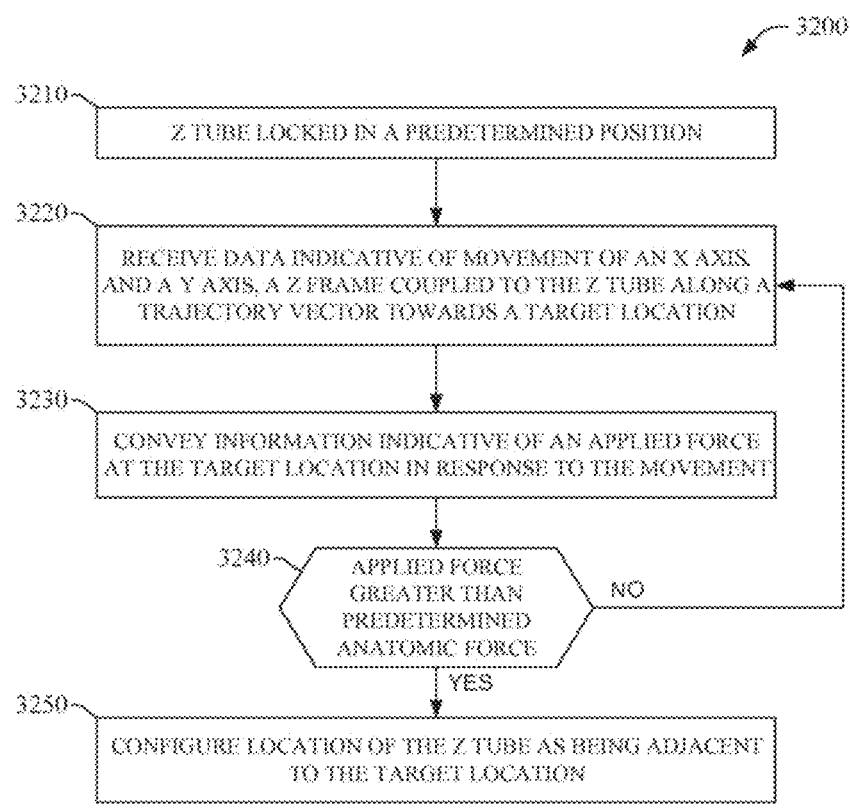
Figure 33:
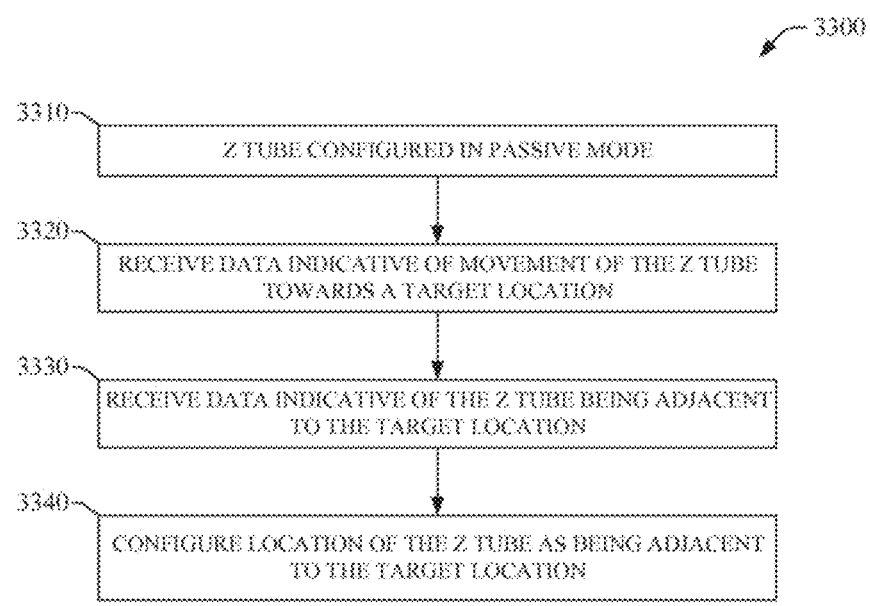

FIG. 31 is a flowchart of a method 3100 for positioning an end-effectuator 30 in space in accordance with one embodiment of the invention. In some embodiments, the positioning can comprise positioning the end-effectuator 30 in a first plane (for example, the x-y plane or horizontal plane) and moving the end-effectuator 30 along a direction substantially normal to the first plane. FIGS. 32-33 are flowcharts of methods for driving an end-effectuator 30 to a procedure location in accordance with one embodiment of the invention. As an example, in some embodiments, the procedure location can be a position at the surface of a bone into which a conventional screw of other piece of hardware is to be inserted. In some embodiments, the end-effectuator 30 can be fitted with a guide tube 50 or conventional dilator. In some embodiments, in scenarios in which a Z-tube 50 of a surgical robot 15 comprising the end-effectuator 30 is to be locked and a Z-frame 72 is to be advanced, the method 3200 can be implemented (i.e., executed). In applications where conventional screws are to be driven into bone, the surgeon may want to move the end-effectuator tip 30, fitted with a guide tube 50 or a conventional dilator, all the way down to the bone (see for example FIG. 62 described below). It should be appreciated that in some embodiments, since the first lateral movement occurs above the level where the patient 18 is lying, the methods depicted in FIGS. 31-33 and 62 can mitigate the likelihood that the robot 15 randomly collides with a patient 18. In some embodiments, the method can also utilize the robot's Cartesian architecture, and the ease with which a coordinated movement down the infinite trajectory vector can be made. That is, in some embodiments, to move down this vector, the roll 62 and pitch 60 axes need no adjustment, while the x-axis 66, y-axis 68, and Z-frame 72 axes are moved at a fixed rate. In certain embodiments, for an articular robot 15 to make such a move, the multiple angular axes would have to be synchronized nonlinearly, with all axes simultaneously moved at varying rates.

FIG. 34 illustrates a block diagram of a computer platform 3400 having a computing device 3401 that enables various features of the invention, and performance of the various methods disclosed herein in accordance with some embodiments of the invention. In some embodiments, the computing device 3401 can control operation of a surgical robot 15 and an optical tracking system 3417 in accordance with aspects described herein. In some embodiments, control can comprise calibration of relative systems of coordinates, generation of planned trajectories, monitoring of position of various units of the surgical robots 15 and/or units functionally coupled thereto, and implementation of safety protocols, and the like. For example, in some embodiments, computing device 3401 can embody a programmable controller that can control operation of a surgical robot 15 as described herein. It should be appreciated that in accordance with some embodiments of the invention, the operating environment 3400 is only an example of an operating environment and is not intended to suggest any limitation as to the scope of use or functionality of operating environment architecture. In some embodiments of the invention, the operating environment 3400 should not be interpreted as having any dependency or requirement relating to any one functional element or combination of functional elements (e.g., units, components, adapters, or the like).

The various embodiments of the invention can be operational with numerous other general purpose or special purpose computing system environments or configurations. Examples of well-known computing systems, environments, and/or configurations that can be suitable for use with the systems and methods of the invention comprise personal computers, server computers, laptop devices or handheld devices, and multiprocessor systems. Additional examples comprise mobile devices, programmable consumer electronics, network PCs, minicomputers, mainframe computers, distributed computing environments that comprise any of the above systems or devices, and the like.

In some embodiments, the processing effected in the disclosed systems and methods can be performed by software components. In some embodiments, the disclosed systems and methods can be described in the general context of computer-executable instructions, such as program modules, being executed by one or more computers, such as computing device 3401, or other computing devices. Generally, program modules comprise computer code, routines, programs, objects, components, data structures, etc., that perform particular tasks or implement particular abstract data types. The disclosed methods also can be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of the computing device 3401. In some embodiments, the components of the computing device 3401 can comprise, but are not limited to, one or more processors 3403, or processing units 3403, a system memory 3412, and a system bus 3413 that couples various system components including the processor 3403 to the system memory 3412. In some embodiments, in the case of multiple processing units 3403, the system can utilize parallel computing.

In general, a processor 3403 or a processing unit 3403 refers to any computing processing unit or processing device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally or alternatively, a processor 3403 or processing unit 3403 can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors or processing units referred to herein can exploit nano-scale architectures such as, molecular and quantum-dot based transistors, switches and gates, in order to optimize space usage or enhance performance of the computing devices that can implement the various aspects of the subject invention. In some embodiments, processor 3403 or processing unit 3403 also can be implemented as a combination of computing processing units.

The system bus 3413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 3413, and all buses specified in this specification and annexed drawings also can be implemented over a wired or wireless network connection and each of the subsystems, including the processor 3403, a mass storage device 3404, an operating system 3405, robotic guidance software 3406, robotic guidance data storage 3407, a network adapter 3408, system memory 3412, an input/output interface 3410, a display adapter 3409, a display device 3411, and a human machine interface 3402, can be contained within one or more remote computing devices 3414a,b at physically separate locations, functionally coupled (e.g., communicatively coupled) through buses of this form, in effect implementing a fully distributed system.

In some embodiments, robotic guidance software 3406 can configure the computing device 3401, or a processor thereof, to perform the automated control of position of the local robot 3416 (for example, surgical robot 15) in accordance with aspects of the invention. Such control can be enabled, at least in part, by a tracking system 3417. In some embodiments, when the computing device 3401 embodies the computer 100 functionally coupled to surgical robot 15, robotic guidance software 3406 can configure such computer 100 to perform the functionality described in the subject invention. In some embodiments, robotic guidance software 3406 can be retained in a memory as a group of computer-accessible instructions (for instance, computer-readable instructions, computer-executable instructions, or computer-readable computer-executable instructions). In some embodiments, the group of computer-accessible instructions can encode the methods of the invention (such as the methods illustrated in FIGS. 24-33 in accordance with some embodiments of the invention). In some embodiments, the group of computer-accessible instructions can encode various formalisms (e.g., image segmentation) for computer vision tracking. Some embodiments include robotic guidance software 3406 that can include a compiled instance of such computer-accessible instructions, a linked instance of such computer-accessible instructions, a compiled and linked instance of such computer-executable instructions, or an otherwise executable instance of the group of computer-accessible instructions.

Some embodiments include robotic guidance data storage 3407 that can comprise various types of data that can permit implementation (e.g., compilation, linking, execution, and combinations thereof) of the robotic guidance software 3406. In some embodiments, robotic guidance data storage 3407 can comprise data associated with intraoperative imaging, automated adjustment of position of the local robot 3416 and/or remote robot 3422, or the like. In some embodiments, the data retained in the robotic guidance data storage 3407 can be formatted according to any image data in industry standard format. As illustrated, in some embodiments, a remote tracking system 3424 can enable, at least in part, control of the remote robot 3422. In some embodiments, the information can comprise tracking information, trajectory information, surgical procedure information, safety protocols, and so forth.

In some embodiments of the invention, the computing device 3401 typically comprises a variety of computer readable media. The readable media can be any available media that is accessible by the computer 3401 and comprises, for example and not meant to be limiting, both volatile and non-volatile media, removable and non-removable media. In some embodiments, the system memory 3412 comprises computer readable media in the form of volatile memory, such as random access memory (RAM), and/or non-volatile memory, such as read only memory (ROM). In some embodiments, the system memory 3412 typically contains data (such as a group of tokens employed for code buffers) and/or program modules such as operating system 3405 and robotic guidance software 3406 that are immediately accessible to, and/or are presently operated-on by the processing unit 3403. In some embodiments, operating system 3405 can comprise operating systems such as Windows operating system, Unix, Linux, Symbian, Android, Apple iOS operating system, Chromium, and substantially any operating system for wireless computing devices or tethered computing devices. Apple® is a trademark of Apple Computer, Inc., registered in the United States and other countries. iOS® is a registered trademark of Cisco and used under license by Apple Inc. Microsoft® and Windows® are either registered trademarks or trademarks of Microsoft Corporation in the United States and/or other countries. Android® and Chrome® operating system are a registered trademarks of Google Inc. Symbian® is a registered trademark of Symbian Ltd. Linux® is a registered trademark of Linus Torvalds. UNIX® is a registered trademark of The Open Group.

In some embodiments, computing device 3401 can comprise other removable/non-removable, volatile/non-volatile computer storage media. As illustrated, in some embodiments, computing device 3401 comprises a mass storage device 3404 which can provide non-volatile storage of computer code (e.g., computer-executable instructions), computer-readable instructions, data structures, program modules, and other data for the computing device 3401. For instance, in some embodiments, a mass storage device 3404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

In some embodiments, optionally, any number of program modules can be stored on the mass storage device 3404, including by way of example, an operating system 3405, and tracking software 3406. In some embodiments, each of the operating system 3405 and tracking software 3406 (or some combination thereof) can comprise elements of the programming and the tracking software 3406. In some embodiments, data and code (for example, computer-executable instructions, patient-specific trajectories, and patient 18 anatomical data) can be retained as part of tracking software 3406 and stored on the mass storage device 3404. In some embodiments, tracking software 3406, and related data and code, can be stored in any of one or more databases known in the art. Examples of such databases comprise, DB2®, Microsoft® Access, Microsoft® SQL Server, Oracle®, mySQL, PostgreSQL, and the like. Further examples include membase databases and flat file databases. The databases can be centralized or distributed across multiple systems.

DB2® is a registered trademark of IBM in the United States.

Microsoft®, Microsoft® Access®, and Microsoft® SQL Server™ are either registered trademarks or trademarks of Microsoft Corporation in the United States and/or other countries.

Oracle® is a registered trademark of Oracle Corporation and/or its affiliates.

MySQL® is a registered trademark of MySQL AB in the United States, the European Union and other countries.

PostgreSQL® and the PostgreSQL® logo are trademarks or registered trademarks of The PostgreSQL Global Development Group, in the U.S. and other countries.

In some embodiments, an agent (for example, a surgeon or other user, or equipment) can enter commands and information into the computing device 3401 via an input device (not shown). Examples of such input devices can comprise, but are not limited to, a camera (or other detection device for non-optical tracking markers), a keyboard, a pointing device (for example, a mouse), a microphone, a joystick, a scanner (for example, a barcode scanner), a reader device such as a radiofrequency identification (RFID) readers or magnetic stripe readers, gesture-based input devices such as tactile input devices (for example, touch screens, gloves and other body coverings or wearable devices), speech recognition devices, or natural interfaces, and the like. In some embodiments, these and other input devices can be connected to the processing unit 3403 via a human machine interface 3402 that is coupled to the system bus 3413. In some other embodiments, they can be connected by other interface and bus structures, such as a parallel port, game port, an IEEE 1394 port (also known as a firewire port), a serial port, or a universal serial bus (USB).

In some further embodiments, a display device 3411 can also be functionally coupled to the system bus 3413 via an interface, such as a display adapter 3409. In some embodiments, the computer 3401 can have more than one display adapter 3409 and the computer 3401 can have more than one display device 3411. For example, in some embodiments, a display device 3411 can be a monitor, a liquid crystal display, or a projector. Further, in addition to the display device 3411, some embodiments can include other output peripheral devices that can comprise components such as speakers (not shown) and a printer (not shown) capable of being connected to the computer 3401 via input/output Interface 3410. In some embodiments, the input/output interface 3410 can be a pointing device, either tethered to, or wirelessly coupled to the computing device 3410. In some embodiments, any step and/or result of the methods can be output in any form to an output device. In some embodiments, the output can be any form of visual representation, including, but not limited to, textual, graphical, animation, audio, tactile, and the like.

In certain embodiments, one or more cameras (for example, camera 8200 shown in FIG. 81) can be contained or functionally coupled to the tracking system 3417, which is functionally coupled to the system bus 3413 via an input/output interface of the one or more input/output interfaces 3410. Such functional coupling can permit the one or more camera(s) to be coupled to other functional elements of the computing device 3401. In one embodiment, the input/output interface, at least a portion of the system bus 3413, and the system memory 3412 can embody a frame grabber unit that can permit receiving imaging data acquired by at least one of the one or more cameras. In some embodiments, the frame grabber can be an analog frame grabber, a digital frame grabber, or a combination thereof. In some embodiments, where the frame grabber is an analog frame grabber, the processor 3403 can provide analog-to-digital conversion functionality and decoder functionality to enable the frame grabber to operate with medical imaging data. Further, in some embodiments, the input/output interface can include circuitry to collect the analog signal received from at least one camera of the one or more cameras. In some embodiments, in response to execution by processor 3403, tracking software 3406 can operate the frame grabber to receive imaging data in accordance with various aspects described herein.

Some embodiments include a computing device 3401 that can operate in a networked environment (for example, an industrial environment) using logical connections to one or more remote computing devices 3414*a,b*, a remote robot 3422, and a tracking system 3424. By way of example, in some embodiments, a remote computing device can be a personal computer, portable computer, a mobile telephone, a server, a router, a network computer, a peer device or other common network node, and so on. In particular, in some embodiments, an agent (for example, a surgeon or other user, or equipment) can point to other tracked structures, including anatomy of a patient 18, using a remote computing device 3414 such as a hand-held probe that is capable of being tracked and sterilized. In some embodiments, logical connections between the computer 3401 and a remote computing device 3414*a,b* can be made via a local area network (LAN) and a general wide area network (WAN). In some embodiments, the network connections can be implemented through a network adapter 3408. In some embodiments, the network adapter 3408 can be implemented in both wired and wireless environments. Some embodiments include networking environments that can be conventional and commonplace in offices, enterprise-wide computer networks, intranets. In some embodiments, the networking environments generally can be embodied in wire-line networks or wireless networks (for example, cellular networks, such as third generation ("3G") and fourth generation ("4G") cellular networks, facility-based networks (for example, femtocell, picocell, wifi networks). In some embodiments, a group of one or more networks 3415 can provide such networking environments. In some embodiments of the invention, the one or more network(s) can comprise a LAN deployed in an industrial environment comprising the system 1 described herein.

As an illustration, in some embodiments, application programs and other executable program components such as the operating system 3405 are illustrated herein as discrete blocks, although it is recognized that such programs and components reside at various times in different storage components of the computing device 3401, and are executed by the data processor(s) of the computer 100. Some embodiments include an implementation of tracking software 3406 that can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer-readable media can comprise "computer storage media," or "computer-readable storage media," and "communications media." "Computer storage media" comprise volatile and non-volatile, removable and non-removable media implemented in any methods or technology for storage of information such as computer readable instructions, data structures, program modules, or other data. In some embodiments of the invention, computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

As described herein, some embodiments include the computing device 3401 that can control operation of local robots 3416 and/or remote robots 3422. Within embodiments in which the local robot 3416 or the remote robot 3422 are surgical robots 15, the computing device 3401 can execute robotic guidance software 3407 to control such robots 3416, 3422, 15. In some embodiments, the robotic guidance software 3407, in response to execution, can utilize trajectories (such as, tip and tail coordinates) that can be planned and/or configured remotely or locally. In an additional or alternative aspect, in response to execution, the robotic guidance software 3407 can implement one or more of the methods described herein in a local robot's computer or a remote robot's computer to cause movement of the remote robot 15 or the local robot 15 according to one or more trajectories.

In some embodiments, the computing device 3401 can enable pre-operative planning of the surgical procedure.

In some embodiments, the computing device 3401 can permit spatial positioning and orientation of a surgical tool (for example, instrument 35) during intraoperative procedures. In some further embodiments, the computing device 3401 can enable open procedures. In some other embodiments, the computing device 3401 can enable percutaneous procedures.

In certain embodiments, the computing device 3401 and the robotic guidance software 3407 can embody a 3D tracking system 3417 to simultaneously monitor the positions of the device and the anatomy of the patient 18. In some embodiments, the 3D tracking system 3417 can be configured to cast the patient's anatomy and the end-effectuator 30 in a common coordinate system.

In some embodiments, the computing device 3401 can access (i.e., load) image data from a conventional static storage device. In some embodiments, the computing device 3401 can permit a 3D volumetric representation of patient 18 anatomy to be loaded into memory (for example, system memory 3412) and displayed (for example, via display device 3411).

In some embodiments, the computing device 3401, in response to execution of the robotic guidance software 3407 can enable navigation through the 3D volume representation of a patient's anatomy.

In some embodiments, the computing device 3401 can operate with a conventional power source required to offer the device for sale in the specified country. A conventional power cable that supplies power can be a sufficient length to access conventional hospital power outlets. In some embodiments, in the event of a power loss, the computing device 3401 can hold the current end-effectuator 30 in a position unless an agent (for example, a surgeon or other user, or equipment) manually moves the end-effectuator 30.

In some embodiments, the computing device 3401 can monitor system physical condition data. In some embodiments, the computing device 3401 can report to an operator (for example, a surgeon) each of the physical condition data and indicate an out-of-range value.

In some embodiments, the computing device 3401 can enable entry and storage of manufacturing calibration values for end-effectuator 30 positioning using, for example, the input/output interface 3410.

In some embodiments, the computing device 3401 can enable access to manufacturing calibration values by an agent (for example, a surgeon or other user, or equipment) authenticated to an appropriate access level. In some embodiments, the data can be retained in robotic guidance data storage 3407, or can be accessed via network(s) 3415 when the data is retained in a remote computing device 3414a.

In some embodiments, the computing device 3401 can render (using for example display device 3411) a technical screen with a subset of the end-effectuator 30 positioning calibration and system health data. The information is only accessible to an agent (for example, a surgeon or other user, or equipment) authenticated to an appropriate level.

In some embodiments, the computing device 3401 can enable field calibration of end-effectuator 30 positioning only by an agent (for example, a surgeon or other user, or equipment) authenticated to an appropriate access level.

In some embodiments, the computing device 3401 can convey the status of local robot 3416, remote robot 3422, and/or other device being locked in position using a visual or aural alert.

In some further embodiments, the computing device 3401 can include an emergency stop control that upon activation, disables power to the device's motors 160 but not to the processor 3403. In some embodiments, the emergency stop control can be accessible by the operator of computing device 3401. In some embodiments, the computing device 3401 can monitor the emergency stop status and indicate to the operator that the emergency stop has been activated.

In some other embodiments, the computing device 3401 can be operated in a mode that permits manual positioning of the end-effectuator 30.

In some embodiments, the computing device 3401 can boot directly to an application representing the robotic guidance software 3406. In some embodiments, computing device 3401 can perform a system check prior to each use. In scenarios in which the system check fails, the computing device 3401 can notify an operator.

In some embodiments, the computing device 3401 can generate an indicator for reporting system status.

Some embodiments include the computing device 3401 that can minimize or can mitigate delays in processing, and in the event of a delay in processing, notify an agent (for example, a surgeon or other user, or equipment). For example, in some embodiments, a delay may occur while a system scan is being performed to assess system status, and consequently the computing device 3401 can schedule (for example, generate a process queue) system scans to occur at low usage times. In some embodiments, a system clock of the computing device 3401 can be read before and after key processes to assess the length of time required to complete computation of a process. In some embodiments, the actual time to complete the process can be compared to the expected time. In some embodiments, if a discrepancy is found to be beyond an acceptable tolerance, the agent can be notified, and/or concurrently running non-essential computational tasks can be terminated. In one embodiment, a conventional system clock (not shown) can be part of processor 3403.

In some embodiments, the computing device 3401 can generate a display that follows a standardized workflow.

In some embodiments, the computing device 3401 can render or ensure that text is rendered in a font of sufficient size and contrast to be readable from an appropriate distance.

In some embodiments, the computing device 3401 can enable an operator to locate the intended position of a surgical implant or tool.

In some further embodiments, the computing device 3401 can determine the relative position of the end-effectuator 30 to the anatomy of the patient 18. For example, to at least such end, the computing device 3401 can collect data the optical tracking system 3417, and can analyze the data to generate data indicative of such relative position.

In some embodiments, the computing device 3401 can indicate the end-effectuator 30 position and orientation.

In some embodiments, the computing device 3401 can enable continuous control of end-effectuator 30 position relative to the anatomy of a patient 18.

In some embodiments, the computing device 3401 can enable an agent (for example, a surgeon or other user, or equipment) to mark the intended position of a surgical implant or tool (for example, instrument 35).

In some embodiments, the computing device 3401 can allow the position and orientation of a conventional handheld probe (or an instrument 35) to be displayed overlaid on images of the patient's anatomy.

In some embodiments, the computing device 3401 can enable an agent (for example, a surgeon or other user, or equipment) to position conventional surgical screws. In some embodiments, the computing device 3401 can enable selection of the length and diameter of surgical screws by the agent. In yet another aspect, the computing device can ensure that the relative position, size and scale of screws are maintained on the display 3411 when in graphical representation. In some embodiments, the computing device 3401 can verify screw path plans against an operation envelope and reject screw path plans outside this envelope. In still another aspect, the computing device 3401 can enable hiding of a graphical screw representation.

In some embodiments, the computing device 3401 can enable a function that allows the current view to be stored. In some embodiments, the computing device 3401 can enable a view reset function that sets the current view back to a previously stored view.

In some embodiments, the computing device 3401 can enable an authentication based tiered access system.

In some embodiments, the computing device 3401 can log and store system activity. In some embodiments, the computing device 3401 can enable access to the system activity log to an agent authorized to an appropriate level.

In some embodiments, the computing device 3401 can enable entry and storage of patient 18 data.

In some embodiments, the computing device 3401 can enable the appropriate disposition of patient 18 data and/or procedure data. For example, in a scenario in which such data are being collected for research, the computing device 3401 can implement de-identification of the data in order to meet patient 18 privacy requirements. In some embodiments, the de-identification can be implemented in response to execution of computer-executable instruction(s) retained in memory 3412 or any other memory accessible to the computing device 3401. In some embodiments, the de-identification can be performed automatically before the patient 18 data and/or procedure data are sent to a repository or any other data storage (including mass storage device 3404, for example). In some embodiments, indicia (e.g., a dialog box) can be rendered (for example, at display device 3411) to prompt an agent (e.g., machine or human) to permanently delete patient 18 data and/or procedure data at the end of a procedure.

FIG. 11 shows a flow chart diagram 1100 for general operation of the robot 15 according to some embodiments is shown. In some embodiments, at step 210, the local positioning system (herein referred to as "LPS") establishes a spatial coordinate measuring system for the room 10 where the invasive procedure is to occur; in other words, the LPS is calibrated. In some embodiments, in order to calibrate the LPS, a conventional mechanical fixture that includes a plurality of attached calibrating transmitters 120 is placed within the room 10 where positioning sensors 12 are located. In some embodiments of the invention, at least three calibrating transmitters 120 are required, but any number of calibrating transmitters 120 above three is within the scope of the invention. Also, in some embodiments, at least three positioning sensors 12 are required, but any number of positioning sensors 12 above three is also within the scope of the invention, and the accuracy of the system is increased with the addition of more positioning sensors.

In some embodiments, the distance between each of the calibrating transmitters 120 relative to each other is measured prior to calibration step 210. Each calibrating transmitter 120 transmits RF signals on a different frequency so that the positioning sensors 12 can determine which transmitter 120 emitted a particular RF signal. In some embodiments, the signal of each of these transmitters 120 is received by positioning sensors 12. In some embodiments, since the distance between each of the calibrating transmitters 120 is known, and the sensors 12 can identify the signals from each of the calibrating transmitters 120 based on the known frequency, using time of flight calculation, the positioning sensors 12 are able to calculate the spatial distance of each of the positioning sensors 12 relative to each other. The system 1 is now calibrated. As a result, in some embodiments, the positioning sensors 12 can now determine the spatial position of any new RF transmitter 120 introduced into the room 10 relative to the positioning sensors 12.

In some embodiments, a step 220a in which a 3D anatomical image scan, such as a CT scan, is taken of the anatomical target. Any 3D anatomical image scan may be used with the surgical robot 15 and is within the scope of the present invention.

In some embodiments, at step 230, the positions of the RF transmitters 120 tracking the anatomical target are read by positioning sensors 110. These transmitters 120 identify the initial position of the anatomical target and any changes in position during the procedure.

In some embodiments, if any RF transmitters 120 must transmit through a medium that changes the RF signal characteristics, then the system will compensate for these changes when determining the transmitter's 120 position.

In some embodiments, at step 240, the positions of the transmitters 120 on the anatomy are calibrated relative to the LPS coordinate system. In other words, the LPS provides a reference system, and the location of the anatomical target is calculated relative to the LPS coordinates. In some embodiments, to calibrate the anatomy relative to the LPS, the positions of transmitters 120 affixed to the anatomical target are recorded at the same time as positions of temporary transmitters 120 placed on precisely known anatomical landmarks also identified on the anatomical image. This calculation is performed by a computer 100.

In some embodiments, at step 250, the positions of the RF transmitters 120 that track the anatomical target are read. Since the locations of the transmitters 120 on the anatomical target have already been calibrated, the system can easily determine if there has been any change in position of the anatomical target.

Some embodiments include a step 260, where the positions of the transmitters 120 on the surgical instrument 35 are read. The transmitters 120 may be located on the surgical instrument 35 itself, and/or there may be transmitters 120 attached to various points of the surgical robot 15.

In some embodiments of the invention, the surgical robot 15 can also include a plurality of attached conventional position encoders that help determine the position of the surgical instrument 35. In some embodiments, the position encoders can be devices used to generate an electronic signal that indicates a position or movement relative to a reference position. In some other embodiments, a position signal can be generated using conventional magnetic sensors, conventional capacitive sensors, and conventional optical sensors.

In some embodiments, position data read from the position encoders may be used to determine the position of the surgical instrument 35 used in the procedure. In some embodiments, the data may be redundant of position data calculated from RF transmitters 120 located on the surgical instrument 35. Therefore, in some embodiments, position data from the position encoders may be used to double-check the position being read from the LPS.

In some embodiments, at step 270, the coordinates of the positions of the transmitters 120 on the surgical instrument 35, and/or the positions read from the position encoders, is calibrated relative to the anatomical coordinate system. In other words, in some embodiments, the position data of the surgical instrument 35 is synchronized into the same coordinate system as the patient's anatomy. In some embodiments, this calculation is performed automatically by the computer 100 since the positions of the transmitters 120 on the anatomical target and the positions of the transmitters 120 on the surgical instrument 35 are in the same coordinate system, and the positions of the transmitters 120 on the anatomical target are already calibrated relative to the anatomy.

In some embodiments, at step 280, the computer 100 superimposes a representation of the location calculated in step 270 of the surgical device on the 3D anatomical image of the patient 18 taken in step 220. In some embodiments, the superimposed image can be displayed to an agent.

In some embodiments, at step 290, the computer 100 sends the appropriate signals to the motors 160 to drive the surgical robot 15. In some embodiments, if the agent preprogrammed a trajectory, then the robot 15 is driven so that the surgical instrument 35 follows the preprogrammed trajectory if there is no further input from the agent. In some embodiments, if there is agent input, then the computer 100 drives the robot 15 in response to the agent input.

In some embodiments, at step 295, the computer 100 determines whether the anatomy needs to be recalibrated. In some embodiments, the agent may choose to recalibrate the anatomy, in which case the computer 100 responds to agent input. Alternatively, in some embodiments, the computer 100 may be programmed to recalibrate the anatomy in response to certain events. For instance, in some embodiments, the computer 100 may be programmed to recalibrate the anatomy if the RF transmitters 120 on the anatomical target indicate that the location of the anatomical target has shifted relative to the RF transmitters 120 (i.e. this spatial relationship should be fixed). In some embodiments, an indicator that the anatomical target location has shifted relative to the transmitters 120 is if the computer 100 calculates that the surgical instrument 35 appears to be inside bone when no drilling or penetration is actually occurring.

In some embodiments, if the anatomy needs to be calibrated, then the process beginning at step 230 is repeated. In some embodiments, if the anatomy does not need to be recalibrated, then the process beginning at step 250 is repeated.

In some embodiments, at any time during the procedure, certain fault conditions may cause the computer 100 to interrupt the program and respond accordingly. For instance, in some embodiments, if the signal from the RF transmitters 120 cannot be read, then the computer 100 may be programmed to stop the movement of the robot 15, or remove the surgical instrument 35 from the patient 18. Another example of a fault condition is if the robot 15 encounters a resistance above a preprogrammed tolerance level.

FIG. 12 shows a flow chart diagram 1200 for a closed screw/needle insertion procedure according to an embodiment of the invention is shown. In a closed pedicle screw insertion procedure, in some embodiments, the robot 15 holds a guide tube 50 adjacent to the patient 18 in the correct angular orientation at the point where a conventional pedicle screw is to be inserted through the tissue and into the bone of the patient 18.

In some embodiments, the distance between each of the calibrating transmitters 120 relative to each other is measured prior to calibration step 300. In some embodiments, each calibrating transmitter 120 transmits RF signals on a different frequency so the positioning sensors 12 can determine which transmitter 120 emitted a particular RF signal. In some embodiments, the signal of each of these transmitters 120 is received by positioning sensors 12. Since the distance between each of the calibrating transmitters 120 is known, and the sensors 12 can identify the signals from each of the calibrating transmitters 120 based on the known frequency, using time of flight calculation, in some embodiments, the positioning sensors 12 are able to calculate the spatial distance of each of the positioning sensors 12 relative to each other. The system 1 is now calibrated. As a result, in some embodiments, the positioning sensors 12 can now determine the spatial position of any new RF transmitter 120 introduced into the room 10 relative to the positioning sensors 12.

In some embodiments, at step 310, a 3D anatomical image scan, such as a CT scan, is taken of the anatomical target. Any 3D anatomical image scan may be used with the surgical robot 15 and is within the scope of the present invention.

In some embodiments, at step 320, the operator selects a desired trajectory and insertion point of the surgical instrument 35 on the anatomical image captured at step 310. In some embodiments, the desired trajectory and insertion point is programmed into the computer 100 so that the robot 15 can drive a guide tube 50 automatically to follow the trajectory.

In some embodiments, at step 330, the positions of the RF transmitters 120 tracking the anatomical target are read by positioning sensors 110. In some embodiments, these transmitters 120 identify the initial position of the anatomical target and any changes in position during the procedure.

In some embodiments, if any RF transmitters 120 must transmit through a medium that changes the RF signal characteristics, the system will compensate for these changes when determining the transmitter's 120 position.

In some embodiments, at step 340, the positions of the transmitters 120 on the anatomy are calibrated relative to the LPS coordinate system. In other words, the LPS provides a reference system, and the location of the anatomical target is calculated relative to the LPS coordinates. In some embodiments, to calibrate the anatomy relative to the LPS, the positions of transmitters 120 affixed to the anatomical target are recorded at the same time as positions of temporary transmitters 120 on precisely known anatomical landmarks also identified on the anatomical image. This calculation is performed by a computer.

In some embodiments, at step 350, the positions of the RF transmitters 120 that track the anatomical target are read. Since the locations of the transmitters 120 on the anatomical target have already been calibrated, in some embodiments, the system can easily determine if there has been any change in position of the anatomical target.

In some embodiments, at step 360, the positions of the transmitters 120 on the surgical instrument 35 are read. In some embodiments, the transmitters 120 may be located on the surgical instrument 35, and/or attached to various points of the surgical robot 15.

In some embodiments, at step 370, the coordinates of the positions of the transmitters 120 on the surgical instrument 35, and/or the positions read from the position encoders, are calibrated relative to the anatomical coordinate system. In other words, the position data of the surgical instrument 35 is synchronized into the same coordinate system as the anatomy. This calculation is performed automatically by the computer 100 since the positions of the transmitters 120 on the anatomical target and the positions of the transmitters 120 on the surgical instrument 35 are in the same coordinate system and the positions of the transmitters 120 on the anatomical target are already calibrated relative to the anatomy.

In some embodiments, at step 380, the computer 100 superimposes a representation of the location calculated in step 370 of the surgical device on the 3D anatomical image of the patient 18 taken in step 310. The superimposed image can be displayed to the user.

In some embodiments, at step 390, the computer 100 determines whether the guide tube 50 is in the correct orientation and position to follow the trajectory planned at step 320. If it is not, then step 393 is reached. If it is in the correct orientation and position to follow the trajectory, then step 395 is reached.

In some embodiments, at step 393, the computer 100 determines what adjustments it needs to make in order to make the guide tube 50 follow the preplanned trajectory. The computer 100 sends the appropriate signals to drive the motors 160 in order to correct the movement of the guide tube.

In some embodiments, at step 395, the computer 100 determines whether the procedure has been completed. If the procedure has not been completed, then the process beginning at step 350 is repeated.

In some embodiments, at any time during the procedure, certain fault conditions may cause the computer 100 to interrupt the program and respond accordingly. For instance, if the signal from the RF transmitters 120 cannot be read, then the computer 100 may be programmed to stop the movement of the robot 15 or lift the guide tube 50 away from the patient 18. Another example of a fault condition is if the robot 15 encounters a resistance above a preprogrammed tolerance level. Another example of a fault condition is if the RF transmitters 120 on the anatomical target shift so that actual and calculated positions of the anatomy no longer match. One indicator that the anatomical target location has shifted relative to the transmitters 120 is if the computer 100 calculates that the surgical instrument 35 appears to be inside bone when no drilling or penetration is actually occurring.

In some embodiments, the proper response to each condition may be programmed into the system, or a specific response may be user-initiated. For example, the computer 100 may determine that in response to an anatomy shift, the anatomy would have to be recalibrated, and the process beginning at step 330 should be repeated. Alternatively, a fault condition may require the flowchart to repeat from step 300. Another alternative is the user may decide that recalibration from step 330 is desired, and initiate that step himself.

Referring now to FIG. 13, a flow chart diagram 1300 for a safe zone surgical procedure performed using the system described herein is shown in accordance with some embodiments of the invention. In a safe zone surgical procedure, there is a defined safe zone around the surgical area within which the surgical device must stay. The physician manually controls the surgical device that is attached to the end-effectuator 30 of the surgical robot 15. If the physician moves the surgical device outside of the safe zone, then the surgical robot 15 stiffens the arm 23 so that the physician cannot move the instrument 35 in any direction that would move the surgical instrument 35 outside the safe zone.

In some embodiments, the distance between each of the calibrating transmitters 120 relative to each other is measured prior to calibration step 400. Each calibrating transmitter 120 transmits RF signals on a different frequency so the positioning sensors 12 can determine which transmitter 120 emitted a particular RF signal. The signal of each of these transmitters 120 is received by positioning sensors 12. Since the distance between each of the calibrating transmitters 120 is known, and the sensors 12 can identify the signals from each of the calibrating transmitters 120 based on the known frequency, the positioning sensors 12 are able to calculate, using time of flight calculation, the spatial distance of each of the positioning sensors 12 relative to each other. The system 1 is now calibrated. As a result, the positioning sensors 12 can now determine the spatial position of any new RF transmitter 120 introduced into the room 10 relative to the positioning sensors 12.

In some embodiments, at step 410, a 3D anatomical image scan, such as a CT scan, is taken of the anatomical target. Any 3D anatomical image scan may be used with the surgical robot 15 and is within the scope of the present invention.

In some embodiments, at step 420, the operator inputs a desired safe zone on the anatomical image taken in step 410. In an embodiment of the invention, the operator uses an input to the computer 100 to draw a safe zone on a CT scan taken of the patient 18 in step 410.

In some embodiments, at step 430, the positions of the RF transmitters 120 tracking the anatomical target are read by positioning sensors. These transmitters 120 identify the initial position of the anatomical target and any changes in position during the procedure.

In some embodiments, if any RF transmitters 120 must transmit through a medium that changes the RF signal characteristics, then the system will compensate for these changes when determining the transmitter's 120 position.

In some embodiments, at step 440, the positions of the transmitters 120 on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters 120 affixed to the anatomical target are recorded at the same time as positions of temporary transmitters 120 on precisely known landmarks on the anatomy that can also be identified on the anatomical image. This calculation is performed by a computer 100.

In some embodiments, at step 450, the positions of the RF transmitters 120 that track the anatomical target are read. Since the locations of the transmitters 120 on the anatomical target have already been calibrated, the system can easily determine if there has been any change in position of the anatomical target.

In some embodiments, at step 460, the positions of the transmitters 120 on the surgical instrument 35 are read. The transmitters 120 may be located on the surgical instrument 35 itself, and/or there may be transmitters 120 attached to various points of the surgical robot 15.

In some embodiments, at step 470, the coordinates of the positions of the transmitters 120 on the surgical instrument 35, and/or the positions read from the position encoders, are calibrated relative to the anatomical coordinate system. In other words, the position data of the surgical instrument 35 is synchronized into the same coordinate system as the anatomy. This calculation is performed automatically by the computer 100 since the positions of the transmitters 120 on the anatomical target and the positions of the transmitters 120 on the surgical instrument 35 are in the same coordinate system and the positions of the transmitters 120 on the anatomical target are already calibrated relative to the anatomy.

In some embodiments, at step 480, the computer 100 superimposes a representation of the location calculated in step 470 of the surgical device on the 3D anatomical image of the patient 18 taken in step 410. In some embodiments, the superimposed image can be displayed to the user.

In some embodiments, at step 490, the computer 100 determines whether the surgical device attached to the end-effectuator 30 of the surgical robot 15 is within a specified range of the safe zone boundary (for example, within 1 millimeter of reaching the safe zone boundary). In some embodiments, if the end-effectuator 30 is almost to the boundary, then step 493 is reached. In some embodiments, if it is well within the safe zone boundary, then step 495 is reached.

In some embodiments, at step 493, the computer 100 stiffens the arm of the surgical robot 15 in any direction that would allow the user to move the surgical device closer to the safe zone boundary.

In some embodiments, at step 495, the computer 100 determines whether the anatomy needs to be recalibrated. In some embodiments, the user may choose to recalibrate the anatomy, in which case the computer 100 responds to user input. Alternatively, in some embodiments, the computer 100 may be programmed to recalibrate the anatomy in response to certain events. For instance, in some embodiments, the computer 100 may be programmed to recalibrate the anatomy if the RF transmitters 120 on the anatomical target indicate that the location of the anatomical target has shifted relative to the RF transmitters 120 (i.e. this spatial relationship should be fixed.) In some embodiments, an indicator that the anatomical target location has shifted relative to the transmitters 120 is if the computer 100 calculates that the surgical instrument 35 appears to be inside bone when no drilling or penetration is actually occurring.

In some embodiments, if the anatomy needs to be calibrated, then the process beginning at step 430 is repeated. In some embodiments, if the anatomy does not need to be recalibrated, then the process beginning at step 450 is repeated.

In some embodiments, at any time during the procedure, certain fault conditions may cause the computer 100 to interrupt the program and respond accordingly. For instance, in some embodiments, if the signal from the RF transmitters 120 cannot be read, then the computer 100 may be programmed to stop the movement of the robot 15 or remove the surgical instrument 35 from the patient 18. Another example of a fault condition is if the robot 15 encounters a resistance above a preprogrammed tolerance level.

Referring now to FIG. 14, a flow chart diagram 1400 for a conventional flexible catheter or wire insertion procedure according to an embodiment of the invention is shown. Catheters are used in a variety of medical procedures to deliver medicaments to a specific site in a patient's body. Often, delivery to a specific location is needed so a targeted diseased area can then be treated. Sometimes instead of inserting the catheter directly, a flexible wire is first inserted, over which the flexible catheter can be slid.

In some embodiments, the distance between each of the calibrating transmitters 120 relative to each other is measured prior to calibration step 500. In some embodiments, each calibrating transmitter 120 transmits RF signals to a different frequency so the positioning sensors 12, 110 can determine which transmitter 120 emitted a particular RF signal. In some embodiments, the signal from each of these transmitters 120 is received by positioning sensors 12, 110. Since the distance between each of the calibrating transmitters 120 is known, and the sensors can identify the signals from each of the calibrating transmitters 120 based on the known frequency, in some embodiments, using time of flight calculation, the positioning sensors 12, 110 are able to calculate the spatial distance of each of the positioning sensors 12, 110 relative to each other. The system is now calibrated. As a result, in some embodiments, the positioning sensors 12, 110 can now determine the spatial position of any new RF transmitter 120 introduced into the room 10 relative to the positioning sensors 12, 110.

In some embodiments, at step 510, reference needles that contain the RF transmitters 120 are inserted into the body. The purpose of these needles is to track movement of key regions of soft tissue that will deform during the procedure or with movement of the patient 18.

In some embodiments, at step 520, a 3D anatomical image scan (such as a CT scan) is taken of the anatomical target. Any 3D anatomical image scan may be used with the surgical robot 15 and is within the scope of the present invention. In some embodiments, the anatomical image capture area includes the tips of the reference needles so that their transmitters' 120 positions can be determined relative to the anatomy.

In some embodiments, at step 530, the RF signals from the catheter tip and reference needles are read.

In some embodiments, at step 540, the position of the catheter tip is calculated. Because the position of the catheter tip relative to the reference needles and the positions of the reference needles relative to the anatomy are known, the computer 100 can calculate the position of the catheter tip relative to the anatomy.

In some embodiments, at step 550, the superimposed catheter tip and the shaft representation is displayed on the anatomical image taken in step 520.

In some embodiments, at step 560, the computer 100 determines whether the catheter tip is advancing toward the anatomical target. If it is not moving to the anatomical target, then step 563 is reached. If it is correctly moving, then step 570 is reached.

In some embodiments, at step 563, the robot 15 arm is adjusted to guide the catheter tip in the desired direction. If the anatomy needs to be calibrated, then in some embodiments, the process beginning at step 520 is repeated. If the anatomy does not need to be recalibrated, then the process beginning at step 540 is repeated.

In some embodiments, at step 570, the computer 100 determines whether the procedure has been completed. If the procedure has not been completed, then the process beginning at step 540 is repeated.

In some embodiments, at any time during the procedure, certain fault conditions may cause the computer 100 to interrupt the program and respond accordingly. For instance, in some embodiments, if the signal from the RF transmitter's 120 cannot be read, then the computer 100 may be programmed to stop the movement of the robot 15 or remove the flexible catheter from the patient 18. Another example of a fault condition is if the robot 15 encounters a resistance above a preprogrammed tolerance level. A further example of a fault condition is if the RF transmitter's 120 on the anatomical target indicate the location of the anatomical target shift so that actual and calculated positions of the anatomy no longer match. In some embodiments, one indicator that the anatomical target location has shifted relative to the transmitter's 120 is if the computer 100 calculates that the surgical instrument 35 appears to be inside bone when no drilling or penetration is actually occurring.

In some embodiments, the proper response to each condition may be programmed into the system, or a specific response may be user-initiated. For example, in some embodiments, the computer 100 may determine that in response to an anatomy shift, the anatomy would have to be recalibrated, and the process beginning at step 520 should be repeated. Alternatively, in some embodiments, a fault condition may require the flowchart to repeat from step 500. In other embodiments, the user may decide that recalibration from step 520 is desired, and initiate that step himself.

Figure 15A:
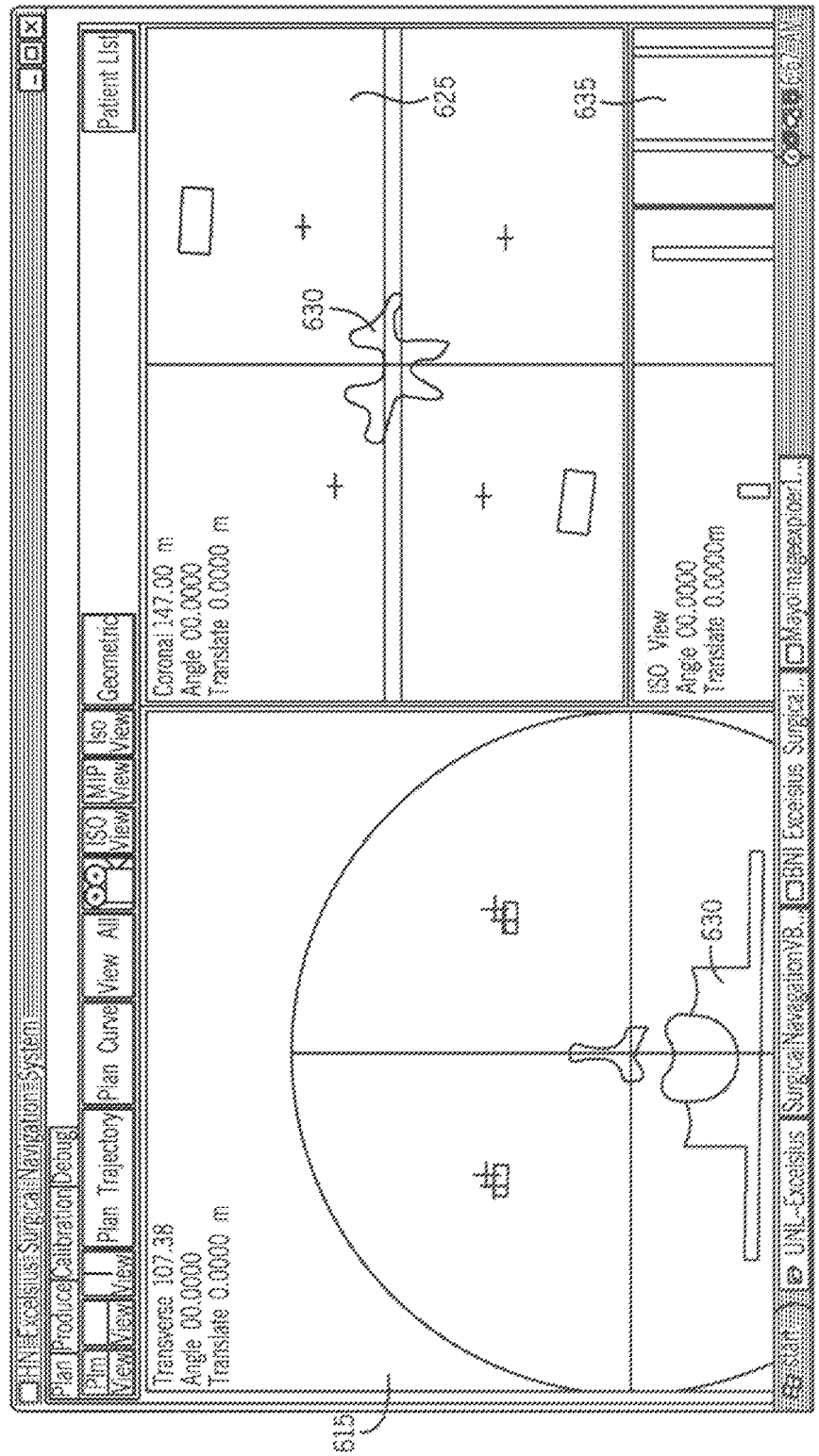
FIG. 15A shows a screenshot of a monitor display showing a set up of the anatomy in X, Y and Z views in accordance with one embodiment of the invention.
Figure 15B:
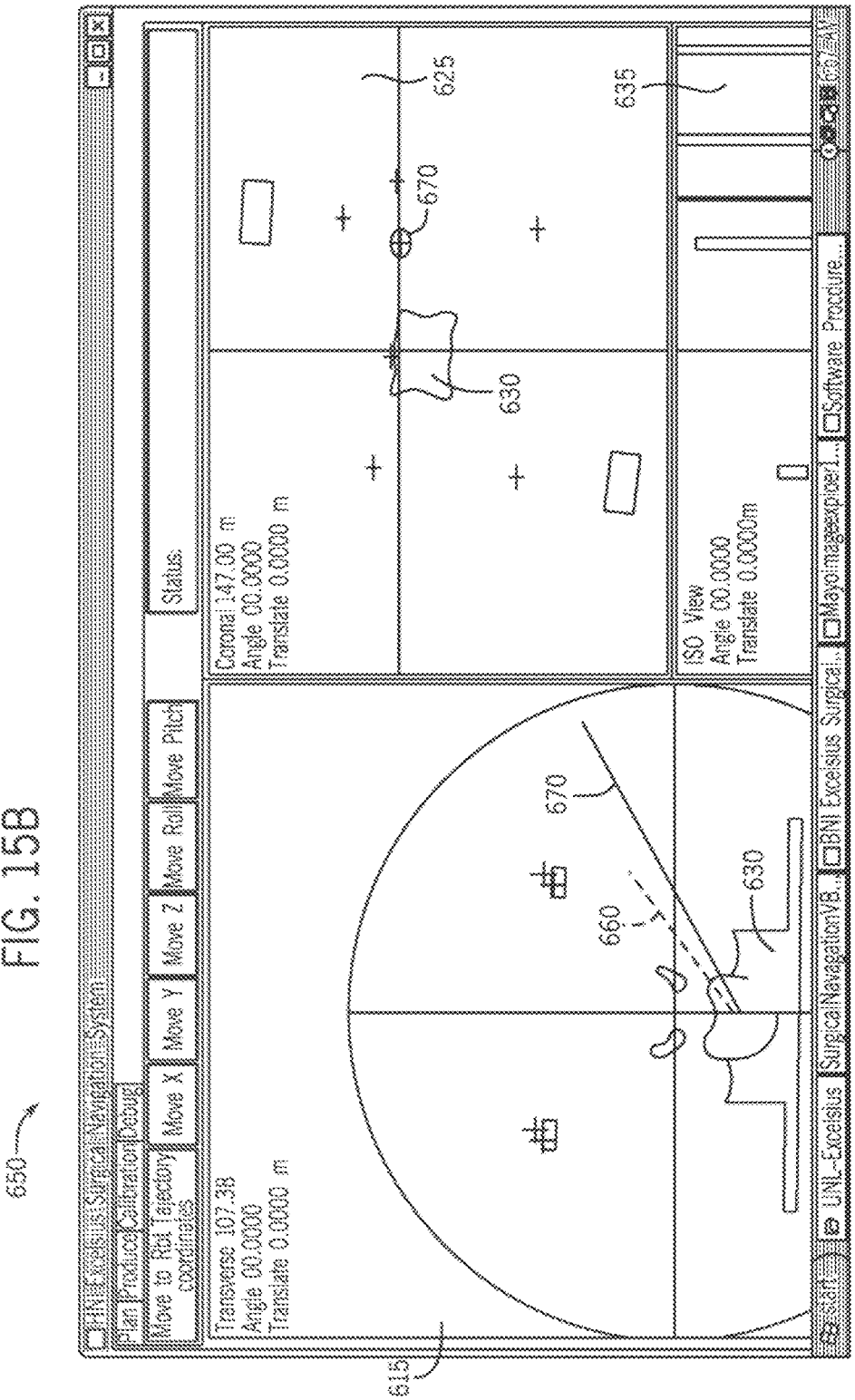
FIG. 15B shows a screenshot of a monitor display showing what the user views during an invasive procedure in accordance with one embodiment of the invention.

Referring now to FIGS. 15A & 15B, screenshots of software for use with the described system is provided in accordance with some embodiments of the invention. The software provides the method to select the target area of surgery, plan the surgical path, check the planned trajectory of the surgical path, synchronize the medical images to the positioning system and precisely control the positioning system during surgery. The surgical positioning system and navigation software includes an optical guidance system or RF Local Positioning System (RF-LPS), which are in communication with the positioning system.

FIG. 15A shows a screen shot 600 of the selection step for a user using a software program as described herein in accordance with some embodiments of the invention. Screen shot 600 includes windows 615, 625, and 635, which show a 3D anatomical image of surgical target 630 on different planes. In this step, the user selects the appropriate 3D image corresponding to anatomical location of where the procedure will occur. In some embodiments, the user uses a graphic control to change the perspective of the image in order to more easily view the image from different angles. In some embodiments, the user can view the surgical target 630 within separate coordinated views for each of the x-axis, y-axis and z-axis coordinates for each anatomical location in the database in each window 615, 625 and 635, respectively.

In some embodiments, after selecting the desired 3D image of the surgical target 630, the user will plan the appropriate trajectory on the selected image. In some embodiments, an input control is used with the software in order to plan the trajectory of the surgical instrument 35. In one embodiment of the invention, the input control is in the shape of a biopsy needle 8110 for which the user can plan a trajectory.

FIG. 15B shows a screen shot 650 during the medical procedure in accordance with some embodiments of the invention. In some embodiments, the user can still view the anatomical target 630 in different x-axis, y-axis and z-axis coordinate views on windows 615, 625, and 635. As shown in screen shot 650, the user can see the planned trajectory line 670 in multiple windows 615 and 625. The actual trajectory and location of the surgical instrument 35 is superimposed on the image (shown as line segment 660). In some embodiments, the actual trajectory and location of the surgical instrument 35 is dynamically updated and displayed, and is shown as a line segment 660. In some other embodiments, the actual trajectory and location of the surgical instrument 35 could be shown as a trapezoid or a solid central line surrounded by a blurred or semi-transparent fringe to represent the region of uncertainty. In some embodiments (under perfect conditions with no bending of the surgical instrument as it enters tissues) the tracking system 3417 and robot 15 encoders calculate that the surgical instrument 35 should be located at the solid line or center of the trapezoid. In some embodiments, due to bending of the instrument 35 that might occur if tissues of different densities are crossed, there might be bending, with the amount of reasonably expected bending displayed as the edges of the trapezoid or fringe. In some embodiments, the size of this edge could be estimated knowing the stiffness and tolerance of the surgical instrument 35 within the guide tube 50, and by using experimental data collected for the same instrument 35 under previous controlled conditions. In some embodiments, displaying this region of uncertainty helps prevent the user from expecting the system to deliver a tool to a target trajectory with a physically impossible level of precision.

As described earlier, in some embodiments, the surgical robot 15 can be used with alternate guidance systems other than an LPS. In some embodiments, the surgical robot system 1 can comprise a targeting fixture 690 for use with a guidance system. In some embodiments, one targeting fixture 690 comprises a calibration frame 700, as shown in FIGS. 20A-20E. A calibration frame 700 can be used in connection with many invasive procedures; for example, it can be used in thoracolumbar pedicle screw insertion in order to help achieve a more accurate trajectory position. In some embodiments, the use of the calibration frame 700 can simplify the calibration procedure. In some embodiments of the invention, the calibration frame 700 can be temporarily affixed to the skin of a patient 18 surrounding a selected site for a medical procedure, and then the medical procedure can be performed through a window defined by the calibration frame.

Figure 20A:
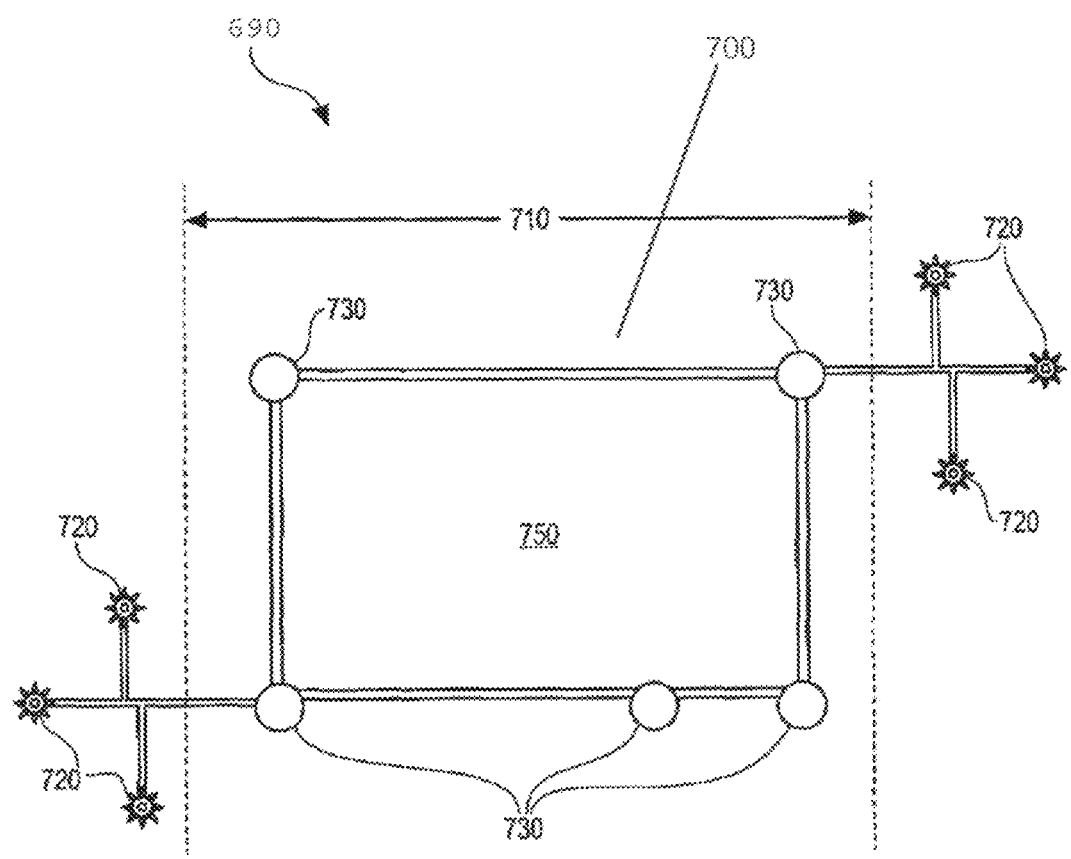
FIGS. 20A-20E show the use of calibration frames with the guidance system in accordance with one embodiment of the invention.
Figure 20B:
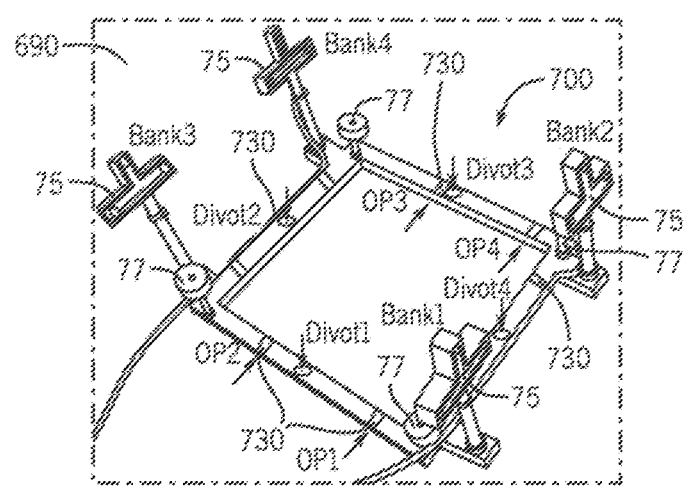
Figure 20C:
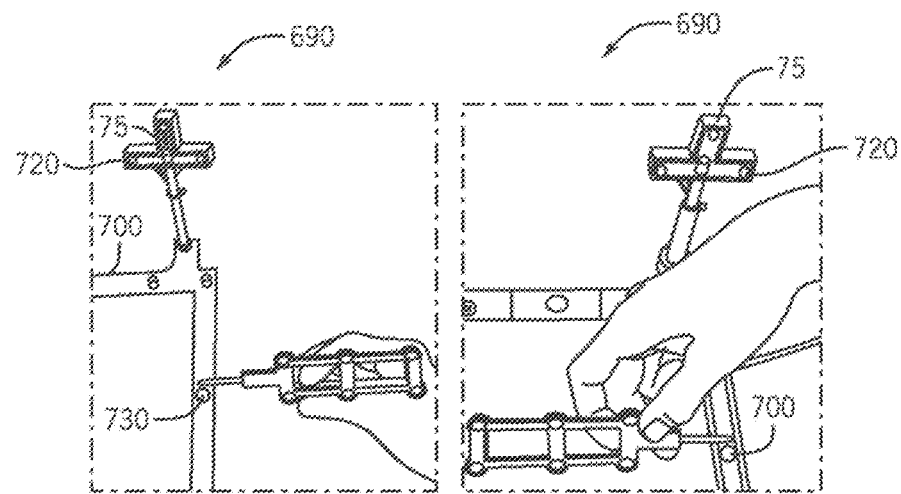

As shown in FIGS. 20A and 20B, in some embodiments of the invention, the calibration frame 700 can comprise a combination of radio-opaque markers 730 and infrared, or "active," markers 720. In some embodiments, the radio-opaque markers 730 can be located within the CT scan region 710, and the active markers 720 can be located outside of the CT scan region 710. In some embodiments, a surgical field 17 (i.e., the area where the invasive procedure will occur) can be located within the perimeter created by radio-opaque markers 730. In some embodiments, the actual distances of the radio-opaque 730 and active markers 720 relative to each other can be measured from a high-precision laser scan of the calibration frame. Additionally or alternatively, in some embodiments, the actual relative distances can be measured by actively measuring the positions of active markers 720 while nearly simultaneously or simultaneously pointing with a pointing device, such as a conventional digitizing probe, to one or more locations on the surface of the radio-opaque markers 730. In certain embodiments, digitizing probes can comprise active markers 720 embedded in a rigid body 690 and a tip extending from the rigid body.

In some embodiments, through factory calibration or other calibration method(s), such as pivoting calibration, the location of the probe tip relative to the rigid body of the probe can be established. In some embodiments, it can then be possible to calculate the location of the probe's tip from the probe's active markers 720. In some embodiments, for a probe with a concave tip that is calibrated as previously described, the point in space returned during operation of the probe can represent a point distal to the tip of the probe at the center of the tip's concavity. Therefore, in some embodiments, when a probe (configured with a concave tip and calibrated to marker 730 of the same or nearly the same diameter as the targeting fixture's radio-opaque marker 730) is touched to the radio-opaque marker 730, the probe can register the center of the sphere. In some embodiments, active markers 720 can also be placed on the robot in order to monitor a position of the robot 15 and calibration frame 700 simultaneously or nearly simultaneously.

In some embodiments, the calibration frame 700 is mounted on the patient's skin before surgery/biopsy, and will stay mounted during the entire procedure. Surgery/biopsy takes place through the center of the frame 700.

In some embodiments, when the region of the plate with the radio-opaque markers 730 is scanned intra-operatively or prior to surgery (for example, using a CT scanner), the CT scan contains both the medical images of the patient's bony anatomy, and spherical representations of the radio-opaque markers 730. In some embodiments, software is used to determine the locations of the centers of the markers 730 relative to the trajectories defined by the surgeon on the medical images. Because the pixel spacing of the CT scan can be conveyed within encoded headers in DICOM images, or can be otherwise available to a tracking software (for example, the robotic guidance software 3406), it can, in some embodiments, be possible to register locations of the centers of the markers 730 in Cartesian coordinates (in millimeters, for example, or other length units). In some embodiments, it can be possible to register the Cartesian coordinates of the tip and tail of each trajectory in the same length units.

In some embodiments, because the system knows the positions of the trajectories relative to the radio-opaque markers 730, the positions of the radio-opaque markers 730 relative to the active markers 720, and the positions of the active markers 720 on the calibration frame 700 relative to the active markers on the robot 15 (not shown), the system has all information necessary to position the robot's end-effectuator 30 relative to the defined trajectories.

In some other embodiments of the invention, the calibration frame 700 can comprise at least three radio-opaque markers 730 embedded in the periphery of the calibration frame 700. In some embodiments, the at least three radio-opaque markers 730 can be positioned asymmetrically about the periphery of the calibration frame 700 such that the software, as described herein, can sort the at least three radio-opaque markers 730 based only on the geometric coordinates of each marker 730. In some embodiments, the calibration frame 700 can comprise at least one bank of active markers 720. In some embodiments, each bank of the at least one bank can comprise at least three active markers 720. In some embodiments, the at least one bank of active markers 720 can comprise four banks of active markers 720. In yet another aspect, the calibration frame 700 can comprise a plurality of leveling posts 77 coupled to respective corner regions of the calibration frame 700. In some embodiments, the corner regions of the calibration frame 700 can include leveling posts 77 that can comprise radiolucent materials. In some embodiments, the plurality of leveling posts 77 can be configured to promote uniform, rigid contact between the calibration frame 700 and the skin of the patient 18. In some embodiments, a surgical-grade adhesive film, such as, for example and without limitation, Ioban™ from 3M™, can be used to temporarily adhere the calibration frame 700 to the skin of the patient 18. 3M™ and Ioban™ are registered trademarks of 3M Company. In some further embodiments, the calibration frame 700 can comprise a plurality of upright posts 75 that are angled away from the frame 700 (see FIG. 20B). In some embodiments, the plurality of active markers 720 can be mounted on the plurality of upright posts 75.

As shown in FIG. 20B, in some embodiments, there are four radio-opaque markers 730 (non-metallic BBs from an air gun) embedded in the periphery of the frame, labeled OP1, OP2, OP3, OP4. In some embodiments, only three markers 730 are needed for determining the orientation of a rigid body in space (the 4th marker is there for added accuracy).

In some embodiments, the radio-opaque markers 730 are placed in an asymmetrical configuration (notice how OP1 and OP2 are separated from each other by more distance than OP3 and OP4, and OP1 and OP4 are aligned with each other across the gap, however OP3 is positioned more toward the center than OP2). The reason for this arrangement is so that a computer algorithm can automatically sort the markers to determine which is which if only given the raw coordinates of the four markers and not their identification.

In some embodiments, there are four banks of active markers 720 (three markers 720 per bank). Only one bank of three markers 720 is needed (redundancy is for added accuracy and so that the system will still work if the surgeon, tools, or robot are blocking some of the markers.

In some embodiments, despite the horizontal orientation of the patient 18, the angulation of the upright posts can permit the active markers 720 to face toward the cameras (for example cameras 8200 shown in FIG. 81). or detection devices of the tracking system (for example, the tracking system 3417). In some embodiments, the upright posts can be angled away from the calibration frame by about 10°.

Figure 20D:
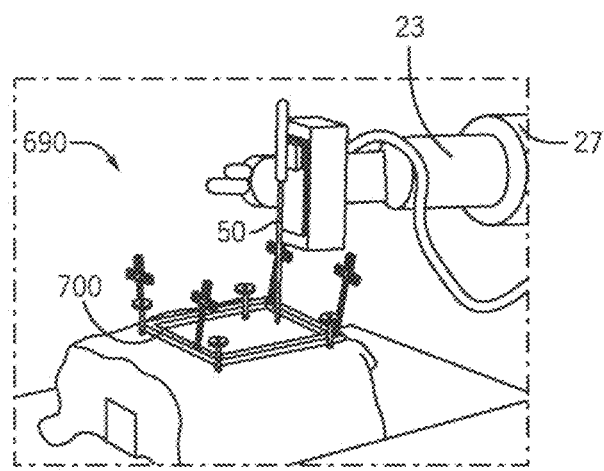

In some applications, to establish the spatial relationship between the active 720 and radio-opaque markers 730, a conventional digitizing probe, such as a 6-marker probe, embedded with active markers 720 in a known relationship to the probe's tip (see for example FIG. 20C) can be used to point to each of the radio-opaque markers 730. In some embodiments, the probe can point to locations on two opposite surfaces of the spherical radio-opaque markers 730 while recording the position of the probe tip and the active markers 720 on the frame 700 simultaneously. Then, the average position of the two surface coordinates can be taken, corresponding to the center of the sphere. An image of the robot 15 used with this targeting fixture 690 is shown in FIG. 20D. For placement of conventional surgical screws, a biopsy, injection, or other procedures, in some embodiments, the robot 15 can work through the window formed by the frame 700. During a surgical procedure, in some embodiments, the working portal is kept on the interior of the frame 700 and the markers 720 on the exterior of the frame 700 can improve accuracy over a system where fiducials are mounted away from the area where surgery is being performed. Without wishing to be bound by theory, simulation, and/or modeling, it is believed that a reason for improved accuracy is that optimal accuracy of tracking markers 720 can be achieved if tracking markers 720 are placed around the perimeter of the frame 700 being tracked.

Figure 20E:
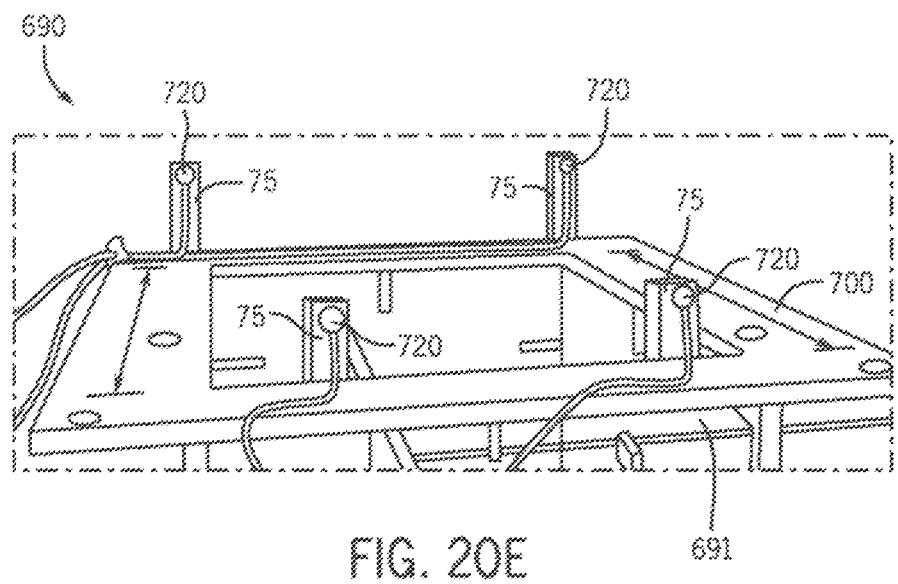

Further embodiments of the invention are shown in FIG. 20E illustrating a calibration frame 700. This fixture 690 is simplified to make it less obstructive to the surgeon. In some embodiments, the calibration frame 700 can comprise four active markers 720 having a lower profile than the active markers 720 described above and depicted in FIGS. 20A-20D. For example, the calibration frame 700 can comprise a plurality of upright posts 75 that are angled away from the calibration frame by about 10°. In some embodiments, the active markers 720 are mounted on the posts 75 that are angled back by 10°, and this angulation keeps the markers 720 facing toward the cameras despite the patient being horizontal.

Moreover, in some embodiments, the front markers 720 can have less chance of obscuring the rear markers 720. For example, posts 75 that are farthest away from the camera or farthest from a detection device of the tracking system 3417 can be taller and spaced farther laterally than the posts 75 closest to the camera.

In some further embodiments of the invention, the calibration frame 700 can comprise markers 730 that are both radio-opaque for detection by a medical imaging scanner, and visible by the cameras or otherwise detectable by the real-time tracking system 3417. In some embodiments, the relationship between radio-opaque 730 and active markers (730, 720) does not need to be measured or established because they are one in the same. Therefore, in some embodiments, as soon as the position is determined from the CT scan (or other imaging scan), the spatial relationship between the robot 15 and anatomy of the patient 18 can be defined.

Figure 21A:
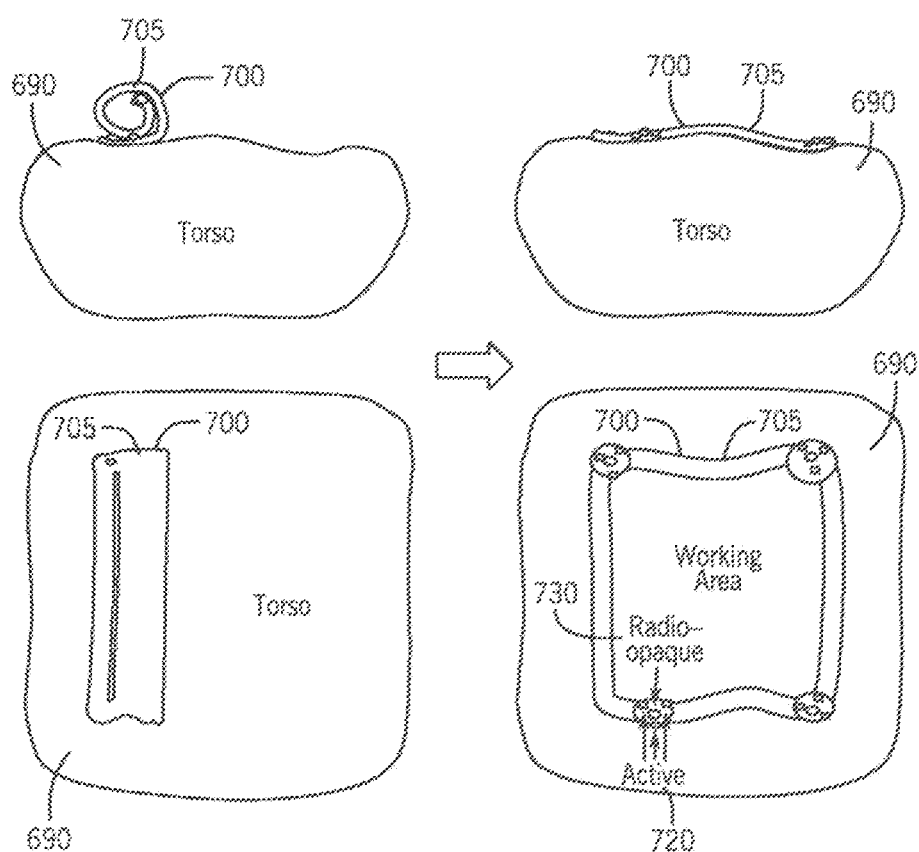
FIG. 21A depicts flexible roll configurations of a targeting fixture in accordance with one embodiment of the invention.

In other embodiments, the targeting fixture 690 can comprise a flexible roll configuration. In some embodiments, the targeting fixture 690 can comprise three or more radio-opaque markers 730 that define a rigid outer frame and nine or more active markers 720 embedded in a flexible roll of material (for example, the flexible roll 705 in FIG. 21A). As described earlier, radio-opaque markers 730 are visible on CT scans and/or other medical diagnostic images, such as MRI, or reconstructions from O-arm or Iso-C scans, and their centroids can be determined from the 3D image. Active markers 720 include tracked markers 720 that have 3D coordinates that are detectable in real-time using cameras or other means. Some embodiments can utilize active marker systems based on reflective optical systems such as Motion Analysis Inc., or Peak Performance. Other suitable technologies include infrared-emitting marker systems such as Optotrak, electromagnetic systems such as Medtronic's Axiem®, or Flock of Birds®, or a local positioning system ("LPS") described by Smith et al. in U.S. Patent Publication No. 2007/0238985.

Flock Of Birds® is a registered trademark of Ascension Technology Corporation.

Axiem is a trademark of Medtronic, Inc., and its affiliated companies.

Medtronic® is a registered trademark used for Surgical and Medical Apparatus, Appliances and Instruments.

In some embodiments of the invention, at least a portion of the flexible roll 705 can comprise self-adhering film, such as, for example and without limitation, 3M™Ioban™ adhesive film (iodine-impregnated transparent surgical drape) similar to routinely used operating room product model 6651 EZ (3M, St. Paul, Minn.). Ioban™ is a trademark of 3M company.

In some embodiments, within the flexible roll 705, the radio-opaque and active markers (730, 720) can be rigidly coupled to each other, with each radio-opaque marker 730 coupled to three or more active markers 720. Alternatively, in some embodiments, the markers can simultaneously serve as radio-opaque and active markers (for example, an active marker 720 whose position can be detected from cameras or other sensors), and the position determined from the 3D medical image can substantially exactly correspond to the center of the marker 720. In some embodiments, as few as three such markers 720 could be embedded in the flexible roll 705 and still permit determination of the spatial relationship between the robot 15 and the anatomy of the patient 18. If radio-opaque markers 730 and active markers 720 are not one in the same, in some embodiments the at least three active markers 720 must be rigidly connected to each radio-opaque marker 730 because three separate non-collinear points are needed to unambiguously define the relative positions of points on a rigid body. That is, if only one or 2 active markers 720 are viewed, there is more than one possible calculated position where a rigidly coupled radio-opaque marker could be.

Figure 21B:
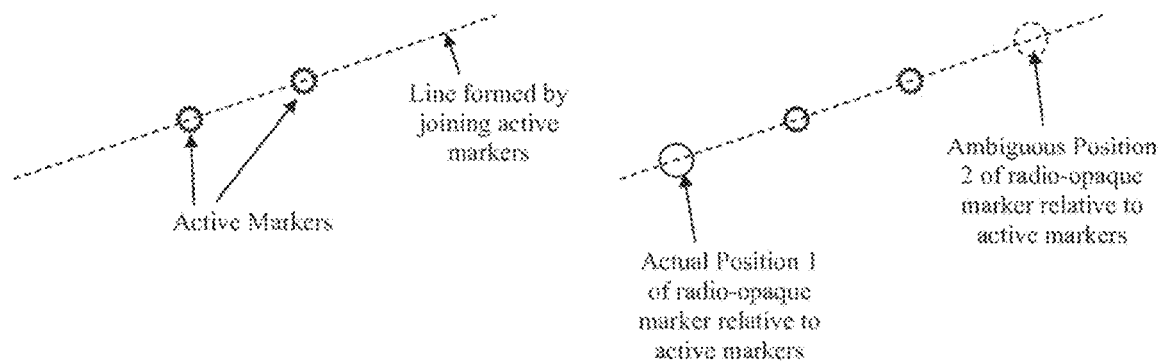
FIG. 21B shows possible positions of markers along a line in space in accordance with one embodiment of the invention.
Figure 21C:
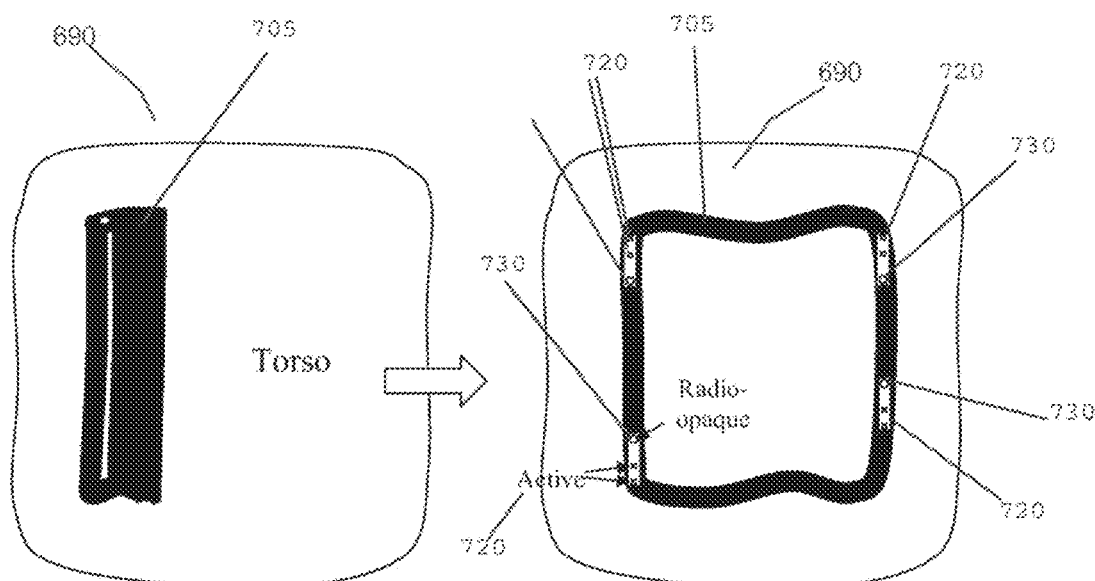
FIG. 21C depicts flexible roll configurations of a targeting fixture in accordance with one embodiment of the invention.

In some embodiments of the invention, other considerations can be used to permit the use of two active markers 720 per radio-opaque marker 730. For example, in some embodiments, if two active markers 720 and one radio-opaque marker 730 are intentionally positioned collinearly, with the radio-opaque marker 730 exactly at the midpoint between the two active markers 720, the location of the radio-opaque marker 730 can be determined as the mean location of the two active markers 720. Alternatively, in some embodiments, if the two active markers 720 and the radio-opaque marker 730 are intentionally positioned collinearly but with the radio-opaque marker 730 closer to one active marker 720 than the other (see for example FIG. 21B), then in some embodiments, the radio-opaque marker 730 must be at one of two possible positions along the line in space formed by the two active markers 720 (see FIG. 21B). In this case, in some embodiments, if the flexible roll 705 is configured so that each pair of active markers 720 is oriented (when in its final position) with one marker 720 more toward the center of the flexible roll 705, then it can be determined from the orientations of all markers or certain combinations of markers from different regions which of the two possible positions within each region is the correct position for the radio-opaque marker 730 (see FIG. 21C showing flexible roll 705 showed rolled on a torso and shown unrolled on a torso with markers 720, 730 in place). As shown, the radio-opaque markers 730 can be positioned toward the inside of the frame 705), with marker groups nearer to the top of the figure having the radio-opaque marker 730 positioned below the active markers 720 and marker groups near the bottom of the figure having the radio-opaque marker positioned above the active markers 720.

In some embodiments, the flexible roll 705 can be positioned across the patient's back or other area, and adhered to the skin of the patient 18 as it is unrolled. In some embodiments, knowing the spatial relationship between each triad of active markers 720 and the rigidly coupled radio-opaque marker 730, it is possible to establish the relationship between the robot 15 (position established by its own active markers 720) and the anatomy (visualized together with radio-opaque markers 730 on MM, CT, or other 3D scan). In some embodiments, the flexible roll 705 can be completely disposable. Alternatively, in some other embodiments, the flexible roll 705 can comprise reusable marker groups integrated with a disposable roll with medical grade adhesive on each side to adhere to the patient 18 and the marker groups 720, 730. In some further embodiments, the flexible roll 705 can comprise a drape incorporated into the flexible roll 705 for covering the patient 18, with the drape configured to fold outwardly from the roll 705.

Figure 21D:
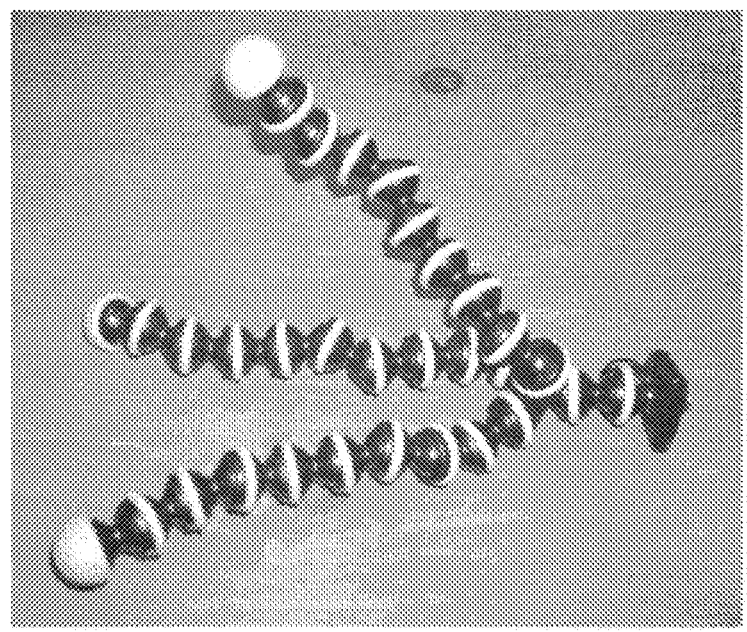
FIG. 21D shows a fixture that can be employed to provide desired stiffness to the unrolled fixture such that it maintains its position after unrolling occurs in accordance with one embodiment of the invention.

In some embodiments, after the roll 705 has been unrolled, the roll 705 can have a desired stiffness such that the roll 705 does not substantially change its position relative to the bony anatomy of the patient 18. In some embodiments of the invention, a conventional radiolucent wire can be embedded in the perimeter of the frame 700. In some embodiments, it a chain of plastic beads, such as the commercially available tripods shown in FIG. 21D, or a commercially available "snake light" type fixture, can be employed to provide desired stiffness to the unrolled fixture such that it maintains its position after unrolling occurs. For example, in some embodiments, the beads of the chain of plastic beads as shown can be affixed to each other with a high friction so that they hold their position once shifted. Further, in some embodiments, chains of beads can be incorporated into, and define, a perimeter of the frame 700. In some embodiments, this type of frame could be loaded with conventional chemicals that mix at the time of application. For example, in some embodiments, components of a conventional two-part epoxy could be held in separate fragile baggies within the frame that pop open when the user first starts to manipulate the beads. In some embodiments, the user would attach the frame to the patient 18, and mold it to the contours of the patient's body. After a short period of time, the frame 700 would solidify to form a very rigid frame, locking the beads in their current orientation.

In some embodiments of the invention, the targeting fixture 690 can be an adherable fixture, configured for temporary attachment to the skin of a patient 18. For example, in some embodiments, the targeting fixture 690 can be temporarily adhered to the patient 18 during imaging, removed, and then subsequently reattached during a follow-up medical procedure, such as a surgery. In some embodiments, the targeting fixture 690 can be applied to the skull of a patient 18 for use in placement of electrodes for deep brain stimulation. In some embodiments, this method can use a single fixture 690, or two related fixtures. In this instance, the two related fixtures can share the same surface shape. However, one fixture 690 can be temporarily attached at the time of medical image scanning, and can include radio-opaque markers 730 (but not active markers 720), and the second fixture 690 can be attached at the time of surgery, and can include active markers 720 (but not radio-opaque markers 730).

In some embodiments, the first fixture (for scanning) can comprise a frame 690 with three or more embedded radio-opaque markers 730, and two or more openings 740 for application of markings (the markings shown as 750 in FIG. 22B). In some embodiments, the device 690 can be adhered to the scalp of a patient 18, and the openings 740 can be used to paint marks on the scalp with, for example, henna or dye (shown as "+" marks 750 in FIG. 22B). With this fixture 690 in place, in some embodiments, the patient 18 can receive a 3D scan (for example an MRI or CT scan) in which the radio-opaque markers 730 are captured. As illustrated by FIG. 22B, in some embodiments, the fixture 690 can then be removed, leaving the dye marks 750 on the scalp. In some embodiments, on a later date (before the dye marks 750 wear off), the patient 18 can return, and the surgeon or technician can attach the 2nd fixture (for surgery) containing active markers 720 for intraoperative tracking (see FIG. 22C-22D). In some embodiments, the fixture 690 shown in FIG. 22C can be mounted to the scalp, spatially positioned and oriented in the same position as the previously adhered first fixture (shown in FIG. 22A) by ensuring that the previously placed dye marks 750 line up with holes in the second fixture 690 (see the alignment arrows depicted in FIG. 22C). Optionally, in some embodiments, the fixture 690 can have a transparent frame for good visualization. The above-described method assumes that the locations of the marks 750 do not change over the period of time between the scan and the return of the patient 18 for surgery. Since the relative positions between the radio-opaque markers 730 from the temporary (first) fixture 690 (which appear in the scan) and the active markers 720 on the second applied fixture 690 are known through a calibration and/or by careful manufacturing of the fixtures 690, the coordinate system of the anatomy and the coordinate system of the active markers 720 can be synchronized so that the robot 15 can target any planned trajectory on the 3D image as described further herein. Further, in some embodiments, this method can enable image guidance with only one pre-op scan and without requiring the patient 18 to go home after a pre-op scan. This circumvents the need for a patient 18 to take care of wounds from targeting screws that are invasively drilled into the skull of the patient 18.

Figure 23:
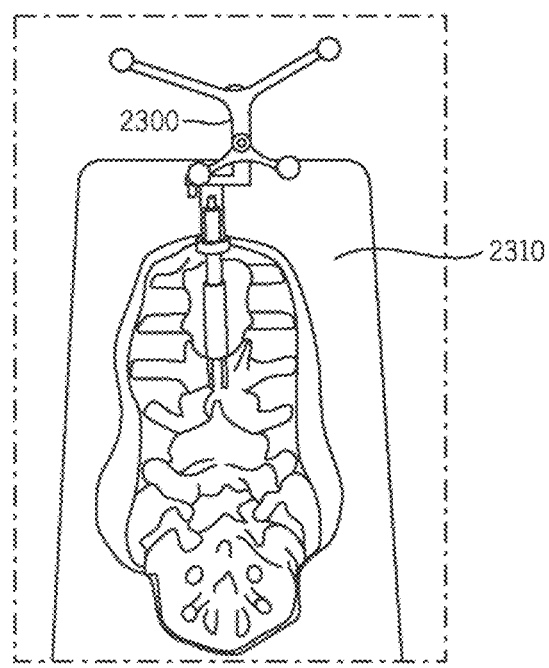
FIG. 23 depicts a dynamic tracking device mounted to the spinous process of the lumbar spine of a patient in accordance with one embodiment of the invention.

In some embodiments of the invention, the targeting fixture 690 can comprise a conventional clamping mechanism for securely attaching the targeting fixture 690 to the patient 18. For example, in some embodiments, the targeting fixture 690 can be configured to clamp to the spinous process 6301 of a patient 18 after the surgeon has surgically exposed the spinous process. FIG. 23 shows a dynamic tracking device 2300 mounted to the spinous process 2310 in the lumbar spine of a patient 18 in accordance with some embodiments of the invention. This targeting fixture is used with Medtronic's StealthStation. This figure is reprinted from Bartolomei J, Henn J S, Lemole G M Jr., Lynch J, Dickman C A, Sonntag V K H, Application of frameless stereotaxy to spinal surgery, Barrow Quarterly 17(1), 35-43 (2001).

StealthStation® is a trademark of Medtronic, Inc., and its affiliated companies.

In some embodiments, during use of a targeting fixture 690 having a conventional clamping mechanism with image guidance, the relationship between the markers 720, 730 and the bony anatomy of the patient 18 can be established using a registration process wherein known landmarks are touched with a digitizing probe at the same time that the markers on the tracker are visible. In some embodiments of the invention, the probe itself can have a shaft protruding from a group of markers 720, 730, thereby permitting the tracking system 3417 to calculate the coordinates of the probe tip relative to the markers 720, 730.

In some embodiments, the clamping mechanism of the targeting fixture 690 can be configured for clamping to the spinous process 2310, or can be configured for anchoring to bone of the patient 18 such that the fixture 690 is substantially stationary and not easily moved. In some further embodiments, the targeting fixture 690 can comprise at least three active markers 720 and distinct radio-opaque markers 730 that are detected on the CT or other 3D image, preferably near the clamp (to be close to bone). In some alternative embodiments, the active markers 720 themselves must be configured to be visualized accurately on CT or other 3D image. In certain embodiments, the portion of the fixture 690 containing a radio-opaque marker 730 can be made to be detachable to enable removal from the fixture after the 3D image is obtained. In some further embodiments, a combination of radio-opaque 730 and active markers 720 can allow tracking with the robot 15 in the same way that is possible with the frame-type targeting fixtures 690 described above.

In some embodiments, one aspect of the software and/or firmware disclosed herein is a unique process for locating the center of the above-described markers 730 that takes advantage of the fact that a CT scan can comprise slices, typically spaced 1.5 mm or more apart in the z direction, and sampled with about 0.3 mm resolution in the x-axis and y-axis directions. In some embodiments, since the diameter of the radio-opaque markers 730 is several times larger than this slice spacing, different z slices of the sphere will appear as circles of different diameters on each successive x-y planar slice. In some embodiments, since the diameter of the sphere is defined beforehand, the necessary z position of the center of the sphere relative to the slices can be calculated to provide the given set of circles of various diameters. Stated similarly, in some embodiments, a z slice substantially exactly through the center of the sphere can yield a circle with a radius R that is substantially the same as that of the sphere. In some embodiments, a z slice through a point at the top or bottom of the sphere can yield a circle with a radius R approximating zero. In some other embodiments, a z slice through a z-axis coordinate Z1 between the center and top or bottom of the sphere can yield a circle with a radius R1=R cos(arcsin(Z1/R)).

In some embodiments of the invention, the observed radii of circles on z slices of known inter-slice spacing can be analyzed using the equation defined by R1=R cos(arcsin(Z1/R)). This provides a unique mathematical solution permitting the determination of the distance of each slice away from the center of the sphere. In cases in which a sphere has a diameter small enough that only a few slices through the sphere appear on a medical image, this process can provide a more precise the center of a sphere.

Some embodiments of the use of the calibration frame 700 are described to further clarify the methods of use. For example, some embodiments include the steps of a conventional closed screw or conventional needle (for example, a biopsy needle 8110) insertion procedure utilizing a calibration frame 700 as follows. In some embodiments, a calibration frame 700 is attached to the patient's 18 skin, substantially within the region at which surgery/biopsy is to take place. In some embodiments, the patient 18 receives a CT scan either supine or prone, whichever positioning orients the calibration frame 700 upward. In some embodiments, the surgeon subsequently manipulates three planar views of the patient's 18 CT images with rotations and translations. In some embodiments, the surgeon then draws trajectories on the images that define the desired position, and strike angle of the end-effectuator 30. In some embodiments, automatic calibration can be performed in order to obtain the centers of radio-opaque makers 730 of the calibration frame 700, and to utilize the stored relationship between the active markers 720 and radio-opaque markers 730. This procedure permits the robot 15 to move in the coordinate system of the anatomy and/or drawn trajectories.

In some embodiments, the robot 15 then will move to the desired position. In some embodiments, if forceful resistance beyond a pre-set tolerance is exceeded, the robot 15 will halt. In some further embodiments, the robot 15 can hold the guide tube 50 at the desired position and strike angle to allow the surgeon to insert a conventional screw or needle (for example, needle 7405, 7410 or biopsy needle 8110). In some embodiments, if tissues move in response to applied force or due to breathing, the movement will be tracked by optical markers 720, and the robot's position will automatically be adjusted.

As a further illustration of a procedure using an alternate guidance system, in some embodiments, the steps of an open screw insertion procedure utilizing an optical guidance system is described. In some embodiments, after surgical exposure, a targeting fixture 690 comprising a small tree of optical markers, for example, can be attached to a bony prominence in the area of interest. In some embodiments, conventional calibration procedures for image guidance can be utilized to establish the anatomy relative to the optical tracking system 3417 and medical images. For another example, the targeting fixture 690 can contain rigidly mounted, substantially permanent or detachable radio-opaque markers 730 that can be imaged with a CT scan. In some embodiments, the calibration procedures consistent with those stated for the calibration frame 700 can be utilized to establish the anatomy relative to the robot 15 and the medical image.

In some embodiments, the surgeon manipulates three planar views of the patient's CT images with rotations and translations. In some embodiments, the surgeon then draws trajectories on the images that define the desired position and strike angle of the end-effectuator 30. In some embodiments, the robot 15 moves to the desired position. In some embodiments, if forceful resistance beyond a pre-set tolerance is exceeded, the robot 15 will halt. In some embodiments, the robot 15 holds the guide tube 50 at the desired position and strike angle to allow the surgeon to insert a conventional screw. In some embodiments, if tissues move in response to applied force or due to breathing, the movement will be tracked by optical markers 720, and the robot's position will automatically be adjusted.

Figure 36:
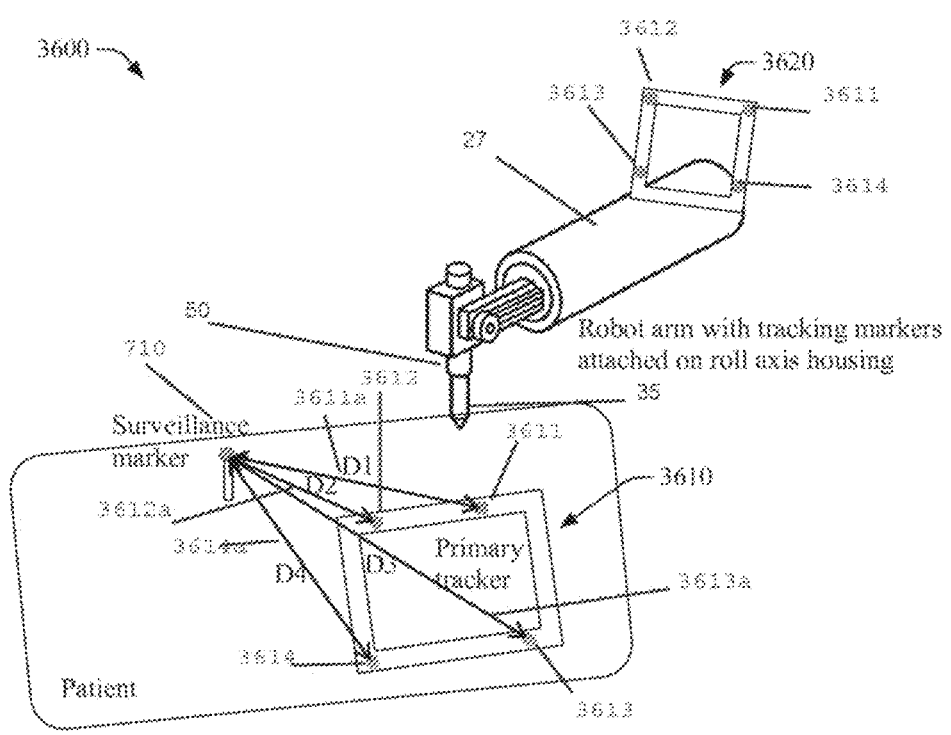
FIG. 36 illustrates a surgical robot system having a surveillance marker in accordance with one or more embodiments described herein.

FIG. 36 illustrates an example embodiment 3600 of surgical robot system 1 that utilizes a surveillance marker 710 in accordance with one or more aspects of the invention. As illustrated, the example embodiment 3600 comprises a 4-marker tracker array 3610 attached to the patient 18 and having a surveillance marker, and a 4-marker tracker array 3620 on the robot 15. In some embodiments, during usage, it may possible that a tracker array, or tracker (3610 in FIG. 36), on a patient 18 inadvertently shifts. For example, a conventional clamp positioned on a patient's 18 spinous process 2310 where the tracker 3610 is attached can be bumped by the surgeon's arm and move (i.e., bend or translate) to a new position relative to the spinous process 2310. Alternatively, a tracker 3610 that is mounted to the skin of the patient 18 can move gradually with the skin, as the skin settles or stretches over time. In this instance, the accuracy of the robot 15 movement can be lost because the tracker 3610 can reference bony anatomy from a medical image that no longer is in the same position relative to the tracker as it had been during the medical image scan. To overcome such problems, some embodiments of the invention provide a surveillance marker 710 as illustrated in FIG. 36. As shown, in some embodiments, the surveillance marker 710 can be embodied or can comprise one or more markers 710 rigidly affixed to a patient 18 in a location different than the location in which a primary tracker array 3610 is affixed; for example, a different spinous process 2310, on the skin, or on a small post drilled into the ilium. Accordingly, in some embodiments, the surveillance marker 710 can be located on the same rigid body as the primary tracker array 3610 but at a different location on the rigid body.

In one embodiment, in response to placement of the surveillance marker 710, execution of a control software application (e.g., robotic guidance software 3406) can permit an agent (e.g., a surgeon, a nurse, a diagnostician) to select "set surveillance marker". At this time, the vector (3D) distances between the surveillance marker 710, and each of the markers 3611, 3612, 3613, and 3614 on the primary tracker array 3610 can be acquired and retained in computer 100 memory (such as a memory of a computing device 3401 executing the control software application). In an embodiment in which a 4-marker tracker array 3610 is utilized (FIG. 36), four distances 3611a, 3612a, 3613a, and 3614a can be acquired and retained, representing the distances between the surveillance marker 710 and markers 3611, 3612, 3613, and 3614. In such embodiment, at each frame of real-time data during a procedure, the surgical robot system 1 disclosed herein can calculate updated distances between each of the markers 3611, 3612, 3613, and 3614 on the primary tracker array 3610 and the surveillance marker 710. The system 1 can then compare the updated distances or a metric thereof (for example, the sum of the magnitude of each distance) to the available values (for example, values retained in the computer 100 memory). In some embodiments, in view that the surveillance marker 710 and tracker array 3610 can be on the same rigid body, the updated distances and/or the metric thereof (such as their sum) can remain substantially fixed unless one or more of the tracker array 3610 or the surveillance marker 710 shifts. In some embodiments, in response to a shift of the tracker array 3610 or the surveillance marker 710, or both, a notification can be issued to alert an agent of a loss in movement accuracy. In some embodiments, if the surveillance marker 710 offset exceeds a pre-set amount, operation of the surgical robot system 1 can be halted. In some embodiments, in response to a user intentionally shifting the tracker array 3610 or the surveillance marker 710 to a new position, execution of the control software application can permit overwriting a set of one or more stored distances with new values for comparison to subsequent frames.

In some embodiments, as illustrated in FIG. 36, embodiment 3600 of surgical robot system 1 utilizes a surveillance marker 710, a 4-marker tracker array 3610 attached to the patient 18, and a 4-marker tracker array 3620 on the robot 15. It should be appreciated that in some embodiments, the 4-marker tracker array 3620 on the robot 15 can experience an unintentional shift in a manner similar to that for the 4-marker array tracker 3610 on the patient 18. Consequently, in certain embodiments, a surveillance marker (not shown) can be attached to a different position on the robot 15 arm than the robot's 4-marker tracker array 3620 to control, at least in part, such unintentional shift. In some embodiments, a surveillance marker on the robot 15 may provide lesser efficiencies than a surveillance marker 710 on the patient 18 in view that the robot 15 arm can be manufactured with negligible or minimal likelihood of the robot's tracker array 3620 or surveillance marker (not shown) shifting. In addition or in the alternative, other embodiments can include means for registering whether the tracker 3620 has shifted can be contemplated for the robot's tracker array 3620. For instance, in some embodiments, the means for registering may not include a surveillance marker, but may comprise the extant robot 15 tracking system 3417 and one or more of the available conventional encoders. In some embodiments, the system 1 and encoder(s) can compare movement registered from the tracker 3620 to movement registered from counts of encoders (not shown) on each robot 15 axis. For example, in some embodiments where the robot's tracker array 3620 is mounted on the housing 27 that rotates with the roll 62 axis (which can be farther away from the base 25 than the z-axis 70, x-axis 66, y-axis 68, and roll 62 axis) then changes in z-axis 70, x-axis 66, y-axis 68, and roll 62 axis encoder counts can provide highly predictable changes in the position of the robot's tracker array 3620 in the coordinate systems of the tracking system 3417 and robot 15. In some embodiments, the predicted movement based on encoder counts and tracked 3D position of the tracker array 3620 after application of known counts can be compared and, if the values differ substantially (or values are above a predetermined threshold), the agent can be alerted to the existence of that an operational issue or malfunction. The operational issue can originate from one or more of a malfunction in the registration of counts (i.e., electromechanical problem), malfunction in registration of the tracker's markers 3621, 3622, 3623, 3624 (for example, outside of tracking system's optimum volume), or shift in the position of the tracker 3620 on the robot's 15 surface during the move.

It should be appreciated that other techniques (for example, methods, systems, and combinations thereof, or the like) can be implemented in order to respond to operational issues that may prevent tracking of the movement of a robot 15 in the surgical robot system 1. In one embodiment, marker reconstruction can be implemented for steadier tracking. In some embodiments, marker reconstruction can maintain the robot end-effectuator 30 steady even if an agent partially blocks markers during operation of the disclosed surgical robot system 1.

Figure 37:
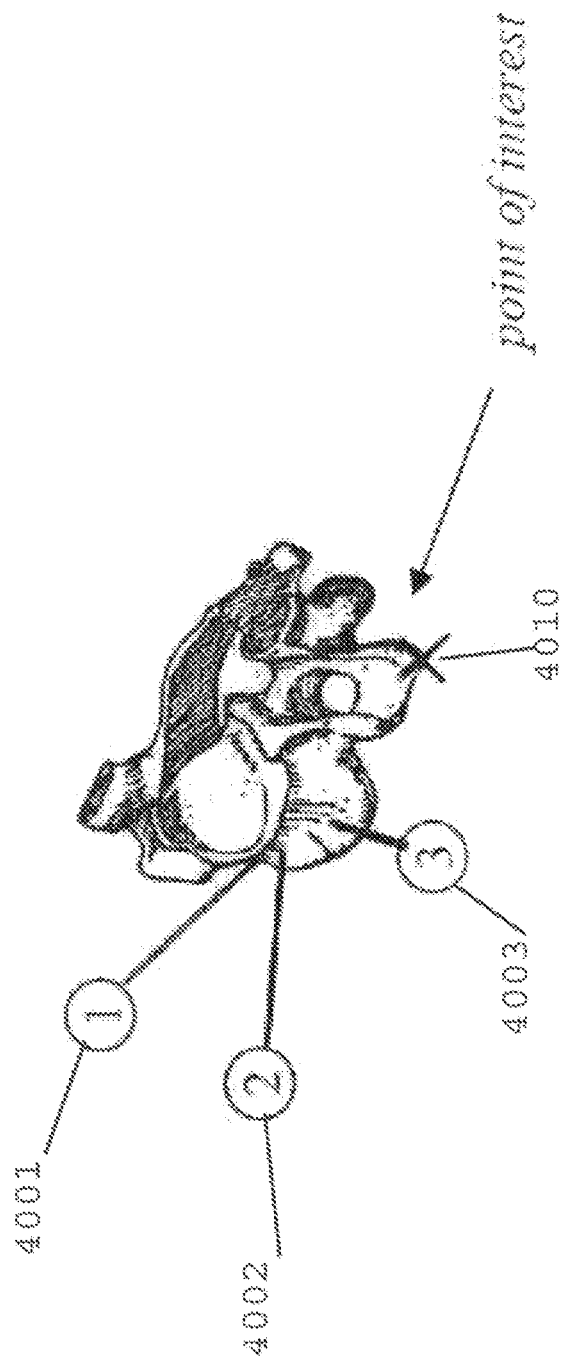
FIG. 37 illustrates an example of a methodology for tracking a visual point on a rigid body using an array of three attached markers in accordance with one embodiment of the invention.

As described herein, in some embodiments, at least some features of tracking movement of the robot's end-effectuator 30 can comprise tracking a virtual point on a rigid body utilizing an array of one or more markers 720, such tracking comprising one or more sequences of translations and rotations. As an illustration, an example methodology for tracking a visual point on a rigid body using an array of three attached markers is described in greater detail herein, such methodology can be utilized to implement marker reconstruction technique in accordance with one or more aspects of the invention. FIG. 37, for example, illustrates an example of a methodology for tracking a visual point 4010 on a rigid body using an array of three attached markers 4001, 4002, 4003. In some embodiments, the method includes contemplating a reference data-frame. In some embodiments, the reference data-frame can be associated with a set of reproducible conditions for the relative positions of the markers 4001, 4002, 4003, but not necessarily defined locations.

Figure 38:
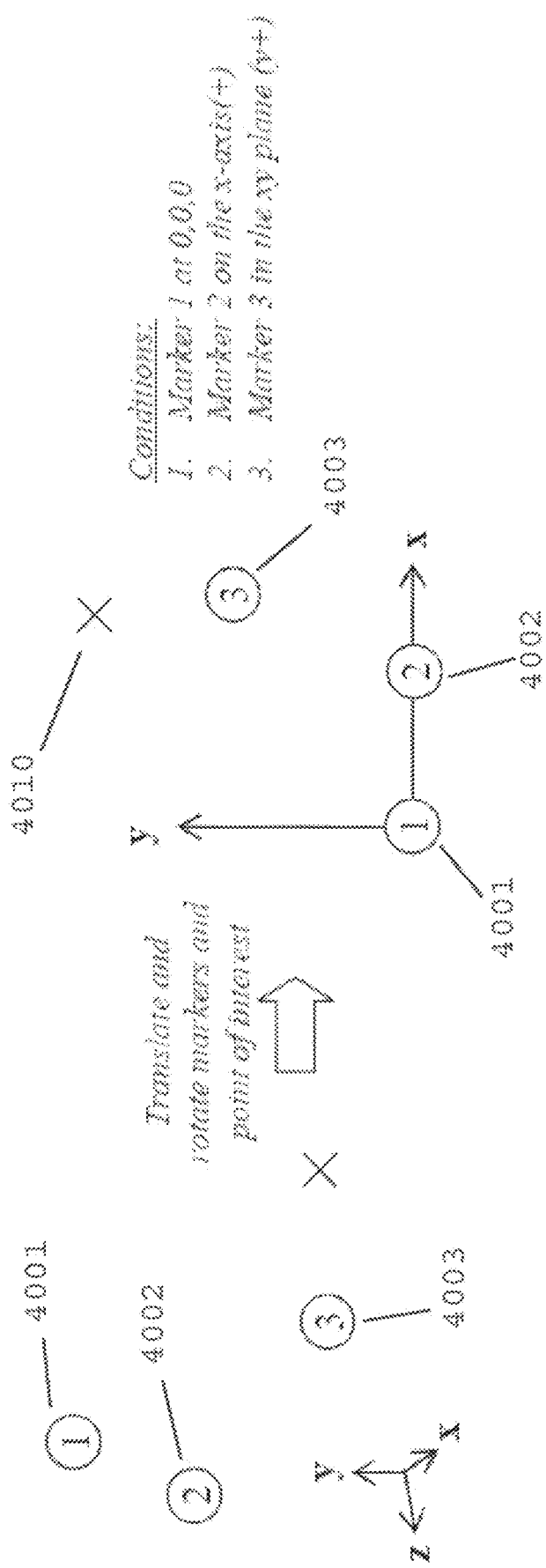
FIG. 38 illustrates a procedure for monitoring the location of a point of interest relative to three markers based on images received form the methodology illustrated in FIG. 37.

FIG. 38 illustrates a procedure for monitoring the location of a point of interest 4010 relative to three markers 4001, 4001, 4003 based on images received form the methodology illustrated in FIG. 37 in accordance with some embodiments of the invention. As shown, the method includes translation and rotating the markers 4001, 4002, 4003 and point of interest 4010 with the conditions as shown. In some embodiments, the method can include saving the x-axis, y-axis, and z-axis coordinates of the point of interest 4010 in this reference frame for future use. In some embodiments, for each subsequent data-frame the method can include the steps of; 1). transform the markers 4001, 4002, 4003 using the conditions defined for the reference frame (keeping track of the rotations and translations), 2). add the point of interest 4010 (which was saved after establishing the reference frame) and 3). transform the point of interest 4010 back to the current location of the markers 4001, 4002, 4003 using inverses of the saved translations and rotations from step 1. In some embodiments, upon or after completing step 1 above, the actual proximity of the markers 4001, 4002, 4003 to their original reference data-frame is dictated by marker noise and rigid body rigidity. In some embodiments, the markers will never overlay perfectly with their counterparts that were stored when establishing the reference frame. In some embodiments, the disclosed method can permit the markers 4001, 4002, 4003 to get as close as possible to their original relative spacing.

Figure 39:
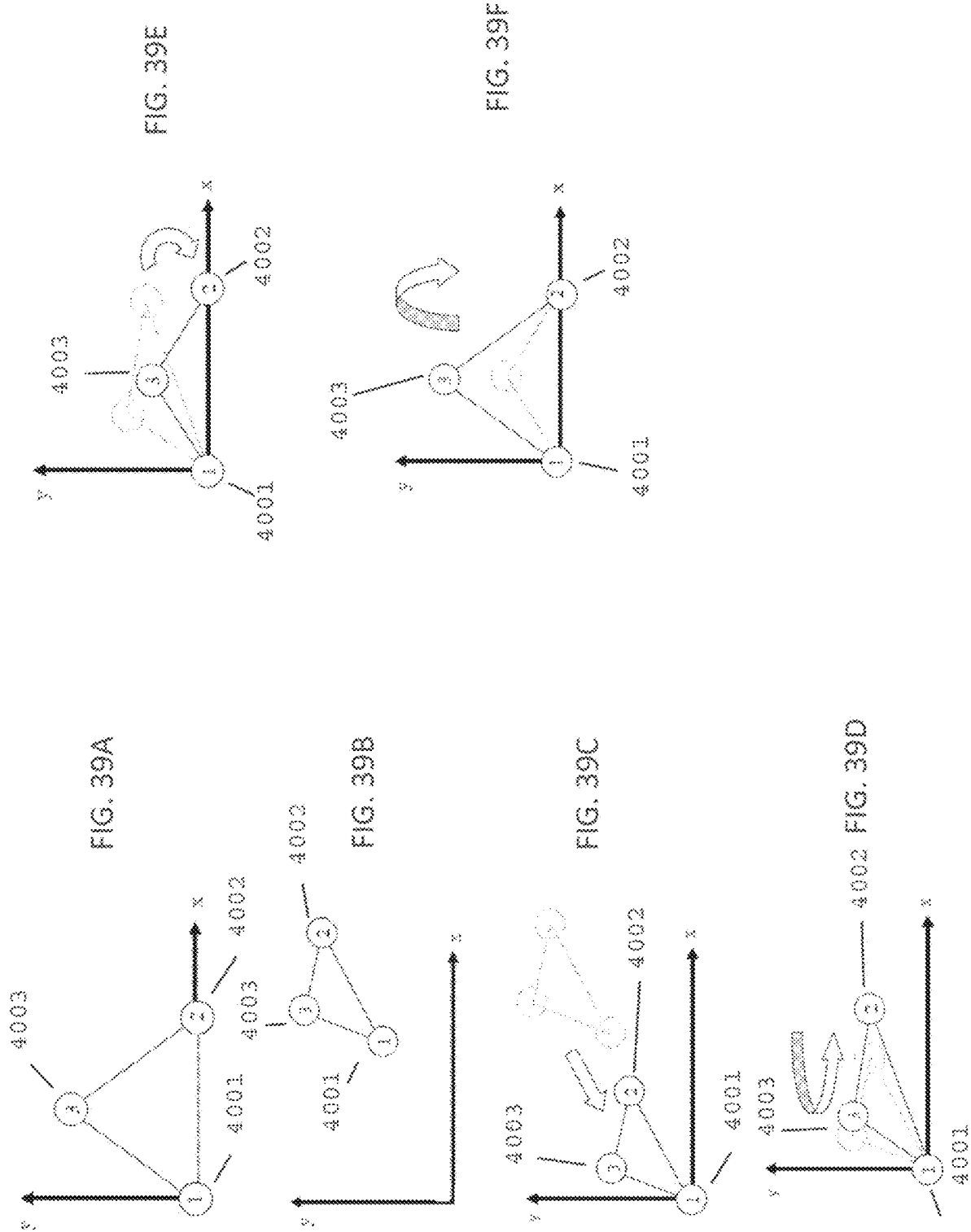
FIGS. 39A-F illustrates examples of tracking methodology based on an array of three attached markers in accordance with one embodiment of the invention.

FIGS. 39A-F illustrate examples of tracking methodology based on an array of three attached markers 4001, 4002, and 4003 in accordance with some embodiments of the invention. In some embodiments, the goal can be marker 4001 on the origin, marker 4002 on the positive x-axis, and marker 4003 in the x-y plan in a positive y direction (shown in FIG. 39A). Assuming a starting configuration as shown in FIG. 39B, in some embodiments, the method can include translating the rigid body so that marker 4001 is at the origin as shown in FIG. 39C. In some embodiments, the method can then include rotation about the y-axis so that marker 4002 is in the x-y plane (i.e., z=0) (see FIG. 39D). In some embodiments, the method can then include rotating the z-axis so that marker 4002 is at y=0, x coordinate positive (as shown in FIG. 39E). Finally, in some embodiments, the method can include rotating about the x-axis so that marker 4003 is at z=0, y coordinate positive. In some embodiments, a record of the translations and rotations can be retained in order to utilize the negative values to transform position(s) back after adding the point of interest. In some embodiments, when translating the rigid body so that the marker 4001 moves to the origin, the vector to add to each marker's position vector is simply the negative 4001 position vector. In some embodiments, to determine the values of θ to plug into the rotation matrices in steps 2, 3, and 4, use the arctangent. For example, rotate marker 4002 about the y-axis to z=0 where:

$$M2 = \begin{bmatrix} 4 \\ 5 \\ 6 \end{bmatrix}$$

Figure 40:
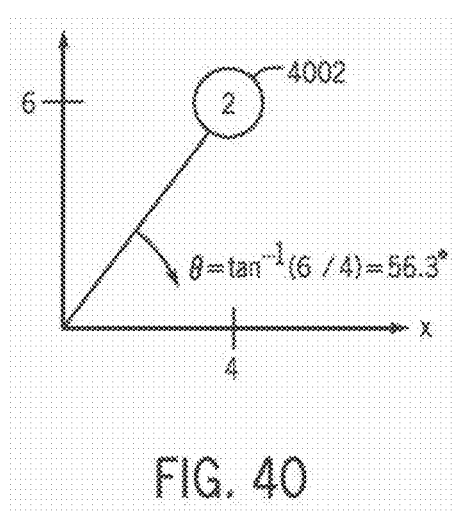
FIG. 40 illustrates an example of a two dimensional representation for rotation about the Y-axis in accordance with one embodiment of the invention.

FIG. 40 illustrates an example of a two dimensional representation for rotation about the y-axis in accordance with some embodiments of the invention. As shown, FIG. 40 illustrates one embodiment showing a two-dimensional representation looking down the axis about which rotation occurs (e.g., y-axis is going into the page). In this example, a position rotation of θ=56.3° about the y-axis is needed to bring 4002 to z=0. It should be appreciated that the appropriate direction (+ or −) of the rotation angle to plug into the rotation matrix can be confusing. In some embodiments, it is beneficial to draw the plane of the rotation with the rotation axis coming out of the plane contained in the page surface (for example, the right-hand rule can provide a suitable orientation), then a counterclockwise rotation is positive and a clockwise rotation is negative. In the foregoing example, the axis was going into the page surface, thus a clockwise rotation was positive.

Figure 41A:
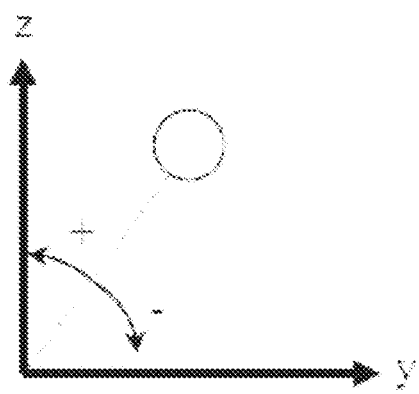
FIG. 41A illustrates an alternative representation of a two dimensional representation for rotation about an X-axis in accordance with one embodiment of the invention.
Figure 41B:
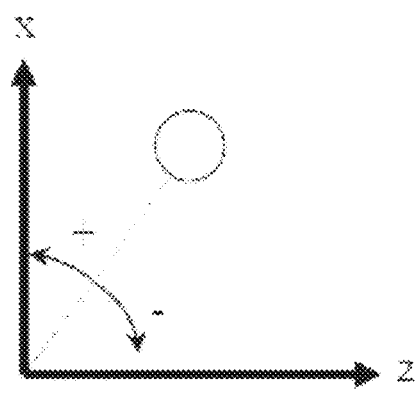
FIG. 41B illustrates an alternative representation of a two dimensional representation for rotation about a Y-axis in accordance with one embodiment of the invention.
Figure 41C:
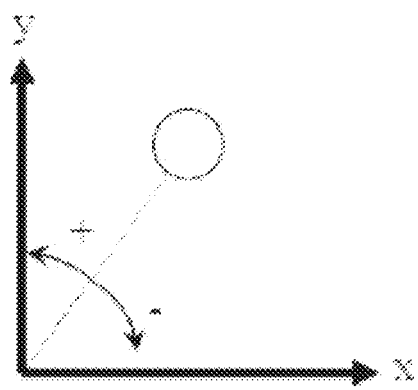
FIG. 41C illustrates an alternative representation of a two dimensional representation for rotation about a Z-axis in accordance with one embodiment of the invention.

FIGS. 41A-C illustrates an alternative representation of two dimensional representations for rotations about the axis, depicting how each plane can be drawn for counterclockwise positive and clockwise negative in accordance with some embodiments of the invention. As shown, FIG. 41A illustrates an alternative representation of a two dimensional representation for rotation about an X-axis. FIG. 41B illustrates an alternative representation of a two dimensional representation for rotation about a Y-axis. FIG. 41C illustrates an alternative representation of a two dimensional representation for rotation about a Z-axis In some embodiments, to rotate the rigid body about the y-axis so that 4002 is in the x-y plane (z=0):

$$\theta_y = +\tan^{-1}\left(\frac{4002_z}{4002_x}\right)$$

In some embodiments, to rotate the rigid body about the z-axis so that 4002 is at y=0, $$\theta_z = -\tan^{-1}\left(\frac{4002_y}{4002_x}\right)$$

In some embodiments, to rotate the rigid body about the x-axis so that 4003 is at z=0:

$$\theta_x = -\tan^{-1}\left(\frac{4003_z}{4003_y}\right)$$

Figure 42:
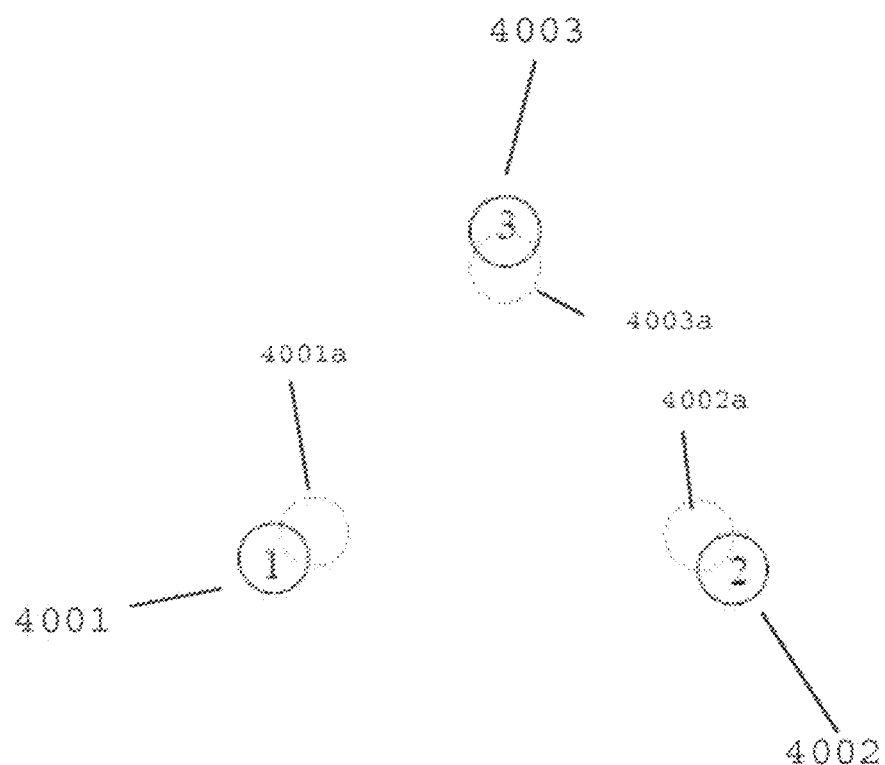
FIG. 42 provides a depiction of a noise within a frame of data.

As described herein, the example method to transform markers 4001, 4002, 4003 as close as possible to the reference frame can comprise; 1). translate the rigid body so that 4001 is at the origin (0, 0, 0), and 2). rotate about the y-axis so that 4002 is in the x-y plane (i.e., z=0), and 3). rotate about the z-axis so that 4002 is at y=0, x coordinate positive, and 4). rotate about the x-axis so that 4003 is at z=0, y coordinate positive. In other embodiments, a method to reach the same reference can comprise: 1). translate the rigid body so that 4001 is at the origin (0, 0, 0), and 2). rotate about the x-axis so that 4002 is in the x-y plane (i.e., z=0), and 3). rotate about the z-axis so that 4002 is at y=0, x coordinate positive, 4). rotate about the x-axis so that 4003 is at z=0, y coordinate positive. It should be appreciated that there are other possible methods and related actions, both in the reference frame chosen and in how the rigid body is manipulated to get it there. The described method is simple, but does not treat markers equally. The reference frame requires 4001 to be restricted the most (forced to a point), 4002 less (forced to a line), and 4003 the least (forced to a plane). As a result, errors from noise in markers are manifested asymmetrically. For example, consider a case where in a certain frame of data, noise causes each of the three markers to appear farther outward than they actually are or were (represented by 4001a, 4002a, and 4003a) when the reference frame was stored (as depicted in FIG. 42.)

Figure 43:
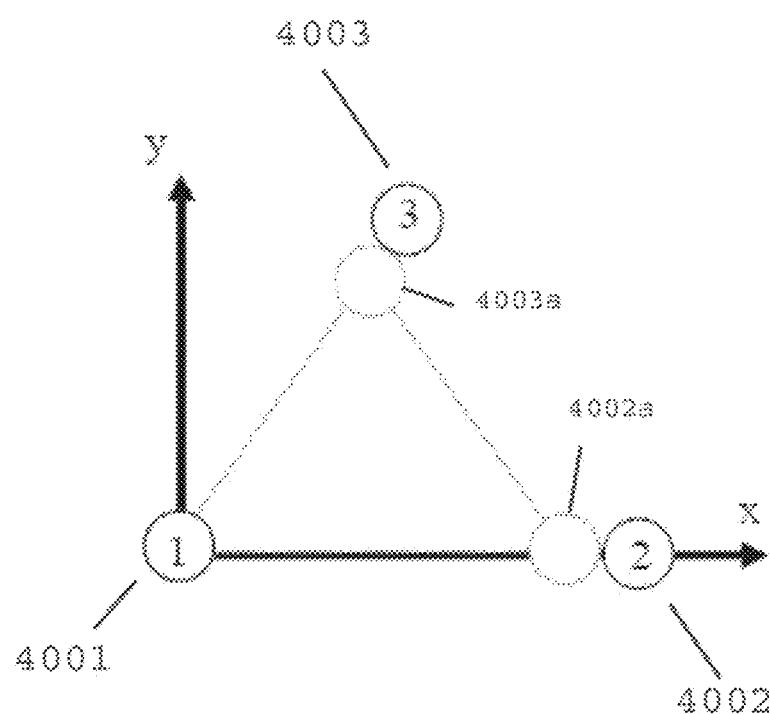
FIG. 43 illustrates the depiction of a noise within a frame of data as shown in FIG. 42 with a stored point of interest.

In some embodiments, when the transformations are done to align the apparent markers "as close as possible" to their stored reference position, they will be offset. For example, when the stored point of interest is added, it will be misplaced in a direction on which marker was chosen as 4001 in the algorithm (see 4003, 4003a and 4002, 4002a for example in FIG. 43).

Some embodiments provide additional or alternative methods for tracking points of interest that can involve more symmetrical ways of overlaying the actual marker positions with the stored reference positions. For example, in some embodiments, for three markers 4001, 4002, 4003, a two-dimensional fitting method typically utilized in zoology can be implemented. (See, e.g., Sneath P. H. A., "Trend-surface analysis of transformation grids," J. Zoology 151, 65-122 (1967)). The method can include a least squares fitting algorithm for establishing a reference frame and transforming markers to lie as close as possible to the reference. In this case, the reference frame is the same as described earlier except that the common mean point (hereinafter referred to as "CMP") is at the origin instead of marker 4001. In some embodiments, the CMP after forcing the markers into the x-y plane is defined in the following equation (and can be represented in FIG. 44):

$$CMP = \begin{bmatrix} \bar{x} \\ \bar{y} \\ 0 \end{bmatrix} = \begin{bmatrix} (M1_x + M2_x + M3_x)/3 \\ (M1_y + M2_y + M3_y)/3 \\ 0 \end{bmatrix}$$

In some embodiments, for the markers to be centered around CMP, the markers can be translated by subtracting the CMP from 4001, 4002, and 4003. It should be noted that the point of interest being tracked is not included in determining $CMP_{ref}$.

In some embodiments, the method to transform markers as close as possible to this reference frame can comprise; 1). translating the rigid body so that 4001 is at the origin (0, 0, 0), and 2). rotating about the y-axis so that 4002 is in the x-y plane (i.e., z=0), and 3). rotating about the z-axis so that 4002 is at y=0, x coordinate positive into the x-ray plane, and 4). rotating about the x-axis so that 4003 is at z=0, y coordinate positive, and finally 5). calculate the CMP for the markers 4001, 4002, 4003 and translating the rigid body so that the CMP is at the origin (i.e., subtract the CMP from each point transformed). In some embodiments, steps 1-5 are done for the original set of markers for which the position of the point of interest was known and for the new set for which you are adding the point of interest. A further step can be included for the new set, for example, 6). rotate about the z-axis to best overlay the stored reference markers. In some embodiments, the rotation angle θ is found using the formula from Sneath:

$$\tan\theta = \frac{\sum x_{pos2} y_{ref} - \sum x_{ref} y_{pos2}}{\sum x_{ref} x_{pos2} + \sum y_{ref} y_{pos2}}$$

In some embodiments, if M1, M2, M3 denote the stored reference markers and M'1, M'2, M'3 denote the position being tracked in this data-frame, the equation can be written:

$$\tan^{-1} = \frac{\begin{bmatrix}(M'1_x M1_y + M'2_x M2_y + M'3_x M3_y) - \\ (M1_x M'1_y + M2_x M'2_y + M3_x M'3_y)\end{bmatrix}}{\begin{bmatrix}(M1_x M'1_x + M2_x M'2_x + M3_x M'3_x) + \\ (M1_y M'1_y + M2_y M'2_y + M3_y M'3_y)\end{bmatrix}}$$

It should be noted that this rotation angle can be small (e.g., smaller than about 1°). In some embodiments, after the markers 4001, 4002, 4003 are overlaid, some embodiments of the invention can include adding the point of interest then transforming the point of interest back to its true present location in the current frame of data. In some embodiments, to transform back, negative values saved from the forward transformation steps 1-6 as discussed above can be utilized. That is, for instance, go from step 6 to step 5 by rotating by negative θ, go from step 5 to step 4 by adding the CMP, etc.)

Figure 44:
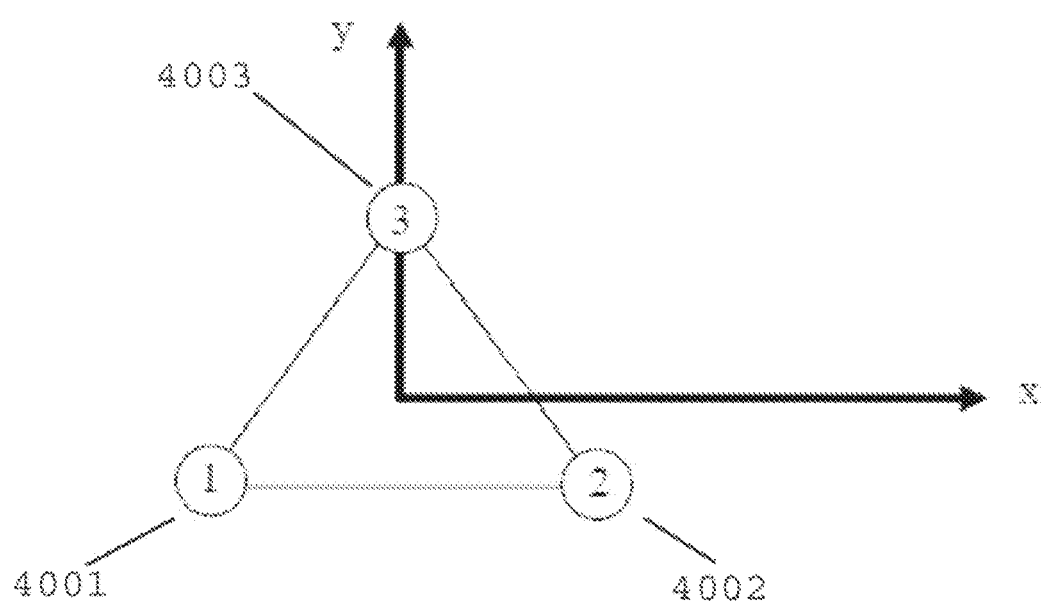
FIG. 44 illustrates a depiction of results of applying a least squares fitting algorithm for establishing a reference frame and transforming markers in accordance with one embodiment of the invention.
Figure 45:
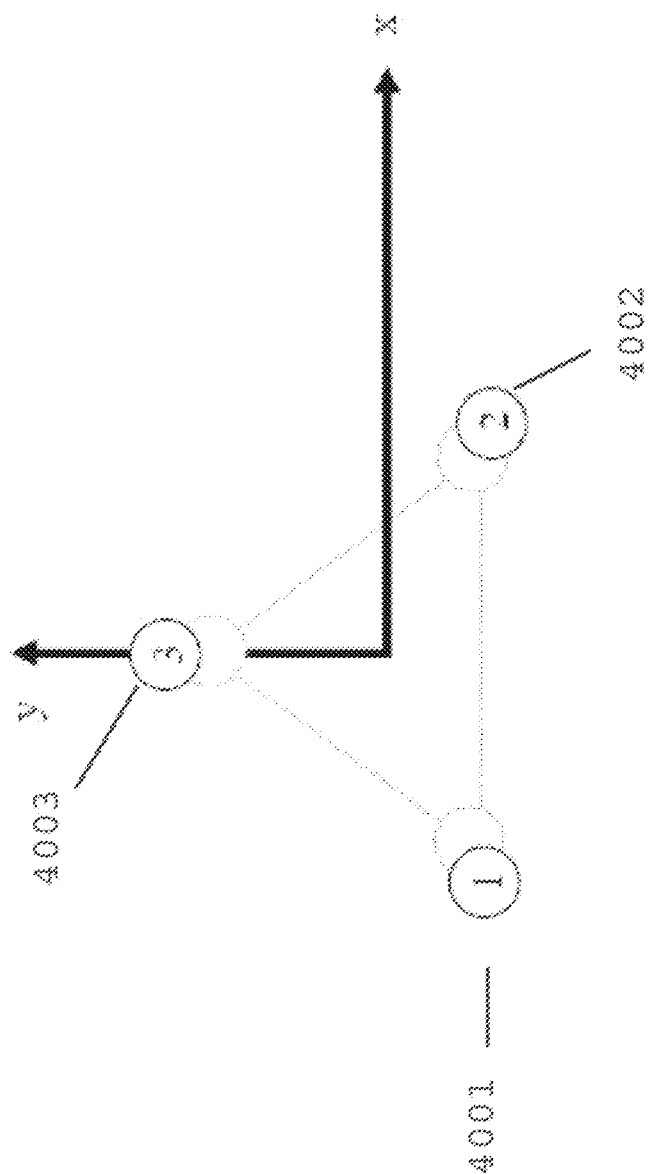
FIG. 45 illustrates a depiction of results of applying a least squares fitting algorithm for establishing a reference frame and transforming markers as shown in FIG. 44 including noise.

In some embodiments, using this least-squares algorithm, noise is manifested more symmetrically and the point of interest will probably be calculated to be closer to its actual location. This can be illustrated in FIG. 45, which illustrates a depiction of results of applying a least squares fitting algorithm for establishing a reference frame and transforming markers 4001, 4002, 4003 as shown in FIG. 44 including noise. Regardless of which method is used, it can be beneficial to monitor the error between the marker locations at a given frame of data and the reference marker locations. In some embodiments, the method can include calculating and sum the vector distances of each marker and report the value in mm.

Figure 46:
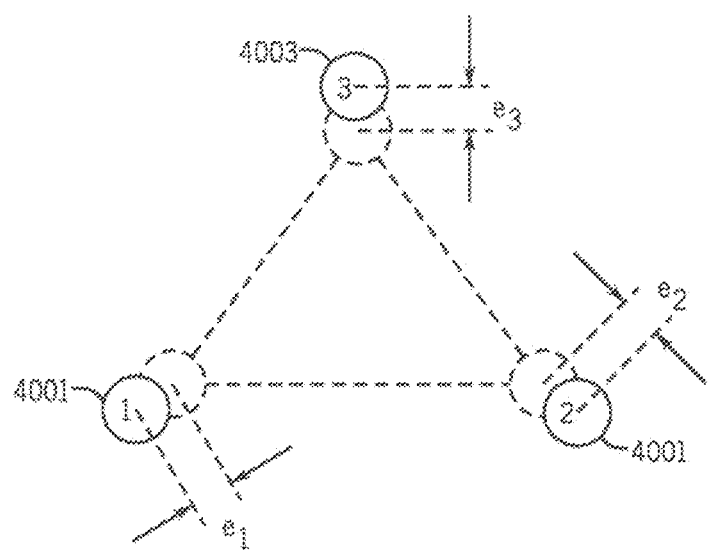
FIG. 46 illustrates a depiction of error calculation for reference frame markers in accordance with one embodiment of the invention.

FIG. 46 for example illustrates a depiction of error calculation for reference frame markers in accordance with some embodiments of the invention. In some embodiments, by continuously displaying this error value, the agent can be alerted if markers 4001, 4002, 4003 have become partially obscured, or if a marker 4001, 4002, 4003 is no longer securely or rigidly attached to the rigid body. In some embodiments, when performing a best fit on more than 3 markers, they cannot be forced into a plane, and therefore the problem becomes much more difficult. In some embodiments, one solution is to inspect all or nearly all possible triangles formed by groups of 3 markers 4001, 4002, 4003 and evaluate which one gives the least standard deviation of the angles of the vertices. See Chèze L, Fregly B. J., Dimnet J, Technical note: A solidification procedure to facilitate kinematic analyses based on video system data," Journal of Biomechanics 28(7), 879-884 (1995). In some other embodiments, the method can include calculating a least squares fit of the vertices of the geometric shape, requiring iteration to perform matrix decomposition (i.e., Newton-Raphson method). For example, see Veldpaus F E, Woltring H J, Dortmans L J M G, '*A least-squares algorithm for the equiform transformation from spatial marker co-ordinates*', *Journal of Biomechanics* 21(1), 45-54 (1988).

In some embodiments, when tracking 3D movement of a rigid body (for example, a robot 15 end-effectuator 30 or a targeted bone) using an array of 3 tracking markers 4001, 4002, 4003 that are rigidly attached to the rigid body, one example method for quantifying motion can include determining the transformations (translation and rotations) for the movement from a first (neutral) position (defined here as "A") to second (current frame) position (herein referred to as "B"). In some embodiments, it may be convenient to describe the rotations as a three by three orientation matrix (direction cosines) of the rigid body in the position B, and to treat the three translation values as a 3×1 vector containing the x, y, z coordinates of the origin of the position A coordinate system transformed to position B. In some embodiments, the direction cosine matrix is a 3×3 matrix, the columns of which contain unit vectors that originally were aligned with the x, y, and z axes, respectively, of the neutral coordinate system. In some embodiments, to build a direction cosine matrix, a 3×3 matrix, A, can be defined in a manner that its columns are unit vectors, i, j, and k, aligned with the x, y, and z axes, respectively:

$$A = \begin{bmatrix} i_x & j_x & k_x \\ i_y & j_y & k_y \\ i_z & j_z & k_z \end{bmatrix} = \begin{bmatrix} 1 & 0 & 0 \\ 0 & 1 & 0 \\ 0 & 0 & 1 \end{bmatrix}$$

Upon or after rotations of the coordinate system occur, in some embodiments, the new matrix (which is the direction cosine matrix, A') is as follows, where the unit vectors i', j', and k' represent the new orientations of the unit vectors that were initially aligned with the coordinate axes:

$$A' = \begin{bmatrix} i'_x & j'_x & k'_x \\ i'_y & j'_y & k'_y \\ i'_z & j'_z & k'_z \end{bmatrix}$$

In some embodiments, to determine the direction cosines and translation vector, the origin and unit vectors can be treated as aligned with the coordinate axes as four tracked points of interest in the manner described herein. For example, if the origin (o) and three unit vectors (i, j, k) are aligned with the coordinate axes, they are treated as virtual tracked points of interest with coordinates of:

$$o = \begin{bmatrix} 0 \\ 0 \\ 0 \end{bmatrix} \rightarrow i = \begin{bmatrix} 1 \\ 0 \\ 0 \end{bmatrix} \rightarrow j = \begin{bmatrix} 0 \\ 1 \\ 0 \end{bmatrix} \rightarrow k = \begin{bmatrix} 0 \\ 0 \\ 1 \end{bmatrix}$$

In some embodiments, these points of interest can provide the direction cosines and translation for the movement when moved along with the three markers from position A to position B. In some embodiments, it may be convenient to implement (for example execute) the method for moving the virtual points to these four points placed into a 3×4 matrix, P.

In some embodiments, the matrix is as follows in position A:

$$P = \begin{bmatrix} o_x & i_x & j_x & k_x \\ o_y & i_y & j_y & k_y \\ o_z & i_z & j_z & k_z \end{bmatrix} = \begin{bmatrix} 0 & 1 & 0 & 0 \\ 0 & 0 & 1 & 0 \\ 0 & 0 & 0 & 1 \end{bmatrix}$$

In some embodiments, the matrix is as follows in position B:

$$P' = \begin{bmatrix} a_x & b_x & c_x & d_x \\ a_y & b_y & c_y & d_y \\ a_z & b_z & c_z & d_z \end{bmatrix} = \begin{bmatrix} o'_x & i'_x + o'_x & j'_x + o'_x & k'_x + o'_x \\ o'_y & i'_y + o'_y & j'_y + o'_y & k'_y + o'_y \\ o'_z & i'_z + o'_z & j'_z + o'_z & k'_z + o'_z \end{bmatrix}$$

In some embodiments, after movement, the direction cosine matrix is $$A' = \begin{bmatrix} i'_x & j'_x & k'_x \\ i'_y & j'_y & k'_y \\ i'_z & j'_z & k'_z \end{bmatrix} = \begin{bmatrix} b_x - a_x & c_x - a_x & d_x - a_x \\ b_y - a_y & c_y - a_y & d_y - a_y \\ b_z - a_z & c_z - a_z & d_z - a_z \end{bmatrix}$$

Figure 47:
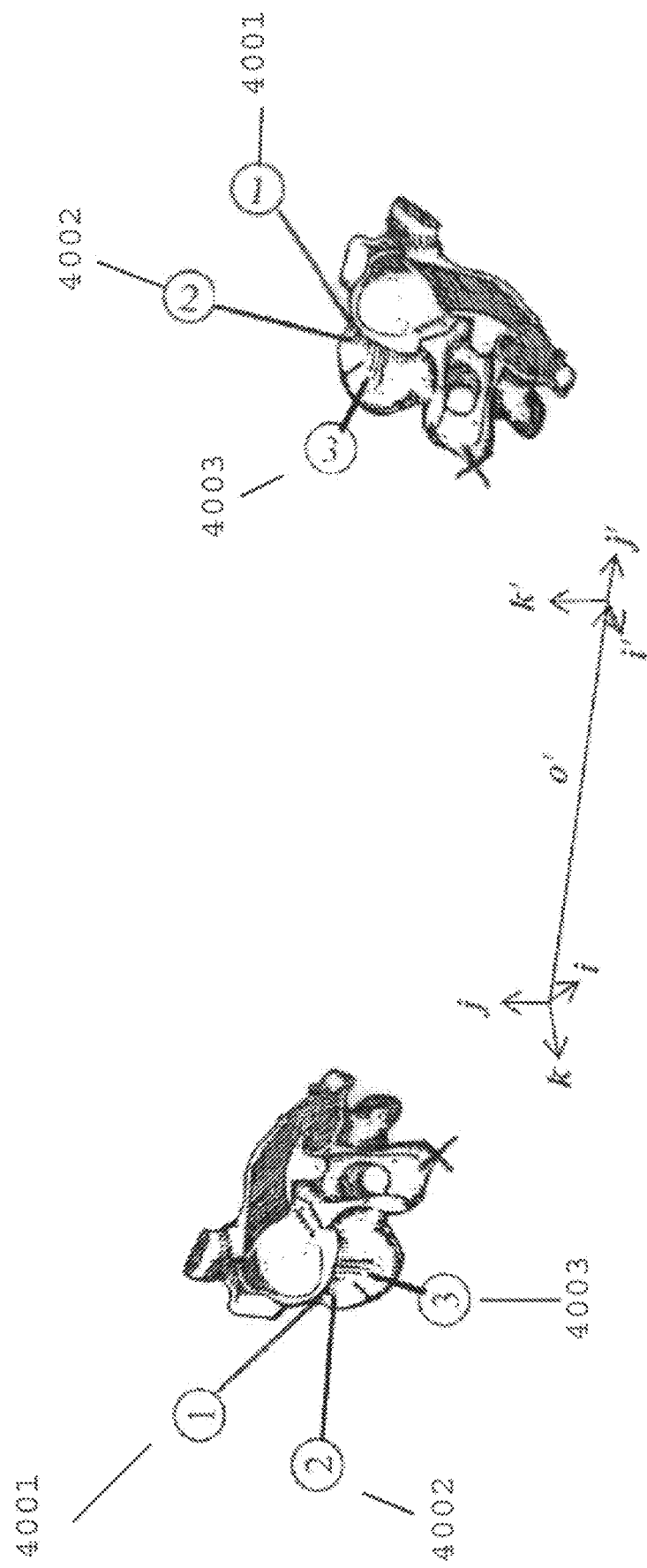
FIG. 47 illustrates a graphical representation of methods of tracking three dimensional movement of a rigid body.

In some embodiments, the vector o' represents the new position of the origin. In some embodiments, after moving the three markers 4001, 4002, 4003 from position A to position B, and bringing the four points (as a 3×4 matrix) along with the three markers 4001, 4002, 4003, the translation of the origin is described by the first column. Further, in some embodiments, the new angular orientation of the axes can be obtained by subtracting the origin from the $2^{nd}$, $3^{rd}$, and $4^{th}$ columns. These methods should be readily apparent from the following graphic representation in FIG. 47, which illustrates a graphical representation of methods of tracking three dimensional movement of a rigid body.

In some embodiments, if more than three markers 4001, 4002, 4003 are utilized for tracking the movement of a rigid body, the same method can be implemented repeatedly for as many triads of markers as are present. For example, in a scenario in which four markers, M1, M2, M3, and M4, are attached to the rigid body, there can be four triads: those formed by {M1, M2, M3}, {M1, M2, M4}, {M1, M3, M4}, and {M2, M3, M4}. In some embodiments, each of these triads can be used independently in the method described hereinbefore in order to calculate the rigid body motion. In some embodiments, the final values of the translations and rotations can then be the average of the values determined using the four triads. In some embodiments, in the alternative or in addition, other methods for achieving a best fit when using more than 3 markers may be used.

In some embodiments, when tracking with four markers, in a scenario in which one of the four markers becomes obscured, it can desirable to switch to tracking the rigid body with the remaining three markers instead of four. However, this change in tracking modality can cause a sudden variation in the results of one or more calculations utilized for tracking. In some embodiments, the variation can occur because the solution from the one remaining triad may be substantially different than the average of 4 triads. In some embodiments, if using the tracked position of the rigid body in a feedback loop to control the position of a robot 15 end-effectuator, the sudden variation in results of the calculation can be manifested as a physical sudden shift in the position of the robot 15 end-effectuator 30. In some embodiments, this behavior is undesirable because the robot 15 is intended to hold a guide tube 50 steady with very high accuracy.

Some embodiments include an example method for addressing the issue of sudden variation that occurs when one of the four markers M1, M2, M3, M4 is blocked, thereby causing the position to be calculated from a single triad instead of the average of four triads, can include reconstructing the blocked marker as a virtual marker. In some embodiments, to implement such reconstructing step with high accuracy, the most recent frame of data in which all four markers M1, M2, M3, M4 are visible can be retained substantially continuously or nearly continuously (for example in a memory of a computing device implementing the subject example method). In some embodiments, if all four markers M1, M2, M3, M4 are in view, the x-axis, y-axis, and z-axis coordinates of each of the four markers M1, M2, M3, and M4 are stored in computer 100 memory. It should be appreciated that in some embodiments, it may unnecessary to log all or substantially all frames and is sufficient to overwrite the same memory block with the most recent marker coordinates from a full visible frame. Then, in some embodiments, at a frame of data in which one of the four markers M1, M2, M3, and M4 is lost, the lost marker's position can be calculated based on the remaining triad, using the example method described herein for remaining three markers. That is, the triad (the three visible markers) is transformed to a reference. The stored set of markers is then transformed to the same reference using the corresponding triad with the fourth marker now acting as a virtual landmark. The recovered position of the lost fourth marker can then be transformed back to the current position in space using the inverse of the transformations that took it to the reference position. In some embodiments, after the lost marker's position is reconstructed, calculation of the rigid body movement can be performed as before, based on the average of the fourth triads, or other best fit method for transforming the rigid body from position A to position B.

In some embodiments, an extension to the methods for reconstructing markers 720 is to use multiple ambiguous synchronized lines of sight via multiple cameras 8200 tracking the same markers 720. For example, two or more cameras 8200 (such as Optotrak® or Polaris®) could be set up from different perspectives focused on the tracking markers 720 on the targeting fixture 690 or robot 15. In some embodiments, one camera unit could be placed at the foot of a patient's bed, and another could be attached to the robot 15. In some embodiments, another camera unit could be mounted to the ceiling. In some embodiments, when all cameras 8200 substantially simultaneously view the markers 720, coordinates could be transformed to a common coordinate system, and the position of any of the markers 720 would be considered to be the average (mean) of that marker's three dimensional position from all cameras used. In some embodiments, even with extremely accurate cameras, an average is needed because with system noise, the coordinates as perceived from different cameras would not be exactly equal. However, when one line of sight is obscured, the lines of sight from other cameras 8200 (where markers 720 can still be viewed) could be used to track the robot 15 and targeting fixture 690. In some embodiments, to mitigate twitching movements of the robot 15 when one line of sight is lost, it is possible that the marker 720 positions from the obscured line of sight could be reconstructed using methods as previously described based on an assumed fixed relationship between the last stored positions of the markers 720 relative to the unobstructed lines of sight. Further, in some embodiments, at every frame, the position of a marker 720 from camera 1 relative to its position from camera 2 would be stored; then if camera 1 is obstructed, and until the line of sight is restored, this relative position is recalled from computer memory (for example in memory of a computer platform 3400) and a reconstruction of the marker 720 from camera 1 would be inserted based on the recorded position of the marker from camera 2. In some embodiments, the method could compensate for temporary obstructions of line of sight such as a person standing or walking in front of one camera unit.

In certain embodiments, when a marker M1, M2, M3, M4 is lost but is successfully reconstructed in accordance with one or more aspect described herein, the marker that has been reconstructed can be rendered in a display device 3411. In one example implementation, circles representing each marker can be rendered graphically, coloring the circles for markers M1, M2, M3, M4 that are successfully tracked in green, markers M1, M2, M3, M4 that are successfully reconstructed in blue, and markers M1, M2, M3, M4 that cannot be tracked or reconstructed in red. It should be appreciated that such warning for the agent can serve to indicate that conditions are not optimal for tracking and that it is prudent to make an effort for all four tracking markers to be made fully visible, for example, by repositioning the cameras or standing in a different position where the marker is not blocked. Other formats and/or indicia can be utilized to render a virtual marker and/or distinguish such marker from successfully tracked markers. In some embodiments, it is possible to extend the method described herein to situations relying on more than four markers. For example, in embodiments in which five markers are utilized on one rigid body, and one of the five markers is blocked, it is possible to reconstruct the blocked marker from the average of the four remaining triads or from another method for best fit of the 4 remaining markers on the stored last visible position of all 5 markers. In some embodiments, once reconstructed, the average position of the rigid body is calculated from the average of the 10 possible triads, {M1, M2, M3}, {M1, M2, M4}, {M1, M2, M5}, {M1, M3, M4}, {M1, M3, M5}, {M1, M4, M5}, {M2, M3, M4}, {M2, M3, M5}, {M2, M4, M5}, and {M3, M4, M5} or from another method for best fit of 5 markers from position A to position B.

Figure 48:
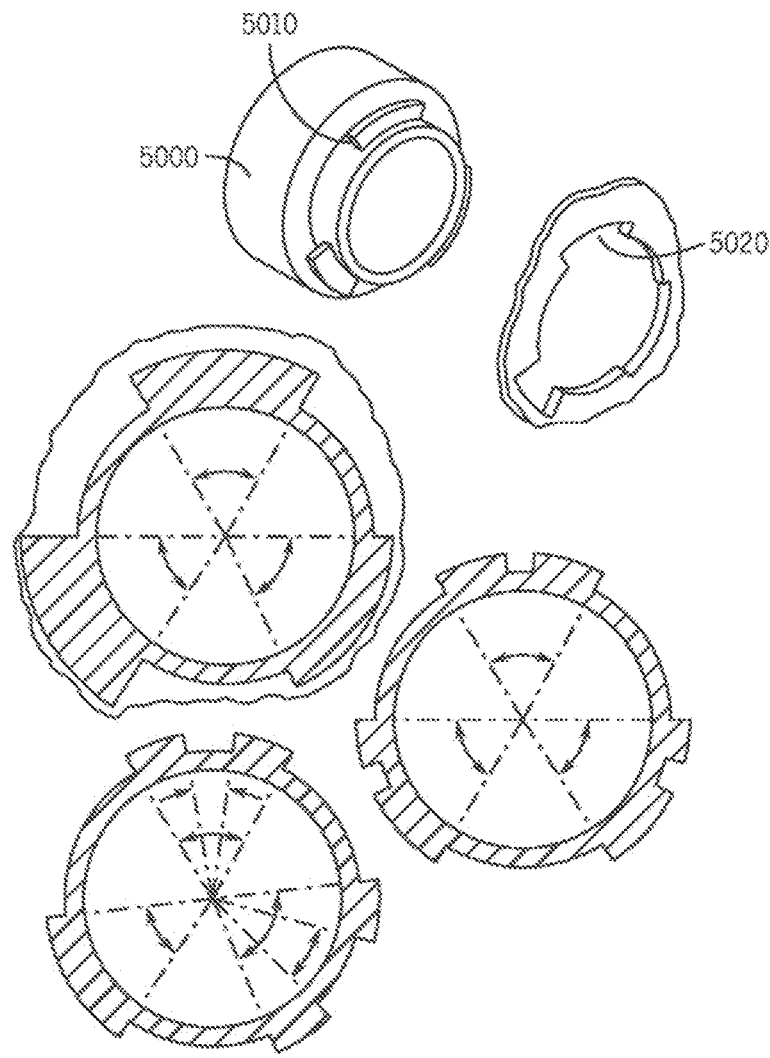
FIG. 48 shows a perspective view illustrating a bayonet mount used to removably couple the surgical instrument to the end-effectuator in accordance with one embodiment of the invention.

As discussed above, in some embodiments, the end-effectuator 30 can be operatively coupled to the surgical instrument 35. This operative coupling can be accomplished in a wide variety of manners using a wide variety of structures. In some embodiments, a bayonet mount 5000 is used to removably couple the surgical instrument 35 to the end-effectuator 30 as shown in FIG. 48. For example, FIG. 48 shows a perspective view illustrating a bayonet mount 5000 used to removably couple the surgical instrument 35 to the end-effectuator 30. In some embodiments, the bayonet mount 5000 securely holds the surgical instrument 35 in place with respect to the end-effectuator 30, enabling repeatable and predictable location of operational edges or tips of the surgical instrument 35.

In some embodiments, the bayonet mount 5000 can include ramps 5010 which allow identification of the surgical instrument 35 and ensure compatible connections as well. In some embodiments, the ramps 5010 can be sized consistently or differently around a circumference of the bayonet mount 5000 coupled to or integral with the surgical instrument 35. In some embodiments, the differently sized ramps 5010 can engage complementary slots 5020 coupled to or integral with the end-effectuator 30 as shown in FIG. 48.

In some embodiments, different surgical instruments 35 can include different ramps 5010 and complementary slots 5020 to uniquely identify the particular surgical instrument 35 being installed. Additionally, in some embodiments, the different ramps 5010 and slots 5020 configurations can help ensure that only the correct surgical instruments 35 are installed for a particular procedure.

In some embodiments, conventional axial projections (such as those shown in U.S. Pat. No. 6,949,189 which is incorporated herein as needed to show details of the interface) can be mounted to or adjacent the ramps 5010 in order to provide automatic identification of the surgical instruments 35. In some embodiments, other additional structures can be mounted to or adjacent the ramps 5010 in order to provide automatic identification of the surgical instruments 35. In some embodiments, the axial projections can contact microswitches or a wide variety of other conventional proximity sensors in order to communicate the identity of the particular surgical instrument 35 to the computing device 3401 or other desired user interface. Alternatively, in some other embodiments of the invention, the identity of the particular surgical instrument 35 can be entered manually into the computing device 3401 or other desired user interface.

Figure 49A:
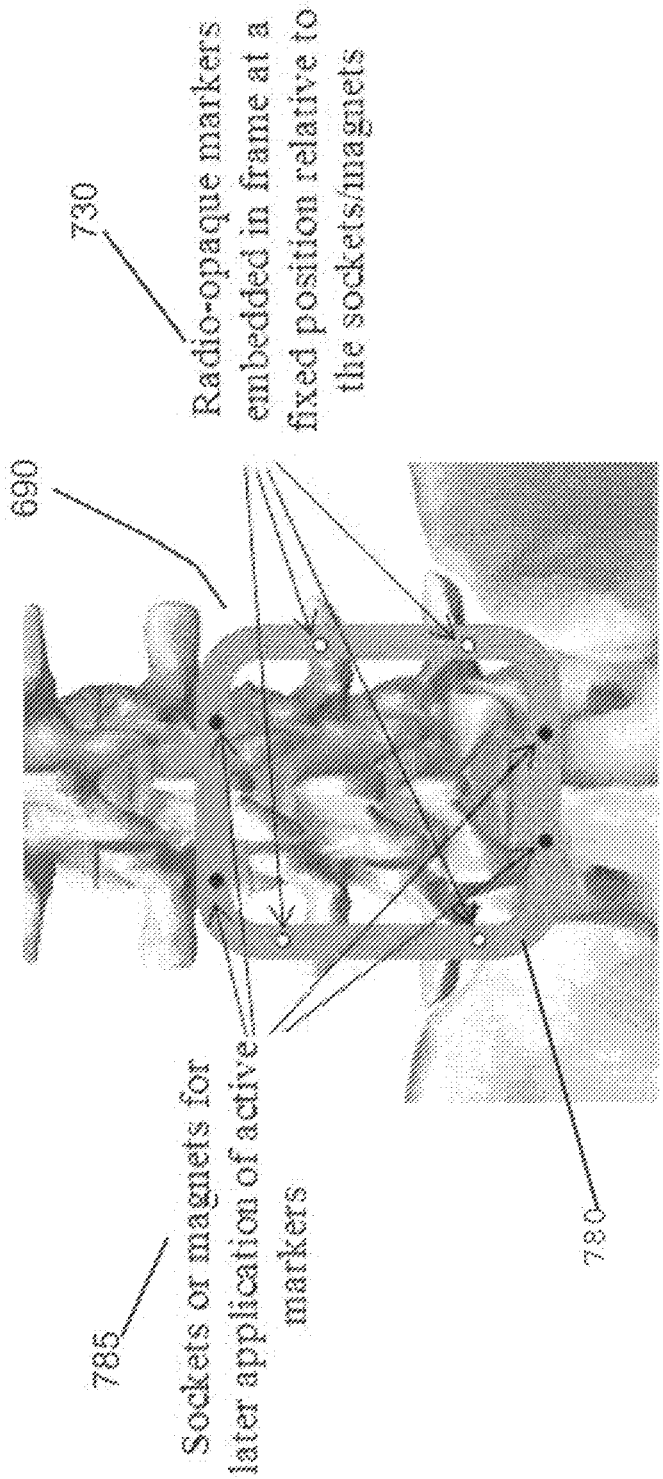
FIGS. 49A-49F depict illustrations of targeting fixtures in accordance with one embodiment of the invention.
Figure 49B:
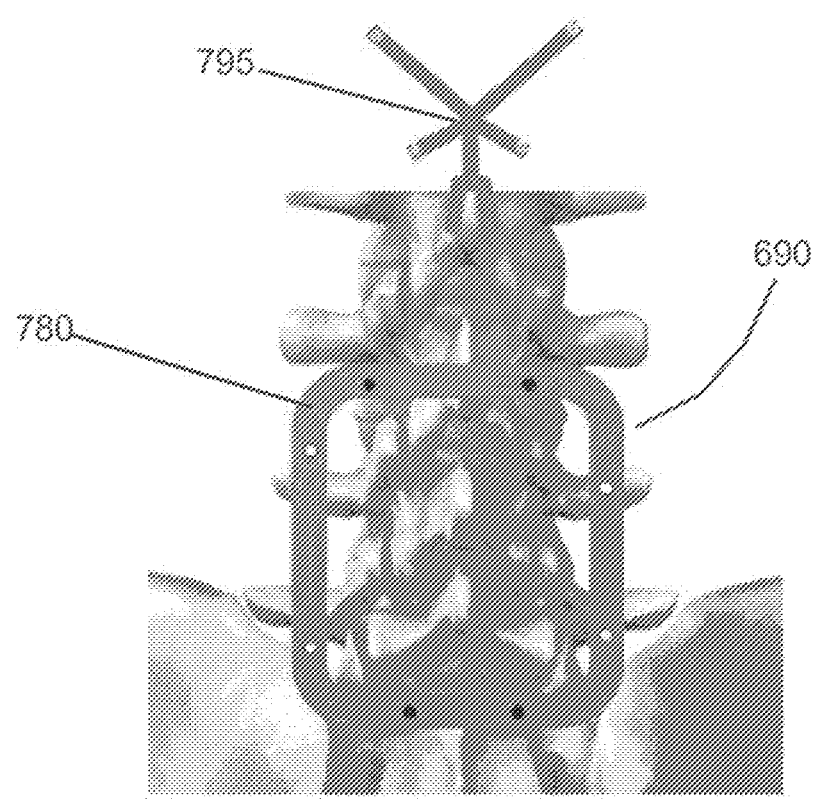
Figure 49C:
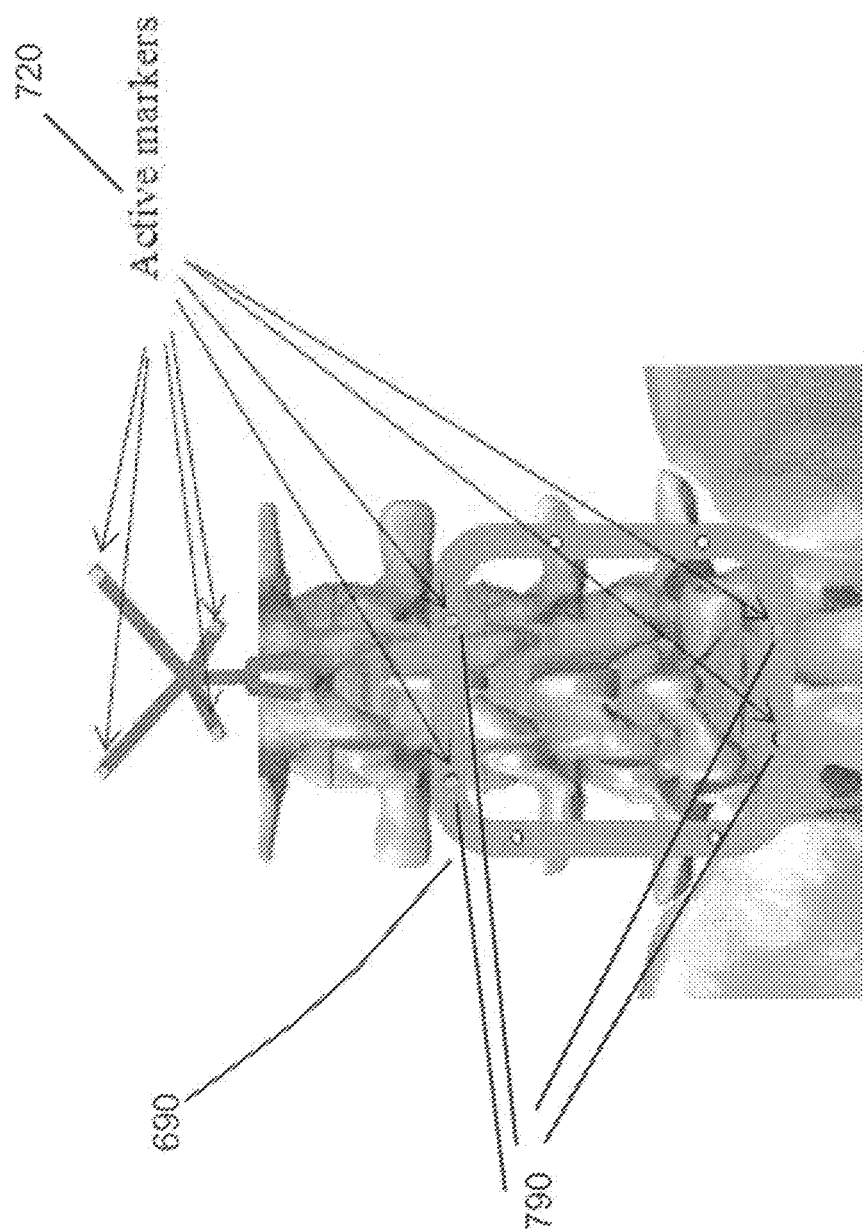
Figure 49D:
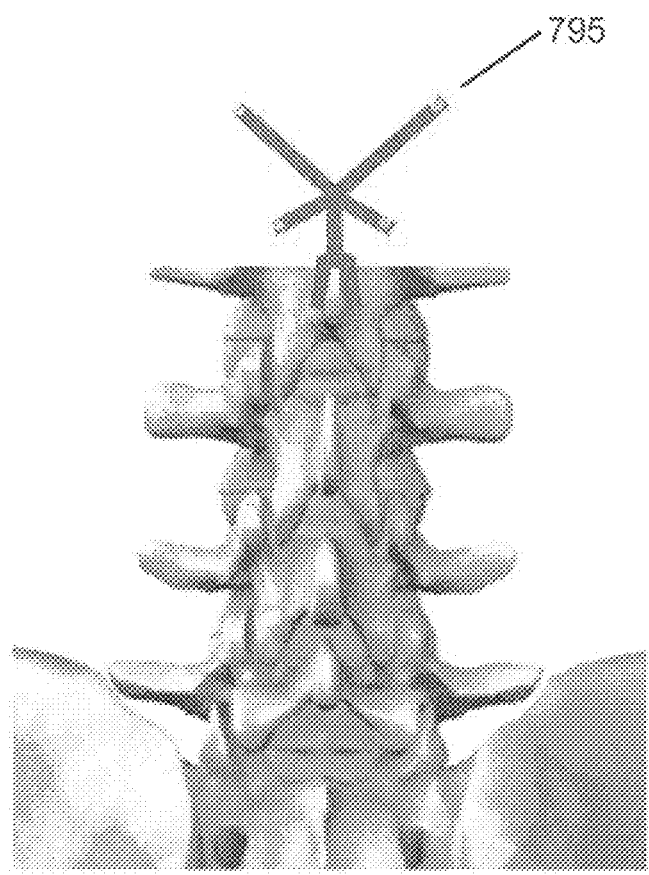
Figure 49E:
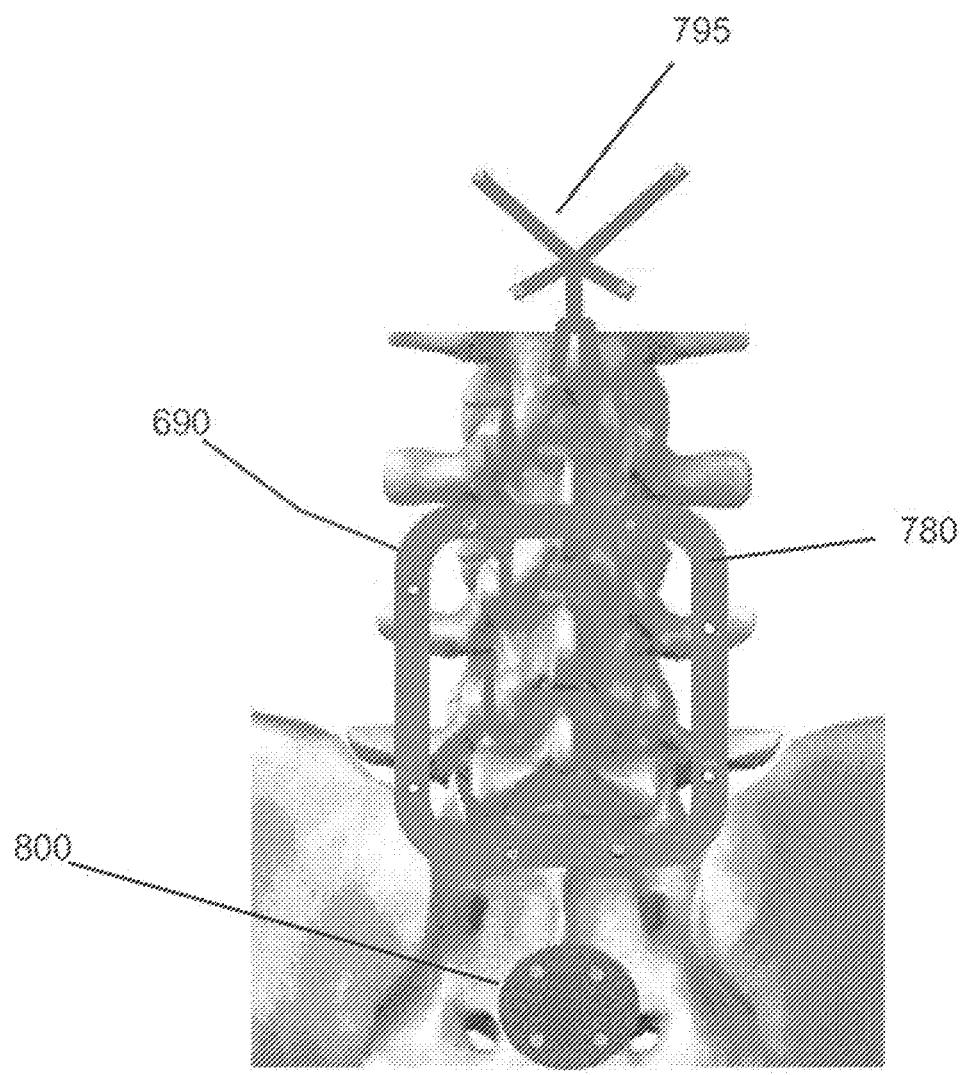
Figure 49F:
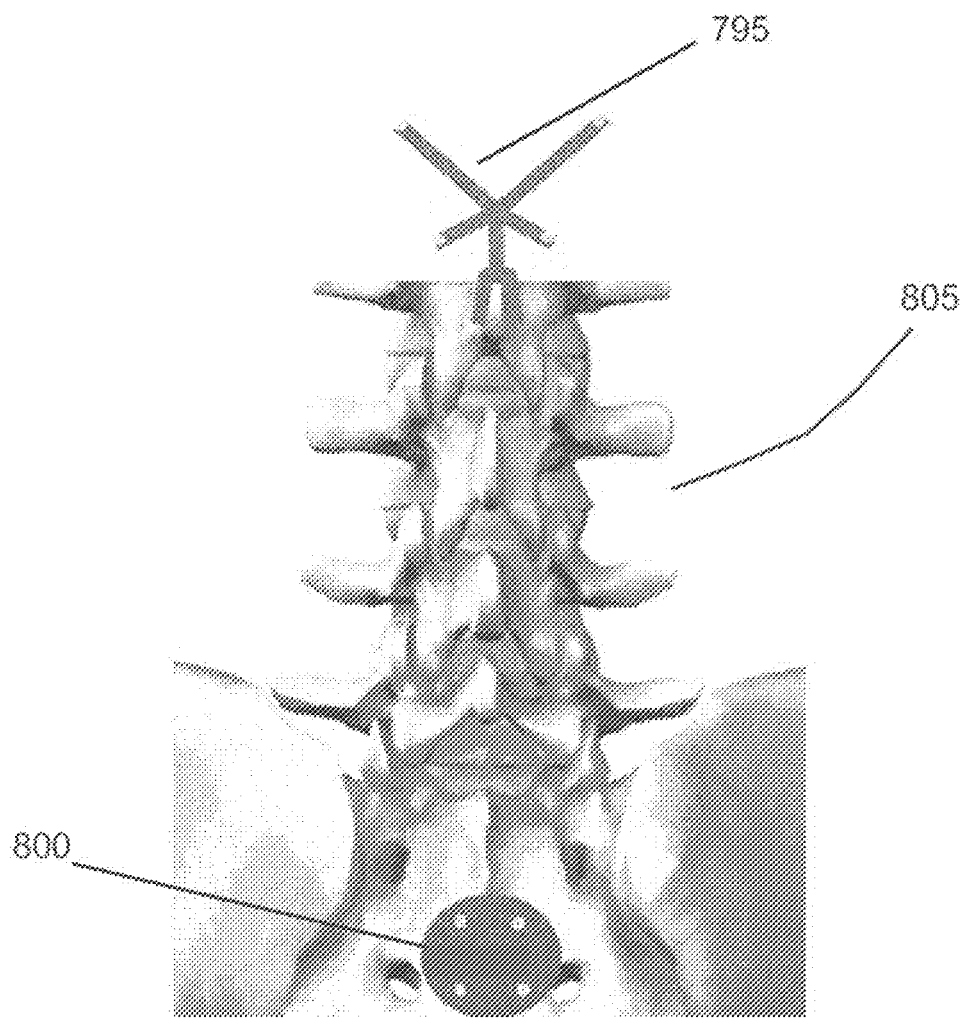

In some embodiments, instead of a targeting fixture 690 consisting of a combination of radio-opaque 730 and active markers 720, it is possible to register the targeting fixture 690 through an intermediate calibration. For example, in some embodiments, an example of such a calibration method could include attaching a temporary rigid plate 780 that contains radio-opaque markers 730, open mounts 785 (such as snaps, magnets, Velcro, or other features) to which active markers 720 can later be attached in a known position. For example, see FIGS. 49A-F which depict illustrations of targeting fixtures 690 coupled to a spine portion 19 of a patient 18 in accordance with one embodiment of the invention). The method can then include scanning the subject (using for example CT, MRI, etc.), followed by attaching a percutaneous tracker 795 such as those described earlier or other array of 3 or more active markers 720 rigidly affixed to the anatomy 19 as for example in FIG. 49B, and then attaching active markers 720 to the temporary plate 780 in the known positions dictated by the snaps, magnets, velcro, etc., as illustrated in FIG. 49C. In some embodiments, a further step can include activating the cameras 8200 to read the position of the tracker 795 rigidly affixed to the anatomy 19 at the same time as the active markers 720 on the temporary plate 780. This step establishes the position of the active markers 720 on the temporary plate 780 relative to the radio-opaque markers 730 on the temporary plate 780 as well as the positions of the active markers 720 on the tracker 795 relative to the active markers 720 on the temporary plate 780, and therefore establishes the position of the anatomy relative to the active markers 720 on the tracker 795. The temporary plate 780 can be removed (as illustrated in FIG. 49D), including the active markers 720 and radio-opaque markers 730. These markers are no longer needed because registration has been performed relative to the active markers on the rigidly affixed tracker 795.

In some alternative embodiments, variants of the order of the above described steps may also be used. For instance, the active markers 720 could already be attached at the time of the scan. This method has advantage that the radio-opaque markers 730 can be positioned close to the anatomy of interest without concern about how they are attached to the tracker 795 with active markers 720. However, it has the disadvantage that an extra step is required in the registration process. In some embodiments, a variant of this method can also be used for improved accuracy in which two trackers of active markers 720 are attached above and below the region of interest. For example, a tracker rostral to the region of interest (shown as 795) could be a spinous process 2310 clamp in the upper lumbar spine and a tracker caudal to the region of interest (shown as 800) could be a rigid array of active markers 720 screwed into the sacrum (see for example FIG. 49E). After calibration, the temporary plate 780 is removed and the area between the two trackers (within the region 805) is registered (see for example FIG. 49F).

Some embodiments can include methods for transferring registration. For example, a registration performed to establish the transformations in order to transpose from a medical image coordinate system (such as the CT-scanned spine) to the coordinate system of the cameras, can later be transferred to a different reference. In the example described in the above related to FIGS. 49A-F, a temporary fixture 780 with radio-opaque markers 730 and active markers 720 is placed on the patient 18 and registered. Then, a different fixture 795 is attached to the patient with active markers 720 only. Then the cameras (for example, camera 8200) are activated, and the active markers 720 on the temporary plate 780 are viewed simultaneously with the active markers 720 on the new tracking fixture 795. The necessary transformations to get from the temporary markers (those on the temporary plate 780) to the new markers (i.e. the markers on fixture 795) are established, after which the temporary plate 780 can be removed. In other words, the registration was transferred to a new reference (fixture 795). In some embodiments, it should be possible to repeat this transferal any number of times. Importantly, in some embodiments, one registration can also be duplicated and transferred to multiple references. In some embodiments, transferal of registration to multiple references would provide a means for tracking relative motion of two rigid bodies. For example, a temporary targeting fixture may be used to register the anatomy to the cameras 8200. Then, two new targeting fixtures may be placed on separate bones that are both included in the medical image used for registration. If the registration from the temporary targeting fixture is transferred to both of the new targeting fixtures, both of these bones may be tracked simultaneously, and the position of the robot end effectuator 30 or any other tracked probe or tool relative to both bones can be visualized. If one bone then moves relative to the other, the end effectuator's position would be located differently relative to the two trackers and the two medical images (for example, see FIGS. 50B-50D showing the two trackers 796 and 797 positioned on a portion of spine 19).

In some embodiments, after registration is transferred to both trackers 796, 797, the robot end effectuator 30 may be perceived by both trackers 796, 797 to be positioned as shown. In some embodiments, it is possible that one of the bones to which a tracker is mounted moves relative to the other, as shown in exaggerated fashion in FIG. 50C. In some embodiments, if the end effectuator 30 is considered fixed, the perception by the tracking system 3417 and software would be that the spine 19 was positioned in two possible relative locations, depending on which tracker is followed (see for example, the representation in FIG. 50D). Therefore, in some embodiments, by overlaying representations of both medical images, it becomes possible to visualize the relative movement of the bones on which the trackers 796, 797 are attached. For example, instead of displaying the re-sliced medical image on the screen and showing the position of the robot end effectuator 30 relative to that image, two re-sliced medical images could be overlapped (each allowing some transparency) and simultaneously displayed, showing one position where the robot end effectuator currently is positioned relative to both images (see FIGS. 50E-50F). However, the duplication of bones would make the representation cluttered, and therefore in some embodiments, it can be possible to automatically or manually segment the medical image such that only bones that do not move relative to a particular tracker 796, 797 are represented on the image (shown in FIG. 50E with the bones 19*a* highlighted as in relation to bone regions meaningful to tracker 796 with regions 19*b* faded, and FIG. 50F with the bones 19*a* highlighted in relation to bone regions meaningful to tracker 797, with regions 19*b* faded). Segmenting would mean hiding, fading, or cropping out the portion of the 3D medical image volume that the user does not want to see (represented as the faded regions 19*b* in FIGS. 50E and 50F).

In some embodiments, segmentation could involve identifying bordering walls on the 3D image volume or bordering curves on 2D slices comprising the medical image. In some embodiments, by segmenting simple six-sided volumes, enough separation of critical elements could be visualized for the task. In some embodiments, bones on the slice from a CT scans depicted in FIGS. 50G and 50H are shown with segmentation into region 20*a*, corresponding to the bone regions 19*a* referred to in FIGS. 50E and 50F, and 20*b*, corresponding to region 19*b*. In some embodiments, the regions 20*a* and 20*b* can be represented in different shades of color (for example, blue for 20*a* and yellow for 20*b*). Furthermore, as shown, the segmentation as displayed is depicted to proceed in and out of the page to include the entire CT volume. Moreover, although it goes right through the disc space, this segmentation cuts through one spinous process 2310 in the image in FIG. 50G, and does not follow the facet joint articulations to segment independently moving bones, as shown in a different slice represented in FIG. 50H. However, the re-sliced images of these overlapped volumes should still be useful when placing, for example, pedicle screws since the pedicles are properly segmented in the images.

An example of transferal of registration to multiple trackers includes conventional pedicle screw placement followed by compression or distraction of the vertebrae. For example, if pedicle screws are being placed at lumbar vertebrae L4 and L5, a tracker could be placed on L3 and registered. In some embodiments, conventional pedicle screws could then be placed at L4 and L5, with extensions coming off of each screw head remaining after placement. In some embodiments, two new trackers (for example, trackers substantially similar to 796, 797) could then be attached to the extensions on the screw heads, one at L4 and one at L5. Then, the registration could be transferred to both of these new trackers and a tracker at L3 could be removed or thereafter ignored. In some embodiments, if the medical image is segmented so that L4 and rostral anatomy is shown relative to the tracker on L4 (while L5 and caudal anatomy is shown relative to the tracker on L5), then it can be possible to see how the L4 and L5 vertebrae move relative to one another, as compressive or distractive forces are applied across that joint. In some embodiments, such compression or distraction might be applied by the surgeon when preparing the disc space for an inter-body spacer, or inserting the spacer, or when compressing the vertebrae together using a surgical tool after the inter-body spacer is in place, and before locking the pedicle screw interconnecting rod.

Figure 50A:
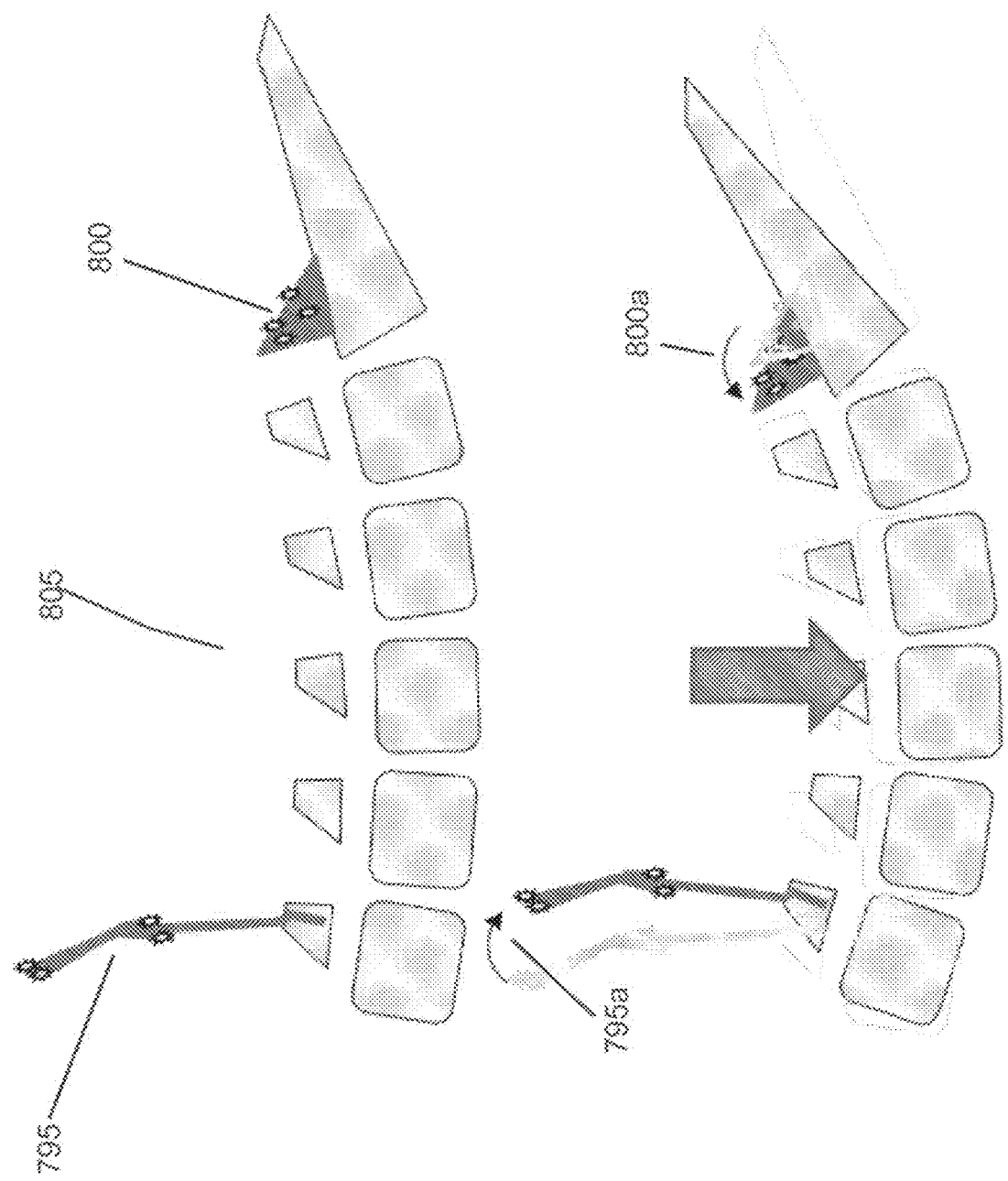
FIG. 50A shows an example illustration of one portion of a spine with markers in accordance with one embodiment of the invention.
Figure 50B:
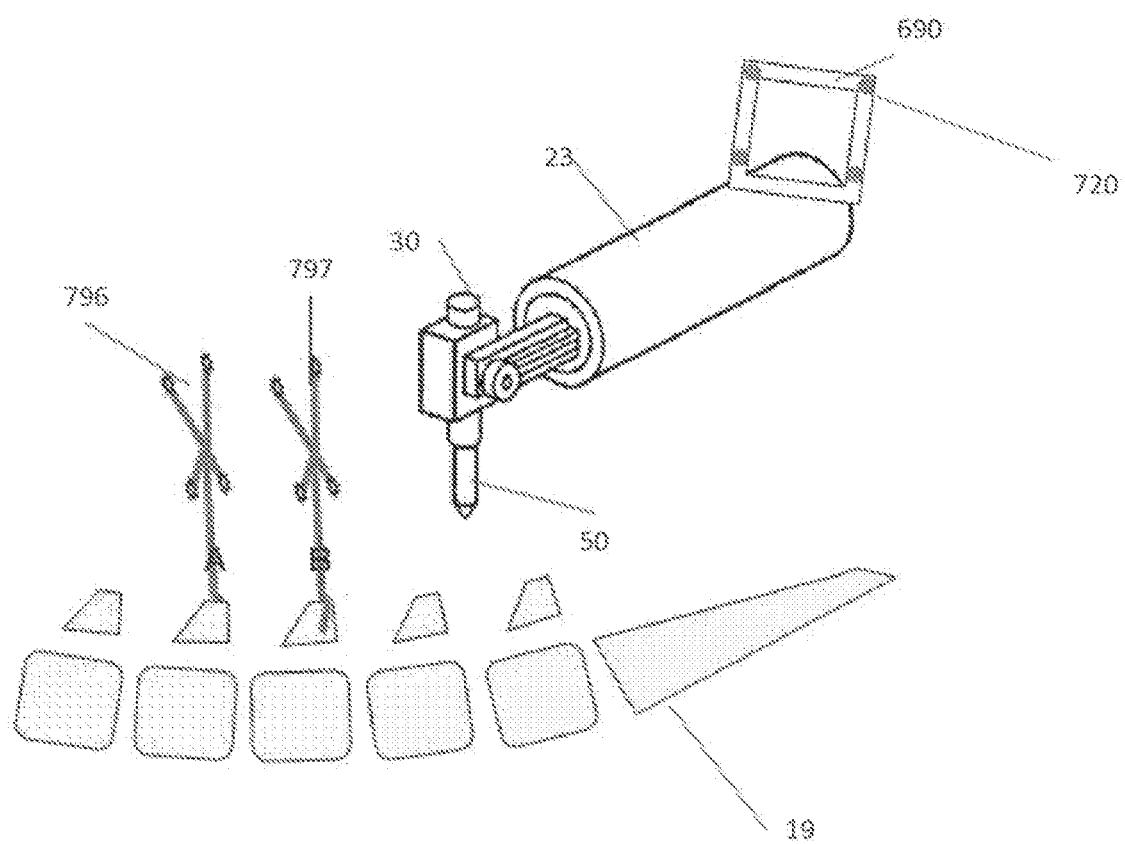
FIGS. 50B-50D show various illustrations of one portion of a spine with two independent trackers with markers in accordance with one embodiment of the invention.
Figure 50C:
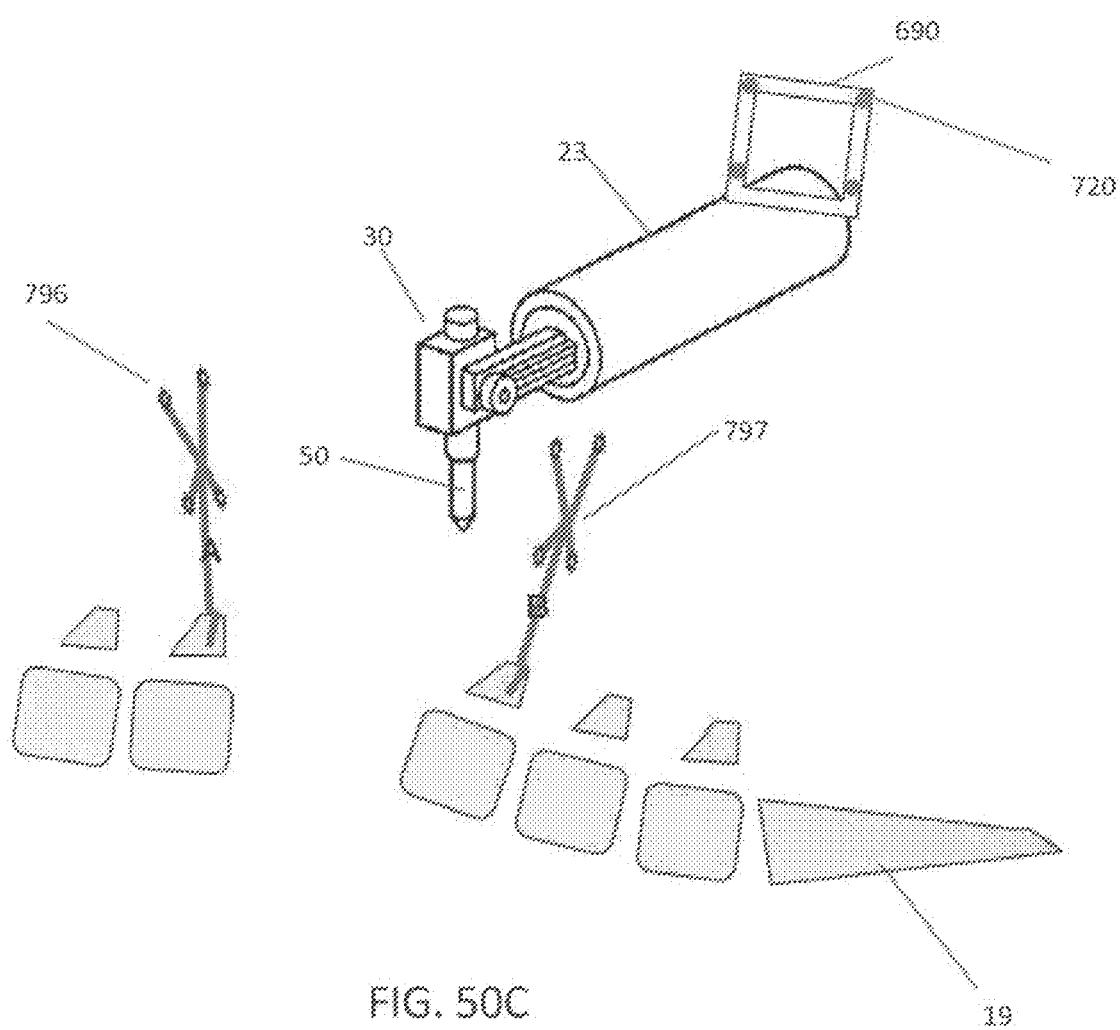
Figure 50D:
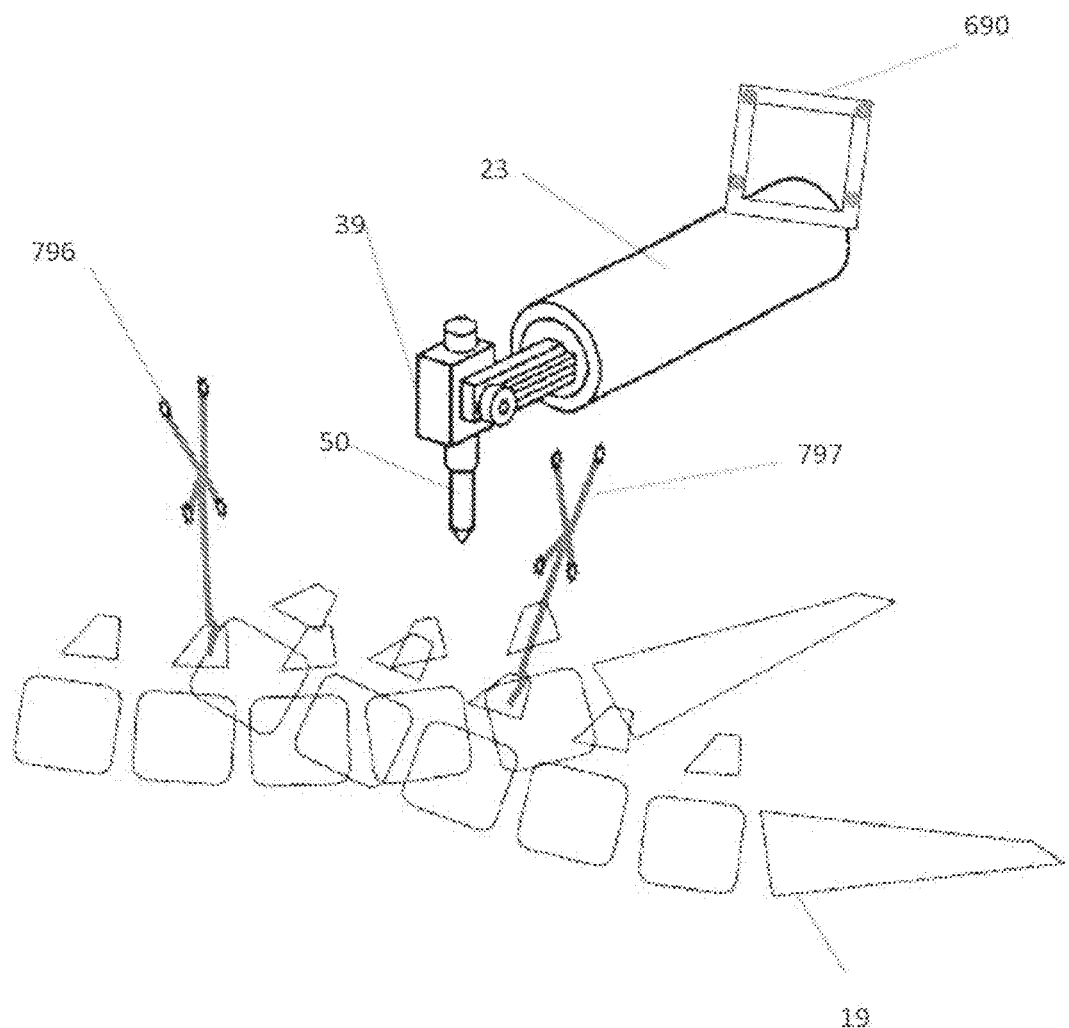
Figure 50E:
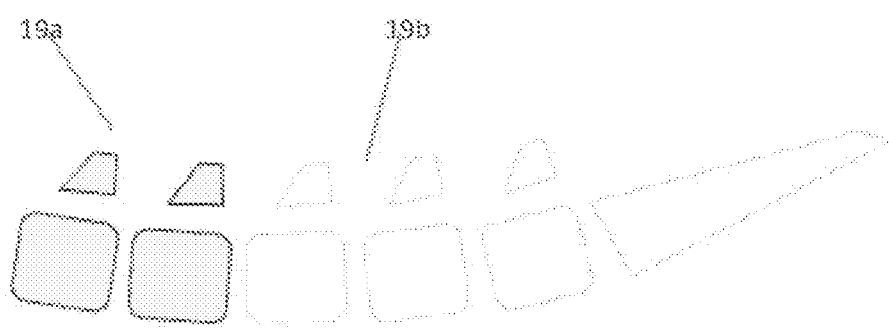
FIG. 50E illustrates a representation of a display of a portion of a spine based on the location of a tracker in accordance with one embodiment of the invention.
Figure 50F:
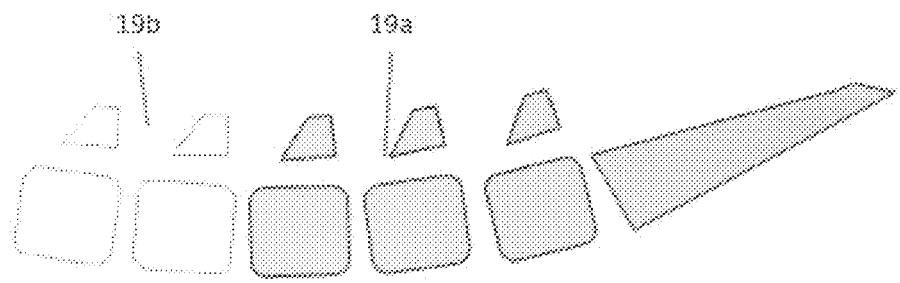
FIG. 50F illustrates a representation of a display of a portion of a spine based on the location of a tracker in accordance with one embodiment of the invention.
Figure 50G:
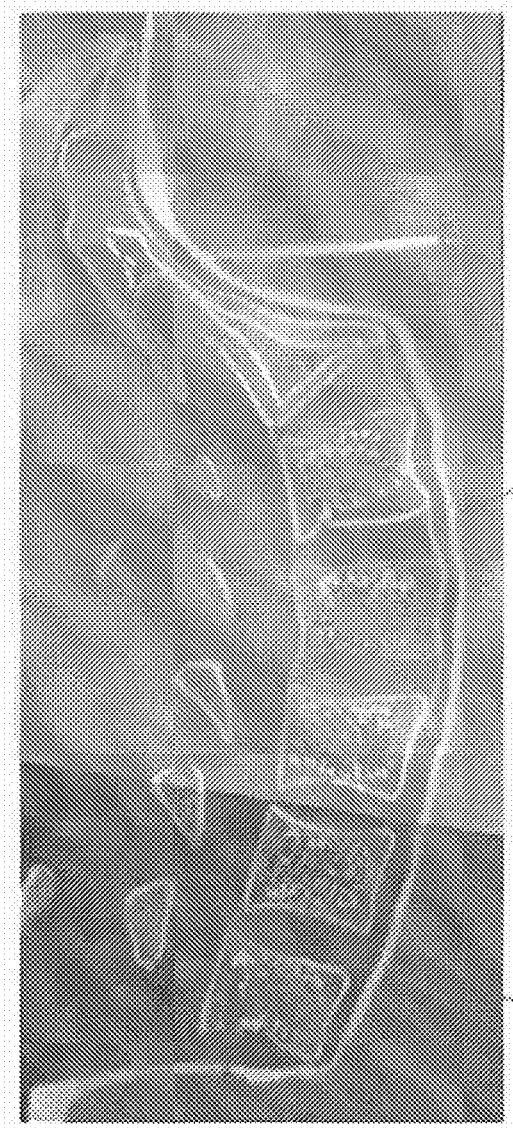
FIGS. 50G-50H represent images of segmented CT scans in accordance with one embodiment of the invention.
Figure 50H:
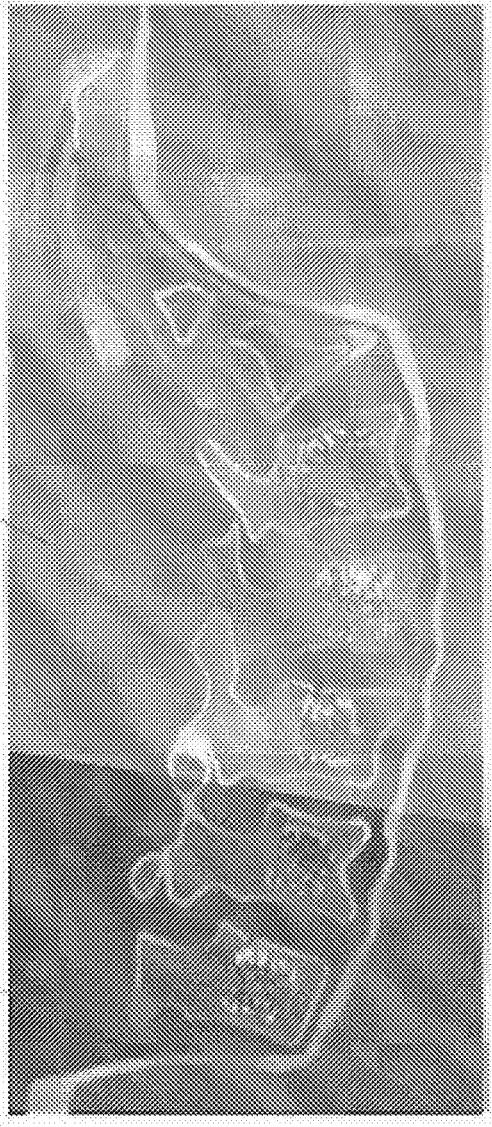

In some embodiments, if there is snaking of the spine, for example, when conventional screws are driven in place or the surgeon applies a focal force on one portion of the spine, the two marker trees will move (illustrated as 795*a* for tracker 795 and 800*a* for tracker 800) by different amounts and to different orientations (illustrated in FIG. 50A). The altered orientations and positions of the trackers 795, 800 can be used to calculate how the spine has snaked and adjust the perceived position of the robot 15 or probe to compensate. In some embodiments, because there are multiple degrees of freedom of the vertebrae, knowledge of how the two trackers' orientations shift does not allow a single unique solution. However, it can be assumed that the bending is symmetrical among all the vertebrae to calculate the new position, and even if this assumption is not perfect, it should provide a reasonably accurate solution. In some embodiments, experiments tracking how cadaveric spines respond to focal forces can be used to collect data that will help to predict how the two ends of the lumbar spine would respond during particular types of external loading.

Figure 51:
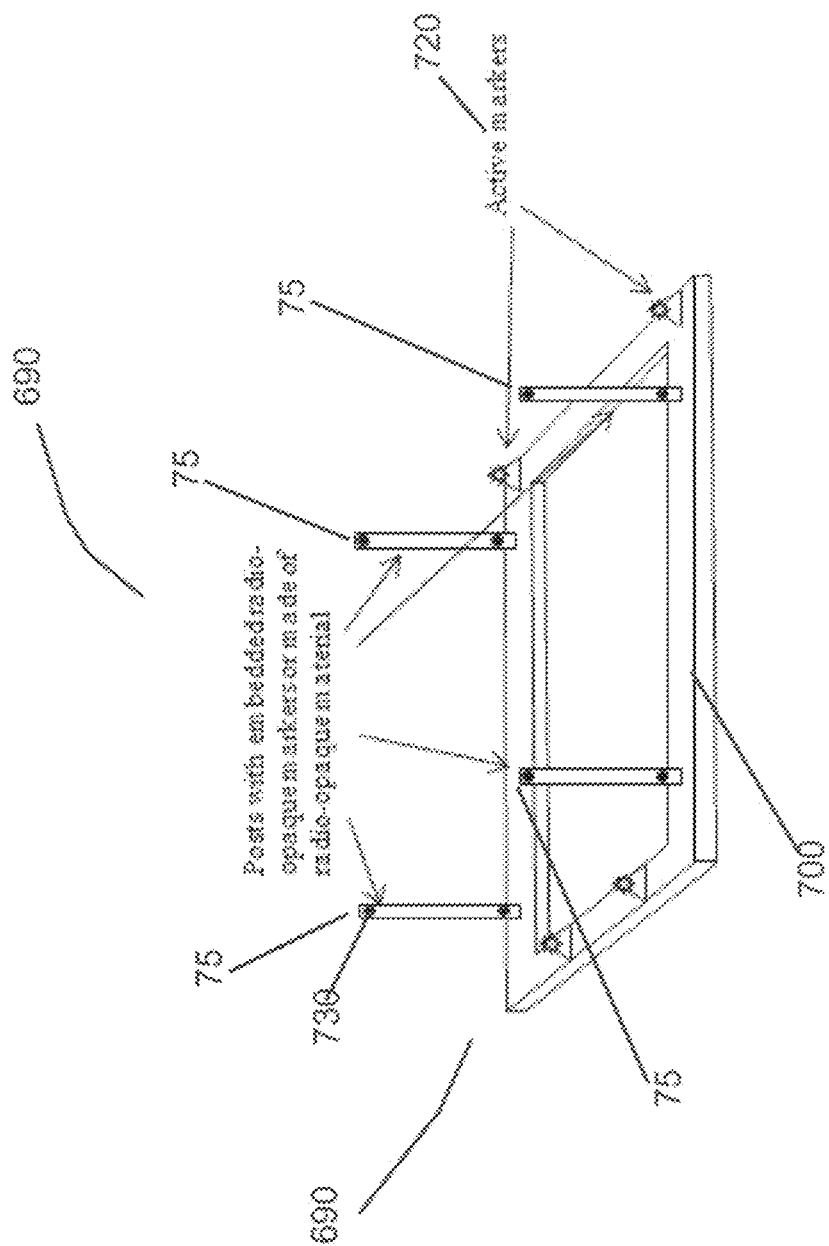
FIG. 51 shows an example of a fixture for use with fluoroscopic views in accordance with one embodiment of the invention.

In some embodiments, it is possible to use the same surgical robot 15 already described for navigation with 3D imaging in a different setting where only 2 fluoroscopic views are obtained. In this instance, the surgical robot 15 will be able to accurately move to a desired position that is pre-planned on these two fluoroscopic views. Since the two fluoroscopic views can represent views to which the surgeon or radiologist is already accustomed, planning trajectories on these views should be straightforward. In obtaining the fluoroscopic views, a method is needed to establish the position of the coordinate system of the anatomy relative to the robot's 15 coordinate system. In some embodiments, a way to fulfill this registration is to obtain the fluoroscopic views while a targeting fixture 690 that includes features that are identifiable on the fluoroscopic images is attached to the patient 18. For example, FIG. 51 shows an example of a fixture for use with fluoroscopic views in accordance with one embodiment of the invention. In some embodiments, the targeting fixture 690 as shown can include features that will appear on 2 fluoroscopic views and active markers 720 for real-time tracking. This targeting fixture 690 has properties that will aid in the ability to set up the coordinate system of the anatomy from the two fluoroscopic images. For example, in some embodiments, the posts 75 as shown are symmetrically spaced around the frame 700 so that posts 75 and/or their embedded markers 730 would overlay on an x-ray image. That is, if there is no parallax, two posts 75 in an aligned position would appear as a single line segment instead of two, or two posts 75, each with two embedded radio-opaque markers 730, would appear as two dots instead of four dots on an x-ray image. These features allow and facilitate the patient 18 or fluoroscopy machine's position to be adjusted until such overlapping is achieved. Similarly, from top or bottom view, the posts 75 and/or their embedded markers 730 would overlap, with a single post appearing as a dot instead of a line segment or two embedded markers 730 in one post appearing as one dot instead of two once the fluoroscopy machine and patient 18 are adjusted to be aligned as desired. In some embodiments, the posts 75 may be designed to be temporarily inserted (i.e., they are present during the scan but are later unplugged from the frame during the procedure so they are not in the way of the user). In some embodiments, the active markers 720 are necessary for later tracking but do not necessarily need to be present during the scan as long as they can be attached with precision to a known position on the frame 700 relative to the radio-opaque makers 730. For example, in some embodiments, conventional sockets on the fixture 690 could later allow the active markers 720 to be snapped in to a location dictated by the manufacturing of the frame 700 or calibrated using a digitizing probe. Furthermore, note that the goal is not necessarily to get perfect lateral and anteroposterior anatomical views of the spine or other anatomy. The goal is to get alignment of the fixture 700 on the x-ray view.

Although it may be beneficial in understanding what it being visualized to also achieve alignment with the anatomical planes, it is unnecessary for registration. An example of how the targeting fixture 690 might appear on anteroposterior or "A-P" and lateral x-rays when affixed to the patient's back but not yet aligned with the x-ray projection is shown in FIGS. 52A-52B.

In some embodiments, after adjusting the position of the patient 18 and fluoroscopy unit, an overlay with good certainty may be obtained for images with radio-opaque markers 730. FIGS. 53A-B for example illustrates expected images on anteroposterior and lateral x-rays of the spine with a well aligned fluoroscopy (x-ray) machine in accordance with one embodiment of the invention. As shown, the fluoroscopic images do not need the frame 700 to be positioned exactly aligned with the anatomy or rotated to be vertical and horizontal. In some embodiments, the fluoroscopically obtained images are not required to have the correct aspect ratio such that the image properly represents a calibrated coordinate system. In some embodiments, it is possible to rescale the image to adjust the aspect ratio using known distances between posts 75 or between markers 730, x-ray visible lengths of posts 75, or assuming the image should be perfectly circular or square. These distances are known in advance of obtaining the images by the manufacturing process, or by calibration using a digitizing probe or other means. In some embodiments, provided parallax is considered, the ratio of known inter-marker distances can be compared to the ratio of inter-marker distances measured on planar images and used to scale the planar image to achieve the correct aspect ratio. In some embodiments, it is not necessary to rescale the image, but it may help the user to better visualize the image and anatomy when it is displayed in the appropriate aspect ratio. In some embodiments, the comparison can also be used to determine the number of pixels per mm on the image for use in determining relative position of radio-opaque markers 730 and planned trajectory tip and tail. In some embodiments, rescaling facilitates equations for mapping between 2D and 3D space because the pixels per mm in the x and y direction are the same value.

In some embodiments, after obtaining two images, the two images can be used to construct a 3D Cartesian coordinate system because they represent images of the same thing (the fixture) from two orthogonal views. For example, the A-P image could be used to represent the X-Z plane, and the lateral image could be used to represent the Y-Z plane. Radio-opaque markers 730 on the A-P image have known x-axis and z-axis coordinates (as recorded from the manufacturing process or by calibration using a digitizing probe or other means), and the same radio-opaque markers 730 have known y-axis and z-axis coordinates on the lateral image. Therefore, in some embodiments, the x-axis, y-axis, and z-axis coordinates of the markers 730 can be found on the two images, and the positions of the anatomy and planned trajectories relative to these reference points can be related to these reference positions. In some embodiments, the mapping of a point from 3D space to the 2D image and vice versa can be performed knowing the constant mm per pixel, C, on coronal or sagittal images, and multiplying or dividing points by these constants if the center of the image and coordinate system have been shifted to overlap.

FIGS. 54A-B illustrates expected images on anteroposterior and lateral x-rays of the spine with a well aligned fluoroscopy (x-ray) machine in accordance with one embodiment of the invention. As shown, FIGS. 54A-B include overlaid computer-generated graphical images showing the planned trajectory (red 6001) and the current actual position of the robot 15 end-effectuator 30 (light blue 6003). The red circle in 6001 is provided for the user to identify the tail of the planned trajectory (as opposed to the tip). In other embodiments, the line segment could have different colored ends or different shapes on each end (pointed vs. blunt) for distinguishing tip from tail.

In some embodiments, assuming the A-P x-ray represents the X-Z plane and the lateral x-ray represents the Y-Z plane, the algorithm for planning a trajectory and relating this planned trajectory to the robot 15 coordinate system can include the following steps; 1). Draw a line on the A-P and lateral x-ray views representing where the desired trajectory should be positioned (see for example FIGS. 54A-54B). In some embodiments, the next step can include; 2). from the A-P view, find the X and Z coordinates of the reference opaque markers and of the tip and tail of the desired trajectory, and 3). from the lateral view, find the Y and Z coordinates of the reference opaque markers and of the tip and tail of the desired trajectory, and 4). based on the known coordinates of the active markers relative to the opaque markers, transform the X,Y,Z coordinates of the tip/tail into the coordinate system of the active markers. In some embodiments, the method can include store the locations of tip and tail in this coordinate system in computer 100 memory for later retrieval. In some embodiments, the next steps of the method can include; 5). at any frame in real time, retrieve the active marker 720 locations in the coordinate system of the cameras 8200, and 6). based on the stored coordinates of the tip and tail relative to the active markers 720 and the current location of the active markers 720 in the coordinate system of the cameras 8200, calculate the current location of the desired tip and tail in the coordinate system of the cameras 8200. In some embodiments, the next steps of the method can include; 7). transform the active marker 720 locations and the trajectory tip/tail locations into the coordinate system of the robot 15 using methods described before in which markers on the robot 15 are utilized as references, and 8). send the robot 15 to the desired tip/tail locations using methods described previously.

In some embodiments, while the robot 15 moves to position itself in the desired orientation and position, it is possible to overlay a graphical representation of the current location of the robot 15 on the fluoroscopic images by a method that can include; 1). retrieve current location of the robot 15 guide tube 50 in the coordinate system of the cameras 8200 based on active markers 720 attached to the robot, and 2). transform the guide tip and tail to the coordinate system of the medical images based on the locations of active markers on the targeting fixture 690, and 3). represent the current positions of tip/tail of the guide tube 50 on the A-P image by a line segment (or other suitable graphical representation) connecting the X,Z coordinates of the tip to the X,Z coordinates of the tail (see for example FIGS. 54A-B), and 4). represent the current positions of tip/tail of the guide tube 50 on the lateral image by a line segment (or other suitable graphical representation) connecting the Y,Z coordinates of the tip to the Y,Z coordinates of the tail.

Figures 55A, 55B:
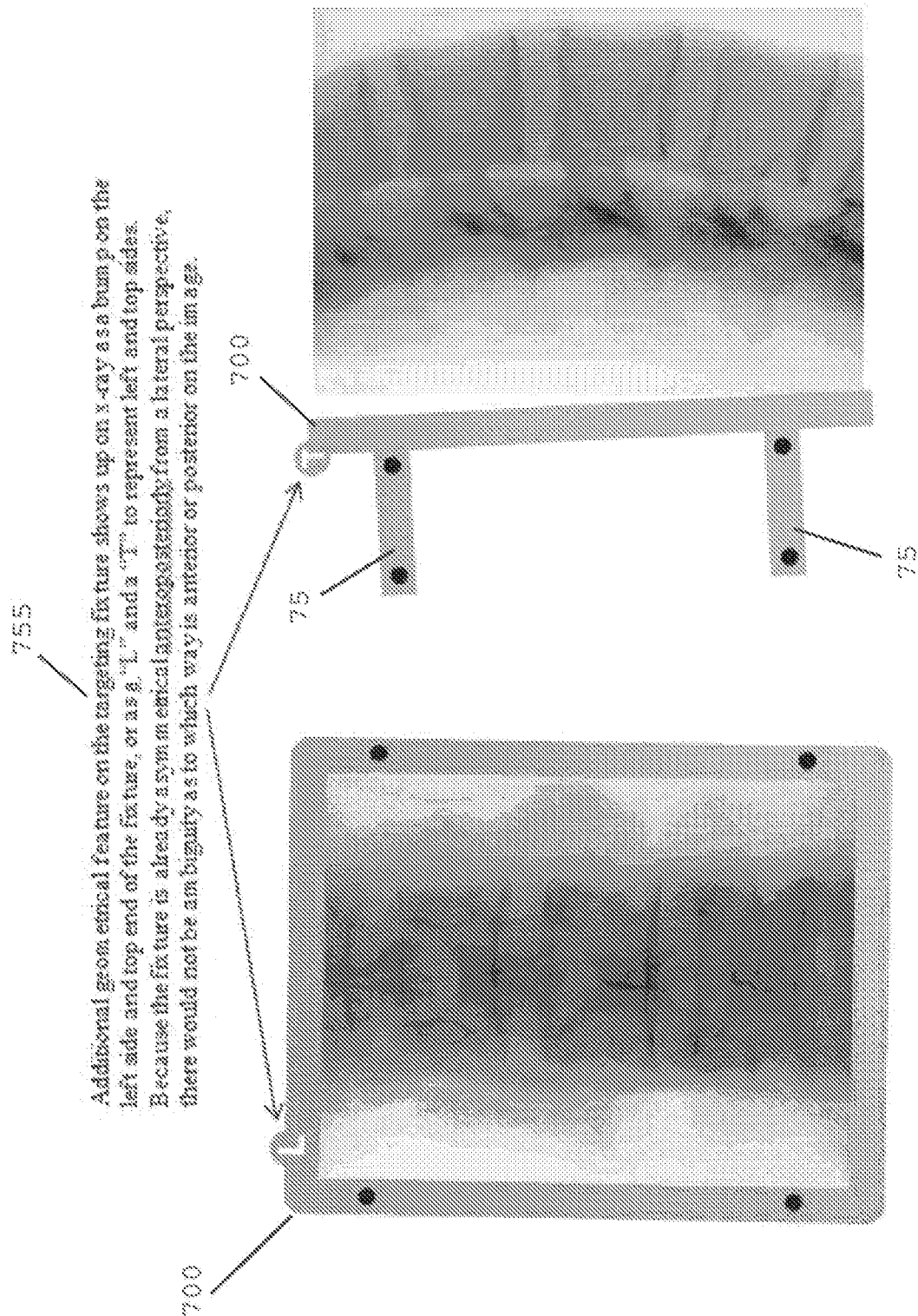
FIGS. 55A-55B illustrates expected images on anteroposterior and lateral x-rays of the spine with a well aligned fluoroscopy (x-ray) machine showing a feature on the targeting fixture designed to eliminate ambiguity about directionality in accordance with one embodiment of the invention.

In some embodiments, in constructing the Cartesian coordinate system based on the two images, it is important to consider directionality. That is, in some embodiments, an x-ray image of the X-Z plane could show positive X to the right and negative X to the left or vice versa. In some embodiments, it could show positive Z upward and negative Z downward or vice versa. In some embodiments, an x-ray image of the Y-Z plane could show positive Y to the right and negative Y to the left or vice versa. In some embodiments, it could show positive Z upward and negative Z downward or vice versa. In some embodiments, if an incorrect assumption is made about the directionality of one of the axes, it would mean that the constructed 3D coordinate system has one or more of its axes pointing in the wrong direction. In some embodiments, this may send the robot 15 to an incorrect position. In some embodiments, one way of ensuring the correct directionality is to query to the user requesting verification of directionality on the images and/or allowing them to flip (mirror) the images on the display 29, 150, 3401. In some embodiments, another way of ensuring the correct directionality is to design the targeting fixture 690 so that the radio-opaque markers 730 are spaced asymmetrically. In some other embodiments, another way of ensuring the correct directionality is to design the targeting fixture 690 with additional radio-opaque features that unambiguously identify top, bottom, left, right, front and rear on images. For example, FIGS. 55A-55B illustrates expected images on anteroposterior and lateral x-rays of the spine with a well aligned fluoroscopy (x-ray) machine. As shown, the targeting fixture 690 illustrated in FIGS. 55A-B includes a feature 755 designed to substantially eliminate ambiguity about directionality in accordance with one embodiment of the invention. As shown, the feature 755 could reveal a "L", "T", or other symbol on the x-ray when the view is correct so as to substantially eliminate directional ambiguity. Furthermore, the "T" feature could be drawn in script (e.g., $\mathscr{T}$) or other asymmetric letter or symbol used so that if an inverted or mirrored x-ray image is presented, the inverted nature is clear and can be compensated.

Figure 56:
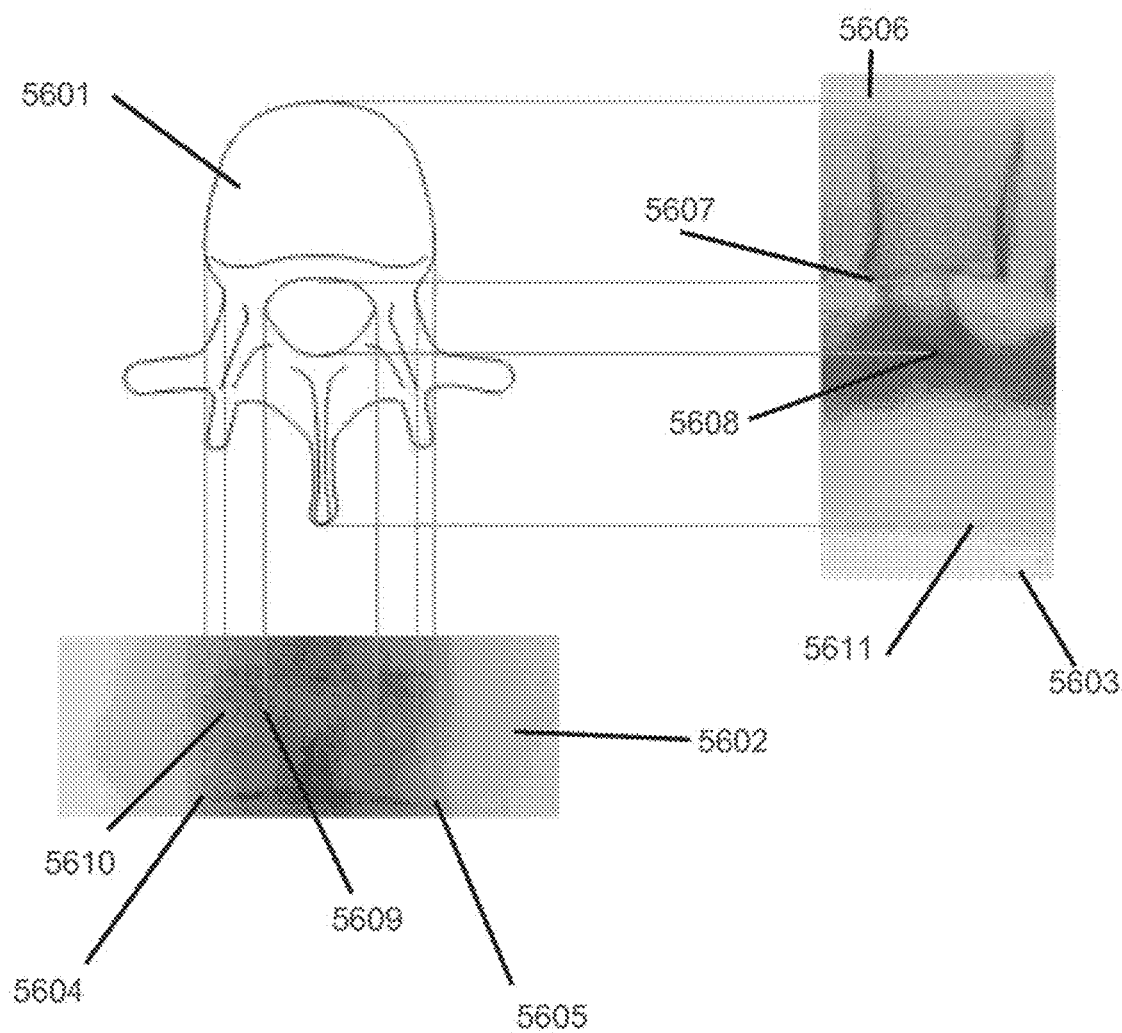
FIG. 56 illustrates an axial view of a spine showing how a cartoonish axial approximation of the spine can be constructed based on lateral and anteroposterior x-rays in accordance with one embodiment of the invention.

In some embodiments, the algorithm described here provides the user with two perpendicular x-ray views from which to plan a trajectory, and provides a visual feedback of the current location of a probe. Typically, these two views might be lateral and anteroposterior (A-P) views. In some embodiments, it might also be desirable for the user to see a third plane (for example, an axial plane). Based on knowledge of the anatomy and landmarks visible on the x-rays, in some embodiments, it is possible to create a rough "cartoon" showing an axial view. In some embodiments, the cartoon may help the user understand the approximate current location of the robot 15 or probe. FIG. 56 shows how such a cartoon can be generated from the x-rays. Note that the cartoon will be imperfect with respect to details such as the curvature of the vertebral body, but key landmarks such as the pedicle boundaries should be reasonably well defined. Such an approach would be based on how a typical vertebra is shaped. For example, FIG. 56 illustrates an axial view of a spine showing how a cartoonish axial approximation of the spine 5601 can be constructed based on a lateral x-ray 5602 and an anteroposterior x-ray 5603 in accordance with one embodiment of the invention. As shown, locations where key landmarks on the adjacent x-ray views intersect the cartoon can be identified with horizontal or vertical lines overlapping the cartoon and x-rays. The user positions these lines using a software interface or software automatically recognizes these features on the x-rays so that the lines intersect the key landmarks, such as a line just tangent to the vertebral body left border 5604, vertebral body right border 5605, vertebral body anterior wall 5606, vertebral body posterior wall 5607, posterior spinal canal 5608, left inner pedicle border 5609, left outer pedicle border 5610, tip of spinous process 5611, etc. After using the software to move these lines so that they intersect correct locations on the x-rays, the software can then stretch and morph the cartoon as needed to fit these anatomical limits. A view on the computer display of the axial plane showing this cartoon and the planned trajectory and current position of robot or probe can be generated by the software to provide additional visual feedback for the user.

Figure 57A:
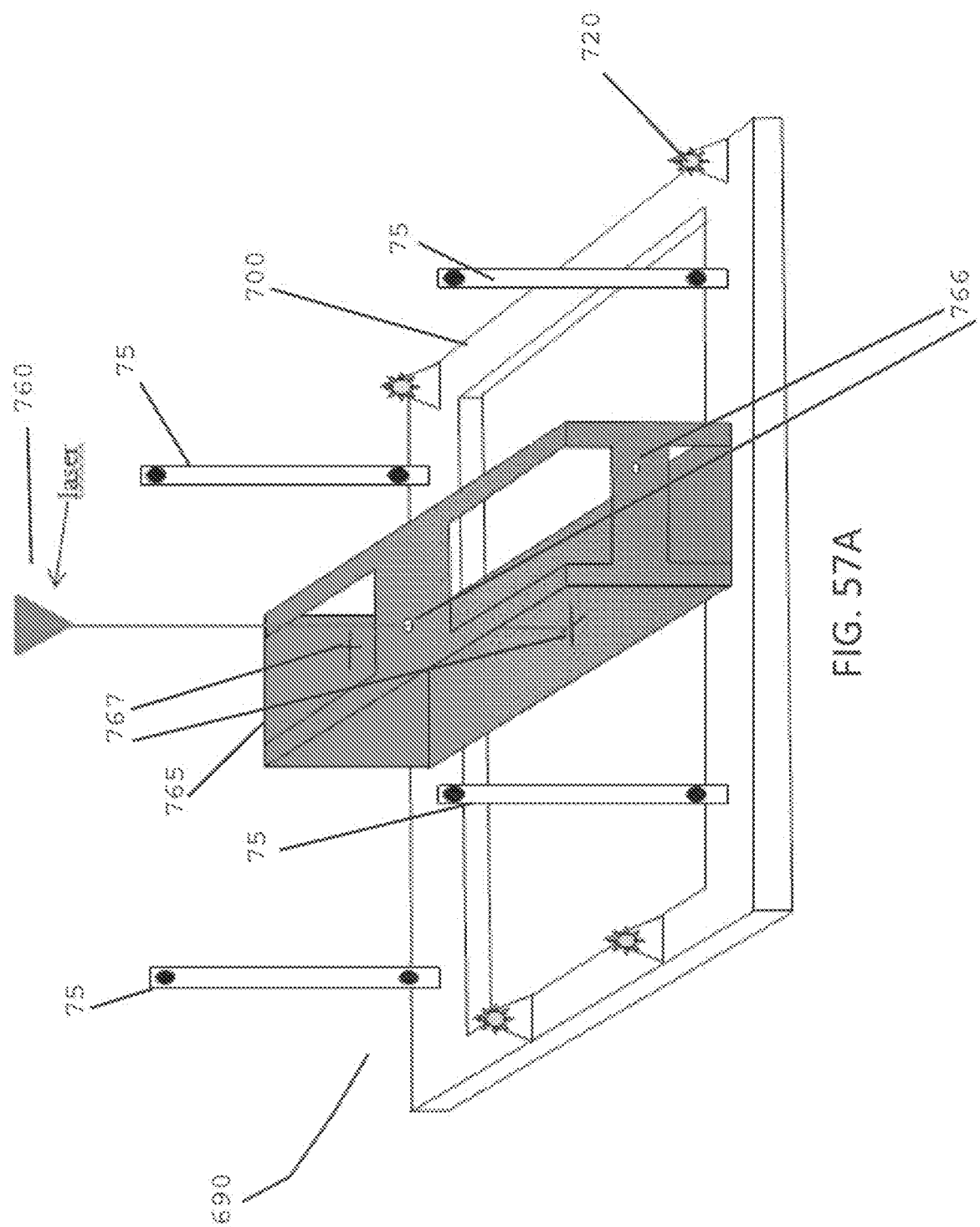
FIGS. 57A-57B illustrates examples of targeting fixtures that facilitate desired alignment of the targeting fixture relative to the x-ray image plane in accordance with one embodiment of the invention.
Figure 57B:
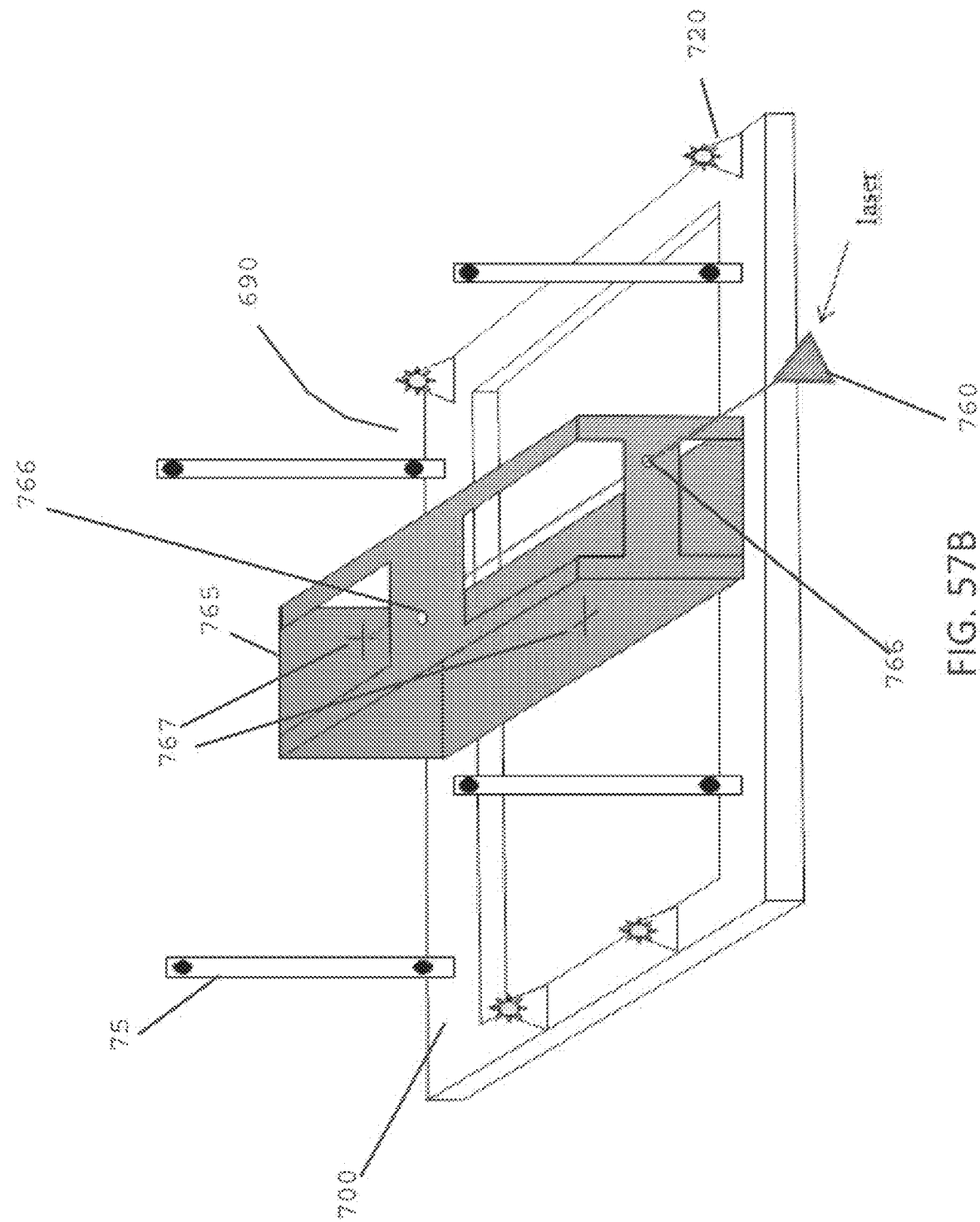

In some embodiments, in order to achieve well aligned x-rays like those shown in FIGS. 53A-B, one possible method is trial and error. For example, the user can try to get the x-ray machine aligned to the targeting fixture 690, attempt to assess alignment by eye, then shoot an x-ray and see how it looks. In some embodiments, if dots are misaligned (for example as shown in FIGS. 52A-52B), adjustments would be made and a new x-ray image can be prepared. This method can be effective but can be dependent on the skill of the operator in assessing alignment and making corrections, and therefore can result in x-ray exposure to the patient 18 and staff. In some embodiments, it is possible to create a tool to assist in the alignment of the targeting fixture 690. In some embodiments, the tool could be a conventional laser that can be attached to the emitter or collector panel of the x-ray machine, capable of passing a laser beam parallel to the direction that the x-rays will travel. In some embodiments, the laser could be attached temporarily (using a conventional magnet or adhesive) or permanently, connected to an arm extending from the x-ray machine and oriented in the correct direction, enabling the directed beam to shine down toward the fixture 690. In some embodiments, if the fixture 690 has a geometric, electronic, or other features capable of visual or other feedback to the user regarding the vector direction of this laser light, it would allow alignment of the x-ray arm without taking any x-rays. An example of such a feature is shown in FIG. 57A and FIG. 57B. FIGS. 57A-B illustrates examples of targeting fixtures 690 that facilitate desired alignment of the targeting fixture 690 relative to the x-ray image plane in accordance with one embodiment of the invention. As shown, some embodiments include a feature 765 temporarily added to the targeting fixture 690 In some embodiments, feature 765 facilitates desired alignment of the targeting fixture 690 relative to the x-ray image plane from an AP view when a laser (attached to the face of the x-ray emitter or collector) is directed through the opening 766 and toward the crosshairs 767 at the base. In some embodiments, if the laser light does not strike the crosshairs 767 dead center, further adjustment of the x-ray unit's orientation is needed. The temporarily added feature 765 that facilitates desired alignment of the targeting fixture 690 relative to the x-ray image plane from a lateral view when a laser (attached to the face of the x-ray emitter or collector) is directed through the opening and toward the crosshairs at the opposite face. In some embodiments, if the laser light does not strike the crosshairs dead center, further adjustment of the x-ray unit's orientation is needed.

In some embodiments, this method for aligning the radio-opaque markers 730 would have the advantage over trial-and-error methods that are affected by parallax effects, and as described below, do not confound the ability to align markers as needed. For example, with parallax, it may not be clear to the user when good alignment of the markers 730 is achieved, depending on how symmetrically spaced the markers 730 are about the center of the image.

Figures 58A, 58B:
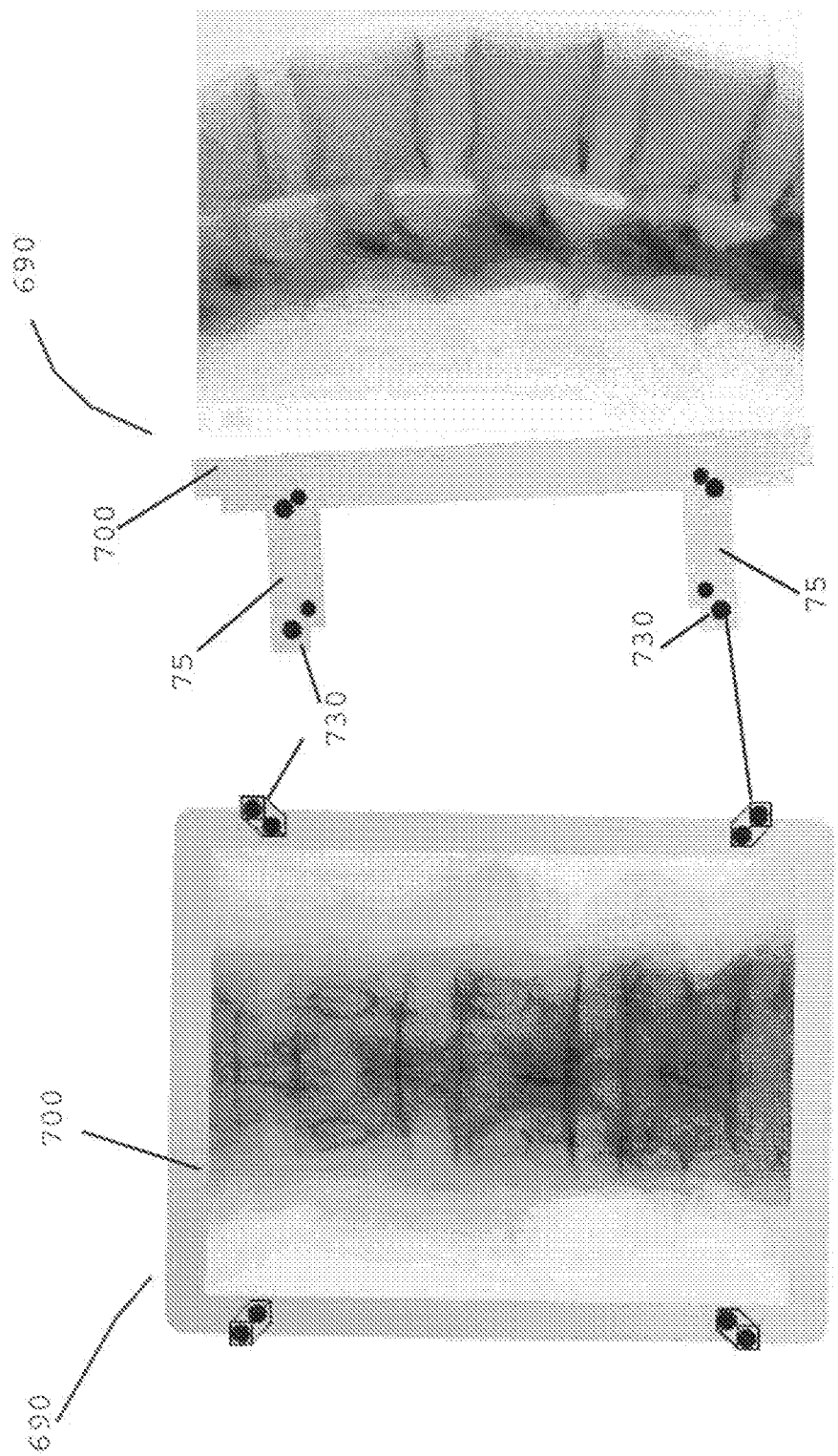
FIGS. 58A-58B illustrates expected images on anteroposterior and lateral x-rays of the spine with a well aligned fluoroscopy (x-ray) machine when parallax is present in accordance with one embodiment of the invention.

With parallax error, the x-rays may not pass through the subject in a straight line and instead travel from emitter to receiver in a conical pattern. This conical path can produce an image where the details of anatomy on the 2D x-ray that are closer to the emitter of the x-rays will appear farther apart laterally than details of the anatomy that are closer to the receiver plate. In the case of x-ray images in FIGS. 53A-B, instead of the radio-opaque markers 730 appearing overlaid, they may appear as shown in FIGS. 58A-B. For example, FIGS. 58A-B illustrates expected images on anteroposterior and lateral x-rays of the spine with a well aligned fluoroscopy (x-ray) machine when parallax is present in accordance with one embodiment of the invention. As shown, parallax affects spacing symmetrically about the x, y center of the image, with locations of markers 730 closer to the receiver plate of the x-ray unit appearing closer to the center of the image.

Further, in the description, two terms used are "near plane" and "far plane"—these terms refer to markers in the 2D views that appear farther apart or closer together because of parallax. The reason markers are farther apart or closer together is because of their proximity to the emitter or collector of the x-ray machine, with markers nearer the emitter appearing farther apart and markers nearer the collector closer together. However, rather than referencing distance from emitter and collector, "near plane" refers to markers that appear magnified (nearer to the eye) and "far plane" refers to markers that appear more distant.

Parallax will affect the image symmetrically about the center of the image. For example, in some embodiments, two markers 730 (one in near plane and one in far plane) that are in the same projected position, and are at the center of the image, may appear to be exactly on top of each other, whereas markers 730 in the near plane and far plane that are in the same projected position, but are close to the edge of the image may appear separated by a substantial distance.

FIG. 59A illustrates two parallel plates with identically positioned radio-opaque markers 730 in accordance with one embodiment of the invention. As shown, this illustrates possible marker 730 separation on an x-ray from markers 730 on two plates that are in the same projected line of sight. FIG. 59B illustrates resulting expected x-ray demonstrating how marker overlay is affected due to parallax using the two parallel plates as shown in FIG. 59A in accordance with one embodiment of the invention. By comparing the two parallel plates with identically positioned radio-opaque markers 730 shown in FIG. 59A, with the resulting expected x-ray in FIG. 59B demonstrates how marker overlay is affected due to parallax. In some embodiments, an algorithm can be implemented to account for this parallax effect. By doing so, the graphical image indicating the position of the probe or robot 15 can be adjusted to more accurately account for the perceived shift caused by parallax.

Figure 60:
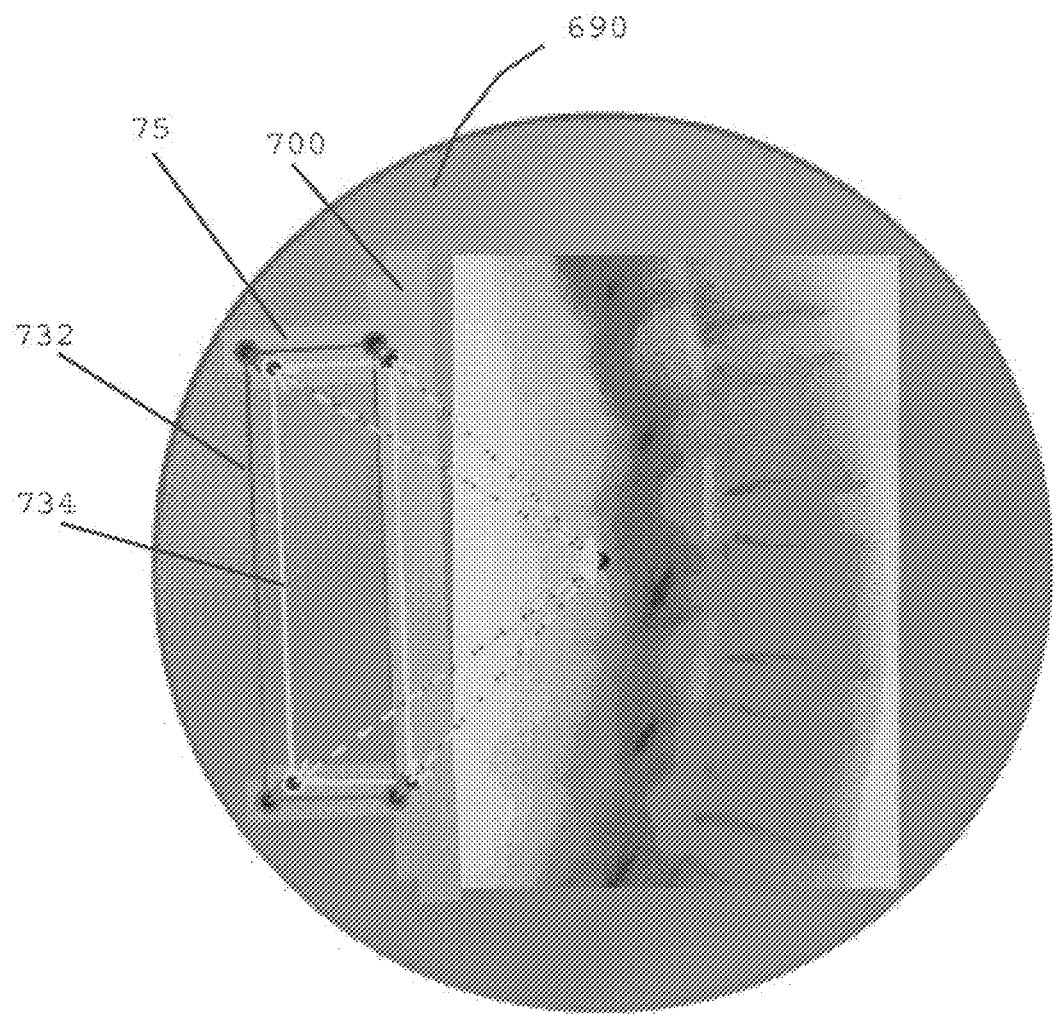
FIG. 60 shows a representation of the rendering of a computer screen with an x-ray image that is affected by parallax overlaid by graphical markers over the radio-opaque markers on two plates that have the same geometry in accordance with one embodiment of the invention.

In some embodiments, the algorithm requires information to be gathered on the near and far plane positions of the markers 730 on the image. That is, the user can indicate, using software or an automatic scan of the image, the spacing between markers 730, as shown in FIG. 60, which shows a representation of the rendering of a computer screen with an x-ray image that is affected by parallax overlaid by graphical markers 732, 734 over the radio-opaque markers 730 on two plates that have the same geometry in accordance with one embodiment of the invention. In some embodiments, the spacing between near plane and far plane markers 730 is known because of earlier calibration of the plates 700 in which the markers 730 are embedded, and the horizontal and vertical positions of the markers 730 are detectable relative to the center of the image. Therefore, in some embodiments, the parallax shift of the markers 730 can be calculated and applied to the mapping of any calculated three dimensional points on to the two dimensional image, and application of any necessary positional shift. For example, in some embodiments, it might be of interest to display a line segment on the two dimensional image representing how the shaft of a probe or robot 15 guide tube 50 (that is being tracked using optical tracking) would appear following x-ray imaging. In some embodiments, the x-axis, y-axis, and z-axis location of each end of the line segment (which has been calculated from optical tracking data) can be shifted based on the known parallax. Further, in some embodiments, a new line segment can be displayed that better represents how this projected object should appear on the 2D x-ray image.

Figure 61:
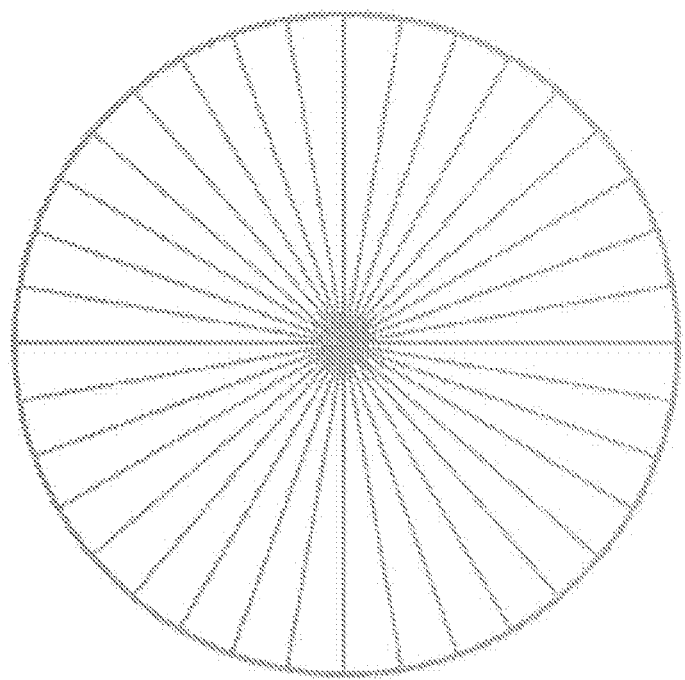
FIG. 61 shows a graphical overlay for the x-ray image screen intended to help the user physically line up the x-ray machine to get a view in which the markers on the two calibration plates shown in FIG. 59A in the case where parallax complicates the view in accordance with one embodiment of the invention.

In some embodiments, a method of implementing this system of two orthogonal fluoroscopy images to control a robot 15 can involve combining a robot 15 and fluoroscopy unit into a single interconnected device. There could be some advantages of this combination. For example, a conventional rotating turntable mechanism could be incorporated that could swing the fluoro arm into place, while at the same time swinging the robot arm 23 out of place (since the robot 15 would typically not be in the surgical field 17 at the same time as the fluoro arm). Furthermore, in some embodiments, the size of the robot arm 23 could be reduced compared to the stand-alone robot 15 because the fluoro arm's mass would serve as a counter-balance weight to help stabilize the robot arm 23. Moreover, in some embodiments, with integration, the fluoroscopy unit can more quickly transfer the image to the computer 100 and overlay with a graphical plot, for instance, as line segments starting at the center of the image and extending radially (similar to pie slices) around the image to facilitate appropriate marker 730 overlay. In some embodiments, overlaid near and far plane markers 730 should always fall on the same ray if the plates 690 with embedded markers 730 on the subject are aligned substantially parallel (see for example FIG. 61 which shows a graphical overlay for the x-ray image screen intended to help the user physically line up the x-ray machine). In some embodiments, the graphical overlay for the x-ray image screen can help the user physically line up the x-ray machine to avoid parallax. With parallax, any pair of corresponding markers on the 2 plates should lie on the same radial line, although the one in the far plane will lie closer to the middle of the image. In some embodiments, this overlay could be a physical object such as transparent film, or a computer-generated graphical image. In some embodiments, lines are spaced radially by 10 degrees, but actual spacing (frequency of lines) and regions in which lines are drawn could be user selectable.

Some embodiments can include mapping a 3D anatomical coordinate system on to two 2D orthogonal views (and vice versa) while considering parallax. For example, in some embodiments, a rigid frame is mounted to the patient and two perpendicular x-rays are taken to create a 3D coordinate system. To define this 3D coordinate system, a method is needed to map points from the 2D views (each with parallax) to the 3D volume and vice versa. The 3D coordinate system has coordinates x, y, z while the two 2D coordinate systems have coordinates $x_{AP}$, $z_{AP}$ and $x_{Lat}$, $z_{Lat}$ ("AP" for "anteroposterior" and "Lat" for "lateral" views).

In some embodiments, it can be assumed that the x-ray path from emitter to receiver is conical, and therefore linear interpolation/extrapolation can be used to adjust the positions of represented points. In some embodiments, software can calculate the distance of each landmark from the center of the image (indicated by dashed or dotted arrows). These distances, together with the known distance between near plane and far plane plates, can provide the necessary information to account for the parallax shift when mapping graphical objects whose positions are known in 3D back on to this 2D image.

Some embodiments can include solving to map x, y, z onto $x_{AP}$, $z_{AP}$ and $x_{Lat}$, $z_{Lat}$. For example, consider two intermediate 2D AP and lateral views represented as follows:

$$x_{ta} = (x - x_{oa})s_{AP}$$

$$z_{ta} = (z - z_{oa})s_{AP}$$

$$y_{tl} = (y - y_{ol})s_{Lat}$$

$$z_{tl} = (z - z_{ol})s_{Lat}$$

Where $x_{ta}$ and $z_{ta}$ can be called temporary scaled values of x and z in the AP plane, $y_{tl}$ and $z_{tl}$ are temporary scaled values of y and z in the Lat plane, $s_{AP}$ is the scaling factor in the AP plane, determined from the known near plane[1] marker spacing. $s_{Lat}$ is the scaling factor in the Lat plane, determined from the known near plane marker spacing of the lateral markers, and $x_{oa}$, $z_{oa}$, $y_{ol}$, and $z_{ol}$ are offsets in AP and Lat planes that position the markers such that they are as they appear centered about the image determined from registered positions of the markers on the images. In other words, $(x_{ta}, z_{ta})=(0, 0)$ represents the center of the AP image and $(y_{tl}, z_{tl})=(0, 0)$ represents the center of the lateral image. These planar values would be enough to display a 2D representation if no parallax were present or near plane markers were only being displayed.

In some embodiments, to find $x_{oa}$, $z_{oa}$, $y_{ol}$, and $z_{ol}$ consider pairs of points on the x-rays, because the ratio of distance from center on the x-ray is the same as the ratio of distance from center on the temporary scaled values. For example:

$$\frac{x_{AP1}}{x_{AP2}} = \frac{x_{ta1}}{x_{ta2}} = \frac{(x_1 - x_{oa})s_{AP}}{(x_2 - x_{oa})s_{AP}}$$

$$\left(\frac{x_{AP1}}{x_{AP2}}\right)(x_2 - x_{oa}) = x_1 - x_{oa}$$

$$x_2\left(\frac{x_{AP1}}{x_{AP2}}\right) - x_1 = x_{oa}\left(\frac{x_{AP1}}{x_{AP2}}\right) - x_{oa}$$

$$x_{oa}\left(\frac{x_{AP1}}{x_{AP2}} - 1\right) = x_2\left(\frac{x_{AP1}}{x_{AP2}}\right) - x_1$$

$$x_{oa} = \frac{x_2\left(\frac{x_{AP1}}{x_{AP2}}\right) - x_1}{\frac{x_{AP1}}{x_{AP2}} - 1}$$

In some embodiments, it can be seen from this equation that it is important to stay away from points where $x_{AP1} \approx x_{AP2}$ because it would result in a divide by zero error. Similar equations can be written for $z_{oa}$, $y_{ol}$, and $z_{ol}$ as follows:

$$z_{oa} = \frac{z_2\left(\frac{z_{AP1}}{z_{AP2}}\right) - z_1}{\frac{z_{AP1}}{z_{AP2}} - 1}$$

$$y_{ol} = \frac{y_2\left(\frac{y_{Lat1}}{y_{Lat2}}\right) - y_1}{\frac{y_{Lat1}}{y_{Lat2}} - 1}$$

$$z_{ol} = \frac{z_2\left(\frac{z_{Lat1}}{z_{Lat2}}\right) - z_1}{\frac{z_{Lat1}}{z_{Lat2}} - 1}$$

This mapping to temporary scaled values gets the near plane markers mapped correctly, but adjustment is needed to account for any position other than near plane as follows:

$$x_{AP} = x_{ta} k_a(y)$$

$$z_{AP} = z_{ta} k_a(y)$$

$$y_{Lat} = y_{tl} k_l(x)$$

$$z_{Lat} = z_{tl} k_l(x)$$

As specified, $k_a$ is a function of y and $k_l$ is a function of x. For $k_a$, this function is a linear interpolation function, in which if y is the y position of the near plane ($y_n$), then $k_a=1$ and if y is the y position of the far plane ($y_f$), then $k_a$ is the ratio of far plane spacing to near plane spacing, $r_a$. For $k_l$, this function is a linear interpolation function, in which if x is the x position of the near plane ($x_n$), then $k_l=1$ and if x is the x position of the far plane ($x_f$), then $k_l$ is the ratio of far plane spacing to near plane spacing, $r_l$. Note that $y_n$, $y_f$, $x_n$, and $x_f$ are in a coordinate system with the origin at the center of the image.

$$k_a = 1 - \left(\frac{y_{tl} - y_n}{y_f - y_n}\right)(1 - r_a)$$

$$k_l = 1 - \left(\frac{x_{ta} - x_n}{x_f - x_n}\right)(1 - r_l)$$

Combining equations, $$x_{AP} = x_{ta}\left[1 - \left(\frac{y_{tl} - y_n}{y_f - y_n}\right)(1 - r_a)\right]$$

$$z_{AP} = z_{ta}\left[1 - \left(\frac{y_{tl} - y_n}{y_f - y_n}\right)(1 - r_a)\right]$$

$$y_{Lat} = y_{tl}\left[1 - \left(\frac{x_{ta} - x_n}{x_f - x_n}\right)(1 - r_l)\right]$$

$$z_{Lat} = z_{tl}\left[1 - \left(\frac{x_{ta} - x_n}{x_f - x_n}\right)(1 - r_l)\right]$$

It should also be possible to map $x_{AP}$, $z_{AP}$, $y_{Lat}$, and $z_{Lat}$ onto x, y, z. Having 4 equations and 4 unknowns:

$$x_{AP} = x_{ta}\left[1 - \left(\frac{y_{tl} - y_n}{y_f - y_n}\right)(1 - r_a)\right]$$

$$1 - \frac{x_{AP}}{x_{ta}} = \left(\frac{y_{tl} - y_n}{y_f - y_n}\right)(1 - r_a)$$

$$\left(1 - \frac{x_{AP}}{x_{ta}}\right)\left(\frac{y_f - y_n}{1 - r_a}\right) = y_{tl} - y_n$$

$$y_{tl} = \left(1 - \frac{x_{AP}}{x_{ta}}\right)\left(\frac{y_f - y_n}{1 - r_a}\right) + y_n$$

Then substitute into this equation:

$$y_{Lat} = y_{tl}\left[1 - \left(\frac{x_{ta} - x_n}{x_f - x_n}\right)(1 - r_l)\right]$$

$$y_{Lat} = \left[\left(1 - \frac{x_{AP}}{x_{ta}}\right)\left(\frac{y_f - y_n}{1 - r_a}\right) + y_n\right]\left[1 - \left(\frac{x_{ta} - x_n}{x_f - x_n}\right)(1 - r_l)\right]$$

And solve for $x_{ta}$:

$$y_{Lat} = \left[\left(\frac{y_f - y_n}{1 - r_a}\right) - \frac{x_{AP}}{x_{ta}}\left(\frac{y_f - y_n}{1 - r_a}\right) + y_n\right]\left[1 - \left(\frac{1 - r_l}{x_f - x_n}\right)(x_{ta} - x_n)\right]$$

$$y_{Lat} = \left[\left[\left(\frac{y_f - y_n}{1 - r_a}\right) + y_n\right] - \left[\frac{x_{AP}}{x_{ta}}\left(\frac{y_f - y_n}{1 - r_a}\right)\right]\right]$$

$$\left[\left[1 + x_n\left(\frac{1 - r_l}{x_f - x_n}\right)\right] - \left[x_{ta}\left(\frac{1 - r_l}{x_f - x_n}\right)\right]\right]$$

$$y_{Lat} = \left[A - \frac{B}{x_{ta}}\right][C - Dx_{ta}]$$

$$y_{Lat} = AC - \frac{BC}{x_{ta}} - ADx_{ta} + BD$$

$$AC + BD - y_{Lat} = \frac{BC}{x_{ta}} + ADx_{ta}$$

$$(AD)x_{ta}^2 + (y_{Lat} - AC - BD)x_{ta} + (BC) = 0$$

Quadratic Formula:

$$x = \frac{-b \pm \sqrt{b^2 - 4ac}}{2a}$$

$$x_{ta} = \frac{-(y_{Lat} - AC - BD) \pm \sqrt{(y_{Lat} - AC - BD)^2 - 4(AD)(BC)}}{2(AD)}$$

Where:

$$A = \left(\frac{y_f - y_n}{1 - r_a}\right) + y_n$$

$$B = x_{AP}\left(\frac{y_f - y_n}{1 - r_a}\right)$$

$$C = 1 + \left(\frac{1 - r_l}{x_f - x_n}\right)x_n$$

$$D = \frac{1 - r_l}{x_f - x_n}$$

Then plug into this equation to solve for $y_{tl}$:

$$y_{tl} = \left(1 - \frac{x_{AP}}{x_{ta}}\right)\left(\frac{y_f - y_n}{1 - r_a}\right) + y_n$$

Then plug into this equation to solve for $z_{tl}$:

$$z_{tl} = z_{Lat} \bigg/ \left[1 - \left(\frac{x_{ta} - x_n}{x_f - x_n}\right)(1 - r_l)\right]$$

Then plug into this equation to solve for $z_{ta}$:

$$z_{ta} = z_{AP} \bigg/ \left[1 - \left(\frac{y_{tl} - y_n}{y_f - y_n}\right)(1 - r_a)\right]$$

Solve differently to give another option for z:

$$y_{Lat} = y_{tl}\left[1 - \left(\frac{x_{ta} - x_n}{x_f - x_n}\right)(1 - r_l)\right]$$

$$\left(\frac{x_{ta} - x_n}{x_f - x_n}\right)(1 - r_l) = 1 - \frac{y_{Lat}}{y_{tl}}$$

-continued $$(x_{ta} - x_n)\left(\frac{1-r_l}{x_f - x_n}\right) = 1 - \frac{y_{Lat}}{y_{tl}}$$

$$x_{ta}\left(\frac{1-r_l}{x_f - x_n}\right) - x_n\left(\frac{1-r_l}{x_f - x_n}\right) = 1 - \frac{y_{Lat}}{y_{tl}}$$

$$x_{ta}\left(\frac{1-r_l}{x_f - x_n}\right) = 1 - \frac{y_{Lat}}{y_{tl}} + x_n\left(\frac{1-r_l}{x_f - x_n}\right)$$

$$x_{ta} = \left(1 - \frac{y_{Lat}}{y_{tl}}\right)\left(\frac{x_f - x_n}{1 - r_l}\right) + x_n$$

Substitute into:

$$x_{AP} = x_{ta}\left[1 - \left(\frac{y_{tl} - y_n}{y_f - y_n}\right)(1 - r_a)\right]$$

$$x_{AP} = \left[\left(1 - \frac{y_{Lat}}{y_{tl}}\right)\left(\frac{x_f - x_n}{1 - r_l}\right) + x_n\right]\left[1 - \left(\frac{y_{tl} - y_n}{y_f - y_n}\right)(1 - r_a)\right]$$

And solve for $y_{tl}$:

$$x_{AP} = \left[\left(\frac{x_f - x_n}{1 - r_l}\right) - \frac{y_{Lat}}{y_{tl}}\left(\frac{x_f - x_n}{1 - r_l}\right) + x_n\right]\left[1 - (y_{tl} - y_n)\left(\frac{1 - r_a}{y_f - y_n}\right)\right]$$

$$x_{AP} = \left[\left[\left(\frac{x_f - x_n}{1 - r_l}\right) + x_n\right] - \left[\frac{y_{Lat}}{y_{tl}}\left(\frac{x_f - x_n}{1 - r_l}\right)\right]\right]$$

$$\left[\left[1 + y_n\left(\frac{1 - r_a}{y_f - y_n}\right)\right] - \left[y_{tl}\left(\frac{1 - r_a}{y_f - y_n}\right)\right]\right]$$

$$x_{AP} = \left[A - \frac{B}{y_{tl}}\right][C - Dy_{tl}]$$

$$x_{AP} = AC - \frac{BC}{y_{tl}} - ADy_{tl} + BD$$

$$AC + BD - x_{AP} = \frac{BC}{y_{tl}} + ADy_{tl}$$

$$(AD)y_{tl}^2 + (x_{AP} - AC - BD)y_{tl} + (BC) = 0$$

Quadratic formula:

$$x = \frac{-b \pm \sqrt{b^2 - 4ac}}{2a}$$

$$y_{tl} = \frac{-(x_{AP} - AC - BD) \pm \sqrt{(x_{AP} - AC - BD)^2 - 4(AD)(BC)}}{2(AD)}$$

Where:

$$A = \left(\frac{x_f - x_n}{1 - r_l}\right) + x_n$$

$$B = y_{Lat}\left(\frac{x_f - x_n}{1 - r_l}\right)$$

$$C = 1 + y_n\left(\frac{1 - r_a}{y_f - y_n}\right)$$

$$D = \frac{1 - r_a}{y_f - y_n}$$

From these equations, it is possible to go from a known x,y,z coordinate to the perceived $x_{AP}$, $z_{AP}$ and $x_{Lat}$, $x_{Lat}$ coordinates on the two views, or to go from known $x_{AP}$, $z_{AP}$ and $x_{Lat}$, $z_{Lat}$ coordinates on the two views to an x,y,z coordinate in the 3D coordinate system. It is therefore possible to plan a trajectory on the $x_{AP}$, $z_{AP}$ and $x_{Lat}$, $z_{Lat}$ views and determine what the tip and tail of this trajectory are, and it is also possible to display on the $x_{AP}$, $z_{AP}$ and $x_{Lat}$, $z_{Lat}$ views the current location of the robot's end effectuator.

In some embodiments, additional measurement hardware (for example, conventional ultrasound, laser, optical tracking, or a physical extension like a tape measure) can be attached to the fluoro unit to measure distance to the attached plates, or other points on the anatomy to ensure that plates are parallel when fluoro images are obtained.

In some embodiments, the identity of the surgical instrument 35 can be used by the control system for the computing device 3401 or other controller for the surgical robot system 1. In some embodiments, the control system 3401 can automatically adjust axial insertion and/or forces and applied torques depending upon the identity of the surgical instrument 35.

In some embodiments, when performing a typical procedure for needle 7405, 7410 or probe insertion (for biopsy, facet injection, tumor ablation, deep brain stimulation, etc.) a targeting fixture 690 is first attached by the surgeon or technician to the patient 18. The targeting fixture 690 is either clamped to bone (open or percutaneously), adhered as a rigid object to the skin, or unrolled and adhered to the skin (for example using the flexible roll shown as 705 in FIG. 21A). In some embodiments, the roll 705 could have a disposable drape incorporated. If a flexible roll 705 is used, reflective markers 720 will then be snapped into place in some embodiments.

In some embodiments, once a targeting fixture 690 is attached, the patient 18 can receive an intraoperative 3D image (Iso-C, O-Arm, or intraoperative CT) with radio-opaque markers 730 included in the field of view along with the region of interest. In some embodiments, for best accuracy and resolution, a fine-slice image is preferred (CT slice spacing=1 mm or less). The 3D scan has to include the radio-opaque markers 730 and the anatomy of interest; not including both would disallow calibration to the robot 15.

In some embodiments, the 3D image series is transferred to (or acquired directly to) the computer 100 of the robot 15. The 3D image has to be calibrated to the robot's position in space using the locations on the 3D image of the radio-opaque markers 730 that are embedded in the targeting fixture 690. In some embodiments, this calibration can be done by the technician scrolling through image slices and marking them using the software, or by an algorithm that automatically checks each slice of the medical image, finds the markers 730, verifying that they are the markers 730 of interest based on their physical spacing (the algorithm is documented herein). In some embodiments, to ensure accuracy, limit subjectivity, and to speed up the process, image thresholding is used to help define the edges of the radio-opaque marker 730, and then to find the center of the marker 730 (the program is documented herein). Some embodiments of the software can do the necessary spatial transformations to determine the location in the room of the robot's markers relative to anatomy through standard rigid body calculations. For example, by knowing the locations of the radio-opaque markers 730 in the coordinate system of the medical image, and knowing the locations of the active markers 720 on the calibration frame 700 relative to these radio-opaque markers 730, and monitoring the locations of the active markers on the robot 15 and targeting fixture 690.

Some embodiments allow the surgeon to use the software to plan the trajectories for needles/probes 7405, 7410. In some embodiments, the software will allow any number of trajectories to be stored for use during the procedure, with each trajectory accompanied by a descriptor.

In some embodiments, the robot 15 is moved next to the procedure table and cameras 8200 for tracking robot 15 and patient 18 are activated. The cameras 8200 and robot 15 are positioned wherever is convenient for the surgeon to access the site of interest. The marker mounts on the robot 15 have adjustable positions to allow the markers 720 to face toward the cameras 8200 in each possible configuration. In some embodiments, a screen can be accessed to show where the robot 15 is located for the current Z-frame 72 position, relative to all the trajectories that are planned. In some embodiments, the use of this screen can confirm that the trajectories planned are within the range of the robot's reach. In some embodiments, repositioning of the robot 15 is performed at this time to a location that is within range of all trajectories. Alternately or additionally, in some embodiments, the surgeon can adjust the Z-frame 72 position, which will affect the range of trajectories that the robot 15 is capable of reaching (converging trajectories require less x-y reach the lower the robot 15 is in the z-axis 70). During this time, substantially simultaneously, a screen shows whether markers 720, 730 on the patient 18 and robot 15 are in view of the cameras 8200. Repositioning of the cameras 8200, if necessary, is also performed at this time for good visibility.

In some embodiments, the surgeon then selects the first planned trajectory and he/she (or assistant) presses "go". The robot 15 moves in the x-y (horizontal) plane and angulates roll 62 and pitch 60 until the end-effectuator 30 tube intersects the trajectory vector (see FIGS. 3A and 3B). In some embodiments, during the process of driving to this location, a small laser light will indicate end-effectuator 30 position by projecting a beam down the trajectory vector toward the patient 18. This laser simply snaps into the top of the end-effectuator 30 tube. In some embodiments, when the robot's end-effectuator 30 tube coincides with the trajectory vector to within the specified tolerance, auditory feedback is provided to indicate that the desired trajectory has been achieved and is being held. Alternately or additionally, in some embodiments, light of a meaningful color is projected on the surgical field 17. For example, in some embodiments, movement of the patient 18 or robot 15 is detected by optical markers 720 and the necessary x-axis 66, y-axis 68, roll 62, and pitch 60 axes are adjusted to maintain alignment.

In some embodiments, the surgeon then drives Z-frame 72 down until the tip of the end-effectuator 30 reaches the desired distance from the probe's or needle's target (typically the skin surface). While moving, the projected laser beam point should remain at a fixed location since movement is occurring along the trajectory vector. Once at the desired Z-frame 72 location, in some embodiments, the surgeon or other user can select an option to lock the Z-tube 50 position to remain at the fixed distance from the skin during breathing or other movement. At this point, the surgeon is ready to insert the probe or needle 7405, 7410. If the length of the guide tube 50 has been specified and a stop on the needle 7405, 7410 or probe is present to limit the guide tube 50 after some length has been passed, the ultimate location of the tip of the probe/needle 7405, 7410 can be calculated and displayed on the medical image in some embodiments. As described earlier, Additionally, in some embodiments, it is possible to incorporate a mechanism at the entry of the guide tube 50 that is comprised of a spring-loaded plunger 54 with a through-hole, and measures electronically the depth of depression of the plunger 54, corresponding to the amount by which the probe or needle 7405, 7410 currently protrudes from the tip of the guide tube 50.

In some embodiments, at any time during the procedure, if there is an emergency and the robot 15 is in the way of the surgeon, the "E-stop" button can be pressed on the robot 15, at which point all axes except the Z-frame axis 72 become free-floating and the robot's end-effectuator 30 can be manually removed from the field by pushing against the end-effectuator 30.

Some embodiments can include a bone screw or hardware procedure. For example, during a typical procedure for conventional screw or hardware insertion in the spine, the patient 18 is positioned prone (or other position) on the procedure table, and is supported. In some embodiments, a targeting fixture 690 is attached to the patient's spine by the surgeon or technician. In some embodiments, the targeting fixture 690 is either clamped to bone (open or percutaneously) or unrolled and adhered to the skin (for example using roll 705). The roll 705 could have a disposable drape incorporated. If a flexible roll 705 is used, reflective markers 720 will then be snapped into place in some embodiments.

In some embodiments, once a targeting fixture 690 is attached, the patient 18 can undergo an intraoperative 3D image (Iso-C, O-Arm, or intraoperative CT) with radio-opaque markers 730 included in the field of view along with the bony region of interest. In some embodiments, for best accuracy and resolution, a fine-slice image is preferred (where the CT slice spacing=1 mm or less). The 3D scan in some embodiments has to include the radio-opaque markers 730 and the bony anatomy; not including both would disallow calibration to the robot 15.

In some embodiments, the 3D image series is transferred to (or acquired directly to) the computer 100 of the robot 15, and the 3D image is calibrated in the same way as described above for needle 7405, 7410 or probe insertion. The surgeon then uses the software to plan the trajectories for hardware instrumentation (e.g., pedicle screw, facet screw). Some embodiments of the software will allow any number of trajectories to be stored for use during the procedure, with each trajectory accompanied by a descriptor that may just be the level and side of the spine where screw insertion is planned.

In some embodiments, the robot 15 is moved next to the table and cameras 8200 for tracking robot 15 and patient 18 are activated. The cameras 8200 are positioned near the patient's head. In some embodiments, the markers for the robot 15 are facing toward the cameras 8200, typically in the positive y-axis 68 direction of the robot's coordinate system. In some embodiments, a screen can be accessed to show where the robot 15 is located relative to all the trajectories that are planned for the current Z-frame 72 position. Using this screen it can be confirmed that the trajectories planned are within the range of the robot's reach. In some embodiments, repositioning of the robot 15 to a location that is within range of all trajectories is performed at this time. Alternately or additionally, in some embodiments, the surgeon can adjust the Z-frame 72 position, which will affect the range of trajectories that the robot 15 is capable of reaching (converging trajectories require less x-y reach the lower the robot 15 is in Z). During this time, simultaneously in some embodiments, a screen shows whether markers 720 on the patient 18 and robot 15 are in view of the cameras 8200. Repositioning of the cameras 8200, if necessary, is also performed at this time for good visibility.

In some embodiments, the surgeon then selects the first planned trajectory and he/she (or assistant) presses "go".

The robot 15 moves in the x-y (horizontal) plane and angulates roll 62 and pitch 60 until the end-effectuator 30 tube intersects the trajectory vector. During the process of driving to this location, in some embodiments, a small laser light will indicate end-effectuator 30 position by projecting a beam down the trajectory vector toward the patient 18. This laser simply snaps into the top of the end-effectuator guide tube 50. When the robot's end-effectuator guide tube 50 coincides with the trajectory vector to within the specified tolerance, auditory feedback is provided in some embodiments to indicate that the desired trajectory has been achieved and is being held. In some embodiments, movement of the patient 18 or robot 15 is detected by optical markers 720 and the necessary x-axis 66, y-axis 68, roll 62, and pitch 60 axes are adjusted to maintain alignment.

In some embodiments of the invention, the surgeon then drives Z-frame 72 down until the tip of the end-effectuator 30 reaches a reasonable starting distance from the site of operation, typically just proximal to the skin surface or the first tissues encountered within the surgical field 17. While moving, the projected laser beam point should remain at a fixed location since movement is occurring along the trajectory vector. Once at the desired location, the user may or may not select an option to lock the Z-tube 50 position to remain at the fixed distance from the anatomy during breathing or other movement.

One problem with inserting conventional guide-wires and screws into bone through any amount of soft tissue is that the screw or wire may sometimes deflect, wander, or "skive" off of the bone in a trajectory that is not desired if it does not meet the bone with a trajectory orthogonal to the bone surface. To overcome this difficulty, some embodiments can use a specially designed and coated screw specifically intended for percutaneous insertion. Some other embodiments can use an end-effectuator 30 tip fitted with a guide tube 50 or dilator, capable of being driven all the way down to the bone. In this instance, the guide tube 50 needs to have a sharp (beveled) leading edge 30*b*, and may need teeth or another feature to secure it well to the bone once in contact. This beveled tube 50 (i.e. guide tube 50 that includes beveled leading edge 30*b*) is driven through soft tissue and next to bone through one of two different methods using the surgical robot system 1 as described.

Figure 62:
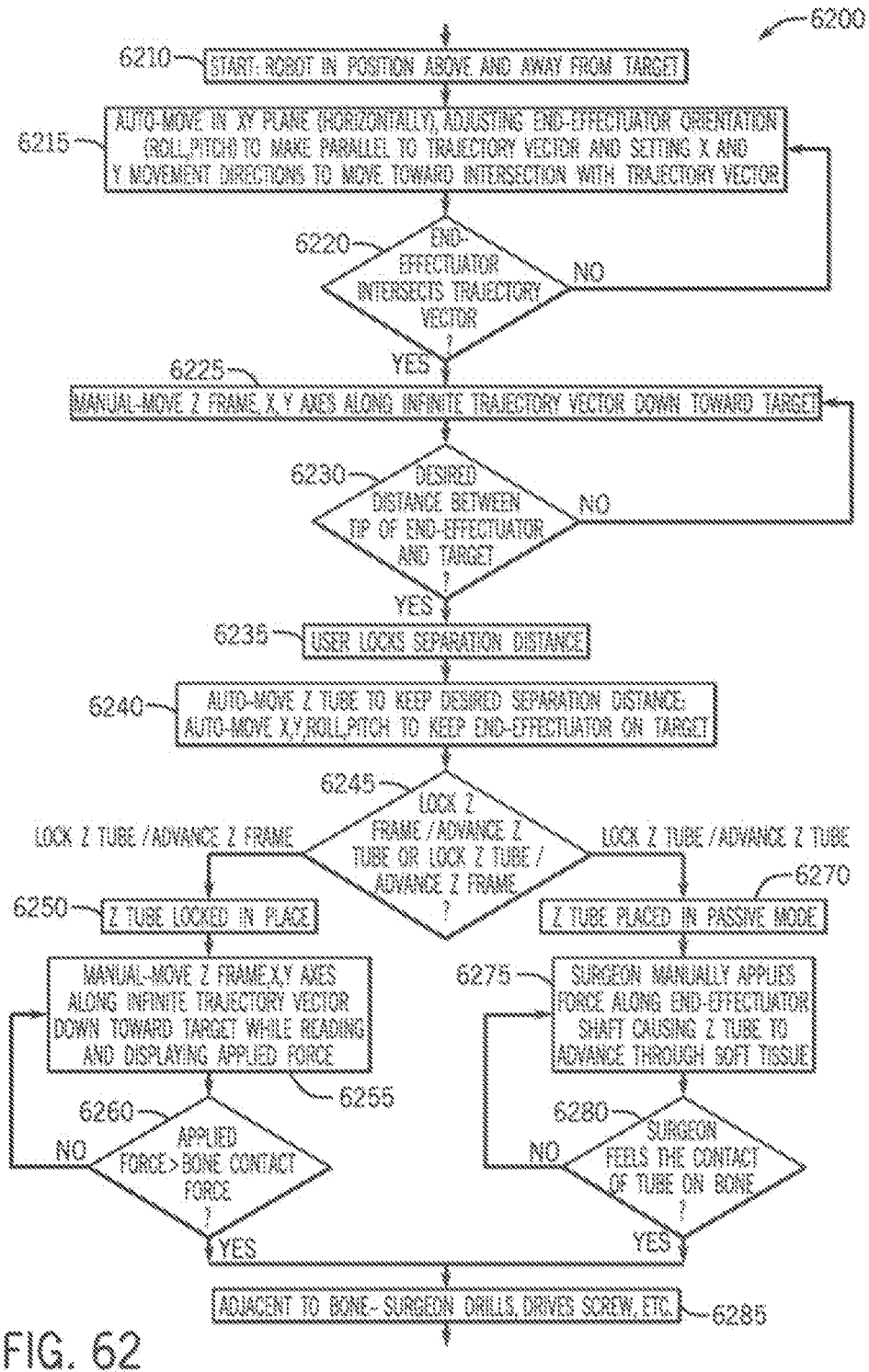
FIG. 62 illustrates a method in accordance with at least one embodiment of the invention.

In applications where conventional screws are to be driven into bone, the surgeon may want to move the end-effectuator tip 30, fitted with a guide tube 50 or a conventional dilator, all the way down to the bone. Referring to FIG. 62 showing steps 6210, 6215, 6220, 6225, 6230, 6235, 6240, 6245, and either 6250, 6255, 6260, and 6260, or 6270, 6275, 6280 and 6285, two embodiments address this need. In some embodiments, the user can insert the tube 50 and force it down the axis Z-tube axis 64 by hand, or with the robot 15 until a peak in force is registered by tactile feel or by a conventional force sensor on the end-effectuator 30 (signaling contact with bone). At this point, it is no longer necessary for the tip of the drill bit 42 to be positioned past the tip of the tube 50 (in fact be better to have it slightly retracted). As described earlier, a drill bit 42 can include a drill stop 46, and the drill bit 42 can be locked and held (see for example FIGS. 17C-17E and 17F-17J). In some embodiments, the stop 46 on the drill bit 42 can then be adjusted by pulling one of the releases 48 and slightly adjusting its position. Then, the tube 50 can be brought up against bone and locked there. Now, the stop 46 can be adjusted to show how much the drill bit 42 would protrude beyond the tip. This same value can be used to offset (extrapolate) the tip of the tube 50 on the software, showing the user where the tip of the drill bit 42 will end up.

In some embodiments, the Z-tube axis 64 is fitted with a conventional force sensor with continuous force readings being displayed on the screen (such as display means 29). In some embodiments, the Z-frame 72 is then driven down into tissue while continuously adjusting the x-axis 66 and y-axis 68 to keep the tube 50 aligned with the trajectory vector. In some embodiments, the steps of 6210, 6215, 6220, 6225, 6230, 6235, 6240, 6245, 6250 and 6255 can be used to drive the tube 50 toward the target. In this instance, roll 62 and pitch 60, defining orientation, should not change while moving x-axis 66, y-axis 68, and the Z-frame 72 as Z-axis 70 along this vector, while holding Z-tube 50 rigidly locked at mid-range. For this procedure, in some embodiments, the Z-tube 50 stiffness must be set very high, and may require a conventional mechanical lock to be implemented. In some embodiments, if Z-tube 50 is not stiff enough, a counter force from the tissues being penetrated may cause it to move back in the opposite direction of Z-frame 72, and the tube 50 will not have any net advancement. In some embodiments, based on the surgeon's previous experience and lab testing, Z-frame 72 is driven down until a force level from the monitored force on Z-tube 50 matches the force typical for collision with bone (step 6260).

In some alternative embodiments, Z-tube 50 is positioned near the top of its range and Z-frame 72 is advanced (while adjusting x-axis 66 and y-axis 68 to stay on the trajectory vector) until the tube 50 tip is near the outermost border of dissected tissue (i.e. skin during percutaneous procedures). In some embodiments, the Z-tube's motor 160 is then deactivated to allow it to move freely while still monitoring its position (step 6270). In some embodiments, the surgeon then pushes the end-effectuator 30 down while x-axis 66, y-axis 68, roll 62, and pitch 60 adjustments can allow the tube 50 to be aligned with the trajectory vector (step 6275). Moreover, since the Z-tube 50 is passive, in some embodiments, the surgeon can manually force the tube 50 to advance until he/she experiences the tactile sense of the tube hitting bone, at which point the Z-tube 50 position is locked (motor 160 activated) by the surgeon or assistant (step 6280, 6285).

At this point, in some embodiments, the guide tube 50 is adjacent to bone and the surgeon may wish to drill into the bone with a conventional guide-wire or drill bit, or insert a screw. For screw prep and insertion, in some embodiments, the surgeon either uses a method that incorporates guide-wires, or a method that does not use guide-wires.

Some embodiments include a guide-wire method. For example, in some embodiments, a guide-wire is drilled into bone through the guide tube 50. After the guide-wire is in place, Z-frame 72 and tube 50 are driven upward along the trajectory vector until outside the body. In some embodiments, the tube is then released with a quick release from the robot's end-effectuator 30 so it can be positioned at the next trajectory. In some embodiments, a cannulated screw, already commonly used in spine surgery, can then be driven in place over the guide-wire.

Some embodiments include a non-guide-wire method. For example, a pilot hole may or may not be drilled first. In some embodiments, a screw is then driven into bone directly through the guide tube 50, which abuts bone. In some embodiments, the tip of the screw may have the special non-skiving design mentioned above.

In some embodiments, if hardware other than a screw is being inserted, the surgeon may wish to dilate soft tissue. In some embodiments, a dilated path would enable larger and/or more tools and implants to be inserted. In some embodiments, dilation is performed by sliding a series of larger and larger diameter tubes over the initial central shaft or tube. In some embodiments, a series of dilators, specially designed to integrate to the robot's end-effectuator 30, sequentially snap on to each other for this purpose.

In some embodiments, after the screw or hardware has been inserted in the first trajectory, the surgeon drives the robot 15 back up the trajectory vector away from the patient 18. In some embodiments, after the end-effectuator 30 is clear of the patient 18 in the Z direction, the next trajectory is selected and the robot 15 repeats the above steps.

In some embodiments, at any time during the procedure, if there is an emergency and the robot 15 is in the way of the surgeon, the "E-stop" button can be pressed on the robot 15, at which point all axes except Z-frame 72 become free-floating, and the robot's end-effectuator 30 can be manually removed from the field by pushing against the end-effectuator.

In some embodiments, for nerve avoidance during medical procedures, a special conventional dilator tube (not shown) that can be used with the robot 15. In some embodiments, the dilator tube can include multiple electrodes at its tip that can be sequentially activated to find not only whether a nerve is nearby, but also to find which radial direction is the nearest direction toward the nerve. Some embodiments incorporate this guide tube 50 and can identify, warn or incorporate automatic algorithms to steer clear of the nerve.

In some embodiments, it is known that pairs of bone screws such as pedicle screws have better resistance to screw pullout if they are oriented so that they converge toward each other. In some embodiments, for the best potential biomechanical stability, a two-screw surgical construct can consist of specially designed conventional screws that would interconnect in the X Z plane (not shown). That is, one screw can have a socket to accept a threaded portion of the other screw so that the screws interconnect at their tips. A procedure such as this requires exceptional accuracy, otherwise the screw tips would not properly intersect, and is therefore especially well-suited for a surgical robot 15. This type of hardware is useful with certain embodiments of the invention.

In some embodiments, instead of only straight lines, the surgeon has several options for trajectory planning—straight, curved or boundary for safe-zone surgery. For curved pathway planning, in some embodiments, the surgeon can draw a path on the medical image that has curvature of a user-selectable radius. In some embodiments, special conventional needles and housings can be used to execute these curved paths. In safe zone surgery (tumor or trauma), in some embodiments, the surgeon first plans a box or sphere around the region on the medical image within which the probe tip, incorporating a drill or ablation instrument, will be allowed to reside. In some embodiments, the robot 15 is driven down along a trajectory vector either automatically or manually as described above to position the tip of the probe to be in the center of the safe zone. In some embodiments, the surgeon would then be able pick the tool's axis of rotation (orthogonal to the long axis) based on the desired impact he/she would like for the purpose of preserving tissue and maximizing efficiency and effectiveness for the task at hand. For example, in some embodiments, an axis of rotation at the surface of the skin could be selected to minimize the amount by which the tool travels laterally and rips the skin.

In some embodiments, the robot 15 uses optical markers for tracking. Some embodiments are able to provide accurate localization of the robot 15 relative to the patient 18, and utilize the LPS because of the advantage of not being limited to line-of-sight. Additionally, in some embodiments, probes utilizing RF emitters on the tip (capable of being tracked by the LPS) can be used for steering flexible probes inside the body. In some embodiments, if the LPS is not yet functional for localization, then localization can be performed using an electromagnetic system such as the Aurora by Northern Digital. Aurora® is a registered trademark of Northern Digital Inc. For example, in this instance, an electromagnetic coil and RF emitters are both present in the probe tip. Some embodiments can offer the option of LPS or electromagnetic localization with steerable needles 7600. In this embodiment of the invention, the surgeon can monitor the current location on the medical image where the probe tip is currently positioned in real-time and activate RF electrodes to advance and steer the probe tip in the desired direction using a joystick.

Figure 63C:
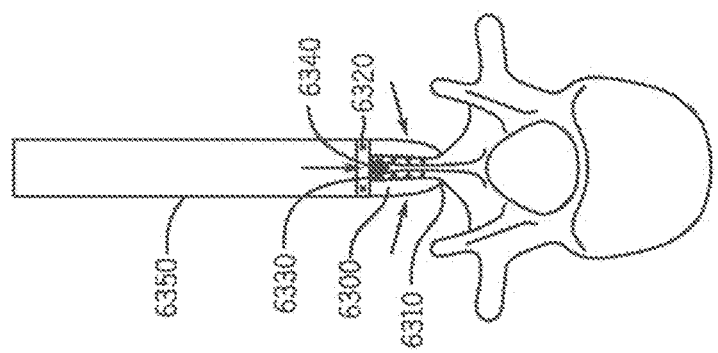
FIGS. 63A-63C illustrates various embodiments of an end-effectuator including a modified mount with a clamping piece in accordance with at least one embodiment of the invention.
Figure 63B:
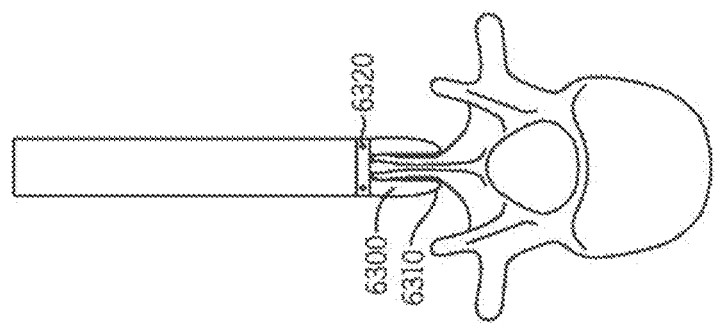
Figure 63A:
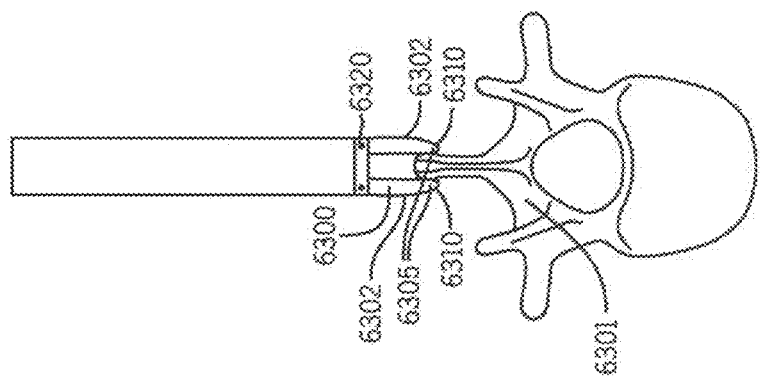

As discussed earlier, in some embodiments, the end-effectuator 30 can include a bayonet mount 5000 is used to removably couple the surgical instrument 35 to the end-effectuator 30 as shown in FIG. 48. Some embodiments can include a modification to the mount 5000 allowing the ability to slide a clamping piece 6300 over the spinous process 6301 without full exposure of the spinous process 6301. See example FIGS. 63A-63B illustrating various embodiments of an end-effectuator 30 including a modified mount 5000 with a clamping piece 6300 in accordance with at least one embodiment of the invention. As shown, the clamping piece 6300 comprises clamps 6302 including at least one beveled edge 6310, and clamp teeth 6330.

In some embodiments, the surgeon would make a stab incision in the midline and then slide the clamps 6302 of the clamping piece 6300 down along the sides of the spinous process 6301, pushing tissue away as the tip of the clamping piece is advanced. In some embodiments, the leading edge of the clamping mechanism 6300 would be beveled (see the leading edges 6305 of each clamp 6302 of the clamping mechanism 6300), and have a shape similar to a periosteal elevator. This allows the clamping mechanism 6300 to separate the muscle tissue from the bony spinous process 6301 as it is advanced. In some embodiments, the leading edges 6305 of the clamping mechanism 6300 can be electrified to enable it to more easily slide through muscle and connective tissues to prevent excessive bleeding.

In some embodiments, a mechanism activated from farther back on the shaft (for example a turn screw 6320, or conventional spring, etc.) can be activated to deploy clamp teeth 6330 on the clamps 6302. The same mechanism or another mechanism would close and compress the clamps 6302 together to firmly secure the clamping mechanism 6300 to the spinous process 6301 (see FIGS. 63B-63C). Additionally, in some embodiments, a screw 6340 aligned with the handle 6350 could deploy to thread into the spinous process 6301 (see for example, FIG. 63C).

The embodiments as described above and shown in FIGS. 63A-63C would be especially well suited to percutaneous pedicle screw-rod surgery because the hole made for mounting the clamping mechanism 6300 could also be used as the hole for inserting the conventional rod to interconnect the conventional pedicle screw heads. Further, the embodiments as described above and shown in FIGS. 63A-63C could also be useful for mounting a marker tree (for example marker tree 795 shown in FIG. 50A) to other bony prominences, such as transverse processes, long bones, skull base, or others.

Figure 64:
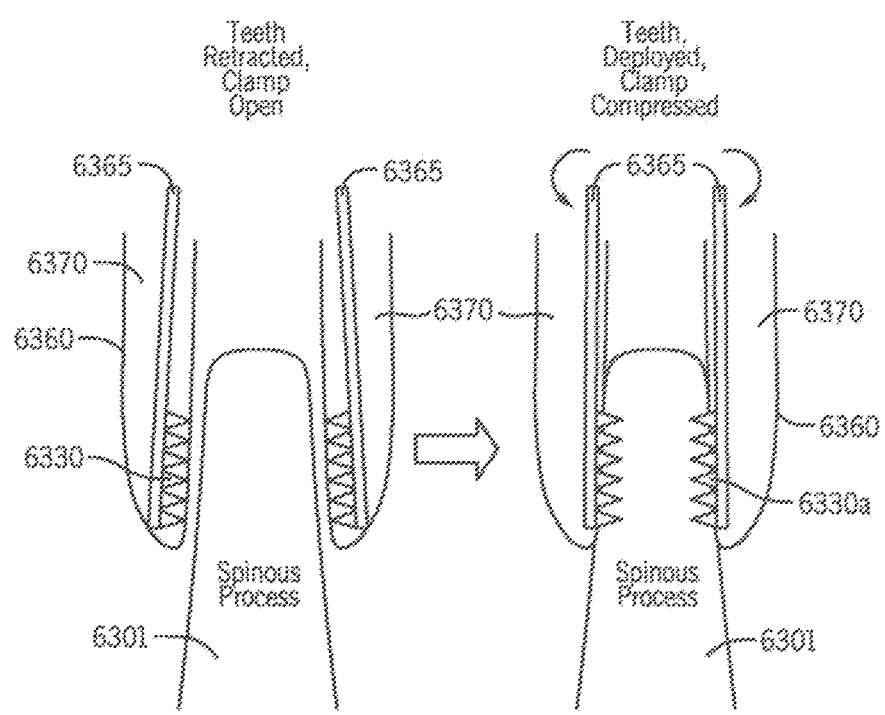
FIGS. 64-65 illustrate embodiments of clamping piece actuation on a spinous process in accordance with some embodiments of the invention.
Figure 65:
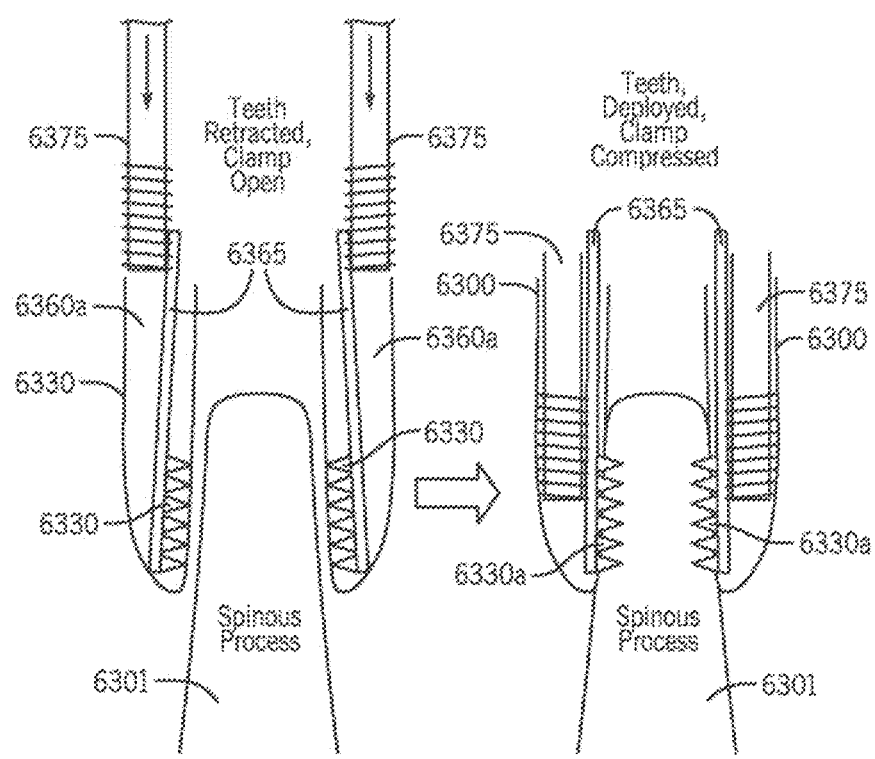

FIGS. 64 and 65 illustrate embodiments of clamping piece 6300 actuation on a spinous process 6301 in accordance with some embodiments of the invention. In some embodiments, the mechanism for deploying the clamp teeth 6330 could be comprised of a hollow tool tip 6360 containing teeth 6330 that are to one side of the hollow cavity 6370 during insertion, but are forced toward the opposite side when the mechanism is deployed, such that the embedded teeth penetrate the bone (see the illustration of penetrated teeth 6330a in FIG. 64).

FIG. 65 shows an alternative embodiment of the clamping piece 6300 actuation on a spinous process 6301. As shown, the groups of teeth 6330 are attached to rods 6365 that run down the hollow cavities 6360a of the hollow tool tips 6360. These rods 6365 pivot farther up the handle 6350 (pivot point not pictured) and the clamp teeth 6330 are forced together. For example, in some embodiments, rods 6365 are driven into the hollow cavity 6360a of the hollow tool tip 6360 on the side away from the bone, forcing the clamp teeth 6330 against and into the bone (for example, see the penetrated teeth 6330a in FIG. 65).

Figure 66A:
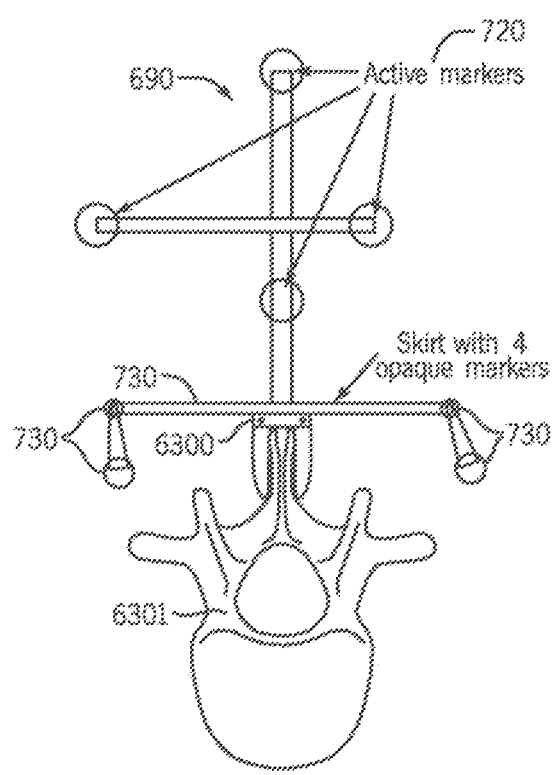
FIG. 66A illustrates a clamping piece modified with a targeting fixture including a temporary marker skirt in accordance with at least one embodiment of the invention.
Figure 66B:
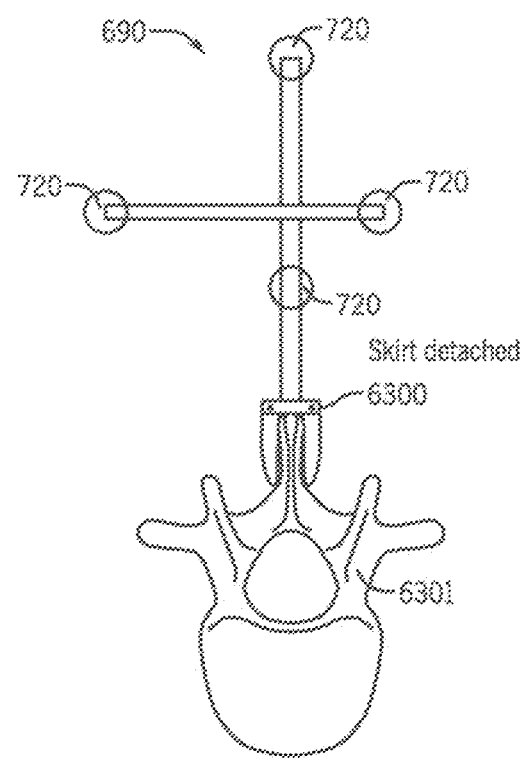
FIG. 66B illustrates a clamping piece modified with a targeting fixture as shown in FIG. 66A with the temporary marker skirt detached in accordance with at least one embodiment of the invention.

As described above, the opaque markers 730 must be included in a CT scan of the anatomy. However, it is desirable to crop CT scans as close as possible to the spine to improve resolution. In some embodiments, instead of using markers 730 near where the active markers 720 are located, an alternative is to have a rigid extension containing opaque markers 730 that are temporarily attached near the spine when the scan is taken. In some embodiments, the clamping piece 6300 can be coupled with, or otherwise modified with a targeting fixture 690. For example, FIG. 66A illustrates a clamping piece 6300 modified with a targeting fixture 690 including a temporary marker skirt 6600 in accordance with at least one embodiment of the invention, and FIG. 66B illustrates a clamping piece 6300 modified with a targeting fixture 690 as shown in FIG. 66A with the temporary marker skirt 6600 detached in accordance with at least one embodiment of the invention. As shown, the temporary marker skirt 6600 includes radio-opaque markers 730 in a temporary "skirt" around the base of the clamping device 6300. The design of the temporary marker skirt 6600 and clamping device 6300 must be such that the markers 730 in the skirt 6600 have known locations relative to the markers 720 for tracking that are farther away. Once the scan is taken, the opaque markers 730 are not needed. Therefore, in some embodiments, by depressing a conventional release, the skirt 6600 can be removed so it will not be in the way of the surgeon (see for example FIG. 66B).

Figure 67:
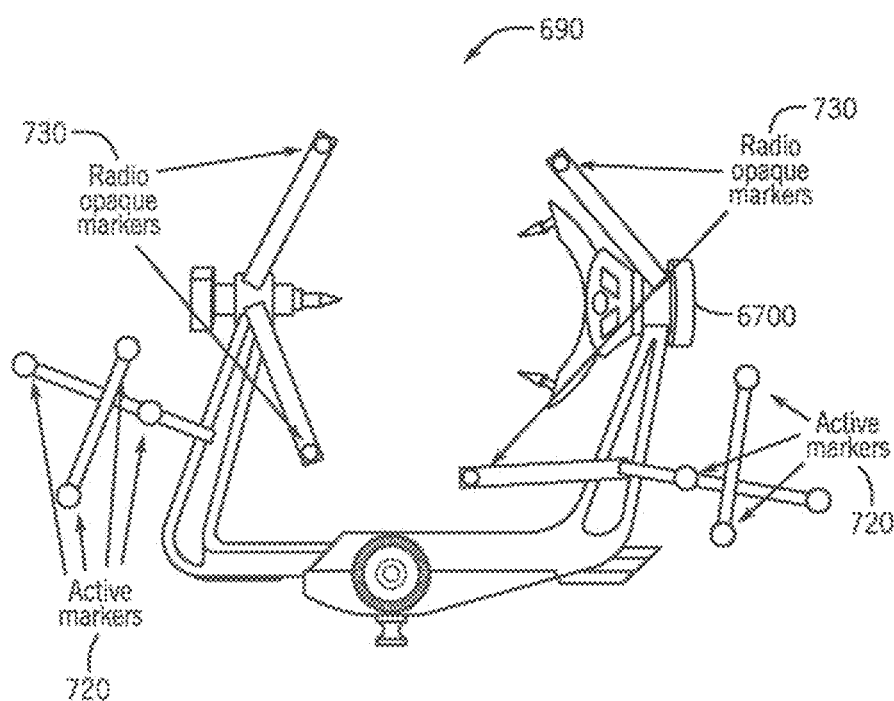
FIG. 67 shows a modified Mayfield frame 6700 including one possible configuration for active and radio-opaque markers in accordance with one embodiment of the invention.

In some embodiments, it may also be desirable to mount the targeting fixture 690 to another piece that is already rigidly attached to the patient 18. For example, for deep brain stimulation or other brain procedure where the patient 18 is positioned in a Mayfield head holder, the head holder could serve as an attachment point for the targeting fixture 690. Since the head holder 6700 and skull form a rigid body, it is possible to track the head holder 6700 under the assumption that the skull moves the same amount as the head holder 6700. Further, in some embodiments of the invention, a surveillance marker (such as surveillance marker 710 as illustrated in FIG. 36) could be used. For this targeting fixture 690, active 720 and radio-opaque 730 markers would be rigidly attached to the head holder 6700. The radio-opaque markers 730 need only be in position when the scan (CT, MM, etc.) is taken and could subsequently be removed. The active markers 720 need not be in position when the scan is taken but could instead be snapped in place when it is necessary to begin tracking. For example, FIG. 67 shows one possible configuration for active 720 and radio-opaque markers 730 attached to a Mayfield frame 6700 in accordance with one embodiment of the invention. As with other targeting fixtures 690, it is required that three or more radio-opaque markers 730 and three or more active markers 720 are attached to same rigid body.

Figure 68:
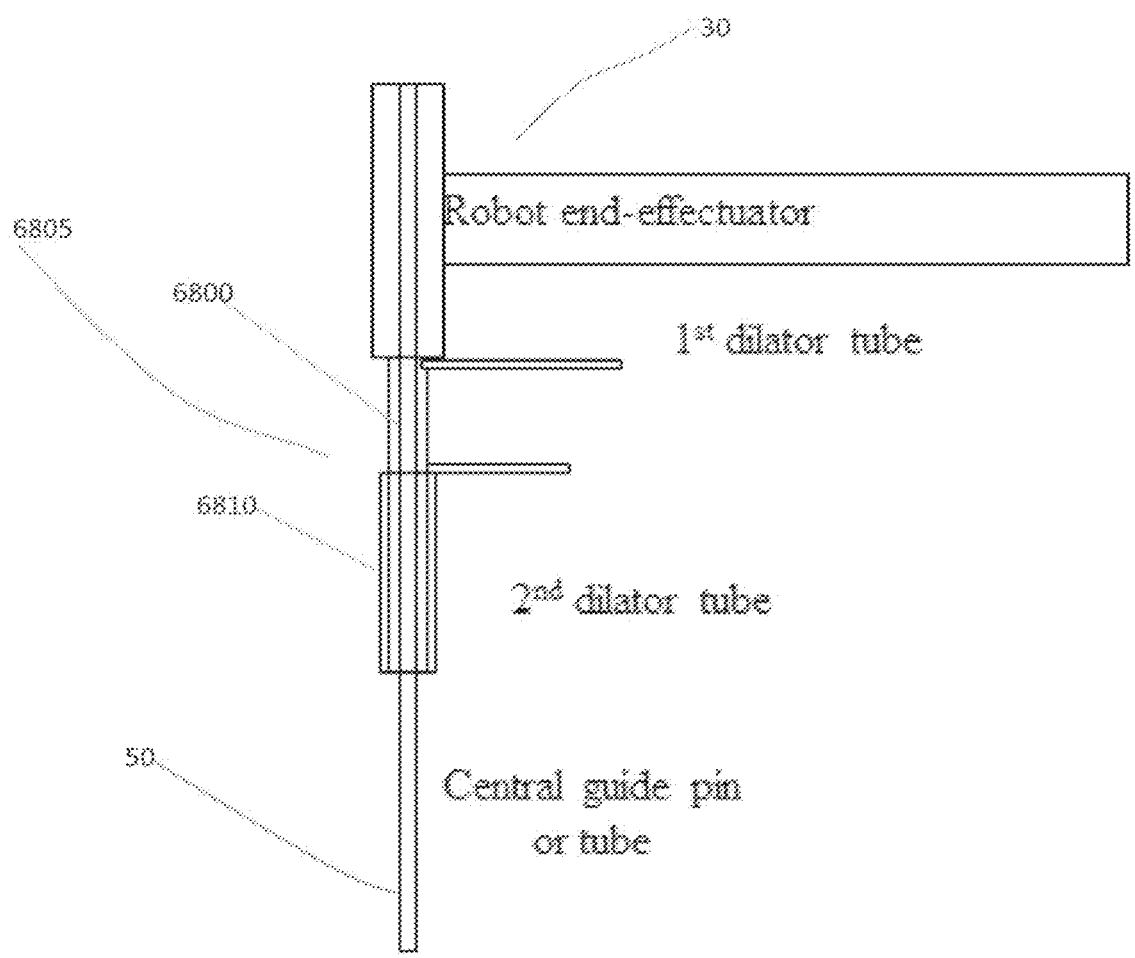
FIG. 68 shows end-effectuator 30 that includes nested dilators in accordance with at least one embodiment of the invention.

One problem with some robotic procedures is that the guide tube 50 must be physically rigidly mounted to the robot's end-effectuator, and therefore mounting one or more dilator tubes can be challenging. To address this problem, in some embodiments, dilators can be placed over the central guide-tube 50 without removing the robot end-effectuator 30. For example, some embodiments can include an end-effectuator 30 that includes at least one dilator tube 6800, 6810. For example, FIG. 68 shows end-effectuator 30 that includes nested dilators 6805 in accordance with at least one embodiment of the invention. As shown, a nested set 6805 of two or more disposable or non-disposable dilators 6800, 6810 can be mounted onto the robot's end-effectuator 30. In some embodiments, each dilator 6800, 6810 may have its own removable conventional handle that allows a surgeon or an automated mechanism to force the dilator down into soft tissue. Some embodiments could include additional dilators, for example, a nested set of three dilators of 7 mm, 11 mm, and 14 mm diameter (not shown) may be useful for creating a portal for minimally invasive screw insertion or application of a surgical implant. In some embodiments, each dilator 6800, 6810 can have greater length as it is closer to the central guide tube 50, allowing the more central tube 50 to be advanced without radially advancing the dilator tubes 6800, 6810 out further.

Figure 69A:
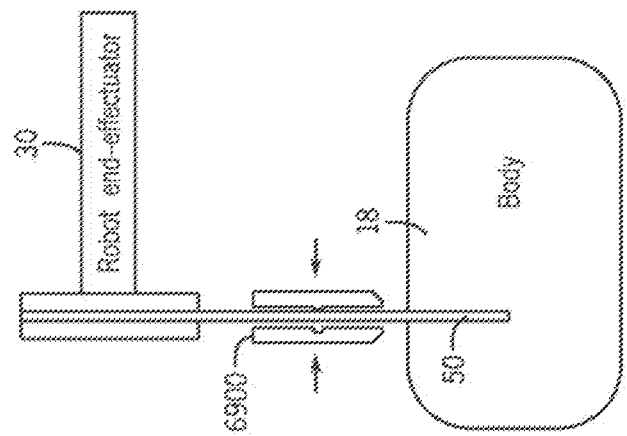
FIGS. 69A-69C illustrates various embodiments of an end-effectuator including cylindrical dilator tubes in accordance with at least one embodiment of the invention.
Figure 69B:
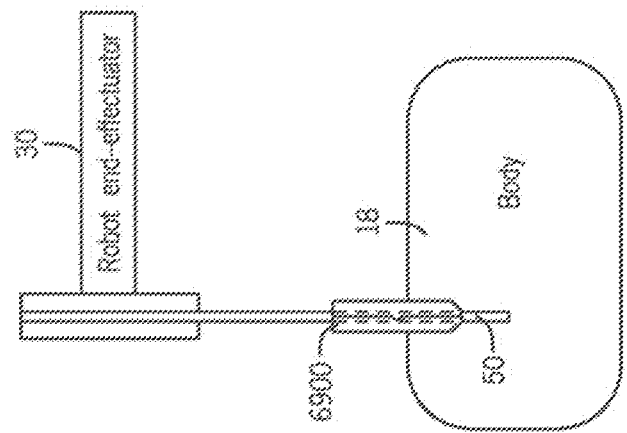
Figure 69C:
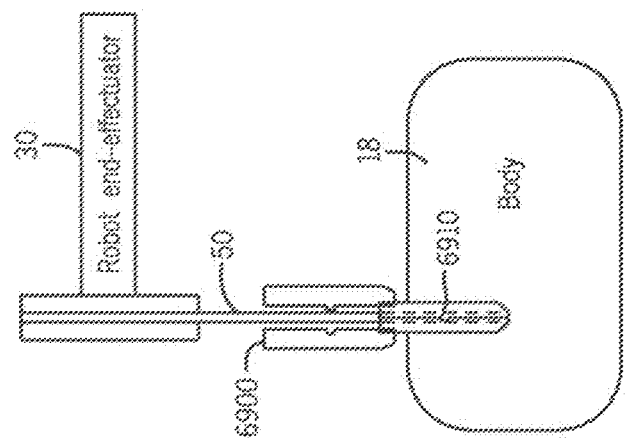

In some further embodiments, the system 1 can include an end-effectuator 30 that is coupled with at least one cylindrical dilator tube 6900. For example, FIGS. 69A-69C illustrate various embodiments of an end-effectuator 30 including cylindrical dilator tubes 6900 in accordance with at least one embodiment of the invention. As shown, in some embodiments, the cylindrical dilator tubes 6900 can be formed from two-halves that snap together. In some embodiments, the cylindrical dilator tubes 6900 can be formed from two-halves that snap together, and in some embodiments, the two-halves snap together over a previous dilator tube 6900. In some embodiments, the tubes 6900 can be fashioned so that they are strong in resisting radial compression, but not necessarily strong in resisting radial expansion (since their opposing force will be the resisting soft tissues). In some embodiments, the tubes 6900 can also benefit from a mechanism for temporarily attaching a conventional handle at the proximal end for easy insertion then removal of the handle following insertion. Moreover, some embodiments include a mechanism for grasping and extracting each tube 6900 or a cluster of tubes 6900, or for attaching one or more tubes 6900 to the central guide tube 50. As depicted in FIGS. 69B and 69C, when the robot's end-effectuator 30 is raised (following the tube 6900 insertion depicted in FIG. 69B), the tube 6900 or cluster of tubes 6900 is extracted with it, leaving behind the outermost dilator 6910a and forming a corridor for surgery. Further, in some embodiments, the surgeon can send the robot's end-effectuator 30 to coincide with the infinite vector defining the desired trajectory, but above the patient 18. In some embodiments, the surgeon then sends the robot's end-effectuator 30 down this vector until the tip of the central guide pin or tube 50 is ready to penetrate soft tissue. In some embodiments, a starter incision may be made to help the central guide tube 50 penetrate the tissue surface. In some embodiments, the surgeon continues to send the robot's end-effectuator 30 down the trajectory vector, penetrating soft tissue, until the target is reached (for example, when the tube 50 abuts bone of a target region). Then, in some embodiments, while the robot 15 holds the central tube 50 steady, each sequential dilator 6900 is slid down the central tube 50 over the previous dilator 6900. When desired dilation is complete, in some embodiments, the proximal end of the dilator tube 6900 may be secured to the patient 18 (or external assembly), and the central tube 50 and all but the outermost dilator tube 6910 would be removed.

Some embodiments include tubes 6900 that comprise a polymeric material. In some embodiments, the tubes 6900 can include at least one either radiolucent or radio-opaque material. In some embodiments, dilators 6900 may be radio-opaque so that their position may be easily confirmed by x-ray. Further, in some embodiments, the outermost dilator 6910 may be radiolucent so that the position of pathology drawn out through the tube, or implants, or materials passed into the patient through the tube, may be visualized by x-ray.

As described earlier, in some embodiments, the use of conventional linear pulse motors 160 within the surgical robot 15 can permit establishment of a non-rigid position for the end-effectuator 30 and/or surgical instrument 35. In some embodiments, the use of linear pulse motors 160 instead of motors with worm gear drive enables the robot 15 to quickly switch between active and passive modes.

The ability to be able to quickly switch between active and passive modes can be important for various embodiments. For example, if there is a need to position the robot 15 in the operative field, or remove the robot 15 from the operative field. Instead of having to drive the robot 15 in or out of the operative field, in some embodiments, the user can simply deactivate the motors 160, making the robot 15 passive. The user can then manually drag it where it is needed, and then re-activate the motors 160.

Figure 70:
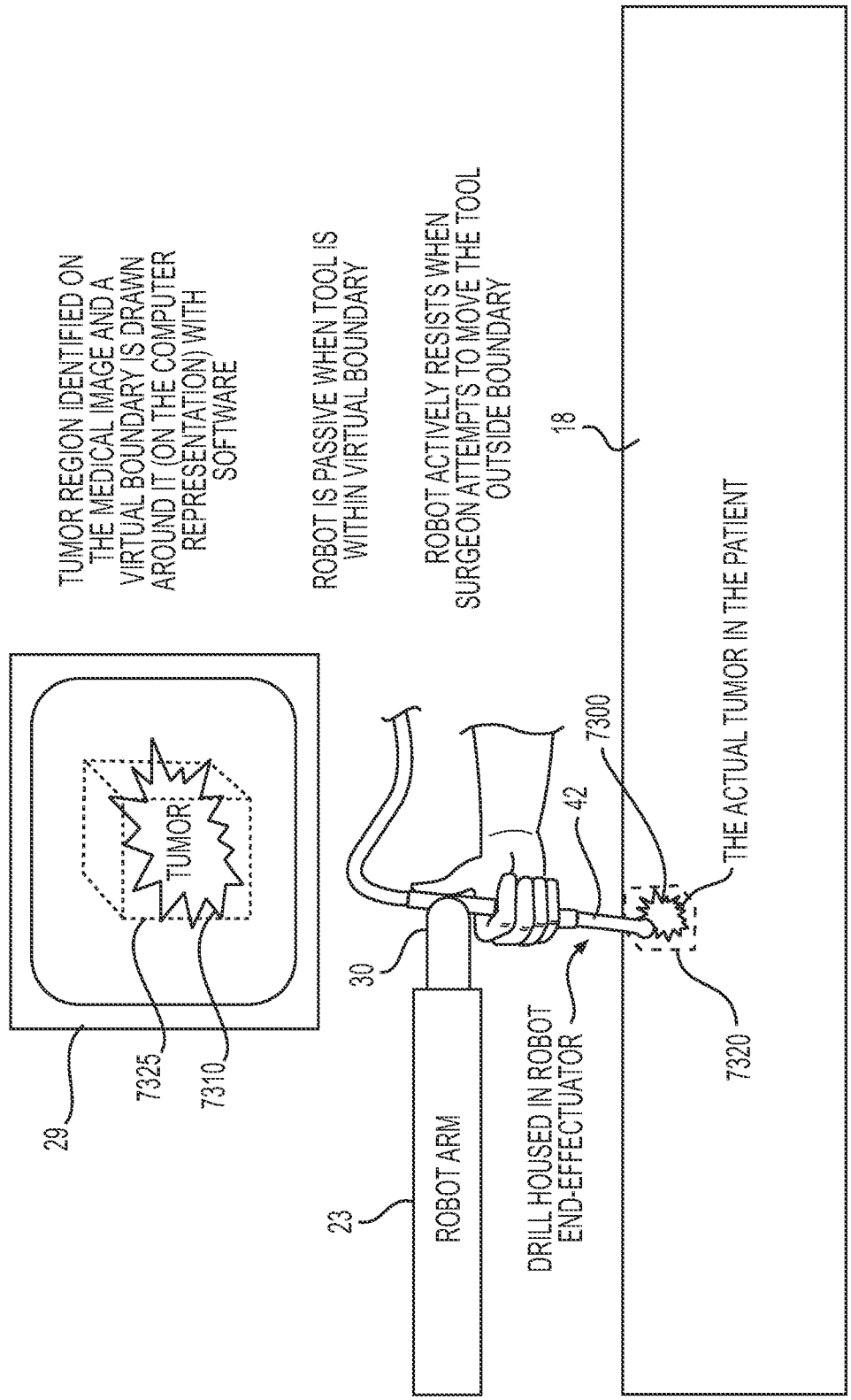
FIG. 70 illustrates a method in accordance with at least one embodiment of the invention.

The ability to be able to quickly switch between active and passive modes can be important for safe zone surgery. In some embodiments, the user can outline a region with pathology (for example a tumor 7300) on the medical images (see for example FIG. 70 showing the displayed tumor 7310 on display means 29). In some embodiments, algorithms may then be implemented where the robot 15 switches from active to passive mode when the boundary of the region is encountered. For example, FIG. 70 shows the boundary region 7320 within the patient 18 displayed as region 7325 on the display means. Anywhere outside the boundary 7320, the robot becomes active and tries to force the end-effectuator 30 back toward the safe zone (i.e. within the boundary 7320). Within the boundary 7320, the robot 15 remains passive, allowing the surgeon to move the tool (such as drill bit 42) attached to the end-effectuator 30.

In some further embodiments, the user can place restrictions (through software) on the range of orientations allowed by the tool within the safe zone (for example, boundary 7320, and displayed as boundary 7325 in FIG. 70). In some embodiments, the tool can only pivot about a point along the shaft that is exactly at the level of the skin. In this instance, the robot 15 freely permits the surgeon to move in and out and pivot the end-effectuator 30, but does not allow left-right or front-back movement without pivoting. For example, in some embodiments, if the surgeon wants to reach a far left point on the tumor 7300, the surgeon must pivot the tool about the pivot point and push it to the appropriate depth of insertion to satisfy the boundary 7320 conditions and force the tip (for example, the tip of the drill bit 42) to that location. This type of limitation can be valuable because it can prevent the surgeon from "ripping" tissue as the drill is moved around to destroy the tumor 7320. Further, it also allows the surgeon to access a safe zone farther distal while keeping clear of a critical structure farther proximal.

Figure 71A:
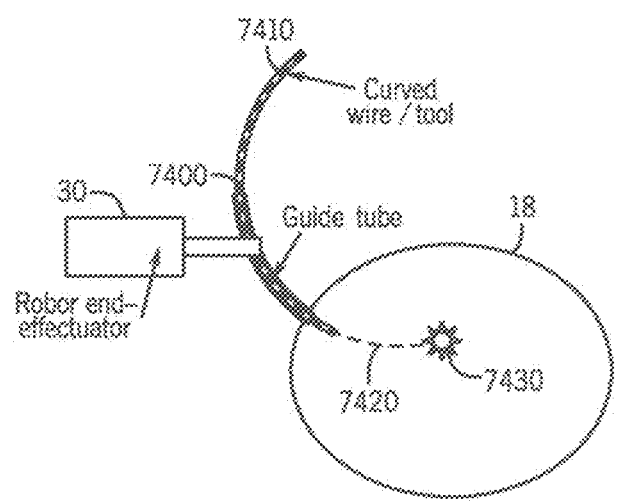
FIG. 71A illustrates a robot end-effectuator coupled with a curved guide tube for use with a curved or straight wire or tool in accordance with at least one embodiment of the invention.

Some embodiments include curved and/or sheathed needles for nonlinear trajectory to a target (for example, such as a tumor 7320 described earlier). In some embodiments, with a curved trajectory, it is possible to approach targets inside the body of a patient 18 that might otherwise be impossible to reach via a straight-line trajectory. For example, FIG. 71A illustrates a robot end-effectuator 30 coupled with a curved guide tube 7400 for use with a curved or straight wire or tool 7410 in accordance with at least one embodiment of the invention. In some embodiments, by forcing a curved or straight wire or tool 7410 through the curved guide tube 7400, at least some curvature will be imparted to the wire or tool 7410. In some embodiments, the curved or straight wire or tool 7410 may comprise a compliant wire capable of forming to the curvature of the guide tube 7400. In some other embodiments, the curved or straight wire or tool 7410 may comprise a non-compliant wire, capable of substantially retaining its shape after entering and exiting the guide tube 7400. A disadvantage of using a very compliant wire is that the tissues that it encounters may easily force it off the desired path. A disadvantage of using a very non-compliant wire is that it would be difficult to achieve a useful amount of curvature. Further, forcing a straight wire of intermediate compliance through a curved guide tube 7400 may produce some curvature of the wire, but less curvature than that of the guide tube 7400. It is possible to mathematically or experimentally model the mechanical behavior of the wire 7410 to determine how much curvature will be imparted. For example, by knowing the orientation of the guide tube 7400, in some embodiments, the robot may be used to accurately guide the curved wire 7410 to a desired target by using computerized planning to predict where the wire 7410 would end up as it traveled through tissue. Further, in some embodiments a very non-compliant wire or tool 7410 can be manufactured in the shape of an arc with a specific radius of curvature, and then fed through a guide tube 7400 with the same radius of curvature. By knowing the orientation of the guide tube 7400 (i.e. substantially the same as wire or tool 7410), computerized planning can be used to predict where the wire or tool 7410 would end up as it traveled through tissue.

Figure 71B:
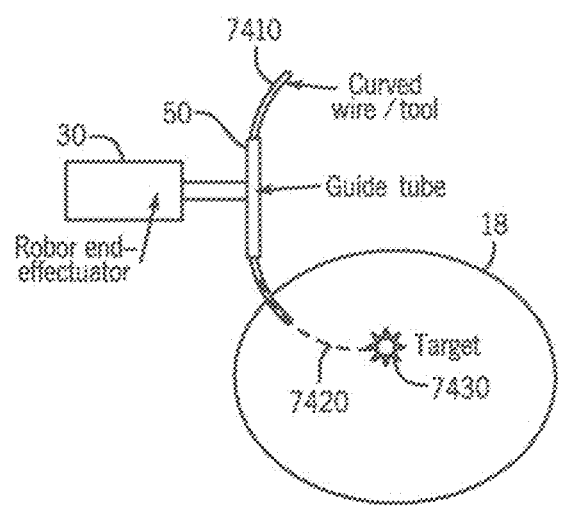
FIG. 71B illustrates a robot end-effectuator coupled with a straight guide tube for use with a curved or straight wire or tool in accordance with at least one embodiment of the invention.

Some other embodiments may use a straight guide tube 50 with a wire or tool 7410 that may be curved or straight. For example, FIG. 71B illustrates a robot end-effectuator 30 coupled with a straight guide tube 50 for use with a curved or straight wire or tool 7405, 7410 in accordance with at least one embodiment of the invention. Some surgical methods may use curved needles 7410 that are manually positioned. In general, the needles consist of a rigid, straight outer guide tube through which is forced an inner needle 7405 with tendency to take on a curved shape. In existing manual devices, the inner needle 7405 is comprised of nitinol, a shape memory alloy, and is formed with significant curvature. This curved needle 7410 is flattened and then fed through the outer guide tube. When it exits the other end of the guide tube, it bends with significant force back toward its original curved configuration. Such a system could be adapted for use with the robot 15 if the curvature of the exiting portion of the needle per unit measure exiting is known, if the radial position of the curved needle 7410 relative to the straight housing is known. In some embodiments, the radial position of the curved needle 7410 can be determined by using marks placed on the curved and straight portions, or through a non-circular cross-section of the straight guide tube and curved needle 7410 (for example, square cross-section of each). In this instance, in some embodiments, it would then be possible to preoperatively plan the path to the target (such as a tumor 7300) and then adjust the robot 15 to guide the curved wire or tool 7410 through this path. In some embodiments, the system 1 can include the ability to electrically stimulate distally while advancing a wire (for example, such as wire 7405, 7410) through soft tissue. For example, some embodiments include a guide tube 7500 capable of being coupled to the robot 15 by end-effectuator 30 that is insulated along its entire shaft but has an electrode 7510 on or near the tip (see for example FIG. 72). In some embodiments, the use of the tube 7500 to perform electromygraphy ("EMG") can enable the system 1 to detect whether nerves come in contact with the guide tube 7500 as the guide tube 7500 is advanced. Some alternative embodiments can include a conventional pin (for example, stainless steel pins such as Kirschner-wires) instead of a tube 7500, insulated along its shaft but not at the tip. In some embodiments, the wire could be connected to a stimulator outside the body and would have the ability to stimulate distally while advancing the pin through soft tissue. In some embodiments, stimulation would allow the ability to identify critical tissue structures (i.e., nerves, plexus).

In some further embodiments, a portion of the leading edge of the guide tube 7500 may be insulated (i.e. comprise a substantially non-electrically conductive area), and a portion of the leading edge may be uninsulated (i.e. the region is inherently electrically conductive area). In this instance, it can be possible to determine the radial direction of the tube 7500 that is closest to the nerve by watching the response as the tube 7500 is rotated. That is, as the tube 7500 is rotated, the EMG nerve detection will have the most pronounced response when the uninsulated portion is nearest the nerve, and the least pronounced response when the uninsulated portion is farthest from the nerve. In some embodiments, it would then be possible for the user to manually steer the robot 15 to automatically steer the tube 7500 farther away from the nerve. In addition, this modified tube 7500 could have a conventional fan-like retractor (not shown) that can be deployed to gently spread the underlying muscle fibers, thereby making an entry point for disk removal, or screw insertion. In some embodiments, the combination of EMG and gentle retraction can enhance the safety and outcomes of robotic assisted spinal surgery.

Figure 72:
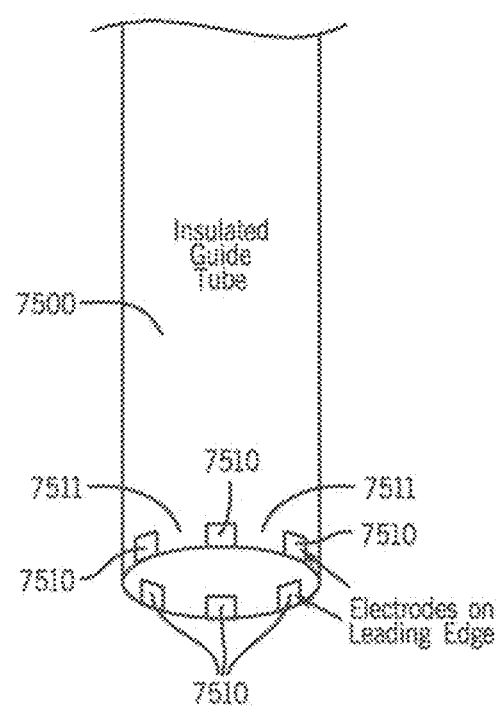
FIG. 72 illustrates a guide tube in accordance with at least one embodiment of the invention.

As described above, one way of taking advantage of the directional electromyographic response is for the user to manually rotate the tube 7500. In some other embodiments, the tube 7500 can be to continuously oscillated back and forth, rotating about its axis while potentials are monitored. In some embodiments, to achieve the same function without rotating the tube 7500, the leading edge of the tube 7500 could have conductive sections that could be automatically sequentially activated while monitoring potentials. For example, in some embodiments, an array of two, three, four, or more electrodes 7510 (shown in FIG. 72) can be positioned around the circumference of the leading edge of the tube 7500. As shown in FIG. 72, regions 7511 between the electrodes 7510 are insulated from each other (because the outer surface of 7500 is insulated). In some embodiments, the electrodes 7510 can be sequentially activated at a very high rate while recording potentials, and correlating which electrode produces the greatest response.

Some embodiments can include a steerable needle capable of being tracked inside the body. For example, U.S. Pat. No. 8,010,181, "System utilizing radio frequency signals for tracking and improving navigation of slender instruments during insertion in the body", herein incorporated by reference, describes a steerable flexible catheter with two or more RF electrodes on the tip, which are used for steering. According to the method described in U.S. Pat. No. 8,010, 181, the side or sides of the tip where the electrodes emit RF have less friction and therefore the probe will steer away from these sides.

Figure 73:
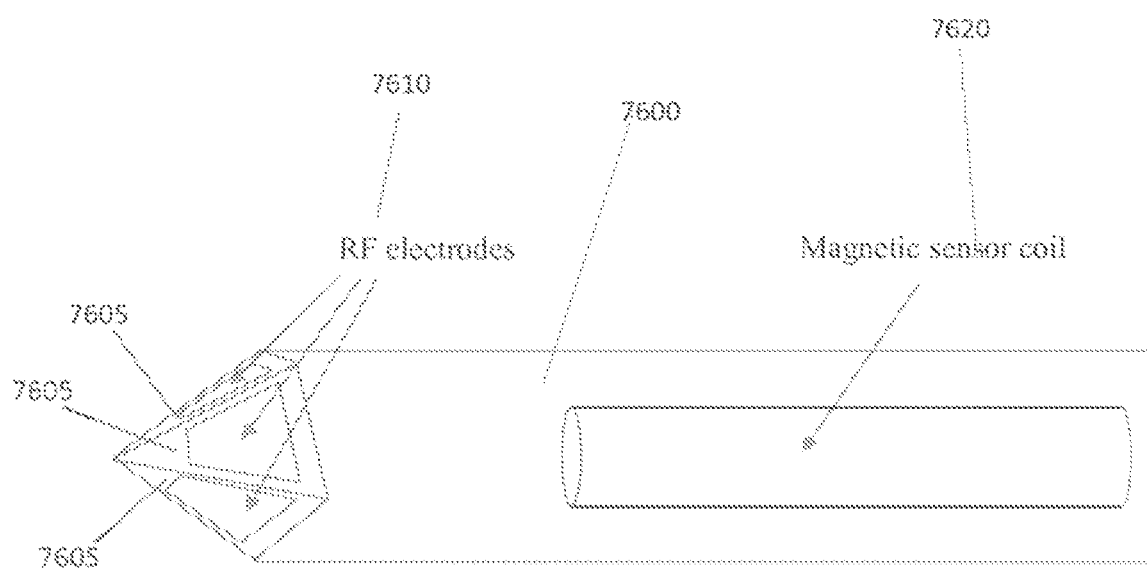
FIG. 73 illustrates a steerable and trackable needle in accordance with at least one embodiment of the invention.

In some embodiments of the invention, a steerable needle 7600 can be coupled with the system 1. In some embodiments, the system 1 can include a steerable needle 7600 coupled with the robot 15 through a coupled end-effectuator 30, the steerable needle 7600 capable of being tracked inside the body of a patient 18. For example, FIG. 73 illustrates a steerable needle 7600 in accordance with at least one embodiment of the invention. In some embodiments, steerable needle 7600 can comprise a plurality of flattened angled bevels 7605 (i.e. facets) on the tip of the probe, with each flat face of each bevel 7605 having an RF electrode 7610. A magnetic coil sensor 7620 embedded within the needle 7600 can enable localization of the tip adjacent to the electrodes 7610. In some embodiments, RF (using for example RF transmitters 120 described earlier) can be used for steering, whereas localization would use electrodes 7610 with the magnetic coil sensor 7620. Some embodiments as described may use off-the-shelf electromagnetic localization system such as the Aurora® from Northern Digital, Inc. (http://www.ndigital.com), which has miniature coils capable of fitting inside a catheter.

Figure 74:
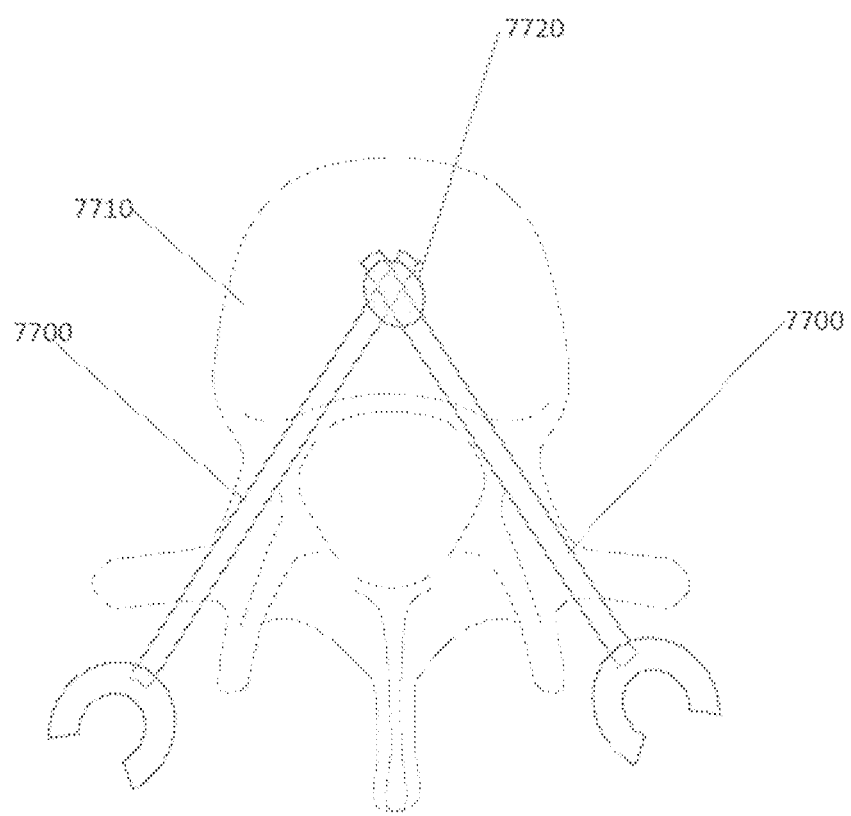
FIG. 74 illustrates one embodiment of intersecting and interlocking bone screws in accordance with at least one embodiment of the invention.

During surgical procedures, pedicle screws or anterior body screws are inserted in two locations. However, there is a chance of failure due to screw pullout. To enhance resistance to pullout, screws are angled toward each other. For example, some embodiments can include intersecting and interlocking bone screws 7700 such as those illustrated in FIG. 74, illustrating one embodiment of intersecting and interlocking bone screws 7700 in accordance with at least one embodiment of the invention. As shown, bone screws 7700 can be coupled and can intersect and interlock 7720. In some embodiments, the intersecting and interlocking bone screws 7700 as shown can be removed without destroying a large area of bone.

Figure 81:
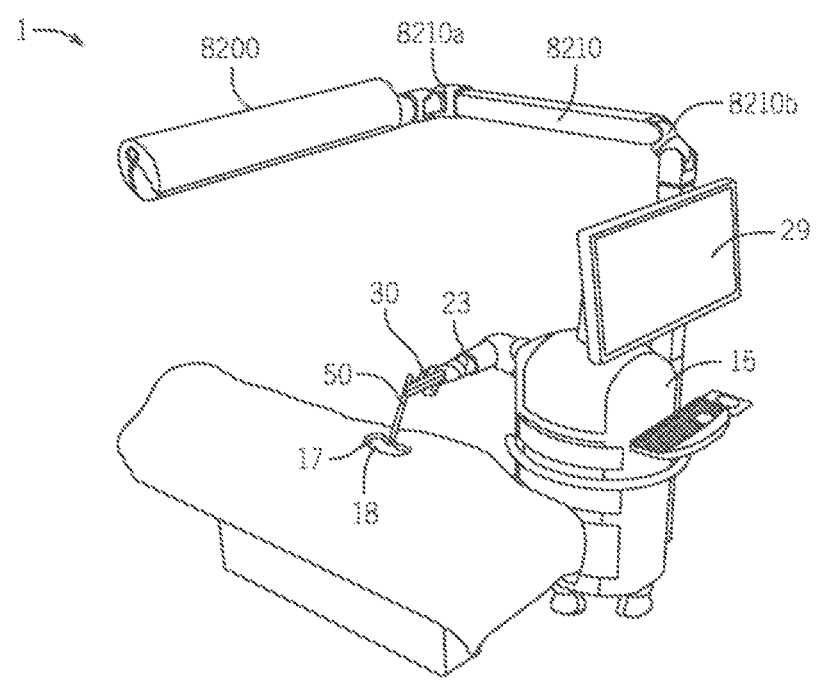
FIG. 81 illustrates a perspective view of a robot system including a camera arm in accordance with one embodiment of the invention.

Some embodiments of the system 1 can include conventional tracking cameras with dual regions of focus. For example, camera units such as Optotrak® or Polaris® from Northern Digital, Inc., can be mounted in a bar so that their calibration volume and area of focus are set. Optotrak® or Polaris® are registered trademarks of Northern Digital, Inc (see for example FIG. 81 showing camera bar 8200). In some embodiments, when tracking the robot 15 and targeting fixture 690 with optical trackers (for example, active markers 720), maintaining markers 720 within the center of the volume can provide the best focus. However, it is not possible for both the targeting fixture's 690 markers and the robot's 15 markers to be substantially centered simultaneously, and therefore both are offset from center by substantially the same distance.

In some embodiments, one solution to this issue is to set up two pairs of cameras 8200 with one camera shared, that is, cameras 1 and 2 form one pair, and cameras 2 and 3 form another pair. This configuration is the same as the Optotrak® system (i.e., three cameras in a single bar), however, the Optotrak® only has one volume and one common focal point. Conversely, some embodiments of the invention would be tuned to have two focal points and two volumes that would allow both the targeting fixture 690 and the robot 15 to be centered at the same time. In some embodiments, the orientations of the lateral cameras can be adjusted by known amounts with predictable impact on the focal point and volume.

In a further embodiment of the invention, two separate camera units (for example, two Polaris® units) can be mounted to a customized conventional bracket fixture including adjustment features (not shown). In some embodiments, this fixture would be calibrated so that the vectors defining the directions of the volumes and distance to focal point can be adjustable by known amounts. In some embodiments, the user could then point one Polaris® unit at the robot's markers, and the other Polaris® unit at the targeting fixture's 690 markers 720. The position of the adjustment features on the bracket would tell the computer what the transformation is required to go from one camera's coordinate system to the other.

In some further embodiments, the cameras 8200 (such as Optotrak® or Polaris®) focused on a particular region could be further improved by a conventional automated mechanism to direct the cameras 8200 at the center of the target. Such a method would improve accuracy because in general, image quality is better toward the center of focus than toward the fringes. In some embodiments, conventional motorized turrets could be utilized to adjust azimuth and elevation of a conventional bracket assembly for aiming the cameras 8200 (and/or in conjunction with movement of cameras 8200 on camera arm 8210 as shown in FIG. 81). In some embodiments, feedback from the current location of active markers 720 within the field of view would be used to adjust the azimuth and elevation until the camera 8200 points directly at the target, regardless of whether the target is the center (mean) of the markers 720 on the robot 15, the center of markers 720 on the targeting fixture 720, or the center of all markers 720. In some embodiments, such a method would allow the center of focus of the cameras 8200 to continuously move automatically as the patient 18 or robot move, ensuring the optimal orientation at all times during the procedure.

Figure 75A:
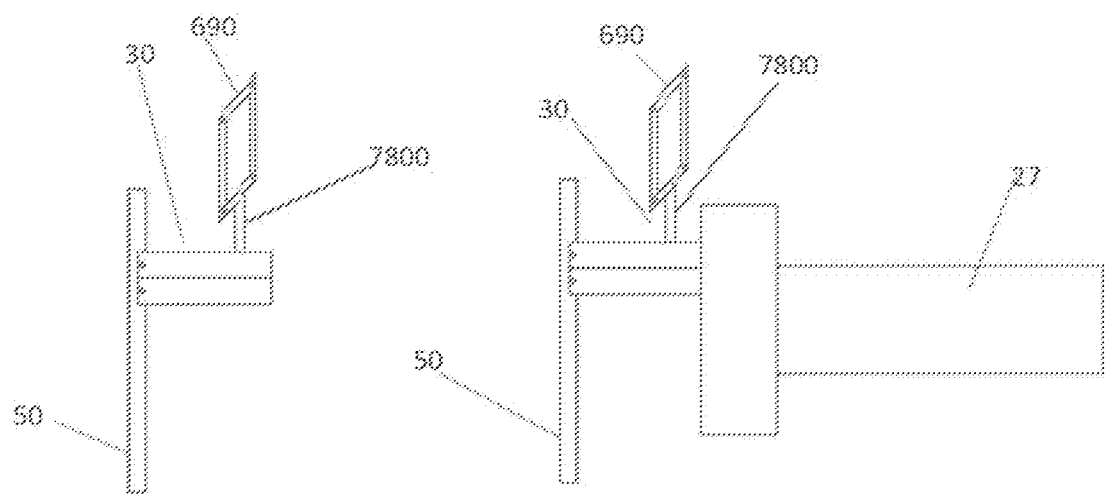
FIG. 75A-75B illustrates configurations of a robot for positioning alongside a bed of a patient that includes a targeting fixture coupled to an end-effectuator using a snap-in post.
Figure 75B:
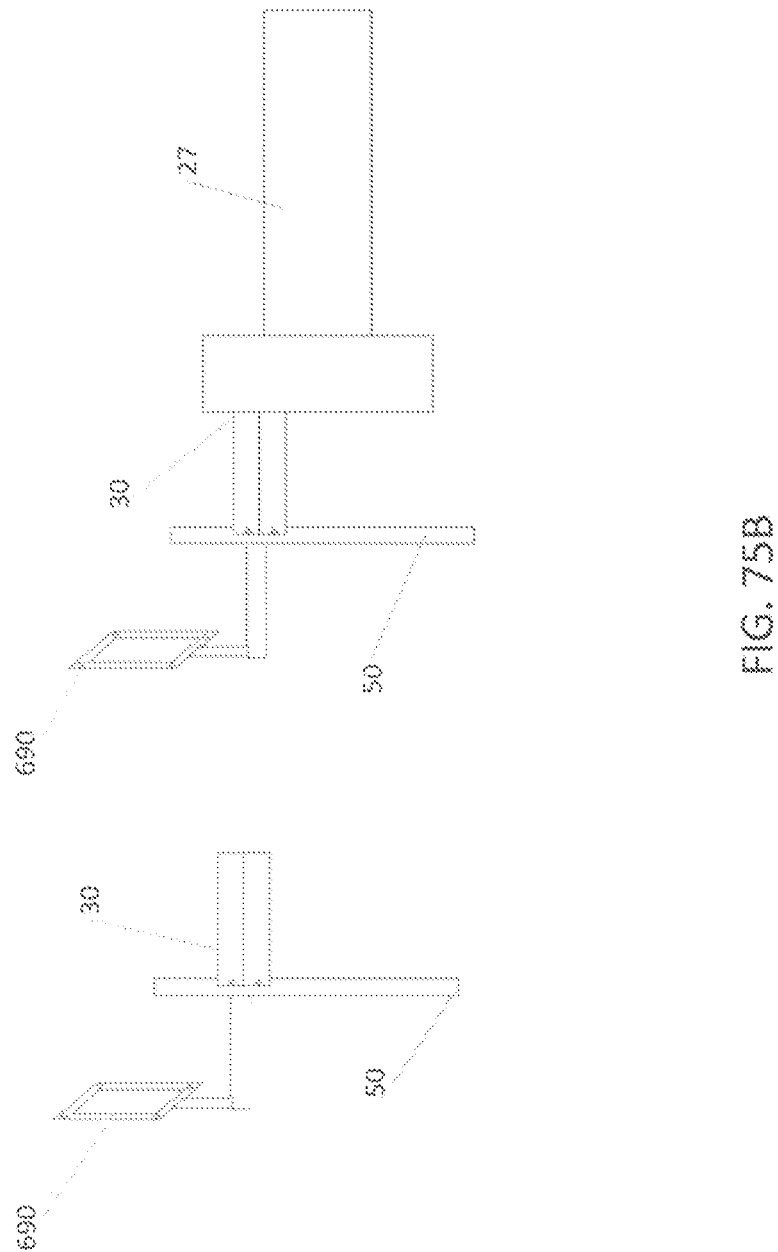

Some embodiments can include a snap-in end-effectuator 30 with attached tracking fixtures 690 (including active markers 720). For example, some embodiments include snap-in posts 7800 attached to the end-effectuator 30 and tracking fixtures 690. In some embodiments, the snap-in posts 7800 can facilitate orienting tracking markers 720 to face cameras 8200 in different setups by allowing markers 720 to be mounted to each end-effectuator 30. FIG. 75A-75B illustrates configurations of a robot 15 for positioning alongside a bed of a patient 18 that includes a targeting fixture 690 coupled to an end-effectuator 30 using a snap-in post 7800. In some embodiments, with the robot 15 in a typical configuration alongside a bed with the patient's 18 head toward the left, one end-effectuator 30 could have right-facing markers 720 (fixture 690) (illustrated in FIG. 75A) for cameras 8200 positioned at the foot of the bed. In some embodiments, the same type of end-effectuator 30 could have left-facing markers 720 (fixture 690) for cameras 8200 positioned at the head of the bed (illustrated in FIG. 75B). In some embodiments, the fixtures 690 are mounted where they would be closer to the cameras 8200 than the end-effectuator 30 so that the surgeon does not block obscure the markers 720 from the camera when using the tube 50. In some further embodiments, each interchangeable end-effectuator 30 could include conventional identification electronics. For example, in some embodiments, each interchangeable end-effectuator 30 could include an embedded conventional chip and a press-fit electrical connector. In some embodiments, when the system 1 includes a snap-in end-effectuator 30 with attached tracking fixtures 690, the computer 100 may recognize which end-effectuator is currently attached using the identification electronics. In some embodiments, when the system 1 includes a snap-in end-effectuator 30 with attached tracking fixtures 690, the computer 100 may recognize which end-effectuator is currently attached using the identification electronics, and apply stored calibration settings.

The robot system 1 contains several unique software algorithms to enable precise movement to a target location without requiring an iterative process. In some embodiments, an initial step includes a calibration of each coordinate axis of the end-effectuator 30. During the calibration, the robot 15 goes through a sequence of individual moves while recording the movement of active markers 720 that are temporarily attached to the end-effectuator (see FIG. 76). From these individual moves, which do not have to fall in a coordinate system with orthogonal axes, the required combination of necessary moves on all axes is calculated.

Figure 76:
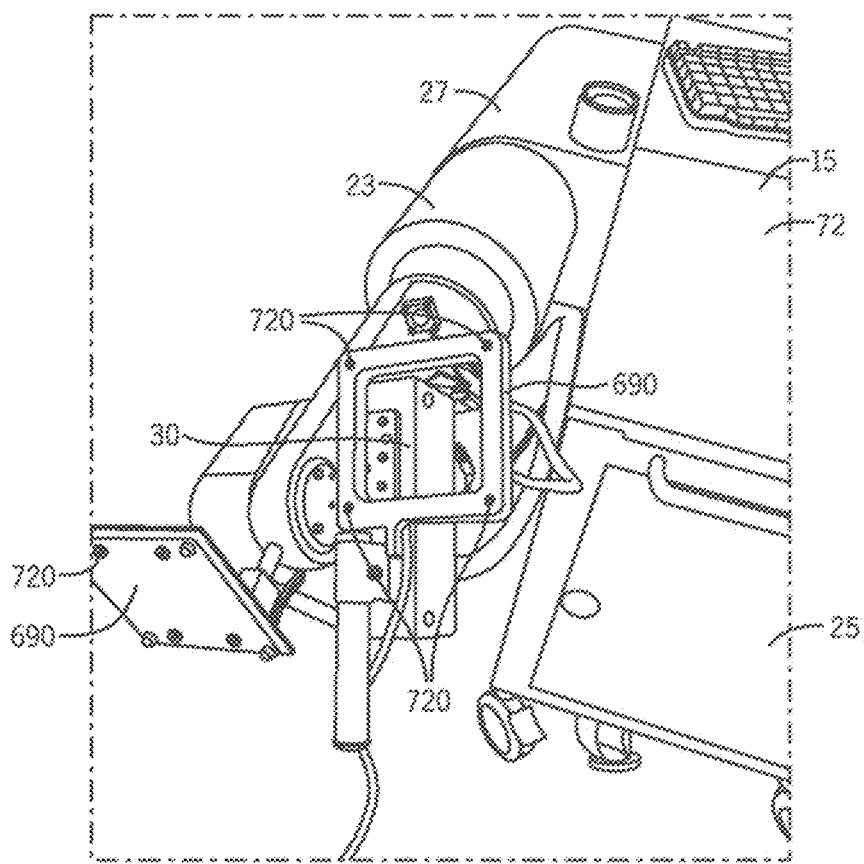
FIG. 76 illustrates a surgical robot having a plurality of optical markers mounted for calibration and tracking movement in accordance with one embodiment of the invention.

In some embodiments, it is possible to mount optical markers 720 for tracking the movement of the robot 15 on the base of the robot 15, then to calculate the orientation and coordinates of the guide tube 50 based on the movement of sequential axes (see earlier description related to FIG. 16). The advantage of mounting markers 720 on the base of the robot 15 is that they are out of the way and are less likely to be obscured by the surgeon, tools, or parts of the robot. However, the farther away the markers 720 are from the end-effectuator 30, the more the error is amplified at each joint. At the other extreme, it is possible to mount the optical markers 720 on the end-effectuator 30 (as illustrated in FIG. 76). The advantage of mounting markers 720 on the end-effectuator is that accuracy is maximized because the markers 720 provide feedback on exactly where the end-effectuator 30 is currently positioned. A disadvantage is that the surgeon, tools, or parts of the robot 15 can easily obscure the markers 720 and then the end-effectuator's 30 position in space cannot be determined.

In some embodiments, it is possible to mount markers 720 at either extreme or at an intermediate axis. For example, in some embodiments, the markers 720 can be mounted on the x-axis 66. Thus, when the x-axis 66 moves, so do the optical markers 720. In this location, there is less chance that the surgeon will block them from the cameras 8200 or that they would become an obstruction to surgery. Because of the high accuracy in calculating the orientation and position of the end-effectuator 30 based on the encoder outputs from each axis, it is possible to very accurately determine the position of the end-effectuator 30 knowing only the position of the markers on the x-axis 66.

Some embodiments include an algorithm for automatically detecting the centers of the radio-opaque markers 730 on the medical image. This algorithm scans the medical image in its entirety looking for regions bounded on all sides by a border of sufficient gradient. If further markers 730 are found, they are checked against the stored locations and thrown out if outside tolerance.

Figure 77:
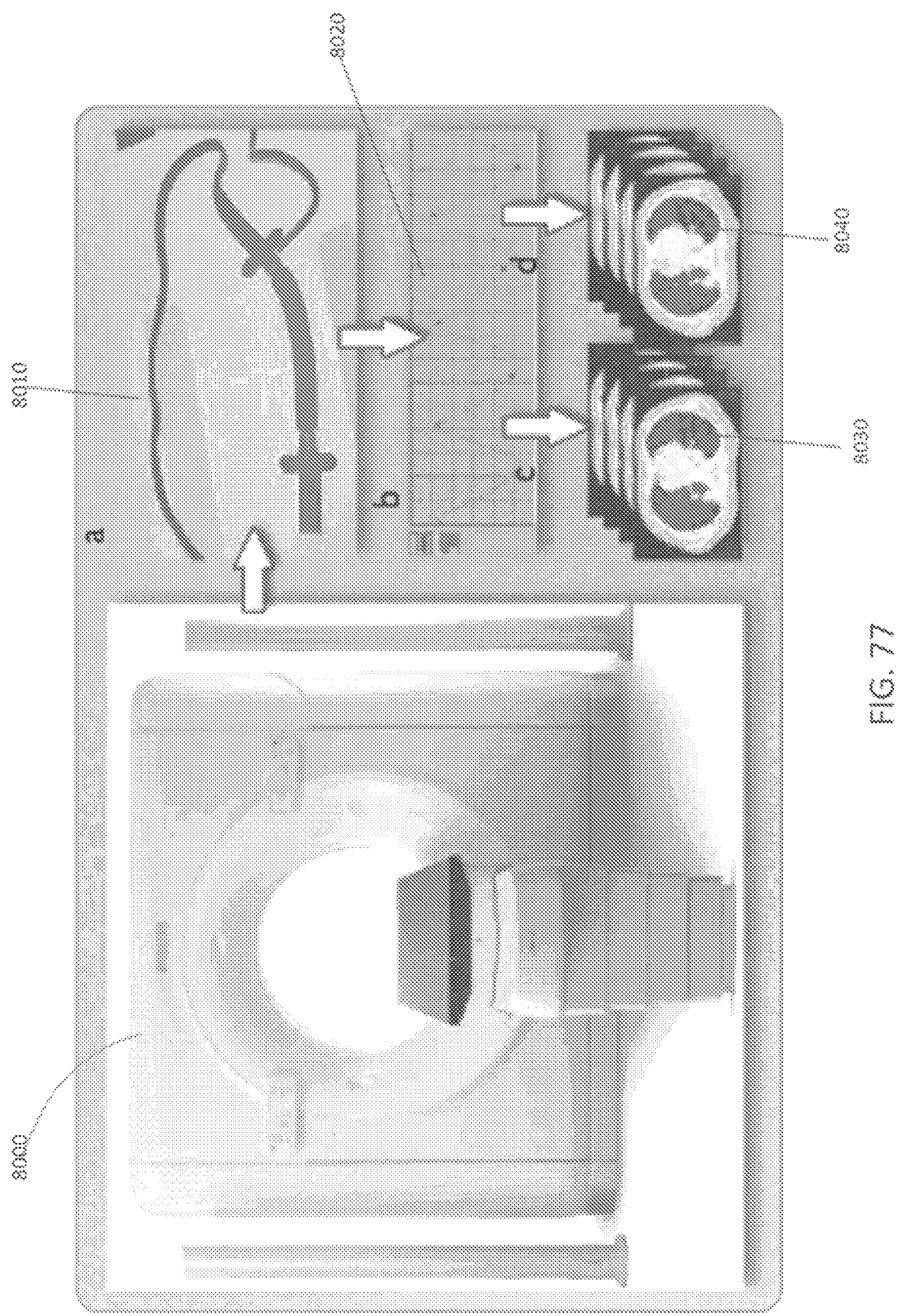
FIG. 77 illustrates a CT scan and methods in accordance with one embodiment of the invention.

Some biopsy procedures can be affected by the breathing process of a patient, for example when performing a lung biopsy. In some procedures, it is difficult for the clinician to obtain a sample during the correct breathing phase. The use of tracking markers 720 coupled to a bone of the patient cannot alone compensate for the breathing induced movement of the target biopsy region. Some embodiments include a method of performing a lung biopsy with breathing correction using the system 1. Currently, for radiation treatment of lung tumors, breathing is monitored during CT scan acquisition using a "bellows" belt (see for example CT scanner 8000 in FIG. 77, with bellows image 8010. The bellows monitors the phase of breathing, and when the clinician tells the patient to hold their breath, CT scan of the patient 18 is performed. The bellows output 8010 shows the phase in which the CT was taken. Later, targeted radiation bursts can be applied when the lung is in the right position as monitored by the bellows during the treatment phase. A CT scan is taken while the bellows monitors the breathing phase and when the patient held their breath during the CT scan. Later, radiation bursts are applied instantaneously when that same phase is reached without requiring the patient 18 to hold their breath again.

Figure 78:
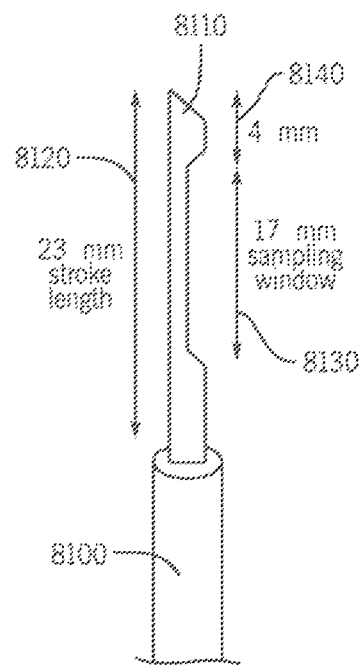
FIG. 78 illustrates a biopsy tool in accordance with one embodiment of the invention.

Some embodiments include a method of performing a lung biopsy with breathing correction using the system 1. In some embodiments, a tracking fixture 690 is attached to the patient 18 near biopsy site and bellows belt on the patient's 18 waist. In some embodiments, a CT scan of the patient 18 is performed with the patient holding their breath, and while monitoring the breathing phase. In some embodiments, a clinician locates the target (for example, a tumor) on the CT volume, and configures the robot 15 to the target using at least one of the embodiments as described earlier. In some embodiments, the robot 15 calibrates according to at least one embodiment described earlier. In some embodiments, the robot 15 moves into position above the biopsy site based the location of at least one tracking marker 720, 730. In some embodiments, the bellows belt remains in place, whereas in other embodiments, the markers 720, 730 on the patient 18 can track the breathing phase. In some embodiments, based on the bellows or tracking markers 720, 730, the computer 100 of the computing device 3401 within platform 3400 can use robotic guidance software 3406 to send a trigger during the calibrated breathing phase to deploy a biopsy gun to rapidly extract a biopsy of the target (such as a tumor). In some embodiments, a conventional biopsy gun (or tool, such as biopsy gun tip 8100 in FIG. 78) could be mounted in the robot's end-effectuator 30 and activated by a conventional mechanism (such as for example, by a toggled digital output port). For example, as shown, the biopsy gun tip 8100 can comprise a biopsy needle 8110 including a stroke length 8120, a sampling window 8130 and a biopsy tip 8140. In some embodiments, the biopsy needle 8110 in the biopsy gun tip 8100 can be mounted to the end-effectuator 30. In some embodiments, the biopsy needle 8110 can be inserted (under guidance by the robot 15) at least partially into the superficial tissues near the target (for example, the moving lung tumor). In some embodiments, the biopsy gun tip 8100 can fire as directed by a software 3406 trigger, requiring only a small penetration to retrieve the biopsy.

Deep brain stimulation ("DBS") requires electrodes to be placed precisely at targets in the brain. Current technology allows CT and MRI scans to be merged for visualizing the brain anatomy relative to the bony anatomy (skull). It is therefore possible to plan trajectories for electrodes using a 3D combined CT/MRI volume, or from CT or MRI alone. Some embodiments include robot 15 electrode placement for asleep deep brain stimulation using the system 1 where the acquired volume can then be used to calibrate the robot 15 and move the robot 15 into position to hold a guide 50 for electrode implantation.

In some embodiments, a Mayfield frame 6700 modified including one possible configuration for active and radio-opaque markers (shown in FIG. 67 in accordance with one embodiment of the invention) can be used for electrode placement for asleep deep brain stimulation. In some embodiments, the active markers 720 do not need to be attached at the time of the scan as long as their eventual position is unambiguously fixed. In some embodiments, the radio-opaque markers 730 can be removed after the scan as long as the relative position of the active markers 720 remains unchanged from the time of the scan. In some embodiments, the marker 730 can be a ceramic or metallic sphere, and for MRI, a suitable marker is a spherical vitamin E capsule. In some embodiments, the end-effectuator 30 can include an interface for feeding in a conventional electrode cannula and securing the electrode housing to the skull of the patient 18 (for example, using a Medtronic StimLoc® lead anchoring device to the skull). StimLoc® is a trademark of Medtronic, Inc., and its affiliated companies.

Figure 79:
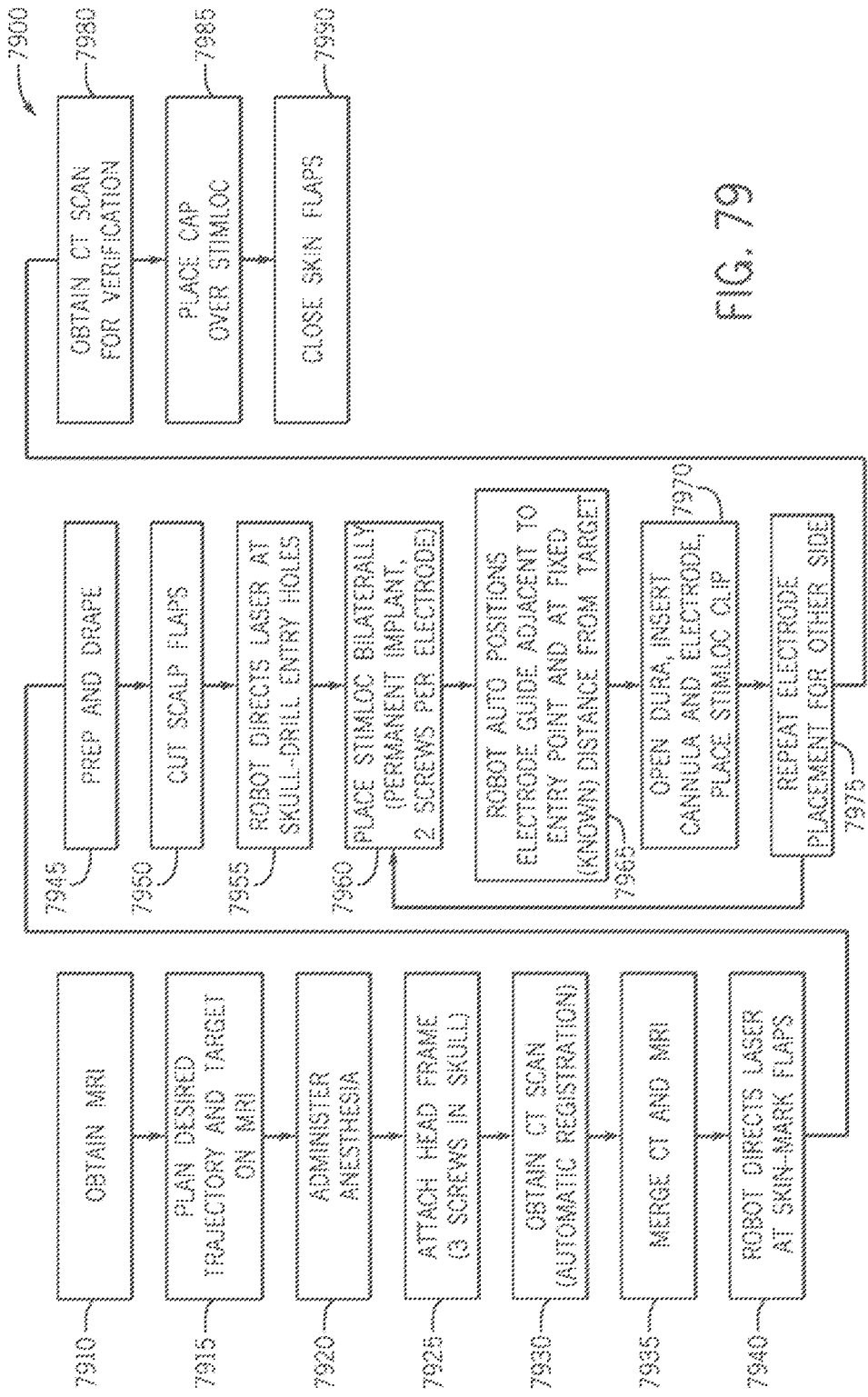
FIG. 79 illustrates a deep brain stimulation electrode placement method performed by the robot system in accordance with one embodiment of the invention.

In some embodiments, the system 1 can perform the method steps 7910-7990 as outlined in FIG. 79 for DBS electrode placement. As show, in some embodiments, the patient 18 can receive an MRI 7910, and the target and trajectory can be planned 7915. Surgery can be initiated under general anesthesia 7920, and the head frame (as shown in FIG. 67) can be attached to the patient 18 with three screws in the skull 7925. In some embodiments, a CT scan can be performed 7930, and the previously obtained MRI 7910 can be merged with the CT scan 7935. During the CT scan, software can automatically register the anatomy relative to the markers 720, 730 that are mounted on the head holder. In some embodiments, the robot 15 can direct a laser at the skin of the patient 18 to mark flaps 7940. In some embodiments, the skin of the patient 18 can be prepared and draped 7945, and scalp flaps can be prepared 7950. As shown, in some embodiments, the robot 15 can laser drill entry holes 7955, and the StimLoc can be secured bilaterally 7960 (permanent implant, 2 screws per electrode). In some embodiments, the robot 15 can auto-position a conventional electrode guide adjacent to entry point at a fixed (known) distance from target 7965. In some embodiments, the dura can be opened, a cannula and electrode inserted, and a StimLoc clip can be positioned 7970. In some embodiments, steps 7965, 7970 are repeated for the other side of the patient's skull 7975. In some embodiments, a verification CT scan is performed 7980, a cap is placed over the StimLoc, and the flaps are closed.

In some embodiments, the robot system 1 includes at least one mounted camera. For example, FIG. 81 illustrates a perspective view of a robot system including a camera arm in accordance with one embodiment of the invention. In some embodiments, to overcome issues with line of sight, it is possible to mount cameras for tracking the patient 18 and robot 15 on an arm 8210 extending from the robot. As shown in FIG. 81, in some embodiments, the arm 8210 is coupled to a camera arm 8200 via a joint 8210*a*, and the arm 8210 is coupled to the system 1 via joint 8210*b*. In some embodiments, the camera arm 8200 can be positioned above a patient (for example, above a patient 18 lying on a bed or stretcher as shown in FIG. 81). In this position, in some embodiments, it might be less likely for the surgeon to block the camera when the system 1 is in use (for example, during a surgery and/or patient examination). Further, in some embodiments, the joints 8210*a*, 8210*b* can be used to sense the current position of the cameras (i.e. the position of the camera arm 8200). Moreover, in some embodiments, the exact position of the end-effectuator 30 in the camera's coordinate system can be calculated based on monitored counts on each robot axis 66, 68, 70, 64, and in some embodiments, the cameras 8200 would therefore only have to track markers 720 on the patient 18.

Figure 82A:
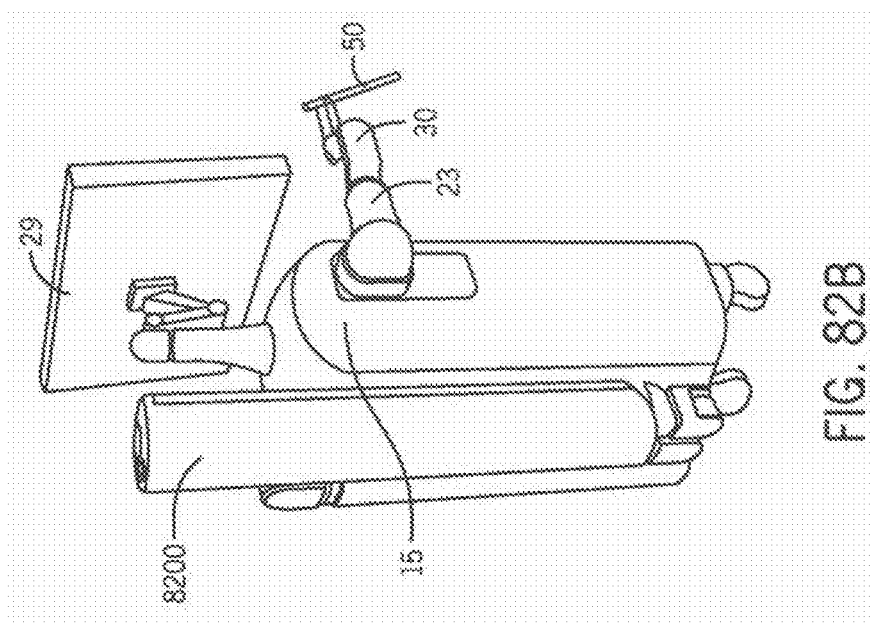
FIG. 82A illustrates a front-side perspective view of a robot system including a camera arm in a stored position in accordance with one embodiment of the invention.
Figure 82B:
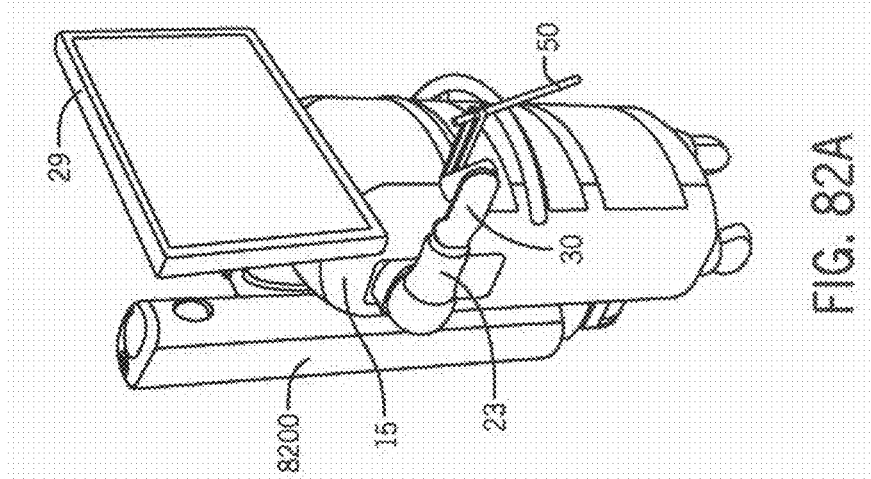
FIG. 82B illustrates a rear-side perspective view of a robot system including a camera arm in a stored position in accordance with one embodiment of the invention.

Some embodiments include an arm 8210 and camera arm 8200 that can fold into a compact configuration for transportation of the robot system 1. For example, FIG. 82A illustrates a front-side perspective view of a robot system including a camera arm in a stored position, and FIG. 82B illustrates a rear-side perspective view of a robot system including a camera arm in a stored position in accordance with one embodiment of the invention.

Some embodiments can include methods for prostate 8330 immobilization with tracking for imaged-guided therapy. In some embodiments, to enable the insertion of a needle (7405, 7410, 7600, 8110 for example) into the prostate 8330 utilizing 3D image guidance, a 3D scan of the prostate 8330 relative to reference markers 720, 730 or other tracking system 3417 is needed. However, the prostate 8330 is relatively mobile and can shift with movement of the patient 18. In some embodiments, it may be possible to immobilize the prostate 8330 while also positioning and securing tracking markers 720 in close proximity to improve tracking and image guidance in the prostate 8330.

Figure 83:
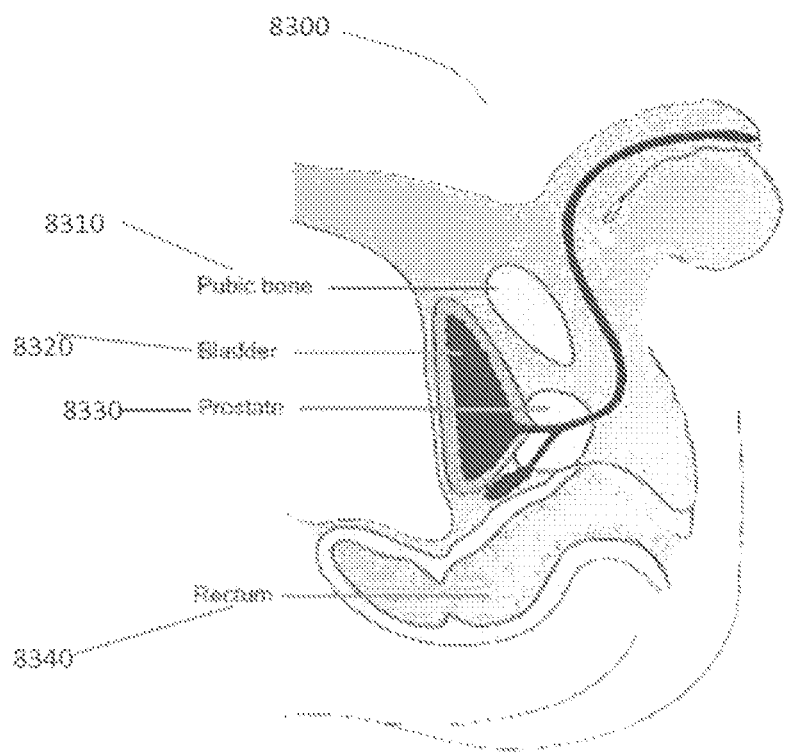
FIG. 83 shows a lateral illustration of a patient lying supine, showing the normal relative positions of the prostate, rectum, bladder, and pubic bone.
Figure 84:
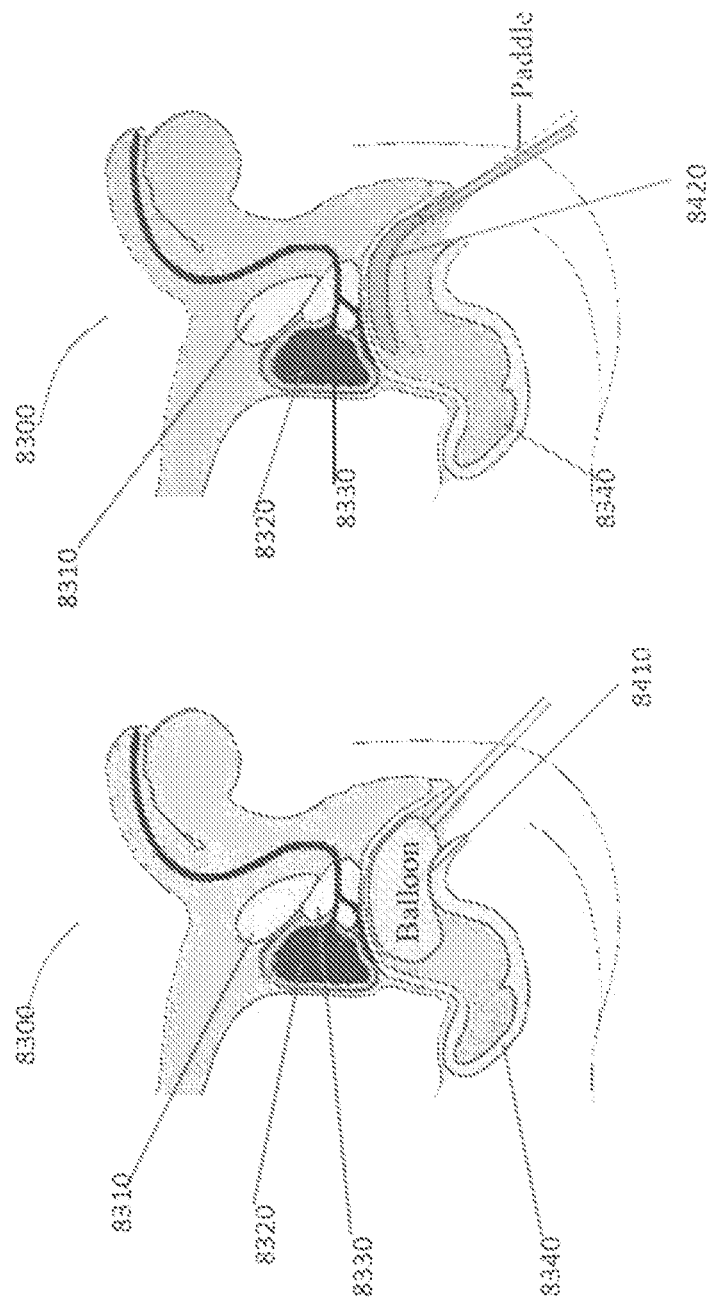
FIG. 84A shows a lateral illustration of a patient lying supine, showing how inflation of a balloon can cause anterior displacement of the prostate toward the pubic bone, and a controllable amount of compression against the pubic bone in accordance with one embodiment of the invention.
FIG. 84B shows a lateral illustration of a patient lying supine, showing how shifting of a paddle in the rectum can cause anterior displacement of the prostate toward the pubic bone, and a controllable amount of compression against the pubic bone in accordance with one embodiment of the invention.

The prostate 8330 is anatomically positioned adjacent to the bladder 8320, the pubic bone 8310, and the rectum 8340 (see for example FIG. 83 showing a lateral illustration of a patient lying supine, depicting the normal relative positions of the prostate 8330, rectum 8340, bladder 8320, and pubic bone 8310). This position facilitates entrapment of the prostate 8330, especially when it is enlarged, against the bladder 8320 and pubic bone 8310 via anterior displacement applied within the rectum 8340. In some embodiments, displacement could be applied using a balloon 8410, a paddle 8420, or a combination of the two elements. For example, FIG. 84A shows a lateral illustration of a patient lying supine, showing how inflation of a balloon can cause anterior displacement of the prostate 8330 toward the pubic bone 8310, and a controllable amount of compression against the pubic bone 8310 in accordance with one embodiment of the invention. Further, FIG. 84B shows a lateral illustration of a patient lying supine, showing how shifting of a paddle in the rectum 8340 can cause anterior displacement of the prostate 8330 toward the pubic bone 8310, and a controllable amount of compression against the pubic bone 8310 in accordance with one embodiment of the invention.

In some embodiments, the balloon 8410 has the advantage that it can be inserted into the rectum 8340 un-inflated, and then when inflated. In some embodiments, it will displace the wall of the rectum 8340 and prostate 8330 laterally toward the pubic bone 8310. In some embodiments, a paddle 8420 can cause lateral displacement of the rectal wall and prostate 8330 if a pivot point near the anus is used.

Figure 85:
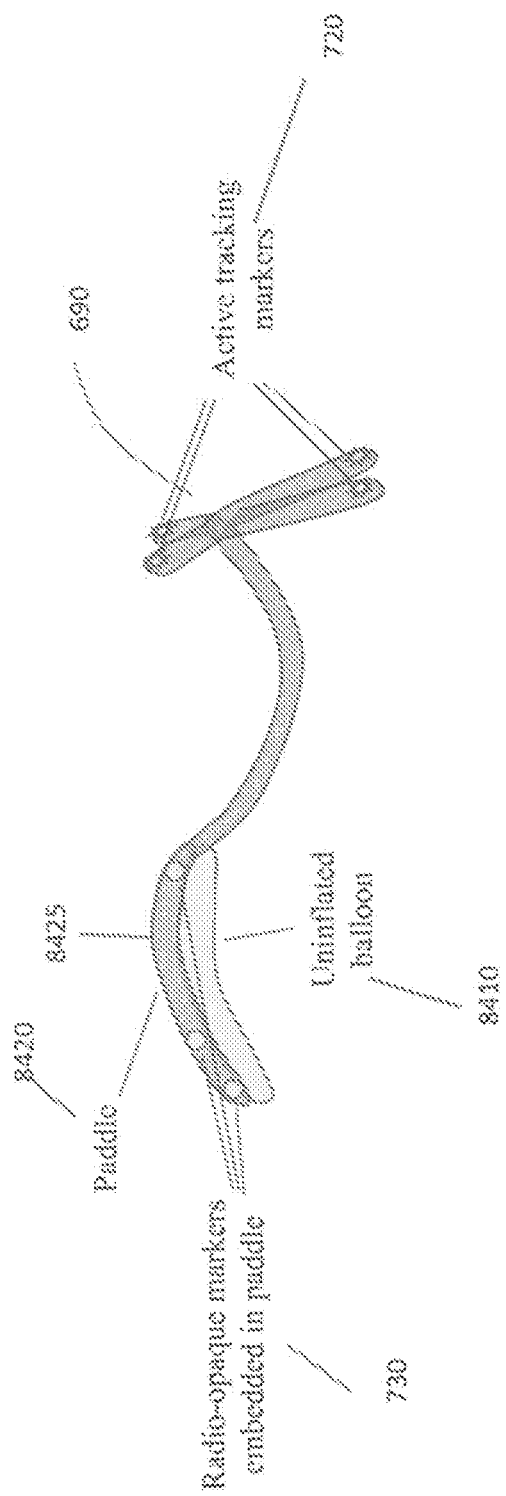
FIG. 85 shows a sketch of a targeting fixture and immobilization device to be used for tracking the prostate during image-guided surgical procedures in accordance with one embodiment of the invention.
Figure 86:
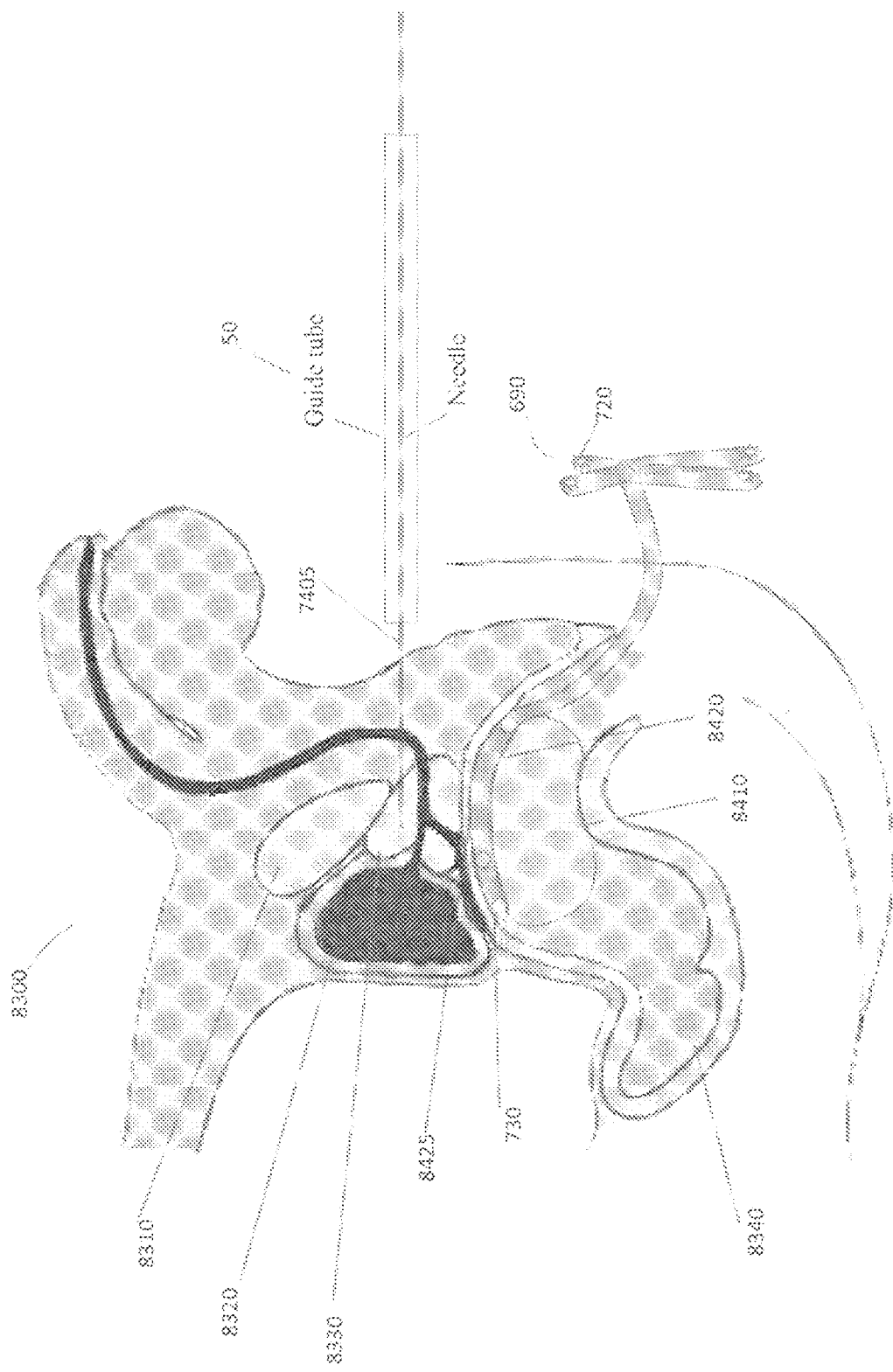
FIG. 86 shows an illustration of the device as illustrated in FIG. 85, in place in the rectum with prostate compressed and immobilized and tracking markers visible protruding caudal to the rectum in accordance with one embodiment of the invention.

In some embodiments, it is possible to configure a device consisting of a balloon 8410 and paddle 8420 such that fiducials are embedded in the device, with these fiducials being detectable on the 3D medical image (for instance, such as MM). For example, FIG. 85 shows a sketch of a targeting fixture and immobilization device to be used for tracking the prostate 8330 during image-guided surgical procedures in accordance with one embodiment of the invention. As shown, active tracking markers 720 can be rigidly interconnected to the paddle element 8420 such that these tracking markers 720 protrude from the rectum 8340 and are visible to tracking cameras (for example, 8200) during the medical procedure. For example, FIG. 86 shows an illustration of the device as illustrated in FIG. 85, in place in the rectum 8340 with prostate 8330 compressed and immobilized and tracking markers visible protruding caudal to the rectum 8340 in accordance with one embodiment of the invention.

In some embodiments, in addition to applying lateral force from the side of the rectum 8340, it is also possible to apply lateral force from the side of the abdomen of the patient 18. In some embodiments, this secondary lateral force, used in conjunction with the force from the rectal wall, may assist in keeping the prostate 8330 immobilized. Additionally, it can serve as a support to which the tracking markers 720 are attached, and can serve as a support to which the rectal paddle/balloon 8420, 8410 can be attached for better stabilization. In some embodiments, the abdominal support can consist of a piece that presses from anterior toward posterior/inferior to press against the top of the bladder 8320 region. For example, conventional straps or pieces that encircle the legs can provide additional support. Since the abdominal shape and leg shape varies among patients, some customization would be beneficial. In some embodiments, adjustable straps and supports made of thermoplastic material could be utilized for customization. In some embodiments, commercially available thermoplastic supports (for example, from Aquaplast Inc) can be used. In some embodiments, the supports are formed by first dipping the support material in hot water to soften it, then applying the support to the patient's skin and molding it. After removing the support material from the hot water, the temperature is low enough that it does not burn the skin, but is warm enough that the support material remains soft for 1-5 minutes. In some embodiments, when the support cools, it maintains the skin contours against which it has been formed. In some embodiments, this type of support could be made for immobilizing the prostate 8330 shaped like moldable briefs. In this instance, the support would be dipped in hot water and then external straps and/or manual pressure would be applied to force the support device to press down toward the prostate 8330. Further, in some embodiments, the support could be manufactured in two halves, formed so that it is molded while two halves are tied together, and then removed (untied) when cool (so that it can later be reattached in the same configuration during the procedure).

In some embodiments, the combination of the elements as described above (including balloon 8410 and/or paddle 8420, enables real-time tracking of the prostate 8330, and manual or robotically assisted insertion of needles (for example, 7405, 7410, 7600, 8110) into the prostate 8330 based on targeting under image guidance. In some embodiments, the procedure can include the conventional abdominal support device as described above. The device would be prepared by dipping in hot water until soft, then applying to the patient such that gentle pressure is maintained from anterior to posterior/inferior against the bladder 8320 region and prostate 8330. In some embodiments, under palpation, the tracking device (paddle 8420 with coupled fixture 690 including markers 720 illustrated in FIG. 85) would be inserted into the rectum 8340 with the paddle 8420 and radio-opaque markers 730 adjacent to the prostate 8330. In this instance, gentle pressure can be manually applied to the protruding handle by the surgeon to maintain the position of the interior paddle 8420. In some embodiments, the balloon 8410 is inflated to maintain gentle compression against the prostate 8330, and to immobilize the prostate 8330 against the pubic bone 8310. In some embodiments, if the conventional abdominal device is used, the abdominal device is interconnected to the rectal device at this point for additional stability. In some embodiments, an MM is obtained. During the MM, the active tracking markers 720 are not attached since they are metallic. In some embodiments, sockets or other conventional quick-connect mechanical device are present in the locations where the markers 720 or marker tree (fixture 690) will later be inserted. In some embodiments, the MM captures an image of the prostate 8330, and the radio-opaque markers 730 embedded in the handle 8425. In some embodiments, the MM can be captured with the patient's legs down to allow the patient 18 to fit into the gantry of the scanner. In some embodiments, the patient 18 is positioned on the procedure table with legs raised. Tracking markers 730 are snapped into the sockets on the protruding handle or the marker tree 690 with markers 720 is otherwise fastened. In some embodiments, registration of the markers 730, 720 is achieved by software (for example, using one or more modules of the software 3406 using the computing device 3401), which automatically detects the positions of the radio-opaque markers 730 on the medical image. In some embodiments, the known relative positions of the active tracking markers 720 and the radio-opaque marker 730 fiducials synchronizes the coordinate systems of the anatomy of the patient 18, tracking system 3417 and software 3406, and robot 15. In some embodiments, the surgeon plans trajectories for needle 7405 insertion into the prostate 8330 on the medical image, and the robot 15 moves the guide tube 50 to the desired 3D location for a needle 7405 of known length to be inserted to the desired depth.

Figure 87:
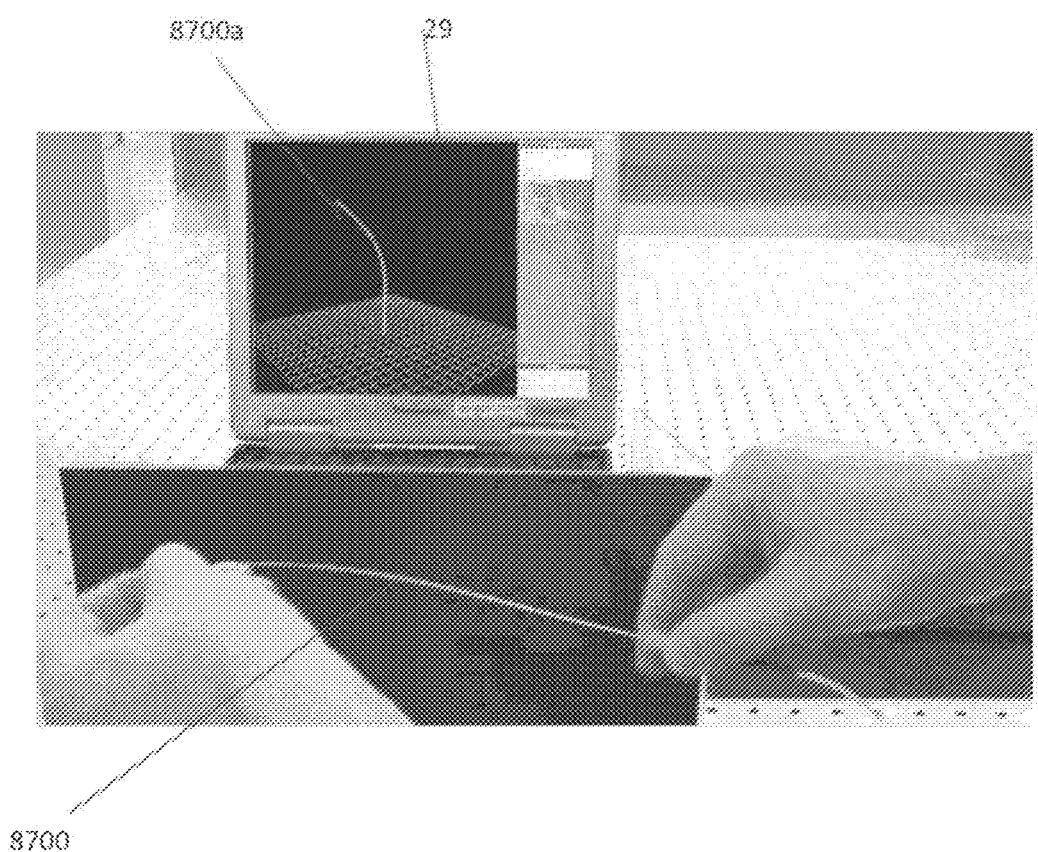
FIG. 87 illustrates a demonstration of a fibre Bragg grating ("FBG") interrogation technology with a flexible fiber optic cable in accordance with one embodiment of the invention.
Figure 88:
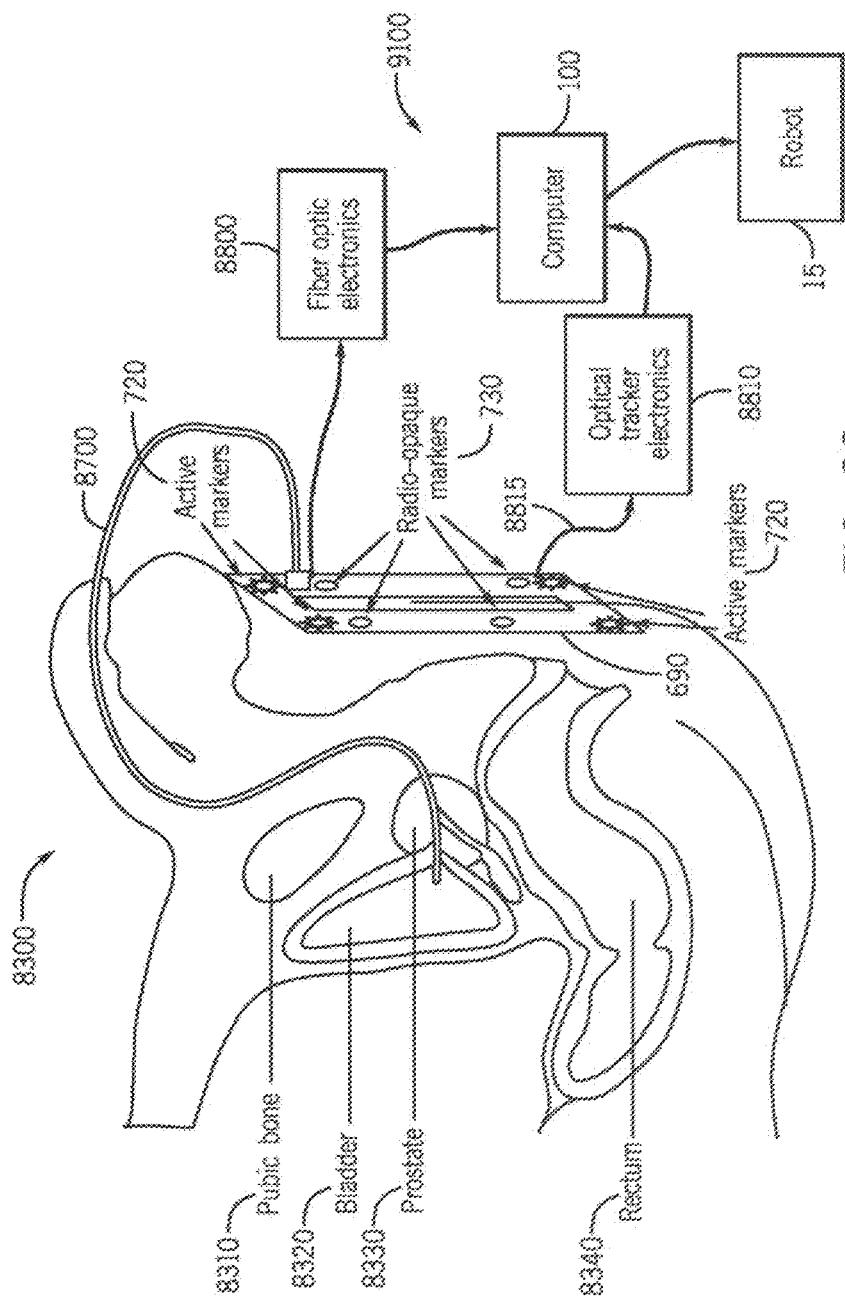
FIG. 88 illustrates a tracker attached to the surface of the skin of a patient and rigidly interconnected to a fiber optic probe to allow accurate tracking of the prostate in accordance with one embodiment of the invention.

Some embodiments can use a dual mode prostate 8330 tracking for image-guided therapy. For example, in some embodiments, it is possible to accurately track the prostate 8330 using a combination of two tracking modalities, including fiber optic tracking. For this alternate method to be used, an optical tracker (fiber optic probe 8700) would first be applied externally. This probe 8700 would be registered to the 3D medical image (for example, using an MM scan) in substantially the same way as previously described, such as for the spine tracking using CT imaging. In some embodiments, after registering and calibrating so that the coordinate systems of the medical image and cameras 8200 are synchronized, a means of updating and correcting for movement of the prostate 8330 can be used. In some embodiments, the probe 8700 can comprise a fiber optic sensor with a Bragg grating. For example, FIG. 87. illustrates a demonstration of a fibre Bragg grating ("FBG") interrogation technology with a flexible fiber optic cable in accordance with one embodiment of the invention. As shown the technology is available from Technobis Fibre Technologies, Uitgeest, Holland. As the fiber optic cable is bent by hand, the system accurately senses the position to which the cable deforms. As depicted in FIG. 88, in some embodiments, the probe 8700 could be inserted into the urethra with the tip of the sensor positioned at the prostate 8330. Since the prostate 8330 surrounds the urethra, a sensor such as probe 8700 positioned in the urethra should show very accurately how the prostate 8330 moves. As shown, the probe 8700 can be coupled with the fixture 690 including markers 720, 730, and coupled to the computer 100 with optical tracker electronics 8810 and fiber optic electronics 800 coupled to the computer 100, coupled to the robot 15.

Figure 89:
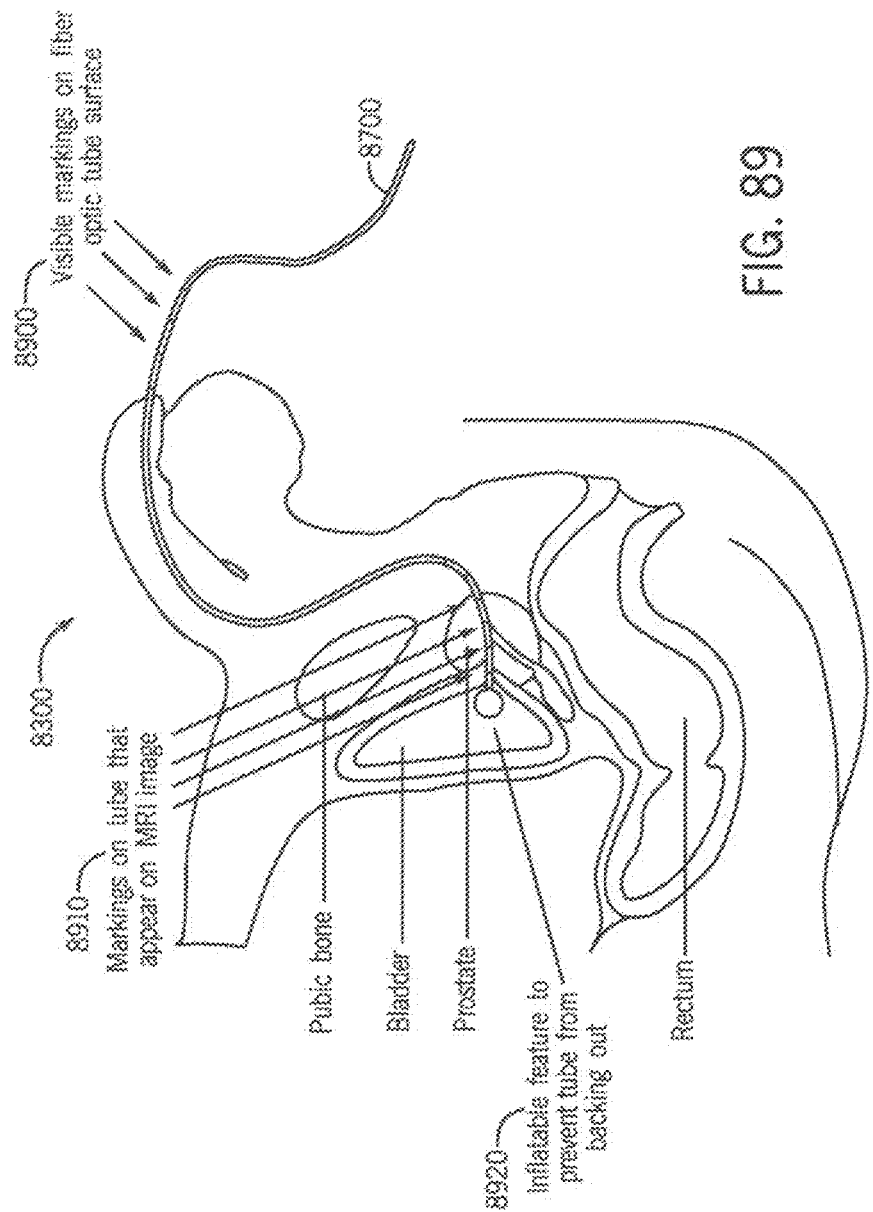
FIG. 89 illustrates the fiber optic probe as depicted in FIG. 88 with optically visible and MRI visible markings in accordance with one embodiment of the invention.

In some embodiments, markings 8910 (gradations) capable of being visualized on MRI can be placed on the outer shaft of the probe 8700 (see for example, FIG. 89). In some embodiments, if the MRI is obtained while the probe 8700 is in position in the urethra, it is possible to determine which point or points along the length of the probe 8700 represent key landmarks within the prostate 8330 (e.g., distal entry, proximal exit, midpoint). In some embodiments, these points can then be tracked by the fiber optic electronics 8800 during the procedure. In some embodiments, the points can then be used to adjust the coordinate system of the prostate 8330 so that the local coordinate system remains properly synchronized with the coordinate system of the optical tracking system 3417 even if the surrounding anatomy (specifically the anatomy to which the tracking markers 720, 730 are attached) shifts relative to the prostate 8330. In other words, the position of the tracking markers 720, 740 on the patient's skin surface gives an approximate estimate of where the prostate 8330 is currently located, and the fiber optic probe 8700 (which is rigidly interconnected to the tracking fixture 690) corrects this position to substantially improve accuracy and account for shifting of the prostate 8330.

Figure 90:
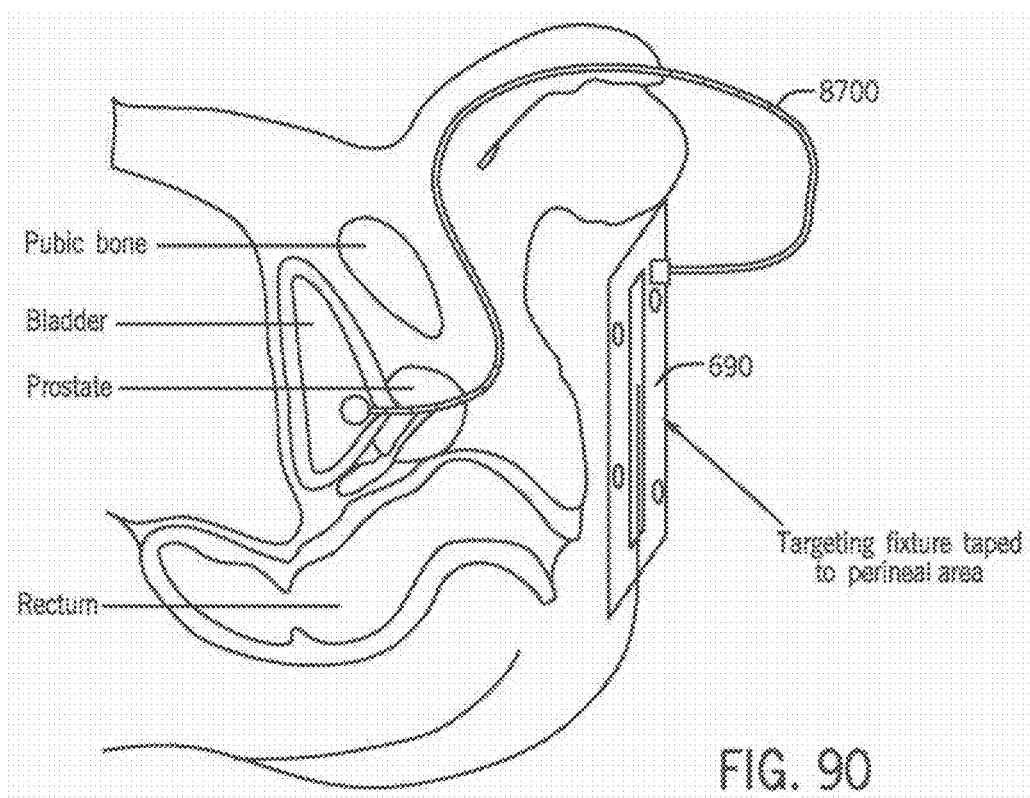
FIGS. 90-93 illustrate various embodiments of a fiber optic probe tracking system to allow accurate tracking of the prostate for image-guided therapy in accordance with one embodiment of the invention.

In some embodiments, image-guided therapy can be performed using one or more of the embodiments as described. For example, in some embodiments, the fiber optic probe as depicted in FIG. 88 can include optically visible 8900 and MM visible 8910. In some embodiments, the probe 8700 is inserted into the penis and advanced until the tip passes into the bladder 8320 (shown in FIG. 89). In some embodiments, the marking 8900, 8910 will provide information about what section of the fiber optic is positioned within the prostate 8330. In some embodiments, the depth of insertion is recorded based on visible markings 8900 on the proximal end that has not entered the penis is recorded. In some embodiments, this information can be used to check whether the probe 8700 has moved, or to reposition the probe 8700 if it is intentionally moved. In some embodiments, the proximal end may be secured (taped) to the penis to prevent advancement or withdrawal with patient 18 movement. In some embodiments, the distal end may have a feature to prevent it from easily sliding back out of the bladder 8320. For example, as shown in FIG. 90, some embodiments include a probe 8700 that comprises an inflatable tip 8920. In some embodiments, the inflatable tip 8920 can be enlarged or flared in the area near the tip. In some embodiments the tip 8920 comprises a balloon that is inflatable after the tip has passed into the bladder 8320, whereas in other embodiments, the tip 8920 comprises conventional soft wings that deploy after the tip has passed into the bladder 8320. As shown in FIG. 90, in some embodiments, a targeting fixture 690 is attached to the patient 18 in the region of the perineum (or abdomen or other suitable surface). The targeting fixture has embedded radio-opaque fiducial markers 730 that will show up on the MM (or other 3D scan), and is equipped with a conventional quick-connect interface that will later accept an attachment with active tracking markers 720. These tracking markers 720 do not need to be present yet, especially if they are not MRI compatible. The targeting fixture 690 can be rigidly interconnected with the proximal end of the fiber optic probe 8700.

Figure 91:
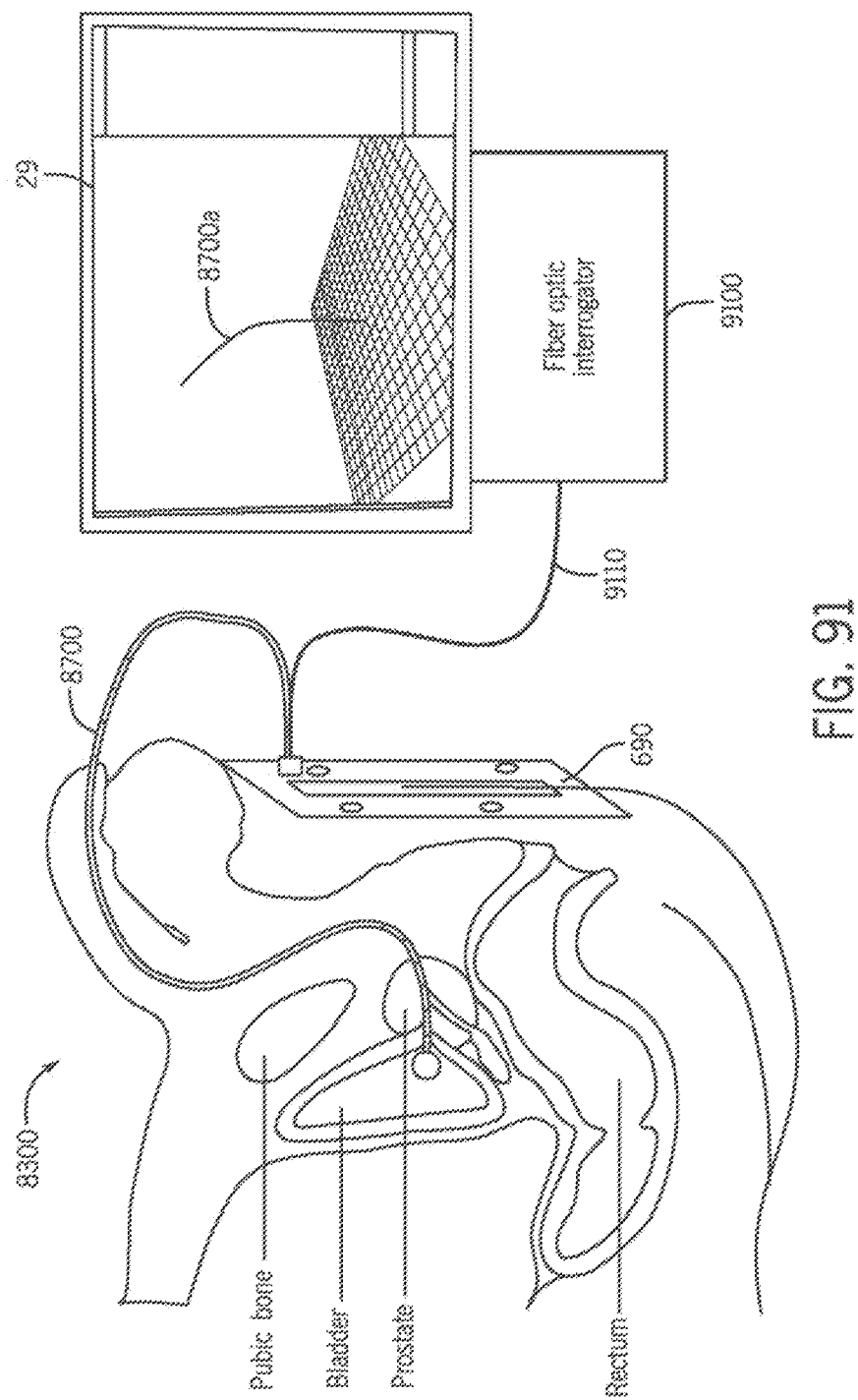

In some embodiments, the patient 18 is positioned outside or in the gantry of the MRI scanner before scanning. In some embodiments, the fiber optic tracking system 9100 is briefly activated to record position of the fiber optic probe 8700 along its entire length for later reference (see FIG. 91). Once recorded, the electronic interface (8800) for the fiber optic tracking system 9100 may be disconnected and removed from the MRI area.

In some embodiments, an MRI scan is obtained. The scan must visualize the prostate 8330, the radio-opaque fiducials 730 on the targeting fixture 690, and the markings 8910 that are present along the urethral tube that will be tracked with fiber optic probe 8700. In some embodiments, the position of the prostate 8330 along the fiber optic probe 8700 at the time of the scan is recorded from the radio-opaque markings 8910 on its surface.

Figure 92:
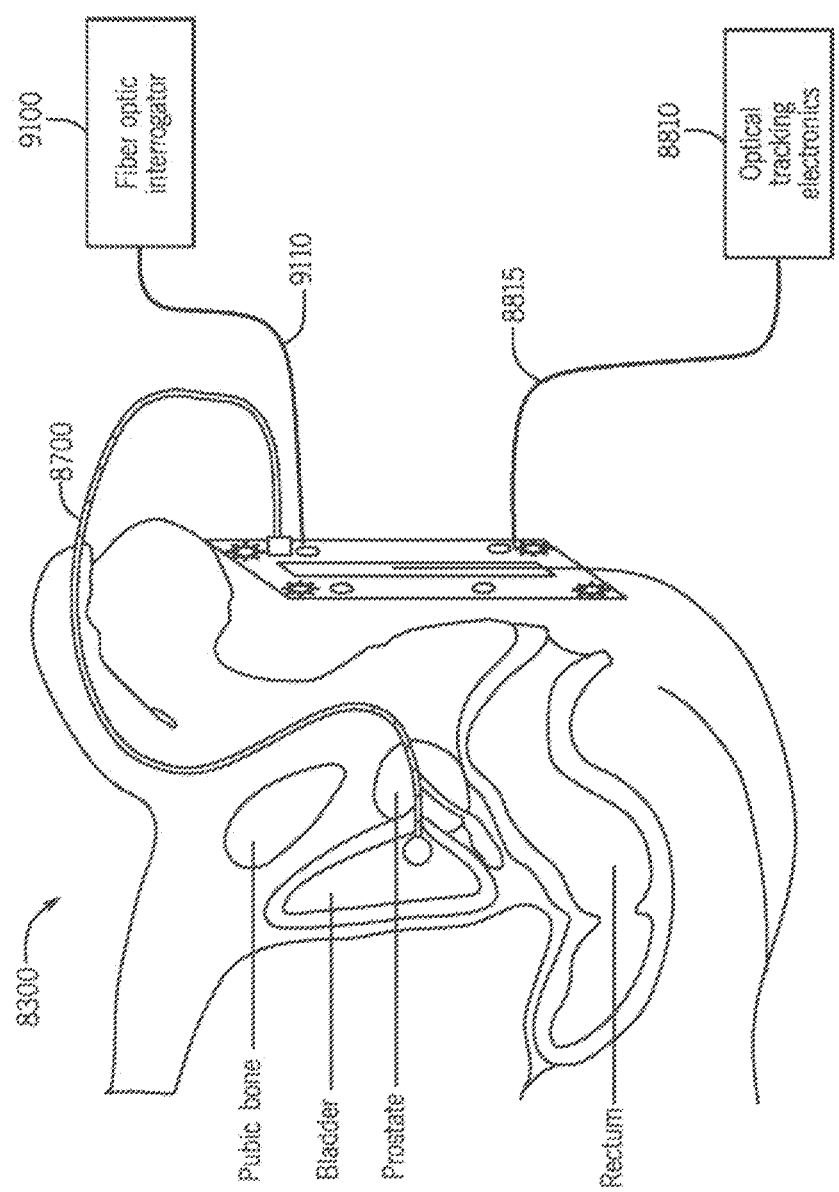

In some embodiments, the patient is positioned on the procedure table, and optical tracking markers 720 are snapped into the targeting fixture (see FIG. 92) and activated. In some embodiments, registration of the markers 720 is achieved by software (for example by one or more modules within the device 3401), which automatically detects the positions of the radio-opaque markers 730 on the medical image. The known relative positions of the active tracking markers 720 and the radio-opaque fiducials 730 synchronizes the coordinate systems of the anatomy, tracking system 3417, and robot 15. The fiber optic tracking system 9100 is activated.

Figure 93:
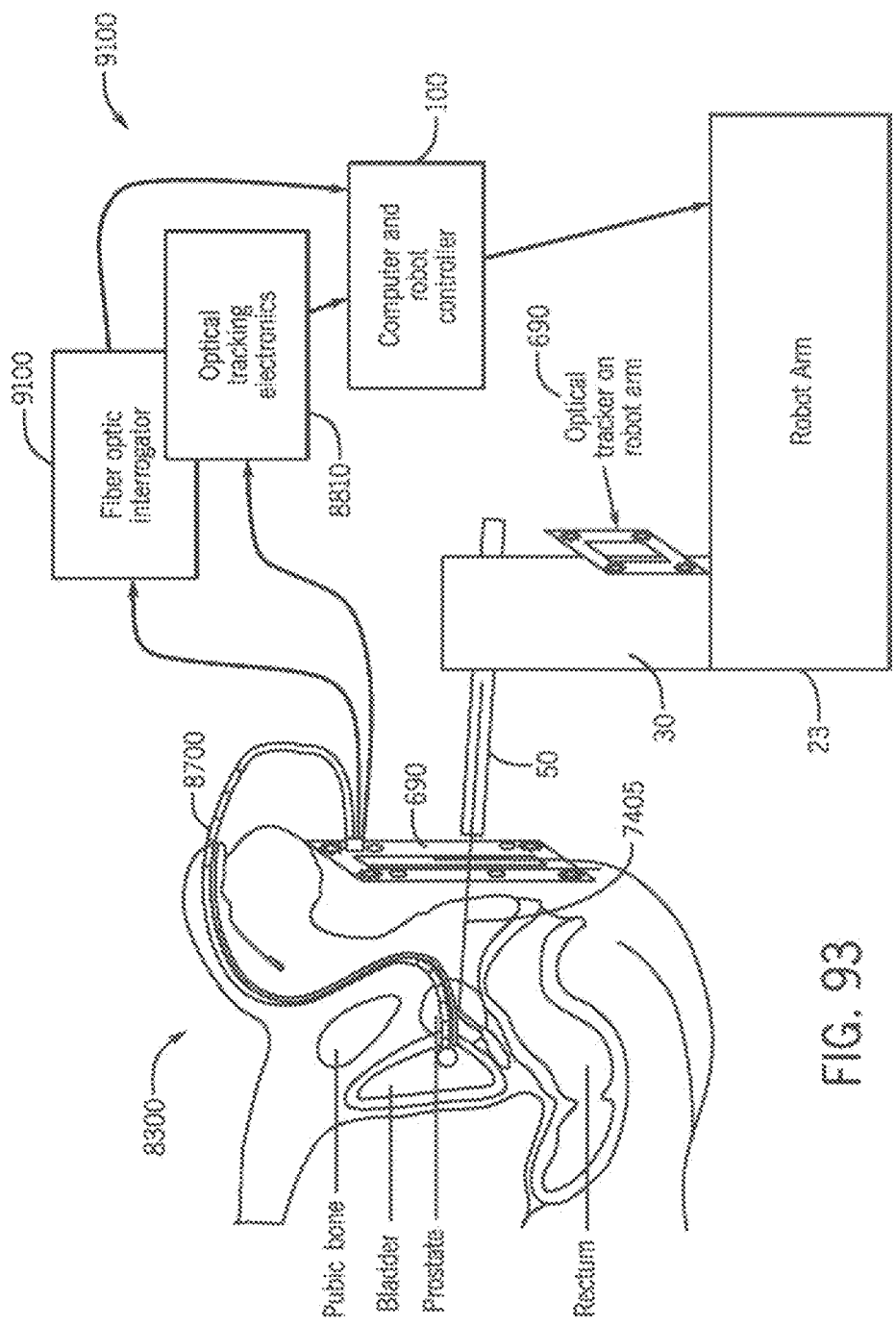

In some embodiments, the offset of the prostate 8330 from the position recorded on the MRI scan is determined as the offset of the prostate 8330 in the optically sensed position of the probe 8700 relative to the position at the time of the MM scan. In some embodiments, the surgeon plans trajectories for insertion of the needle 7405 into the prostate 8330 (from the medical image), and the robot 15 moves the guide tube 50 to the desired 3D location for a needle 7405 to be inserted to the desired depth (see FIG. 93). In some embodiments, an offset necessary to ensure that the correct region of the prostate 8330 is targeted, is determined from the probe 8700 sensed offset, and the position of the guide tube 50.

In some other embodiments, the probe 8700 could be inserted down the esophagus to track movement of the stomach, intestines, or any portion of the digestive system. In some embodiments, it could be inserted into a blood vessel to track the position of major vessels inside the body. In some embodiments, it could be inserted through the urethra into the bladder, ureters, or kidney. In all cases, it would help localize internal points for better targeting for therapy.

In some further embodiments, the probe 8700 could be combined with a conventional catheter for other uses. For example, fluid could be injected or withdrawn through a hollow conventional catheter that is attached along its length to the probe 8700. Further, in some embodiments, a conventional balloon catheter could also be utilized. The balloon could be temporarily inflated to secure a portion of the probe 8700 within the urethra, or other position inside the body, ensuring that the probe 8700 does not move forward or backward once positioned where desired.

A number of technologies for real-time 3D visualization of deforming soft tissue and bony anatomy without the radiation are available and/or are in development. In some embodiments, the surgical robot 15 can use these technologies during surgery, or other image-guided therapy. In some embodiments, the use of real-time 3D visualization, automated non-linear path planning and automated steering and advancement of flexible catheters or wires (for example wires 7405, 7410, 8600, or 8110) in a non-linear path becomes increasingly important.

In some embodiments, it may be possible to visualize soft tissues in real time by combining MRI (magnetic resonance imaging) and ultrasound or contrast enhanced ultrasound ("CEUS"). For example, in some embodiments, an MRI scan and a baseline ultrasound scan would be obtained of the anatomy of interest. In some embodiments, landmarks visualized on the ultrasound would be correlated to the MM (for example, borders of organs, blood vessels, bone, etc.). In some embodiments, a discrete set of key landmarks could be correlated such that the movement of other points of interest between these landmarks could be interpolated. In some embodiments, a computerized geometric model (with its unmoved baseline position corresponding to the anatomy seen on the MRI) would be created. Then, when movements of the landmark points are detected on ultrasound, the positions of the corresponding tissues visualized on the model can be adjusted. In some embodiments, the ultrasound would be allowed to run continuously, providing real-time data on the positions of the landmarks. In some embodiments, changes in landmark position would be used to update the model in real time, providing an accurate 3D representation of the soft tissues without exposure to radiation. In some embodiments, optical tracking markers 720 attached to the conventional ultrasound probes could provide data on the movement of the probes relative to the anatomy, which would affect the model calibration. In some embodiments, for accurate 3D positions of the points on the soft tissues, it may be necessary to utilize several conventional ultrasound probes locked in a rigid orientation relative to each other. In other embodiments, the ultrasound probes can be synchronized so that their relative positions are known or can be extracted. In some embodiments, optical markers 720 on multiple conventional ultrasound probes would allow registration of the multiple ultrasound probe orientations in the same coordinate system.

In some further embodiments of the invention, other methods for assessing distance to tissues of interest, such as electrical conductivity, capacitance, or inductance of the tissues as mild electrical current is applied.

In the modeling approach described above for visualizing soft tissues, it should be recognized that tracking a large number of landmarks helps ensure that the model is accurate. However, there is a trade-off that tracking a large number of landmarks may slow down the process, and disallow real-time updating or require a lengthy registration process. In some embodiments, as fewer landmarks are tracked, tissue modeling to predict deformation of the non-tracked parts of the model becomes increasingly important. In some embodiments, for tissue modeling, the elasticity and other mechanical qualities of the tissues are needed. It may be possible to assess the status of the tissues through a mechanism such as spectroscopy, where absorbance of light passed through tissue might provide information on the composition of tissues, electrical conductivity, DEXA scan, MRI scan, CT scan or other means. This information could be provided to the computer model to allow better estimation of soft tissue deformation.

Another possible mechanism for visualizing soft tissues can include injecting a conventional liquid tracer into the patient 18 that causes different tissues to become temporarily detectable by an external scan. For example, the tracer could comprise a radioactive isotope that is attracted more to certain types of cells than others. Then, when the patient is placed near an array of conventional radiation sensors, the sensors could detect the concentrations of the isotope in different spatial locations.

Some embodiments include a mechanism to allow the user to control the advancement and direction of a flexible catheter or wire (for example wire 7405, 7410, 7600, or 8110) through an interface with the robot 15. In some embodiments, this mechanism can snap or lock into the robot's end-effectuator 30. In some embodiments, the guide tube 50 on the robot's end-effectuator 30 provides accurately controlled orientation and position of the catheter or wire at the point where it enters the patient. In some embodiments, the mechanism would then allow the user to control the rate and amount of advancement of the tube 50, the rate and amount of rotation of the tube 50, and activation of steering RF energy (for example, as described earlier with regard to steerable needle 7600 in FIG. 73). In some embodiments, based on assumptions about the condition of the soft tissues, and locations of obstacles such as blood vessels, nerves, or organs between entry into the patient and the target, a non-linear path is planned by the software 3406 with parameters under the user's control. For example, in some embodiments, the method can include a command sequence such as "advance 5 mm, activate steering toward an azimuth of +35°, continue advancing 5 mm while rotating at 1° per second," etc. In some embodiments, during advancement of the catheter or wire 7600 (or other wire 7405, 7410, or 8110), the real-time location of the tip is tracked using LPS or other visualization means. In some embodiments, the path plan is recalculated based on divergence from the expected path and advancement continues. In some embodiments, this advancing/turning snap-in mechanism can also be used with beveled needles, taking advantage of the direction of the bevel, and the beveled face deflection force that moves the needle laterally away from the face when advanced. In some embodiments, software 3406 would plan which direction the bevel should be oriented during different phases of needle advancement.

In some embodiments, a mechanism similar to the one described above can also be used for automatic hole preparation and insertion of screws. For example, in some embodiments, the end-effectuator 30 could have a conventional mechanism that would allow a tool to be retrieved from a conventional tool repository located somewhere outside the surgical field 17 In some embodiments, features on the tool holder would allow easy automated engagement and disengagement of the tool. In some embodiments, after retrieving the tool, the end effectuator 30 would move to the planned screw location and drill a pilot hole by rotating the assembly at an optimal drilling speed while advancing. In some embodiments, the system 1 would then guide the robot 15 to replace the drill in the repository, and retrieve a driver with appropriately sized screw. In some embodiments, the screw would then be automatically positioned and inserted. In some embodiments, during insertion of the screw, thrust and torque should be coordinated to provide good bite of the screw into bone. That is, the appropriate amount of forward thrust should be applied during rotation so the screw will not strip the hole.

Some embodiments of the method also include algorithms for automatically positioning conventional screws. For example, in some embodiments, different considerations may dictate the decision of where the screw should be placed. In some embodiments, it may be desirable to place the screw into the bone such that the screw is surrounded by the thickest, strongest bone. In some embodiments, algorithms can be used to locate the best quality bone from CT or DEXA scans, and to find an optimized trajectory such that the width of bone around the screw is thickest, or remains within cortical instead of cancellous bone for the greatest proportion. In some embodiments, it may be desirable to place the screw into the bone at an entry point that is most perpendicular to the screw, or is at a "valley" instead of a peak or slope on the bony articulations. In some embodiments, by placing the screw in this way, it is less likely to skive or rotate during insertion and therefore likely to end up in a more accurate inserted location. In some embodiments, algorithms can be used to assess the surface and find the best entry point to guide the screw to the target, while penetrating the bone perpendicular to the bone surface. In other embodiments, it may be desirable to place screws in a multi-level case such that all the screw heads line up in a straight line or along a predictable curve. In some embodiments, by aligning screw heads in this way, the amount by which the surgeon must bend the interconnecting rod is minimized, reducing the time of the procedure, and reducing weakening of the metal rod due to repeated bending. In some embodiments, algorithms can be used that keep track of anticipated head locations as they are planned, and suggest adjustments to trajectories that provide comparable bony purchase, but better rod alignment.

Some embodiments of the invention can use an LPS system that uses time-of-flight of RF signals from an emitter to an array of receivers to localize the position of the emitter. In some embodiments, it may be possible to improve the accuracy of the LPS system by combining it with other modalities. For example, in some embodiments, it may be possible use a magnetic field, ultrasound scan, laser scan, CT, MRI or other means to assess the density and position of tissues and other media in the region where the RF will travel. Since RF travels at different rates through different media (air, tissue, metal, etc.), knowledge of the spatial orientation of the media through which the RF will travel will improve the accuracy of the time-of-flight calculations.

In some embodiments, an enhancement to the robot 15 could include inserting a conventional ultrasound probe into the guide tube 50. In some embodiments, the ultrasound probe could be used as the guide tube 50 penetrates through soft tissue to help visualize what is ahead. As the guide tube 50 advances, penetrating soft tissue and approaching bone, the ultrasound probe would be able to detect contours of the bone being approached. In some embodiments, this information could be used as a visual reference to verify that the actual anatomy being approached is the same as the anatomy currently being shown on the 3D re-sliced medical image over which the robot is navigating. For example, in some embodiments, if a small protrusion of bone is being approached dead center on the probe/guide tube 50 as it is pushed forward, the region in the center of the ultrasound field representing the raised bone should show a short distance to bone, while the regions toward the perimeter should show a longer distance to bone. In some embodiments, if the position of the bony articulation on the re-sliced medical image does not appear to be lined up with the 2D ultrasound view of where the probe is approaching, this misalignment could be used to adjust the registration of the robot 15 relative to the medical image. Similarly, in some embodiments, if the distance of the probe tip to bone does not match the distance perceived on the medical image, the registration could also be adjusted. In some embodiments, where the guide tube 50 is approaching something other than bone, this method may also be useful for indicating when relative movement of internal soft tissues, organs, blood vessels, and nerves occurs.

Figure 94:
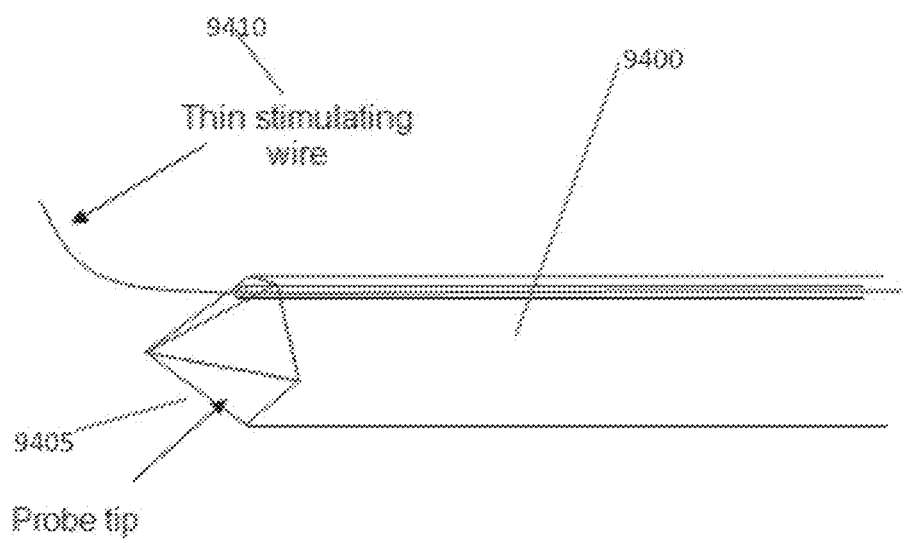
FIG. 94 illustrates one embodiment of a nerve sensing probe.

Some embodiments can include a nerve sensing probe. For example, in some embodiments, for sensing whether a penetrating probe is near a nerve, an electromyography ("EMG") response to applied current could be used, enabling the ability of the robot 15 to steer around nerves. For example, as shown in FIG. 94, a probe 9400 could be used, with 1 or more cannulation offset from the probe's 9400 central axis that would enable a thin wire 9410 to extend from the tip 9405, ahead and to one side of the tip 9405. A beveled tip 9405 (or a conical or rounded tip) could be used.

In some embodiments, the probe 9400 could be advanced manually or automatically and stopped, then the stimulating wire 9410 could be extended and current applied. In some embodiments, the EMG could be checked to verify whether a nerve is in proximity. In some embodiments, the simulating wire 9410 could be retracted, and probe 9400 rotated so that the portal for the stimulating wire 9410 is positioned at a different azimuth index. In some embodiments, the probe 9400 could again be extended to check for the presence of nerves in a different region ahead. In some embodiments, if a nerve is encountered, it would be known which direction the nerve is located, and which direction the probe 9400 would need to be steered to avoid it. In some embodiments, instead of a single wire 9410 extending and checking for a nerve, multiple wires 9410 could simultaneously be extended from several portals around the probe 9400. In some embodiments, the wires 9410 could be activated in sequence, checking for EMG signals and identifying which wire 9410 caused a response to identify the direction to avoid or steer. In some embodiments, it could be necessary to fully retract the stimulating wires 9410 before attempting to further advance the probe 9400 to avoid blocking progress of the probe 9400. In some embodiments, the stimulating wires 9410 would have a small enough diameter so as to be able to penetrate a nerve without causing nerve damage.

As noted elsewhere in this application, the robot 15 executed trajectories for paths into a patient 18 are planned using software (for example, at least one module of the software 3406 running on the computing device 3401 including computer 100) where the desired vectors are defined relative to radio opaque markers 730 on the image and therefore relative to active markers 720 on the targeting fixture 690. In some embodiments, these trajectories can be planned at any time after the image is acquired, before or after registration is performed. In some embodiments, it is possible that this trajectory planning can be done on another computerized device. For example, in some embodiments, a conventional portable device (such as a tablet computer, or a laptop computer, or a smartphone computer) could be used. In some embodiments, the 3D image volume would be transferred to the portable device, and the user would then plan and save the desired trajectories. In some embodiments, when robotic control is needed, this same image volume could be loaded on the console that controls the robot 15 and the trajectory plan could be transferred from the portable device. In some embodiments, using this algorithm, it would therefore be possible for a series of patients 18 to each to have a targeting fixture 690 applied and an imaging scan, such as a CT scan. In some embodiments, the 3D volume for each patient 18 could be exported to different portable devices, and the same or different surgeons could plan trajectories for each patient 18. In some embodiments, the same or different robot 15 could then move from room to room. In some embodiments, in each room, the robot 15 would be sterilized (or have sterile draping applied, and would receive the scan and trajectory plan. The robot 15 would then execute the plan, and then move to the next room to repeat the process. Similarly, the portion of the registration process in which the 3D image volume is searched for radio-opaque markers 730 could be performed on the portable device. Then, in some embodiments, when the robot 15 arrives, the registration information and the trajectories are both transferred to the robot 15 console. In some embodiments, by following this procedure, the time of computation of the image search algorithm on the robot 15 console is eliminated, increasing efficiency of the overall process when the robot 15 is required in multiple rooms.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

What is claimed is:

1. A surgical robot system comprising:
a processor;
a dynamic reference base attached to a patient fixture instrument, wherein the dynamic reference base has tracking markers, which are configured to be tracked by a camera system, indicating a position of the patient fixture instrument in a camera coordinate system associated with the camera system; and
a calibration frame having tracking markers and radiopaque markers, the tracking markers configured to be trackable by the camera system for indicating a location of a target anatomical structure in the camera coordinate system and the radiopaque markers indicating a location of the target anatomical structure in an image coordinate system defined by an imaging system,
a hand-held probe having tracking markers configured to be trackable by the camera system, a rigid body and a tip extending from the rigid body, the tip being adapted to physically contact a selected location of the calibration frame so as to determine the location of at least one of the tracking and radiopaque markers of the calibration frame, wherein the surgical robot system is configured to establish a spatial relationship between the tracking markers and the radiopaque markers of the calibration frame by recording, via the processor, the locations of two opposite surfaces of each of the radiopaque markers of the calibration frame pointed to by the tip of the hand-held probe while simultaneously recording, via the processor, the position of the tracking markers of the calibration frame, wherein an average position of the locations of each of the two opposite surfaces is used by the processor to determine a center of each radiopaque marker;
wherein the surgical robot system is configured to associate a spatial location of the radiopaque markers of the calibration frame in the image coordinate system to a spatial location of the tracking makers of the calibration frame in the camera coordinate system for a registration of the target anatomical structure in the camera coordinate system,
wherein the surgical robot system is configured to transfer the registration of the target anatomical structure to the dynamic reference base,
wherein the dynamic reference base is configured to track the target anatomical structure in the camera coordinate system after registration occurs.

2. The surgical robot system of claim 1, wherein the calibration frame is removably attached to the patient in proximity to the target anatomical structure.

3. The surgical robot system of claim 2, wherein the calibration frame is removed from the patient after registration of the target anatomical structure is transferred to the dynamic reference base.

4. The surgical robot system of claim 1, wherein the radio-opaque markers of the calibration frame can be located within a CT scan region and the tracking markers can be located outside of the CT scan region.

5. The surgical robot system of claim 1, wherein a surgical field can be located within a perimeter created by radio-opaque markers.

6. The surgical robot system of claim 1, wherein the calibration frame comprises an asymmetrical arrangement of the radiopaque markers of the registration fixture device.

7. The surgical robot system of claim 1, wherein at least some of the radiopaque markers are placed in an asymmetrical configuration on the calibration frame and the hand-held probe tip has a concave shape to receive the radiopaque markers.

8. The surgical robot system of claim 1, wherein a probe is used to register the coordinates of the radiopaque markers and the tracking markers.

9. The surgical robot system of claim 1, wherein the tracking markers are positioned on a portion of a robot arm in order to monitor a position of the robot arm and the calibration frame or dynamic reference base simultaneously.

10. A surgical robot system comprising:
   a robot base having a processor, a display, and an arm;
   a dynamic reference base attached to a patient fixture instrument, wherein the dynamic reference base has tracking markers, which are configured to be tracked by a camera system, indicating a position of the patient fixture instrument in a camera coordinate system associated with the camera system; and
   a calibration frame having tracking markers and radiopaque markers, the tracking markers configured to be trackable by the camera system for indicating a location of a target anatomical structure in the camera coordinate system and the radiopaque markers indicating a location of the target anatomical structure in an image coordinate system defined by an imaging system,
   a hand-held probe having tracking markers configured to be trackable by the camera system, a rigid body and a tip extending from the rigid body, the tip being adapted to physically contact a selected location of the calibration frame so as to determine the location of at least one of the tracking and radiopaque markers of the calibration frame, wherein the surgical robot system is configured to establish a spatial relationship between the tracking markers and the radiopaque markers of the calibration frame by recording, via the processor, the locations of two opposite surfaces of each of the radiopaque markers of the calibration frame pointed to by the tip of the hand-held probe while simultaneously recording, via the processor, the position of the tracking markers of the calibration frame, wherein an average position of the locations of each of the two opposite surfaces is used by the processor to determine a center of each radiopaque marker;
   wherein the surgical robot system is configured to associate a spatial location of the radiopaque markers of the calibration frame in the image coordinate system to a spatial location of the tracking makers of the calibration frame in the camera coordinate system for a registration of the target anatomical structure in the camera coordinate system,
   wherein the surgical robot system is configured to transfer the registration of the target anatomical structure to the coordinate system of the dynamic reference base,
   wherein the dynamic reference base is configured to track the target anatomical structure in the camera coordinate system after registration occurs,
   wherein the robot arm is configured to operated based on the coordinate system of the dynamic reference base.

11. The surgical robot system of claim 10, wherein the calibration frame is removably attached to the patient.

12. The surgical robot system of claim 11, wherein the calibration frame is removed from the patient after registration of the target anatomical structure is transferred to the dynamic reference base.

13. The surgical robot system of claim 11, wherein the radio-opaque markers of the calibration frame can be located within a CT scan region and tracking markers can be located outside of the CT scan region.

14. The surgical robot system of claim 11, wherein a surgical field can be located within a perimeter created by radio-opaque markers.

15. The surgical robot system of claim 11, wherein the calibration frame comprises an asymmetrical arrangement of the radiopaque markers of the registration fixture device.

16. The surgical robot system of claim 11, wherein three radiopaque markers are placed in an asymmetrical configuration on the calibration frame.

17. The surgical robot system of claim 11, wherein a probe is used to register the coordinates of the radiopaque markers and the tracking markers.

18. The surgical robot system of claim 11, wherein the tracking markers are positioned on a portion of the robot arm in order to monitor a position of the robot arm and the calibration frame or dynamic reference base simultaneously.

19. The surgical robot system of claim 11, wherein a processor of the surgical robot system is configured to map and identify the radiopaque markers and the tracking markers based on the raw coordinates.

20. A surgical robot system comprising:
   a robot base having a processor, a display, and an arm;
   a dynamic reference base attached to a patient fixture instrument, wherein the dynamic reference base has tracking markers, which are configured to be tracked by a camera system, indicating a position of the patient fixture instrument in a camera coordinate system associated with the camera system;
   a calibration frame having tracking markers and radiopaque markers, the tracking markers configured to be trackable by the camera system for indicating a location of a target anatomical structure in the camera coordinate system and the radiopaque markers indicating a location of the target anatomical structure in an image coordinate system defined by an imaging system; and
   a hand-held probe embedded with tracking markers and in a known relationship with a tip of the probe, the tip being adapted to physically contact a selected location of the calibration frame,
   wherein the surgical robot system is configured to associate a spatial location of the radiopaque markers of the calibration frame in the image coordinate system to a spatial location of the tracking makers of the calibration frame in the camera coordinate system for a registration of the target anatomical structure in the camera coordinate system; and wherein the surgical robot system is configured to transfer the registration of the target anatomical structure to the coordinate system of the dynamic reference base;

wherein the dynamic reference base is configured to track the target anatomical structure in the camera coordinate system after registration occurs, wherein the surgical robot system is configured to establish a spatial relationship between the tracking markers and the radiopaque markers of the calibration frame by recording, via the processor, the locations of two opposite surfaces of each of the radiopaque markers of the calibration frame pointed to by the tip of the hand-held probe while simultaneously recording, via the processor, the position of the tracking markers of the calibration frame, wherein an average position of the locations of each of the two opposite surfaces is used by the processor to determine a center of each radiopaque marker.

* * * * *